United States Patent
Bhatia et al.

(10) Patent No.: US 9,340,772 B2
(45) Date of Patent: May 17, 2016

(54) GENERATING INDUCED PLURIPOTENT STEM CELLS AND PROGENITOR CELLS FROM FIBROBLASTS

(75) Inventors: Mickie Bhatia, Hamilton (CA); Eva Szabo, Hamilton (CA); Shravanti Rampalli-Deshpande, Hamilton (CA); Ruth Munoz Risueno, Hamilton (CA)

(73) Assignee: McMaster University, Hamilton, Ontario (CA)

( * ) Notice: Subject to any disclaimer, the term of this patent is extended or adjusted under 35 U.S.C. 154(b) by 0 days.

(21) Appl. No.: 13/504,745

(22) PCT Filed: Oct. 29, 2010

(86) PCT No.: PCT/CA2010/001708
§ 371 (c)(1),
(2), (4) Date: Apr. 27, 2012

(87) PCT Pub. No.: WO2011/050470
PCT Pub. Date: May 5, 2011

(65) Prior Publication Data
US 2012/0214236 A1    Aug. 23, 2012

Related U.S. Application Data

(60) Provisional application No. 61/256,170, filed on Oct. 29, 2009.

(51) Int. Cl.
*C12N 5/00*    (2006.01)
*C12N 5/02*    (2006.01)
*C12N 5/079*    (2010.01)
*C12N 5/078*    (2010.01)
*C12N 5/074*    (2010.01)
*A61K 35/12*    (2015.01)

(52) U.S. Cl.
CPC ............ *C12N 5/0618* (2013.01); *C12N 5/0634* (2013.01); *C12N 5/0696* (2013.01); *A61K 35/12* (2013.01); *C12N 2501/105* (2013.01); *C12N 2501/11* (2013.01); *C12N 2501/115* (2013.01); *C12N 2501/119* (2013.01); *C12N 2501/13* (2013.01); *C12N 2501/26* (2013.01); *C12N 2501/41* (2013.01); *C12N 2501/602* (2013.01); *C12N 2501/603* (2013.01); *C12N 2501/605* (2013.01); *C12N 2501/608* (2013.01); *C12N 2506/1307* (2013.01); *C12N 2510/00* (2013.01)

(58) Field of Classification Search
None
See application file for complete search history.

(56) References Cited

U.S. PATENT DOCUMENTS

2010/0021437 A1    1/2010 Isacson et al.
2012/0021519 A1*   1/2012 Ichida et al. .......... 435/377
2012/0282229 A1*  11/2012 Kannemeier et al. .... 424/93.21
2013/0177912 A1*   7/2013 Rao et al. .............. 435/6.11
2013/0210138 A1*   8/2013 Thomson et al. ........ 435/366

FOREIGN PATENT DOCUMENTS

| EP | 1970446 A1 | 9/2008 |
|---|---|---|
| EP | 2096169 A1 | 9/2009 |
| WO | WO/2007/016037 A2 | 2/2007 |
| WO | WO/2007/064090 A1 | 6/2007 |
| WO | 2008/118820 A2 | 10/2008 |
| WO | 2008/124133 A1 | 10/2008 |
| WO | 2009/007852 A2 | 1/2009 |
| WO | WO/2009/067757 A1 | 6/2009 |
| WO | WO2009/117439 A2 | 9/2009 |
| WO | 2010/052904 A1 | 5/2010 |
| WO | WO/2010/051526 A1 | 5/2010 |

OTHER PUBLICATIONS

Takahashi, K. et al., Induction of pluripotent stem cells from adult human fibroblasts by defined factors. Cell. Nov. 30, 2007; vol. 131 (5), pp. 861-872. ISSN: 0092-8674.
Wernig, M. et al., In vitro reprogramming of fibroblasts into a pluripotent ES-cell-like state. Nature. Jul. 19, 2007; vol. 448 (7151), pp. 318-324. ISSN: 0028-0836.
Patel, M. et al., Advances in reprogramming somatic cells to induced pluripotent stem cells. Stem Cell Reviews. Sep. 2010; vol. 6 (3), pp. 367-380. ISSN: 1550-8943.
Schenke-Layland, K. et al., Reprogrammed mouse fibroblasts differentiate into cells of the cardiovascular and hematopoietic lineages, Stem Cells, 26:1537-1546 (2008).
Choi K-D et al., Hematopoietic and endothelial differentiation of human induced pluripotent stem cells, Stem Cells, 27:559-567 (2009).
Grinnell, K. L., et al. De-differentiation of mouse interfollicular keratinocytes by the embryonic transcription factor, Oct. 4, Journal of Investigative Dermatology, 127:372-380 (2007), (published online Aug. 24, 2006).
Kong, K.Y., et al., Expression of Scl in mesoderm rescues hematopoiesis in the absence of Oct-4 Blood, vol. 114:60-63 (prepublished online Mar. 25, 2009).
Shimozaki, K et al., Involvement of Oct3/4 in the enhancement of neuronal differentiation of ES cells in neurogenesis-inducing cultures, Development, 130: 2505-2512 (2003).

(Continued)

*Primary Examiner* — Michail Belyavskyi
(74) *Attorney, Agent, or Firm* — Robert C. Netter, Jr.; Dann, Dorfman, Herrell and Skillman

(57) ABSTRACT

The present disclosure provides a method of generating progenitor cells, such as hematopoietic or neural progenitor cells, from fibroblasts, such as dermal fibroblasts, comprising providing fibroblasts that express or are treated with a POU domain containing gene or protein and culturing the cells under conditions that allow production of progenitor cells, without traversing the pluripotent state. Also provided is a method of isolating a subpopulation of fibroblasts with reprogramming potential comprising providing fibroblasts that express an Oct-4-reporter and isolating cells that are positive for the reporter. Further provided is a method of generating reprogrammed fibroblast-derived induced pluripotent stem cells. Also provided are uses and assays of the cells produced by the methods of the disclosure.

6 Claims, 46 Drawing Sheets

(56) References Cited

OTHER PUBLICATIONS

Takeda, J. et al., Human Oct3 gene family: cDNA sequences, alternative splicing, gene organization, chromosomal location, and expression at low levels in adult tissues. 1992, Nucleic Acids Research, vol. 20, No. 17, 4613-4620.

Byrne, J. A. et al., Enhanced Generation of Induced Pluripotent Stem Cells from a Subpopulation of Human Fibroblasts, PLoS one, Sep. 23, 2009, vol. 4, Issue 9, e7118.

Racila D. et al., Transient expression of OCT4 is sufficient to allow human keratinocytes to change their differentiation pathway, Gene Therapy (2011) 18, 294-303, (published online Oct. 28, 2010).

Buitrago, W. and Roop, D. R., The Almighty POUripotent Regulator? Journal of Investigative Dermatology (2007), vol. 127, 260-262.

Masip, M. et al., Reprogramming with Defined Factors: from induced pluripotency to induced transdifferentiation, Mol. Hum. Reprod., (2010), vol. 16, No. 11, 856-868.

Yu, J., et al., Induced pluripotent stem cell lines derived from human somatic cells. Science 318, (2007), 1917-1920.

Feng, Ru et al., PU.1 and C/EBP$\alpha/\beta$ convert fibroblasts into macrophage-like cells, PNAS, Apr. 22, 2008, vol. 105, No. 16, 6057-6062.

Goolsby, J. et al., Hematopoietic progenitors express neural genes, PNAS, Dec. 9, 2003, vol. 100, No. 25, 14926-14931.

Graf, T. and Enver, T. Forcing cells to change lineages, Nature, vol. 462, Dec. 3, 2009, 587-594.

Ieda, M. et al., Direct Reprogramming of Fibroblasts into Functional Cardiomyocytes by Defined Factors, Cell 142, Aug. 6, 2010, 375-386.

Kim, J. B. et al., Direct reprogramming of human neural stem cells by OCT4, Nature, vol. 461, Oct. 1, 2009, 649-654.

Lengner, C. J. et al, The pluripotency regulator Oct4, Cell Cycle 7:6;Mar. 15, 2008, 725-728.

Toma, J. G. et al., Isolation and Characterization of Multipotent Skin-Derived Precursors from Human Skin; Stem Cells 2005; 23:727-737.

Vierbuchen, T. and Wernig, M., Direct lineage conversions: unnatural but useful?, Nature Biotechnology, vol. 29 No. 10, Oct. 2011, 892-907.

Vierbuchen, T. et al., Direct conversion of fibroblasts to functional neurons by defined factors, Nature, vol. 463, Feb. 25, 2010, 1035-1042.

Hotta, A. et al., Isolation of Human iPS Cells Using EOS Lentiviral Vectors to Select for Pluripotency, Nature Methods, vol. 6, No. 5, May 2009 (Published online Apr. 26, 2009), pp. 370-376.

Lowry, W.E. et al., Generation of Human Induced Pluripotent Stem Cells from Dermal Fibroblasts, PNAS, Feb. 26, 2008, vol. 105, No. 8, pp. 2883-2888.

Chang, C-W et al., Polycistronic Lentiviral Vector for "Hit and Run" Reprogramming of Adult Skin Fibroblasts to Induced Pluripotent Stem Cells, Stem Cells, May 1, 2009, vol. 27, No. 5, (Published online Feb. 12, 2009) pp. 1042-1049.

Huangfu, D., et al., "Induction of Pluripotent Stem Cells from Primary Human Fibroblasts with only Oct4 and Sox2," Nature Biotechnol. (2008) 26(11):1269-1275.

Feng, B., et al., "Reprogramming of Fibroblasts into Induced Pluripotent Stem Cells with Orphan Nuclear Receptor Esrrb," Nature Cell Biol. (2009) 11(2):197-203.

\* cited by examiner

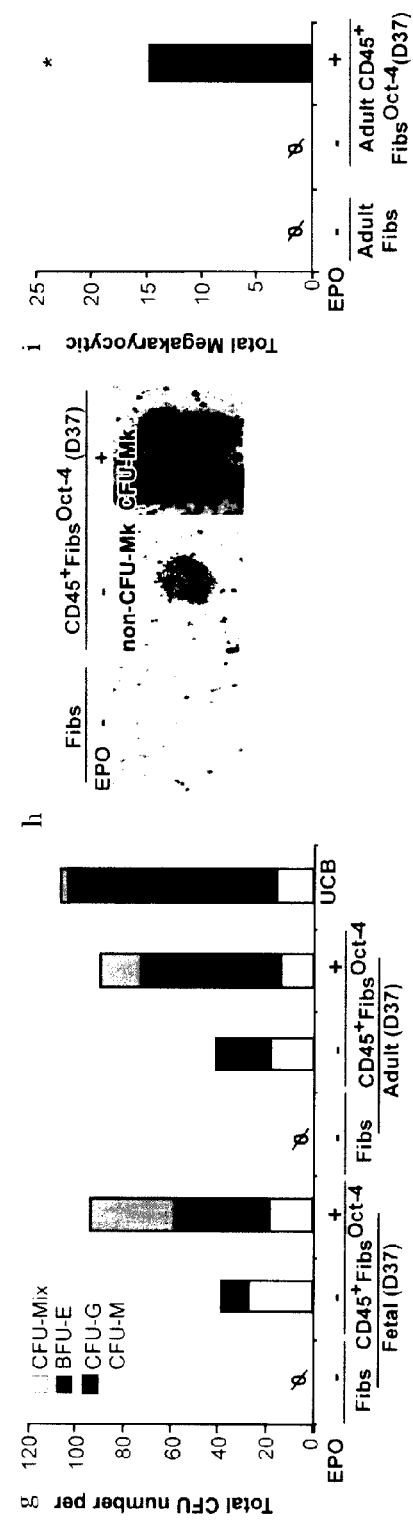

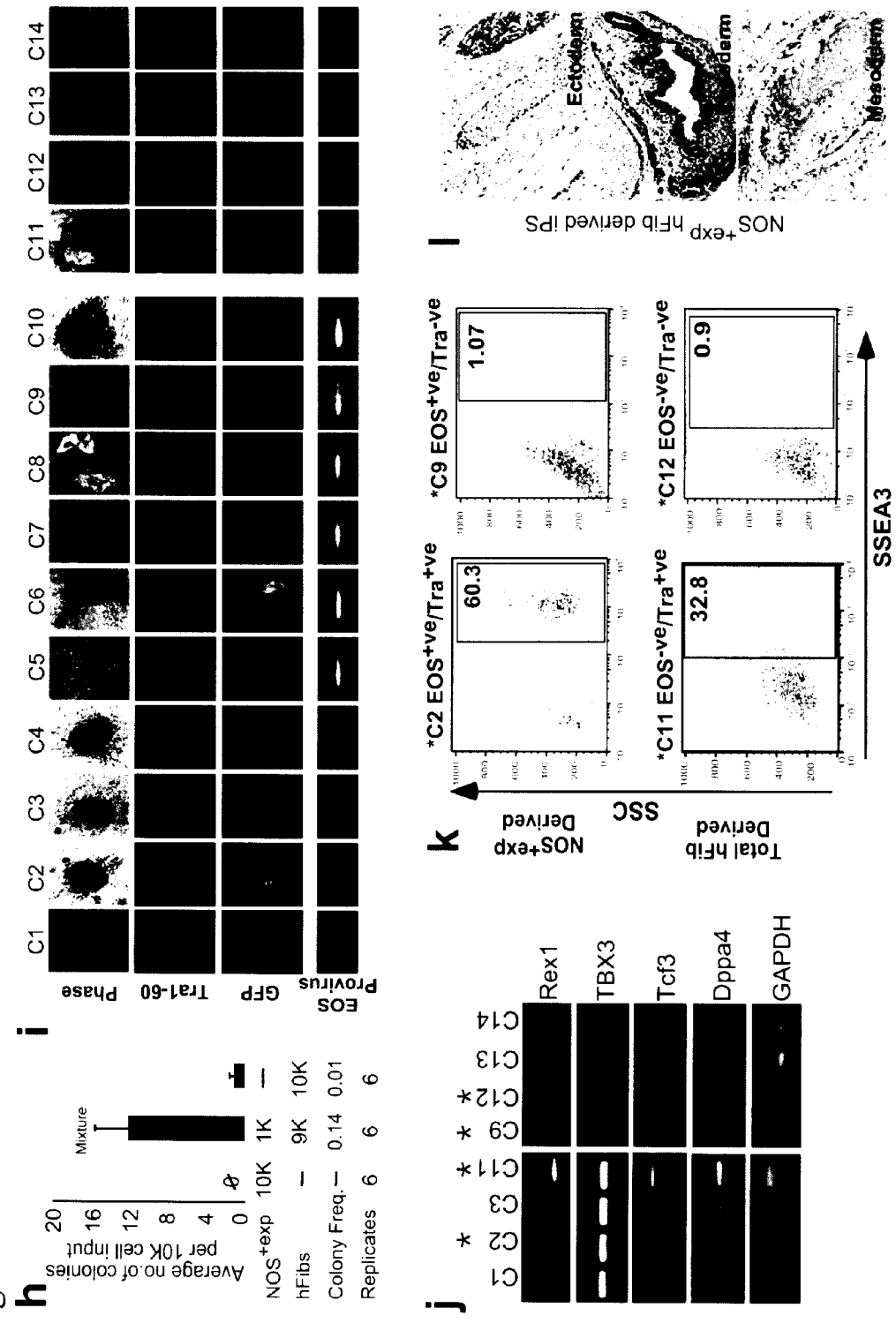

SEQUENCE LISTING

<160> NUMBER OF SEQ ID NOS: 80

<210> SEQ ID NO 1
<211> LENGTH: 9
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (7)..(9)
<223> OTHER INFORMATION: n is a, c, g, or t

<400> SEQUENCE: 1 ntgcaannn                                                                                      9

<210> SEQ ID NO 2
<211> LENGTH: 7
<212> TYPE: DNA
<213> ORGANISM: Homo sapiens

<400> SEQUENCE: 2 tttgcat                                                                                        7

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
gggataattt cagctgacta aacag                                                                   25

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
ttccgtttag ttaggtgcag ttatc                                                                   25

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ctgaagcaga agaggatcac                                                                         20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gaccacatcc ttctcgagcc                                                                         20

```
<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
cgaagaatag caatggtgtg acg                                              23

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
ttccaaagca gcctccaagt c                                                21

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
aacgtttgcc ttaaacaaga ccac                                             24

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
cgagataaac atggcaatca aatg                                             24

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ctagagatct ggctgtgggg                                                  20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
tcataactcc ggtccctctg                                                  20

<210> SEQ ID NO 13
<211> LENGTH: 20
<212> TYPE: DNA
<213> ORGANISM: Artificial Sequence
<220> FEATURE:
<223> OTHER INFORMATION: Primer
```

```
<400> SEQUENCE: 13
ccgagaacct cgaagacatc                                              20

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
gtctgaccct catggctgt                                               19

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
catggtgcag cagctgagtc ct                                           22

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
ccatctcata gggggaaggt                                              20

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
aagtctgccg ttactgccc                                               19

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
catgagcctt caccttaggg t                                            21

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
gggggaagta ggtcttggtc                                              20

<210> SEQ ID NO 20
<211> LENGTH: 20
```

```
<212> TYPE: DNA
<213> ORGANISM: Artificial Sequence
<220> FEATURE:
<223> OTHER INFORMATION: Primer

<400> SEQUENCE: 20
catcattgtg tccatgtggg                                              20

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
atggtgcatt ttactgctga gg                                           22

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
gggagacgac aggtttccaa a                                            21

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
atgagcctcg aatccacata gt                                           22

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
tcctcgttct gataagcagt ca                                           22

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
acggatctat accaacgcca                                              20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
```

```
ggggtggaag tcccagtaat                                              20

<210> SEQ ID NO 27
<211> LENGTH: 19
<212> TYPE: DNA
<213> ORGANISM: Artificial Sequence
<220> FEATURE:
<223> OTHER INFORMATION: Primer

<400> SEQUENCE: 27
gggatcacac tgagcttgc                                               19

<210> SEQ ID NO 28
<211> LENGTH: 19
<212> TYPE: DNA
<213> ORGANISM: Artificial Sequence
<220> FEATURE:
<223> OTHER INFORMATION: Primer

<400> SEQUENCE: 28
acccctgatt ctggtgtgg                                               19

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
gggctaggga acagatcgac g                                            21

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
gcagcagtca ggtgcggagg                                              20

<210> SEQ ID NO 31
<211> LENGTH: 25
<212> TYPE: DNA
<213> ORGANISM: Artificial Sequence
<220> FEATURE:
<223> OTHER INFORMATION: Primer

<400> SEQUENCE: 31
gaaatcccat caccaatctt ccagg                                        25

<210> SEQ ID NO 32
<211> LENGTH: 22
<212> TYPE: DNA
<213> ORGANISM: Artificial Sequence
<220> FEATURE:
<223> OTHER INFORMATION: Primer

<400> SEQUENCE: 32
gcaattgagc cccagccttc tc                                           22

<210> SEQ ID NO 33
<211> LENGTH: 20
<212> TYPE: DNA
<213> ORGANISM: Artificial Sequence
```

<220> FEATURE:
<223> OTHER INFORMATION: Primer

<400> SEQUENCE: 33
cagtcatgaa atcggcaaaa                                               20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
aaacgattgc agggtttcac                                               20

<210> SEQ ID NO 35
<211> LENGTH: 26
<212> TYPE: DNA
<213> ORGANISM: Artificial Sequence
<220> FEATURE:
<223> OTHER INFORMATION: Primer

<400> SEQUENCE: 35
ttagaaggca gatagagcca ctgacc                                        26

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
tgcctgtctg tgagggatga tgtt                                          24

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
agctctatcc cccagcactc g                                             21

<210> SEQ ID NO 38
<211> LENGTH: 21
<212> TYPE: DNA
<213> ORGANISM: Artificial Sequence
<220> FEATURE:
<223> OTHER INFORMATION: Primer

<400> SEQUENCE: 38
gagaaagcga gagctcctcg c                                             21

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
aacgtttgcc ttaaacaaga ccac                                          24

```
<210> SEQ ID NO 40
<211> LENGTH: 24
<212> TYPE: DNA
<213> ORGANISM: Artificial Sequence
<220> FEATURE:
<223> OTHER INFORMATION: Primer

<400> SEQUENCE: 40
cgagataaac atggcaatca aatg                                          24

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
aatgcctttg ggtgagggac                                               20

<210> SEQ ID NO 42
<211> LENGTH: 19
<212> TYPE: DNA
<213> ORGANISM: Artificial Sequence
<220> FEATURE:
<223> OTHER INFORMATION: Primer

<400> SEQUENCE: 42
tccgtgcctt tttttgggg                                                19

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
gcgtggctgc tttcaacttt cctt                                          24

<210> SEQ ID NO 44
<211> LENGTH: 24
<212> TYPE: DNA
<213> ORGANISM: Artificial Sequence
<220> FEATURE:
<223> OTHER INFORMATION: Primer

<400> SEQUENCE: 44
tgggtcggtt tctgtaatgg gtgt                                          24

<210> SEQ ID NO 45
<211> LENGTH: 22
<212> TYPE: DNA
<213> ORGANISM: Artificial Sequence
<220> FEATURE:
<223> OTHER INFORMATION: Primer

<400> SEQUENCE: 45
aacacgccgg gaatggatgg at                                            22

<210> SEQ ID NO 46
<211> LENGTH: 24
<212> TYPE: DNA
<213> ORGANISM: Artificial Sequence
<220> FEATURE:
<223> OTHER INFORMATION: Primer
```

```
<400> SEQUENCE: 46
gcggctttgg tggacatata ggaa                                              24

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47
agaggccaaa gacagaagtg gaga                                              24

<210> SEQ ID NO 48
<211> LENGTH: 24
<212> TYPE: DNA
<213> ORGANISM: Artificial Sequence
<220> FEATURE:
<223> OTHER INFORMATION: Primer

<400> SEQUENCE: 48
agagccacag gctacatcaa tcca                                              24

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
aaactgcgcc gtatcctctg ctaa                                              24

<210> SEQ ID NO 50
<211> LENGTH: 24
<212> TYPE: DNA
<213> ORGANISM: Artificial Sequence
<220> FEATURE:
<223> OTHER INFORMATION: Primer

<400> SEQUENCE: 50
tcttctgcaa gcctccctaa caca                                              24

<210> SEQ ID NO 51
<211> LENGTH: 24
<212> TYPE: DNA
<213> ORGANISM: Artificial Sequence
<220> FEATURE:
<223> OTHER INFORMATION: Primer

<400> SEQUENCE: 51
aatagcagga gcagcaacag aagg                                              24

<210> SEQ ID NO 52
<211> LENGTH: 24
<212> TYPE: DNA
<213> ORGANISM: Artificial Sequence
<220> FEATURE:
<223> OTHER INFORMATION: Primer

<400> SEQUENCE: 52
ttaaaggagc cgcgcatttg acag                                              24

<210> SEQ ID NO 53
```

```
<211> LENGTH: 25
<212> TYPE: DNA
<213> ORGANISM: Artificial Sequence
<220> FEATURE:
<223> OTHER INFORMATION: Primer

<400> SEQUENCE: 53
atctagctca agggtatcgt acaaa                                              25

<210> SEQ ID NO 54
<211> LENGTH: 27
<212> TYPE: DNA
<213> ORGANISM: Artificial Sequence
<220> FEATURE:
<223> OTHER INFORMATION: Primer

<400> SEQUENCE: 54
cacactttgt gcaaatggaa ataaccc                                            27

<210> SEQ ID NO 55
<211> LENGTH: 24
<212> TYPE: DNA
<213> ORGANISM: Artificial Sequence
<220> FEATURE:
<223> OTHER INFORMATION: Primer

<400> SEQUENCE: 55
cagagacttc ctgtatgtag cgca                                               24

<210> SEQ ID NO 56
<211> LENGTH: 24
<212> TYPE: DNA
<213> ORGANISM: Artificial Sequence
<220> FEATURE:
<223> OTHER INFORMATION: Primer

<400> SEQUENCE: 56
agggccagca caagttcctg attt                                               24

<210> SEQ ID NO 57
<211> LENGTH: 22
<212> TYPE: DNA
<213> ORGANISM: Artificial Sequence
<220> FEATURE:
<223> OTHER INFORMATION: Primer

<400> SEQUENCE: 57
agttggactg ccttggtcac tt                                                 22

<210> SEQ ID NO 58
<211> LENGTH: 24
<212> TYPE: DNA
<213> ORGANISM: Artificial Sequence
<220> FEATURE:
<223> OTHER INFORMATION: Primer

<400> SEQUENCE: 58
acaaacctcc gcctttcctc taca                                               24

<210> SEQ ID NO 59
<211> LENGTH: 22
<212> TYPE: DNA
<213> ORGANISM: Artificial Sequence
<220> FEATURE:
<223> OTHER INFORMATION: Primer

<400> SEQUENCE: 59
```
attacaggcc aggagatgcc ca                                           22

<210> SEQ ID NO 60
<211> LENGTH: 18
<212> TYPE: DNA
<213> ORGANISM: Artificial Sequence
<220> FEATURE:
<223> OTHER INFORMATION: Primer

<400> SEQUENCE: 60
cccggggaag ggcggttg                                                18

<210> SEQ ID NO 61
<211> LENGTH: 24
<212> TYPE: DNA
<213> ORGANISM: Artificial Sequence
<220> FEATURE:
<223> OTHER INFORMATION: Primer

<400> SEQUENCE: 61
attagaagag aggaggccac agga                                         24

<210> SEQ ID NO 62
<211> LENGTH: 23
<212> TYPE: DNA
<213> ORGANISM: Artificial Sequence
<220> FEATURE:
<223> OTHER INFORMATION: Primer

<400> SEQUENCE: 62
ttatcctgcc aaccctcagc caa                                          23

<210> SEQ ID NO 63
<211> LENGTH: 24
<212> TYPE: DNA
<213> ORGANISM: Artificial Sequence
<220> FEATURE:
<223> OTHER INFORMATION: Primer

<400> SEQUENCE: 63
gacgcatttg gaagggtctc cttt                                         24

<210> SEQ ID NO 64
<211> LENGTH: 24
<212> TYPE: DNA
<213> ORGANISM: Artificial Sequence
<220> FEATURE:
<223> OTHER INFORMATION: Primer

<400> SEQUENCE: 64
tccttctctc tcccatgctg gttt                                         24

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
tccatgaggg tgtttgatga                                              20

<210> SEQ ID NO 66
<211> LENGTH: 21
<212> TYPE: DNA

```
<213> ORGANISM: Artificial Sequence
<220> FEATURE:
<223> OTHER INFORMATION: Primer

<400> SEQUENCE: 66
cgctgggaca taaatctttg a                                              21

<210> SEQ ID NO 67
<211> LENGTH: 23
<212> TYPE: DNA
<213> ORGANISM: Artificial Sequence
<220> FEATURE:
<223> OTHER INFORMATION: Primer

<400> SEQUENCE: 67
acctcagaag aagataccaa tcc                                            23

<210> SEQ ID NO 68
<211> LENGTH: 18
<212> TYPE: DNA
<213> ORGANISM: Artificial Sequence
<220> FEATURE:
<223> OTHER INFORMATION: Primer

<400> SEQUENCE: 68
aaggcacaca ggcgctta                                                  18

<210> SEQ ID NO 69
<211> LENGTH: 23
<212> TYPE: DNA
<213> ORGANISM: Artificial Sequence
<220> FEATURE:
<223> OTHER INFORMATION: Primer

<400> SEQUENCE: 69
gcgtacgcaa attaaagtcc aga                                            23

<210> SEQ ID NO 70
<211> LENGTH: 25
<212> TYPE: DNA
<213> ORGANISM: Artificial Sequence
<220> FEATURE:
<223> OTHER INFORMATION: Primer

<400> SEQUENCE: 70
cagcatccta aacagctcgc agaat                                          25

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
tgcaccacca actgcttagc                                                20

<210> SEQ ID NO 72
<211> LENGTH: 21
<212> TYPE: DNA
<213> ORGANISM: Artificial Sequence
<220> FEATURE:
<223> OTHER INFORMATION: Primer

<400> SEQUENCE: 72
ggcatggact gtggtcatga g                                              21
```

<210> SEQ ID NO 73
<211> LENGTH: 24
<212> TYPE: DNA
<213> ORGANISM: Artificial Sequence
<220> FEATURE:
<223> OTHER INFORMATION: Primer

<400> SEQUENCE: 73
acgattcgca gttaatcctg gcct                                          24

<210> SEQ ID NO 74
<211> LENGTH: 24
<212> TYPE: DNA
<213> ORGANISM: Artificial Sequence
<220> FEATURE:
<223> OTHER INFORMATION: Primer

<400> SEQUENCE: 74
atagtatggg caagcaggga gcta                                          24

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
gactgagctg gttgcctcat                                               20

<210> SEQ ID NO 76
<211> LENGTH: 22
<212> TYPE: DNA
<213> ORGANISM: Artificial Sequence
<220> FEATURE:
<223> OTHER INFORMATION: Primer

<400> SEQUENCE: 76
ggcagcttta agactttct gg                                             22

<210> SEQ ID NO 77
<211> LENGTH: 26
<212> TYPE: DNA
<213> ORGANISM: Artificial Sequence
<220> FEATURE:
<223> OTHER INFORMATION: Primer

<400> SEQUENCE: 77
ggataacatt gtactgggaa gggaca                                        26

<210> SEQ ID NO 78
<211> LENGTH: 29
<212> TYPE: DNA
<213> ORGANISM: Artificial Sequence
<220> FEATURE:
<223> OTHER INFORMATION: Primer

<400> SEQUENCE: 78
caaagtttct tttattcgta tgtgtgagc                                     29

<210> SEQ ID NO 79
<211> LENGTH: 22
<212> TYPE: DNA
<213> ORGANISM: Artificial Sequence
<220> FEATURE:

```
<223> OTHER INFORMATION: Primer

<400> SEQUENCE: 79
aggcgcgaga acagcactac ta                                              22

<210> SEQ ID NO 80
<211> LENGTH: 24
<212> TYPE: DNA
<213> ORGANISM: Artificial Sequence
<220> FEATURE:
<223> OTHER INFORMATION: Primer

<400> SEQUENCE: 80
atgtttgcac ctccatcaaa gcgg                                            24
```

GENERATING INDUCED PLURIPOTENT STEM CELLS AND PROGENITOR CELLS FROM FIBROBLASTS

CROSS REFERENCE TO RELATED APPLICATIONS

The present application is §371 application of PCT/CA2010/001708 filed on Oct. 29, 2010 which claims priority from U.S. provisional application 61/256,170 filed on Oct. 29, 2009, the contents of each of the foregoing applications is incorporated herein by reference in their entirety.

FIELD OF THE DISCLOSURE

The disclosure relates to reprogramming of fibroblasts. In particular, the disclosure relates to methods of generating progenitor cells and induced pluripotent stems cells derived from fibroblasts and the cells produced by the methods.

BACKGROUND OF THE DISCLOSURE

Several groups have demonstrated the ability to reprogram human fibroblasts to induced pluripotent stem cells (iPSCs) following transduction with Oct-4 together with other factors (Takahashi et al., 2007; Takahashi and Yamanaka, 2006; Yu et al., 2007). For example, dermal fibroblasts can be reprogrammed to a pluripotent state by ectopic expression of a cocktail of pluripotent factors including Oct-4 (POU5F1), Sox-2, Klf-4, c-Myc, Nanog, and Lin28 (Takahashi et al., 2007; Yu et al., 2007), With the exception of Oct4, further studies indicated that the majority of these factors could be eliminated by use of unique stem/progenitor cells (Heng et al.; Aasen et al. 2008; Eminli et al. 2008; Eminli et al. 2009; Kim et al. 2009) or, alternatively, by addition of chemicals targeting the epigenome of dermal fibroblast sources (Shi et al. 2008; Lyssiotis et al. 2009). These studies demonstrate there are several approaches and methods for generation of iPSCs, however, the cellular and molecular mechanisms underlying reprogramming to the pluripotent state remain largely unknown (Jaenisch and Young, 2008). Although iPSCs can be differentiated towards the blood fate, the resulting hematopoietic cells preferentially generate primitive blood cells that utilize embryonic programs. Moreover, the methods remain inefficient, making it difficult to contemplate transplantation or modeling hematological diseases (Lengerke and Daley, 2010). Characterization of these processes is further complicated by cellular intermediates that fail to establish a stable pluripotent state, potentially due to the inability to achieve the correct combination, stoichiometry, or expression levels of reprogramming factors ideal for complete pluripotency induction (Chan et al., 2009; Kanawaty and Henderson, 2009; Lin et al., 2009; Mikkelsen et al., 2008). Consistent with this idea, intermediate cells derived from fibroblasts have been shown to co-express genes associated with several differentiated lineages (neurons, epidermis, and mesoderm) (Kanawaty and Henderson, 2009; Mikkelsen et al., 2008), nevertheless the exact identity and differentiation potential of these cell types remain elusive. This creates the possibility that under unique conditions the fibroblasts expressing a small subset of transcription factors can be induced to differentiate towards specified lineages without achieving pluripotency, as recently been demonstrated by converting fibroblasts into specific cell types such as neurons, cardiomyocytes, and macrophage-like cells (Feng et al., 2008; Ieda et al., 2010; Vierbuchen et al., 2010).

While these studies have examined fibroblast conversion in the murine model, this concept remains to be extrapolated for human applications.

Previous studies have shown that proteins containing POU domains, such as Oct-4, along with Oct-2 (POU2F2) and Oct-1 (POU2F1) bind similar DNA target motifs (Kang et al., 2009). Whilst both Oct-2 and Oct-1 play a role in hematopoietic development (Brunner et al., 2003; Emslie et al., 2008; Pfisterer et al., 1996), Oct-4 is yet to be implicated in this process. Nonetheless, recent studies have predicted that Oct-4 possesses the capacity to bind to the promoters of the hematopoietic genes Runx1 and CD45, thus potentially regulating their expression (Kwon et al., 2006; Sridharan et al., 2009). Despite the similarities in binding and regulation, the exact functional role of individual Oct family members appears to be cell context specific (Kang et al., 2009; Pardo et al., 2010).

The ability to generate pluripotent stem cells from human dermal fibroblasts allows for generation of complex genetic disease models, and provides an unprecedented source for autologous transplantation without concern of immune rejection (Takahashi and Yamanaka 2006; Hanna et al. 2007; Yu et al. 2007; Okita et al. 2008; Park et al. 2008; Park et al. 2008b; Soldner et al. 2009).

Although a variety of somatic cell types can be reprogrammed, the vast majority of studies aimed at characterizing the mechanisms that govern the reprogramming process utilize fibroblasts (Takahashi and Yamanaka 2006; Takahashi et al. 2007; Wernig et al. 2007; Yu et al. 2007; Aoi et al. 2008; Brambrink et al. 2008; Eminli et al. 2008; Hanna et al. 2008; Huangfu et al. 2008; Lowry et al. 2008; Stadtfeld et al. 2008; Zhou et al. 2008; Carey et al. 2009; Feng et al. 2009; Gonzalez et al. 2009; Guo et al. 2009; Kaji et al. 2009; Utikal et al. 2009; Woltjen et al. 2009; Yusa et al. 2009; Zhou et al. 2009). As such, the current understanding of the molecular mechanisms and cellular nature of reprogramming is nearly exclusively derived from fibroblast-based reprogramming. Fibroblasts can be generated from multiple tissue sites including dermal skin, however, little is known about the origins and composition of fibroblasts used experimentally.

Cellular reprogramming to the pluripotent state was originally demonstrated using in vitro cultured mammalian fibroblasts (Takahashi and Yamanaka 2006). To date, iPSCs have been derived from a number of other tissue-derived cells including liver, pancreas, intestine, stomach, adipose, melanocytes, and hematopoietic sources (Aoi et al. 2008; Hanna et al. 2008; Zhou et al. 2008; Eminli et al. 2009; Sun et al. 2009; Utikal et al. 2009) using a variety of transcription factors including the oncogenes c-myc and klf4 (Takahashi and Yamanaka 2006; Takahashi et al. 2007; Aasen et al. 2008; Hanna et al. 2008; Park et al. 2008; Eminli et al. 2009; Hanna et al. 2009; Woltjen et al. 2009; Zhao et al. 2009). To date, the reprogramming process remains inefficient, but can be enhanced by utilization of initial cell types that already possess stem/progenitor proliferative capacity (Kim et al. 2009; Eminli et al. 2008; Eminli et al. 2009), or by enhancing cell cycle state by knocking down inhibitors of cell cycle progression such as p53/p21 (Kawamura et al. 2009; Li et al. 2009; Utikal et al. 2009). However, altering cell cycle regulators or introduction of oncogenes increases the risk of uncontrolled growth and tumor formation and thus raises potential safety concerns for future human therapeutic applications (Lebofsky and Walter 2007; Okita et al. 2007; Nakagawa et al. 2008; Markoulaki et al. 2009).

SUMMARY OF THE DISCLOSURE

The present inventors used human dermal fibroblasts to investigate direct conversion of the fibroblasts into hematopoietic cells (CD45+ cells) and to investigate reprogramming fibroblasts to induced pluripotent stem cells.

Accordingly, in one embodiment, the disclosure provides a method of generating progenitor cells from fibroblasts comprising:

a) providing fibroblasts that express or are treated with POU domain containing gene or protein; and b) culturing the cells of step (a) under conditions to allow production of progenitor cells without traversing the pluripotent state.

In one embodiment, fibroblasts that express a gene or protein containing a POU domain include overexpression of an endogenous gene or protein containing a POU domain or ectopic expression of a gene or protein containing a POU domain. In an embodiment, the fibroblasts do not additionally overexpress or ectopically express or are not treated with Nanog or Sox-2. In another embodiment, fibroblasts that express a POU domain containing gene or protein are produced by transfecting or transducing the fibroblasts with a vector comprising the POU domain. In an embodiment, fibroblasts that express a gene or protein containing a POU domain are produced by lentiviral transduction. In an embodiment, the POU domain containing gene or protein is Oct-1, -2, -4 or -11. In another embodiment, the POU domain containing gene or protein is Oct-4. The POU domain containing gene or protein includes, without limitation, functional variants and fragments thereof as well as small molecule mimetics.

Conditions that allow production of progenitor cells are known in the art and include, without limitation, colony forming assays for a culture period from 15-25 days, optionally 21 days. In another embodiment, the fibroblasts are dermal fibroblasts. In yet another embodiment, the progenitor cells are hematopoietic progenitor cells and the conditions are hematopoietic conditions. In a further embodiment, the progenitor cells are neural progenitor cells and the conditions are neural conditions.

In another embodiment, the method further comprises culturing the cells produced in step (b) in differentiation medium under conditions that allow production of differentiated cells. Such conditions include culturing the cells in medium for a culture period from 10 to 21 days, optionally 16 days. In one embodiment, the differentiation medium is hematopoietic medium comprising a hematopoietic cytokine, such as, Flt3 ligand, SCF and/or EPO. In an embodiment, the differentiated hematopoietic cells are of the myeloblast lineage, such as monocytes or granulocytes. In another embodiment, the differentiated hematopoietic cells are of the erythroid or megakaryocytic lineage. In another embodiment, the differentiation medium is neural medium comprising neural basal media supplemented with fibroblast growth factor and epidermal growth factor. In an embodiment, the differentiated neural cells are neurons and/or glial cells including oligodendrocytes and or astrocytes.

Also provided herein are the isolated progenitor and differentiated cells generated by the methods described herein and uses of the cells for engraftment and transplantation. The hematopoietic progenitor cells are also useful as a source of blood, cellular and acellular blood components, blood products and hematopoietic cells.

Further provided herein is a screening assay comprising
a) preparing a culture of progenitor cells or cells derived therefrom by the methods described herein;
b) treating the cells of a) with a test agent or agents; and
c) subjecting the treated progenitor cells or cells derived therefrom to analysis.

In one embodiment, the progenitor cells are differentiated prior to treating with the test agent.

In another aspect, there is provided a method of isolating a subpopulation of fibroblasts with increased reprogramming potential comprising
a) providing fibroblasts that express an Oct-4-reporter; and
b) isolating cells positive for the reporter.

In one embodiment, the reporter gene comprises a fluorescent protein (such as GFP) and the cells are isolated in step (b) by detection of the fluorescence. In another embodiment, the reporter gene encodes a gene conferring antibiotic resistance, such as to puromycin, and the cells are isolated by survival in the presence of the antibiotic. In an embodiment, the fibroblasts that express an Oct-4-reporter gene are produced by lentiviral transduction. In an embodiment, the fibroblasts are dermal fibroblasts. In another embodiment the fibroblasts are foreskin fibroblasts.

The disclosure further provides a method of generating reprogrammed fibroblast-derived induced pluripotent stem (iPS) cells at higher efficiency comprising
a) providing (i) a population of fibroblasts with increased expression of Oct-4 and (ii) a mixed population of fibroblasts or a population of Oct-4 negative fibroblasts;
b) treating the cells of a) with Oct-4, Nanog, Sox2 and Lin28; and
c) culturing the treated cells of b) under conditions that allow the production of iPS cells.

The method optionally further comprises analyzing and selecting cells that express a marker of undifferentiated stem cells, such as TRA-1-60, SSEA-3, Sox2, Nanog, SSEA4, TRA-1-81, IGF1 receptor, connexin 43, E-cadherin, Alkaline phosphatase, REX1, CRIPTO, CD24, CD90, CD29, CD9 and CD49f. In a particular embodiment cells are selected for expression of TRA-1-60 and/or SSEA-3.

In one embodiment, the population of fibroblasts with increased expression of Oct-4 are produced by the method of isolating a subpopulation of fibroblasts with reprogramming potential as described herein. In an embodiment, the ratio of the cells of i) to the cells of ii) in (a) is 50:50, 25:75 or 10:90. In an embodiment, the fibroblasts are dermal fibroblasts.

Also provided herein are isolated induced pluripotent stem cells generated by the method described herein and cells differentiated therefrom and uses of the cells for engraftment, transplantation and as a source of induced pluripotent stem cells.

Further provided herein is a screening assay comprising
a) preparing a culture of induced pluripotent stem cells by the methods described herein or cells differentiated therefrom;
b) treating the cells with a test agent or agents; and
c) subjecting the treated cells to analysis.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

transduced Fibs, untransduced fetal fibroblasts (Fetal Fibs) and Oct-4 transduced fetal Fibs (Fetal Fibs$^{Oct-4}$) at day 21 post-transduction (D21) (colonies—dashed lines and arrows) (n=6). b. Relative gene expression of Sox-2, Nanog and Oct-4 in Fibs, Fetal Fibs, Fibs$^{Oct-4}$, Fibs$^{Sox-2}$ and Fibs$^{Nanog}$ Fetal Fibs$^{Oct-4}$ in comparison with the expression of these genes in established iPSCs (n=3, *p<0.001). c. Representative FACS plots of the CD45 levels in Fibs$^{Oct-4}$ and Fetal Fibs$^{Oct-4}$ compared with untransduced-Fibs or -Fetal Fibs, Fibs$^{Sox-2}$ or Fibs$^{Nanog}$ (n=6).

Figure 2:
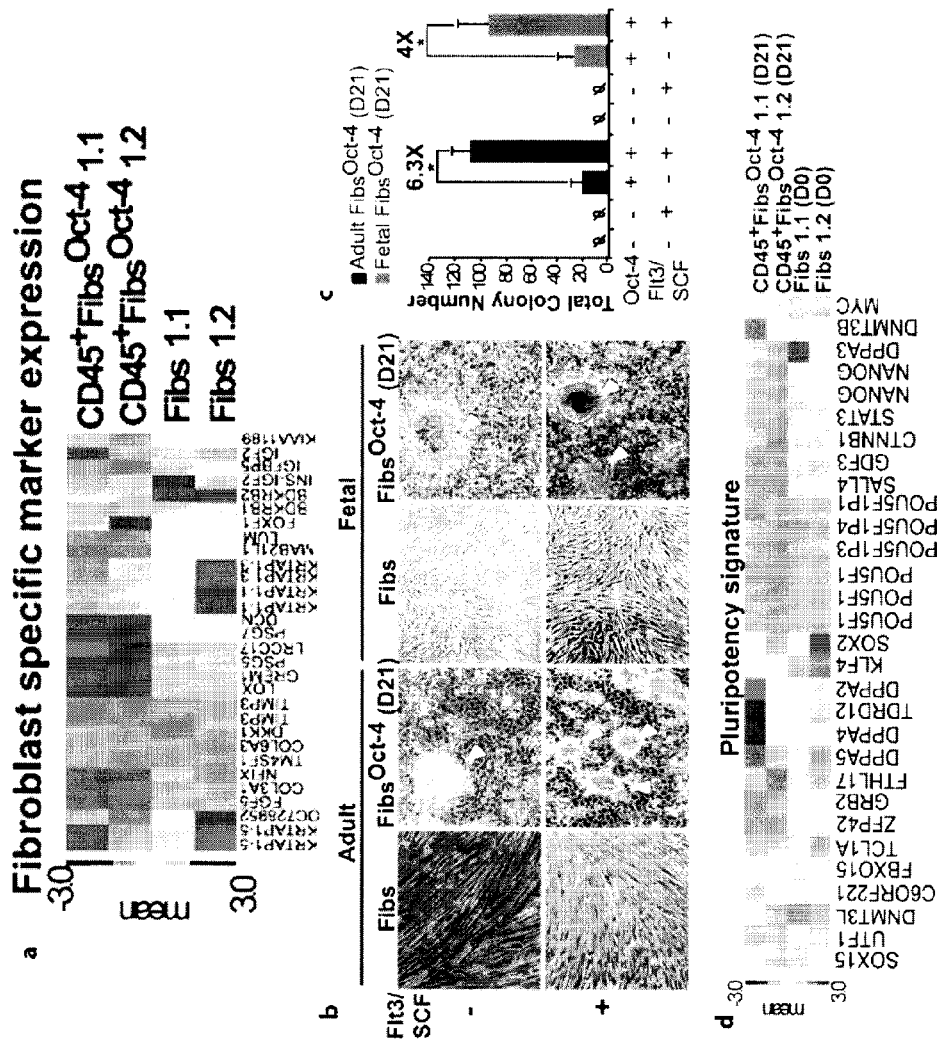

FIG. 2 shows a. Global gene analysis based on fibroblasts specific marker expression over the course of CD45$^{+ve}$ cell emergence in Fibs and sorted CD45$^+$ Fibs$^{Oct-4}$. b. Representative bright field images of Fibs, Fetal Fibs, and Fibs$^{Oct-4}$ or Fetal Fibs$^{Oct-4}$ plus/minus Flt3 and SCF at day 21 (D21) (n=6). c. Enumeration of colonies in Fibs, Fetal Fibs, and Fibs$^{Oct-4}$ or Fetal Fibs$^{Oct-4}$ plus/minus SCF and Flt-3 at day 21 (D21) (colonies-white arrows; n=6; *p<0.001). d. Pluripotency gene signature of Fibs and sorted CD45$^+$ Fibs$^{Oct-4}$.

Figure 3:
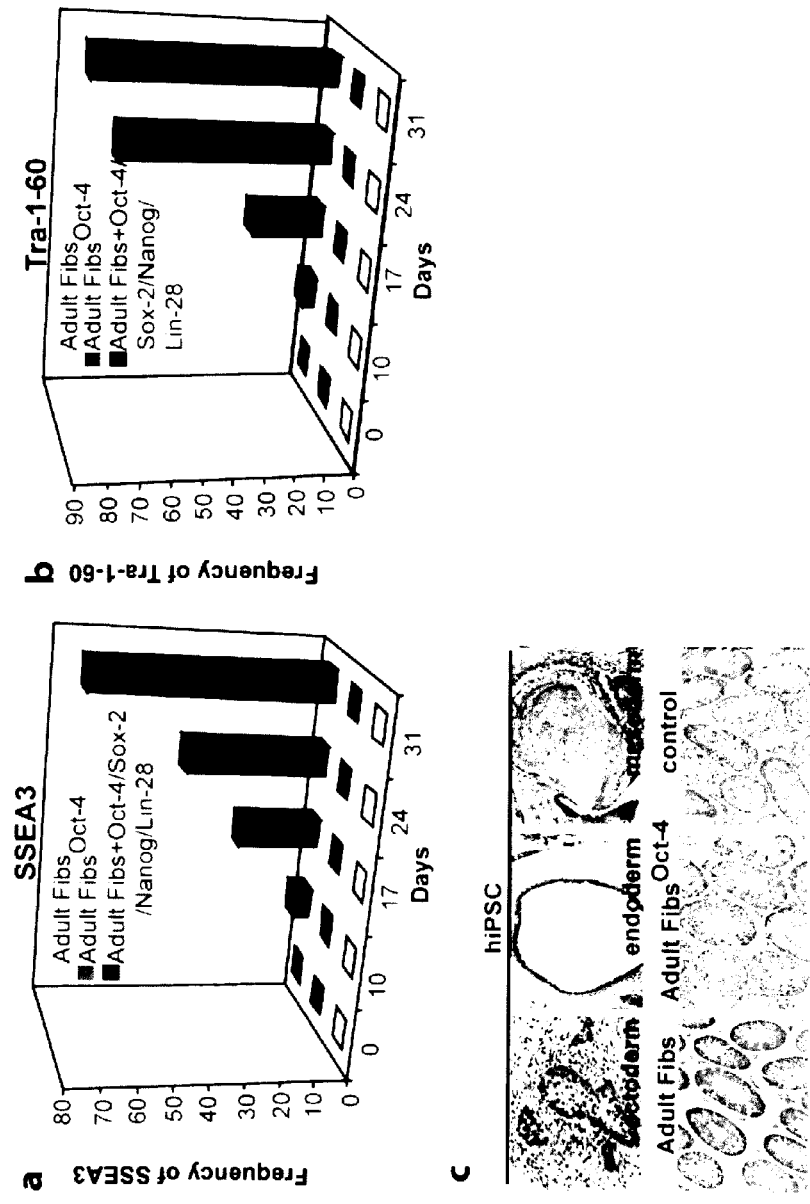

FIG. 3 shows Oct-4 transduced human dermal fibroblasts bypass the pluripotency. a. Quantitative analysis of SSEA3 levels, and b. Tra-1-60 levels over the 31-day timeline of hiPSC derivation in Fibs and Fibs$^{Oct-4}$ plus/minus SCF and Flt-3 and Fibs transduced with Oct-4, Sox-2, Nanog and Lin-28 (n=3). c. Teratomas derived from hiPSCs showing mesoderm, endoderm and ectoderm and testicular sections representing the lack of teratomas from Fibs and Fibs$^{Oct-4}$ plus/minus Flt3 and SCF (Control-saline injected).

Figure 4:
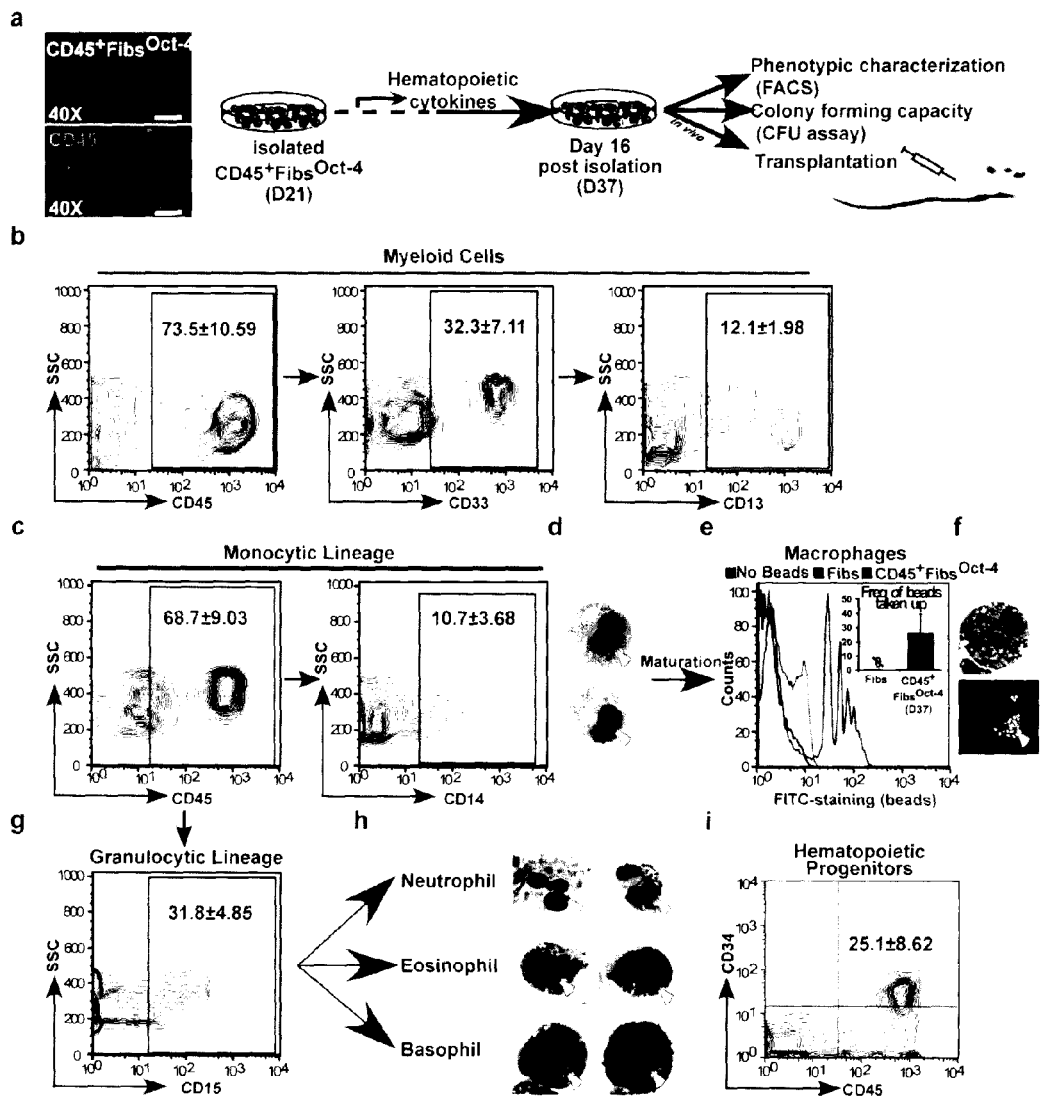
Figure 4:
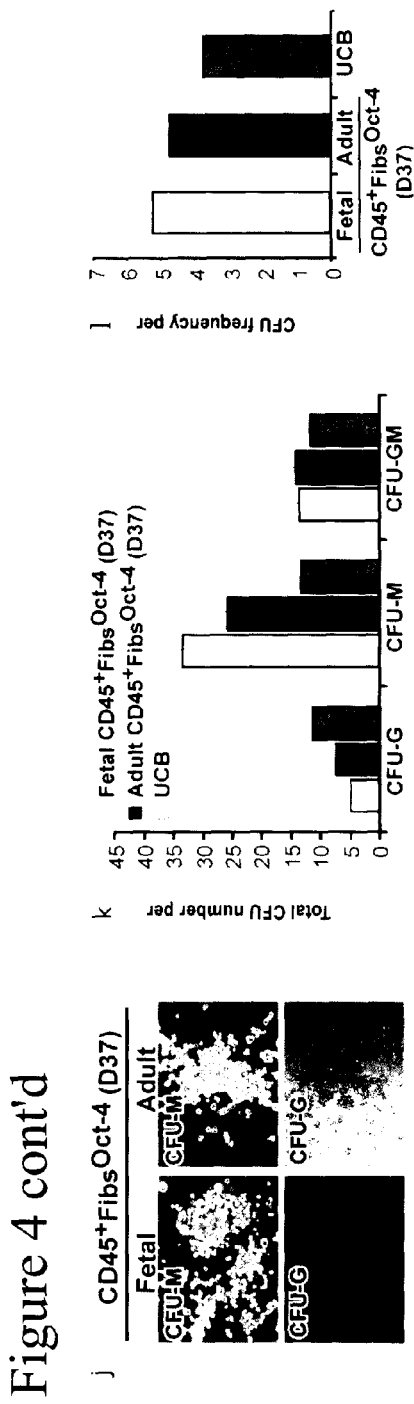

FIG. 4 shows in vitro reconstitution of the myeloid lineage by hematopoietic cytokine treated Oct-4 transduced CD45 positive Fibs. a. Schema presenting Oct-4 transduced CD45$^{+ve}$ Fibs (CD45$^+$Fibs$^{Oct-4}$) isolation and subsequent hematopoietic cytokine treatment, followed by in vitro and in vivo analysis. In vitro analysis includes colony forming unit (CFU) assay and FACS analysis; and the in vivo analysis is the hematopoietic reconstitution assay using NOD/SCID IL2Rγc null (NSG) mice. b. FACS analysis of myeloid cells (CD45$^+$CD13$^+$ and CD13$^+$CD33$^+$ cells) derived from CD45$^+$Fibs$^{Oct-4}$ (n=6). c. Representative FACS plots of monocytes (CD45$^+$CD14$^+$ cells) and d. corresponding Giemsa-Wright images of monocytes with distinguishing nuclear morphology (white arrow) derived from CD45$^+$Fibs$^{Oct-4}$ (n=6). e. Representative FACS plots of FITC-labeled latex-bead uptake indicating the presence of macrophages in the CD45$^+$Fibs$^{Oct-4}$ population versus Fibs (no beads). Upper panel graph shows quantitative analysis of FITC-labeled latex-bead uptake by CD45$^+$Fibs$^{Oct-4}$ and Fibs (n=3). f. Representative Giemsa Wright stained image of a macrophage and immunofluorescence image of FITC-beads (white arrow) taken up by macrophages. g. Representative FACS plot of granulocytes (CD45$^+$CD15$^+$ cells) derived from CD45$^+$Fibs$^{Oct-4}$ (n=6). h. Giemsa Wright stained CD45$^+$CD15$^+$ granulocytes containing neutrophils, eosinophils and basophils (characteristic nuclear morphology-white arrows) (n=6). i. CD45$^+$Fibs$^{Oct-4}$ hematopoietic cytokine treated cells give rise to hematopoietic progenitors (CD45$^+$CD34$^+$ cells) (n=9). j. Representative images of granulocytic (CFU-G), monocytic (CFU-M) colony forming units (CFU) derived from adult dermal or fetal foreskin CD45$^{+ve}$ cells (20×). k. Quantitation of granulocytic (CFU-G), monocytic (CFU-M) and mixed granulocytic and monocytic (CFU-GM) CFU formation from 1000 sorted CD45$^+$CD34$^+$ cells derived from adult dermal Fibs, fetal foreskin Fibs and umbilical cord blood (UCB) (n=3). l. CFU formation frequency in adult and fetal CD45$^+$Fibs$^{Oct-4}$ cells and UCB derived hematopoietic progenitors (n=3; *p<0.001).

Figure 5:
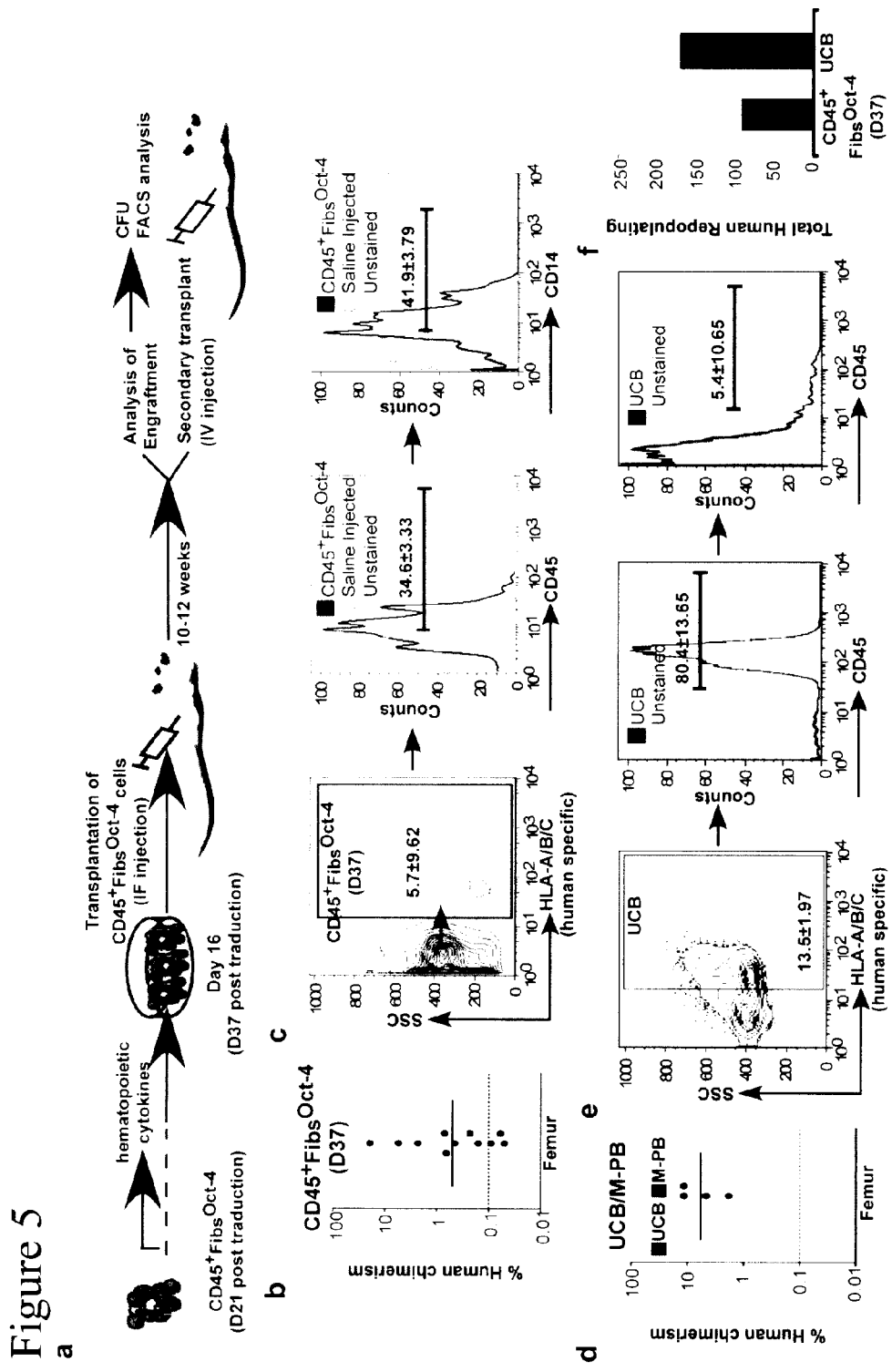

FIG. 5 shows in vivo reconstitution capacity of CD45+ Fibs$^{Oct-4}$ cells. a. Schematic representation of the xenograft models used for primary and secondary injection of CD45$^{+ve}$ cells into adult NOD/SCID IL2Rγc null mice and subsequent analysis of the engrafted cells. b. Graph representing human chimerism at week 10 following intrafemoral injection of CD45$^+$Fibs$^{Oct-4}$ cells treated with cytokines (n=12). c. Representative FACS histograms of engrafted CD45$^+$Fibs$^{Oct-4}$ cells (HLA A/B/C$^{+ve}$ cells) showing the presence of CD45$^{+ve}$ and CD14$^{+ve}$ population (n=12) in engrafted mice versus saline injected mice. d. Graph representing human chimerism at week 10 following intrafemoral injection of cord blood (UCB) derived progenitors and mobilized-peripheral blood (M-PB) cells (n=4). e. Representative FACS histograms of engrafted UCB and M-PB cells showing the presence of CD45$^{+ve}$ and CD14$^{+ve}$ population (n=4). f. Colony formation capacity per 1000 mouse cell depleted CD45$^{+ve}$ cells derived from engrafted CD45$^+$Fibs$^{Oct-4}$ cells versus UCB (n=3).

Figure 6:
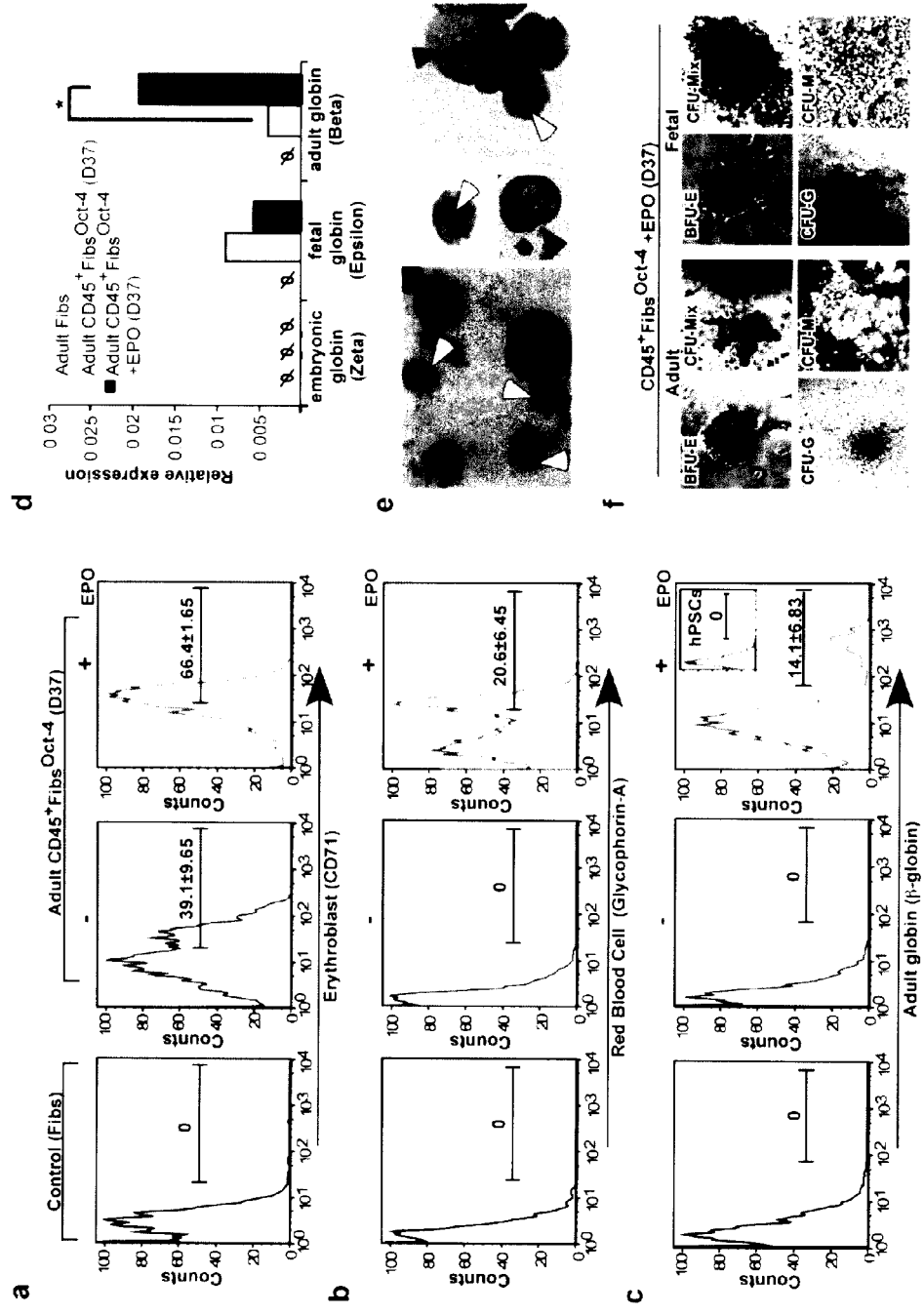

FIG. 6 shows CD45$^+$Fibs$^{Oct-4}$ cells are able to reconstitute the erythroid and megakaryocytic lineages following EPO treatment. a. Representative FACS histograms of erythroblast marker, CD71, levels in Fibs, CD45$^+$Fibs$^{Oct-4}$ cells and CD45$^+$Fibs$^{Oct-4}$ cells treated with EPO (n=3). b. Representative FACS histograms of Glycophorin A (red blood cell marker) levels in Fibs, CD45$^+$Fibs$^{Oct-4}$ and CD45$^+$Fibs$^{Oct-4}$ cells treated with EPO (n=3). c. Representative FACS histograms of adult globin, beta-globin, levels in Fibs, CD45$^+$Fibs$^{Oct-4}$ and CD45$^+$Fibs$^{Oct-4}$ cells treated with EPO (upper panel is FACS analysis of differentiated human pluripotent stem cells (hPSCs)) (n=3). d. Relative mRNA expression of the embryonic globin (zeta), fetal-globin (epsilon) and adult globin (beta) in Fibs, CD45$^+$Fibs$^{Oct-4}$ cells and CD45$^+$Fibs$^{Oct-4}$ cells treated with EPO (n=3; *p<0.001). e. Giemsa Wright stained EPO treated CD45$^+$Fibs$^{Oct-4}$ cells showing primitive (black arrow) and mature (white arrow) erythrocyte morphologies. f. Representative CFU images of EPO treated adult and fetal fibroblast derived CD45$^+$Fibs$^{Oct-4}$ cells (20×; n=3). (Erythroid blast forming units—BFU-E; granulocyte colony forming units—CFU-G; monocyte colony forming units—CFU-M; Colony forming units containing all lineages—CFU-Mix) g. Quantitative analysis of CFU formation in adult and fetal Fibs, CD45$^+$Fibs$^{Oct-4}$ and CD45$^+$Fibs$^{Oct-4}$ cells treated with or without EPO versus UCB (n=3). h. Representative megakaryocytic CFU (CFU-Mk) images (CD41$^{+ve}$ cells) (20×) derived from Fibs (left panel), CD45$^+$Fibs$^{Oct-4}$ cells treated with (right panel) or without EPO (left panel) (n=3). i. Quantitative representation of megakaryocytic CFU formation (right panel, n=3; *p<0.001).

Figure 7:
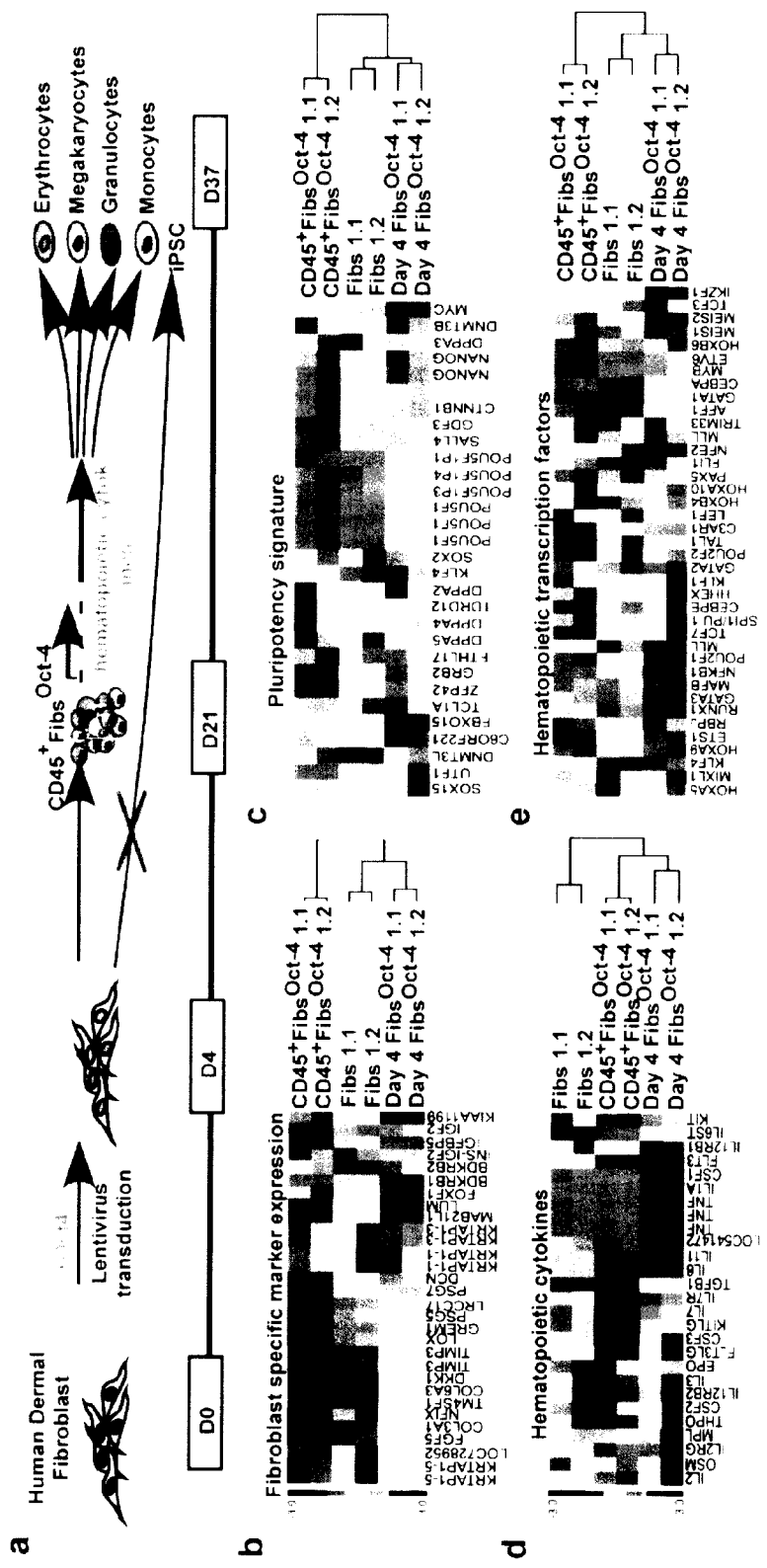
Figure 7:
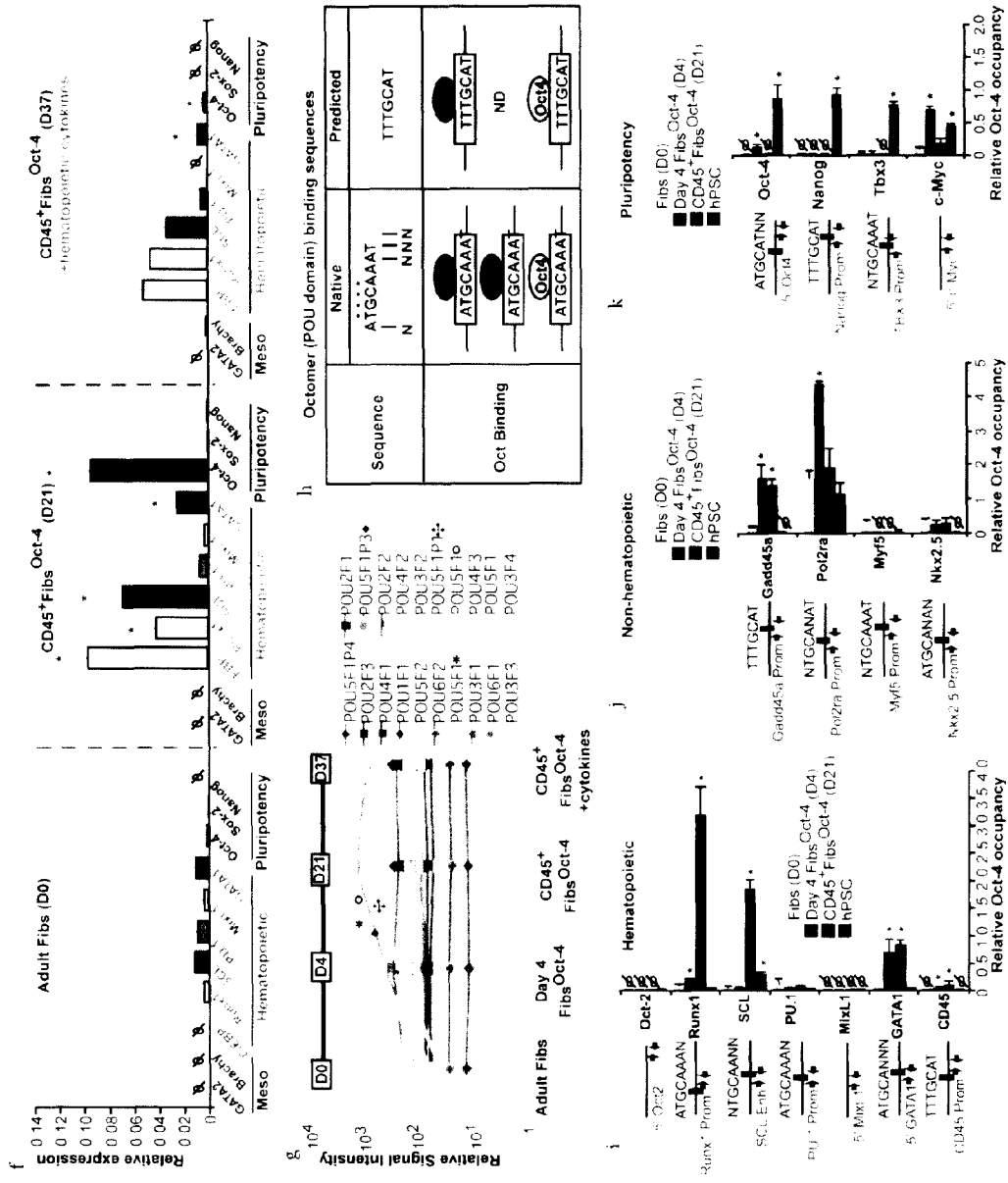

FIG. 7 shows Oct-4 transduction results in hematopoietic program activation in human dermal fibroblasts. a. Proposed model for hematopoietic fate conversion following transduction of Fibs with Oct-4 alone over the time course of CD45$^{+ve}$ cell emergence (day 0 (D0), 4 (D4), 21 (D21) and 37 (D37)) versus hematopoietic differentiation from human iPSCs. Global gene culturing based on fibroblasts specific marker expression (b), pluripotency signature (c), hematopoietic cytokines (d) and hematopoietic transcription factors (e) over the course of CD45$^{+ve}$ cell emergence; i.e. in Fibs (D0), puromycin selected Day 4 Fibs$^{Oct-4}$ (D4) and sorted CD45$^+$ Fibs$^{Oct-4}$ (D21). f. Relative mRNA expression analysis of mesodermal genes (GATA2, Brachyury), hematopoietic specific genes (SCL, MixL1, Runx1, GATA1, PU.1 and C/EBPα) and pluripotency genes (Oct-4, Sox-2 and Nanog) in Fibs (D0) versus sorted CD45$^+$Fibs$^{Oct-4}$ cells at D21 and hematopoietic cytokine treated sorted CD45$^+$Fibs$^{Oct-4}$ cells at D37 (n=4, *p<0.001). g. Gene expression profile of POU family of genes (including Oct-4-POU5F1) over the time course of CD45$^{+ve}$ cell emergence; i.e. in Fibs (D0), puromycin selected Day 4 Fibs$^{Oct-4}$ (D4), sorted CD45$^+$Fibs$^{Oct-4}$ cells (D21) and hematopoietic cytokine treated sorted CD45$^+$Fibs$^{Oct-4}$ cells (D37). h. Schematic representation of the known native (SEQ ID NO:1) and predicated octamer (SEQ ID NO:2) (POU domain) binding sequences that Oct-4, Oct-1 and Oct-2 can occupy (N—can be any nucleotide (A, T, C or G); starred and underlined region represent the core conserved octamer binding region). i. Right panel—Relative Oct-4 occupancy of hematopoietic specific gene SCL, Runx1, CD45, GATA1, PU.1, Oct-2 and C/EBPα promoter or enhancer regions over the course of CD45$^{+ve}$ cell emergence compared to hFib control (n=3; *p<0.001). j. Right panel—Relative Oct-4 occupancy of non-hematopoietic gene Gadd45a, Pol2ra, Myf5 and Nkx2.5 over the course of CD45$^{+ve}$ cell emergence compared to hFib control (n=3; *p<0.001). k. Right panel—Relative Oct-4 occupancy of pluripotency gene Oct-4, Sox-2, Tbx3 and c-Myc promoter regions over the course of CD45$^{+ve}$ cell emergence compared to hFib control (n=3; *p<0.001). i-k. Left panel—proximity of primer designed at a resolution 500-1000 bp (arrows) relative to the native or predicted octamer-binding region (Black box). Pluripotent stem cells—hPSCs; Fibroblasts—Fibs (D0); Puromycin selected Day 4 Oct-4 transduced hFibs—Day 4 Fibs$^{Oct-4}$ (D4) and Oct-4 transduced CD45$^{+ve}$ cells—CD45$^+$Fibs$^{Oct-4}$ (D21).

Figure 8:
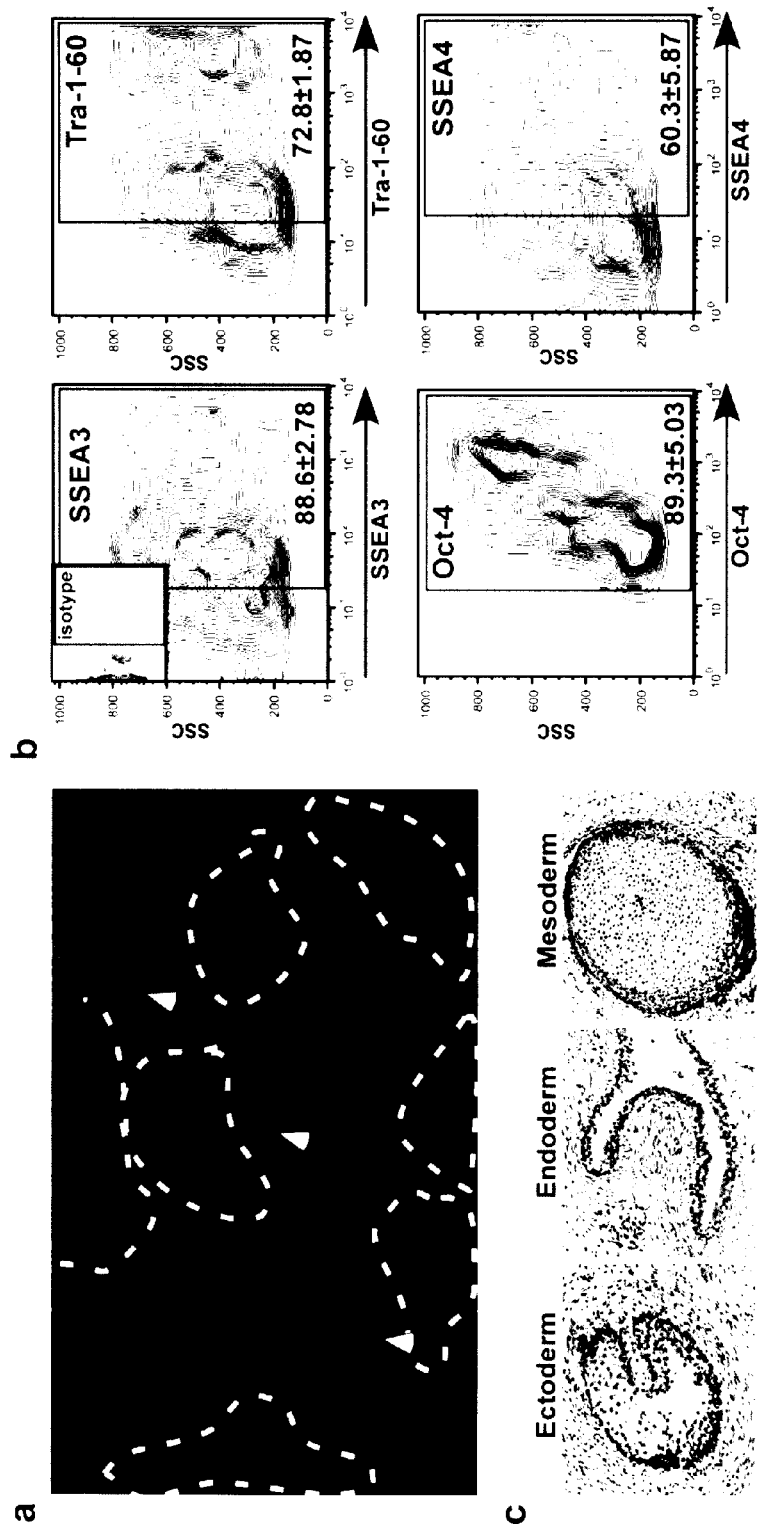

FIG. 8 shows characterization of the iPSC derived from human dermal fibroblasts (Fibs) transduced with Oct-4, Nanog, Sox-2 and Lin-28. a. Representative images of iPSC colonies (dashed lines and arrows) derived from human Fibs transduced with Oct-4, Nanog, Sox-2 and Lin-28 (20x). b. Representative FACS plots of pluripotency markers, SSEA-3, Tra1-60, Oct-4 and SSEA-4, in iPSCs (n=4). c. Intratesticular injection of iPSCs into immunodeficient mice (NOD/SCID) resulted in teratoma formation containing all 3 germ layers: ectoderm (skin), endoderm (lumen with goblet cells) and mesoderm (cartilage) (20x; n=6).

Figure 9:
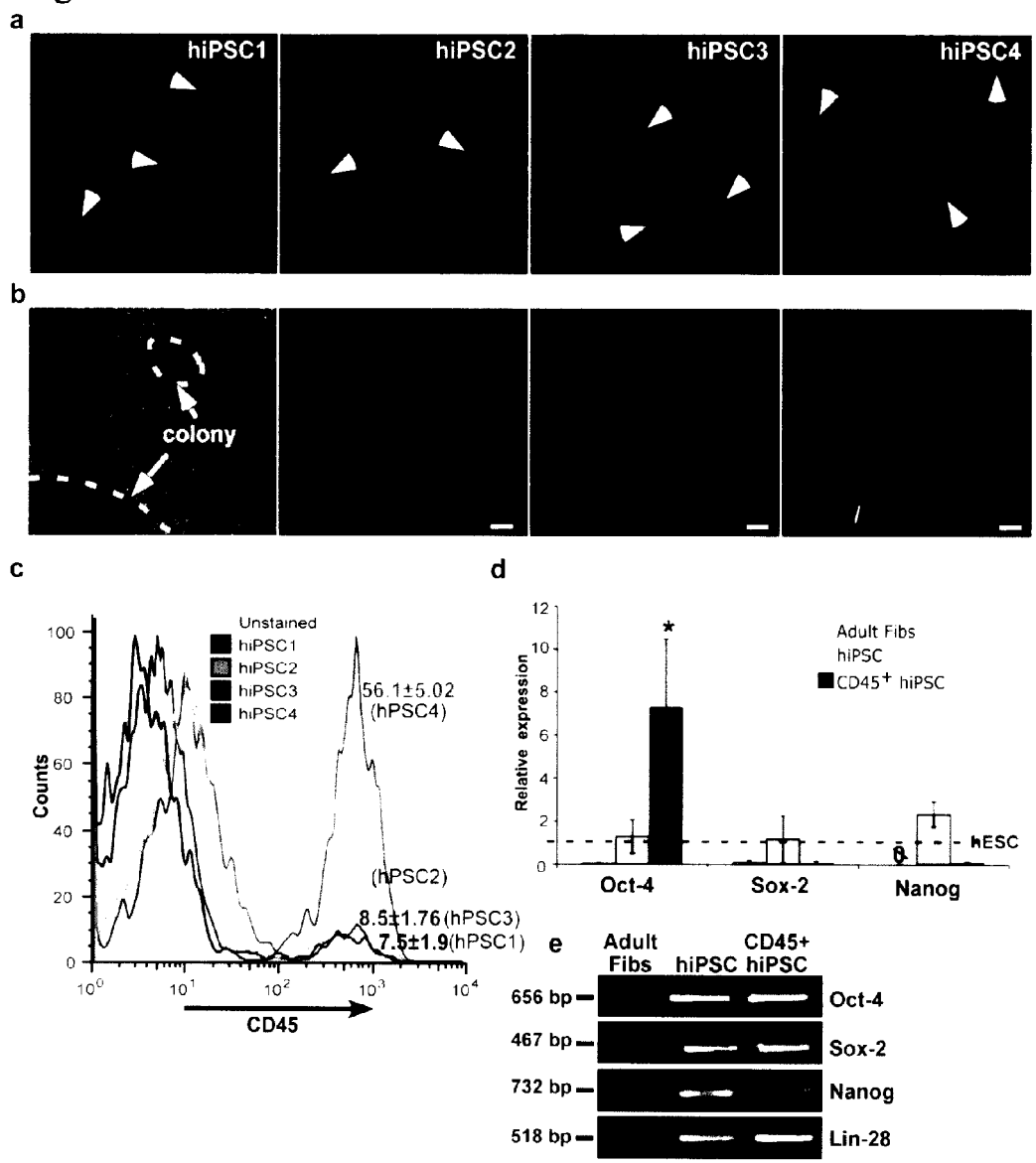

FIG. 9 shows intermediate colonies derived during iPSC derivation have a hematopoietic phenotype. a. Intermediate colonies (arrows) possessing a hematopoietic cellular morphology (rounded cells) were present in four different iPSC lines (1-4). b. Live staining for CD45 positive hematopoietic cells (green) and Tra-1-60 positive iPS colonies (red) showing that CD45 is exclusive to intermediate colonies, while Tra-1-60 is present only in iPSCs (20x; n=4). c. Representative FACS histogram of CD45 levels in four independent iPSC lines (n=4). d. Relative Oct-4, Sox-2 and Nanog mRNA expression: 1, in sorted CD45$^{+ve}$ cells derived from the 4 different iPSC lines; 2, in manually isolated iPS colonies and 3, Fibs (n=4; *p<0.001). Levels were normalized to human embryonic stem cells (hESCs). e. Lentiviral integration of Oct-4, Sox-2, Nanog and Lin-28 in Fibs (untransduced), iPSCs and sorted CD45$^{+ve}$ iPSC (n=4).

Figure 10:
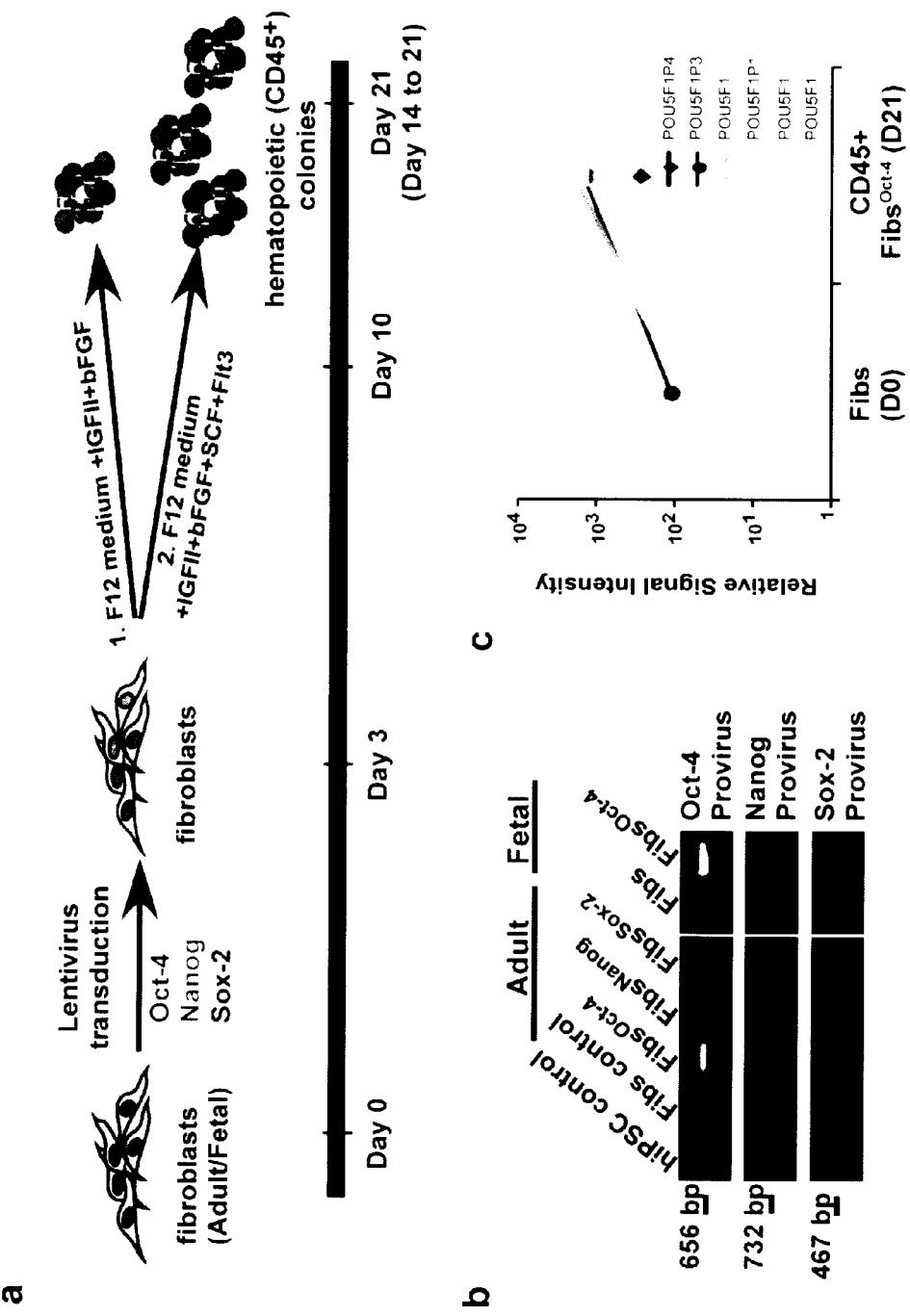

FIG. 10 shows a schematic representation of CD45 positive cell derivation from human dermal fibroblasts (Fibs). a. Human dermal Fibs were transduced with Oct-4 lentivirus on matrigel. On day 3-post transduction the cells were transferred onto matrigel coated dishes containing either 1. F12 medium supplemented with IGFII and bFGF or 2. F12 medium supplemented with IGFII, bFGF, Flt3 and SCF. Hematopoietic CD45 positive colonies were enumerated between days 14 and 21 post Oct-4 transduction. b. Representative blot showing integration of Oct-4 (Fibs$^{Oct-4}$), Sox-2 (Fibs$^{Sox-2}$) and Nanog (Fibs$^{Nanog}$)-lentivectors; human iPSCs derived from dermal Fibs transduced with Oct-4, Sox-2, Lin-28 and Nanog were used as the positive control (lane 1) and untransduced Fibs or Fetal Fibs were used as a negative control (lane 2 and 6). (n=6). c. Global Oct-4 gene expression (POU5F1 probe sets) following Oct-4 transduction over the course of CD45$^{+ve}$ cell emergence from Fibs (Day 0—D0 and Day 21 (D21)—CD45$^+$Fibs$^{Oct-4}$). POU5F1 (Oct-4) specific probe sets increase upon Oct-4 transduction over the time line of CD45$^{+ve}$ cell emergence from hFIbs irrespective of the probe set used for detection.

Figure 11:
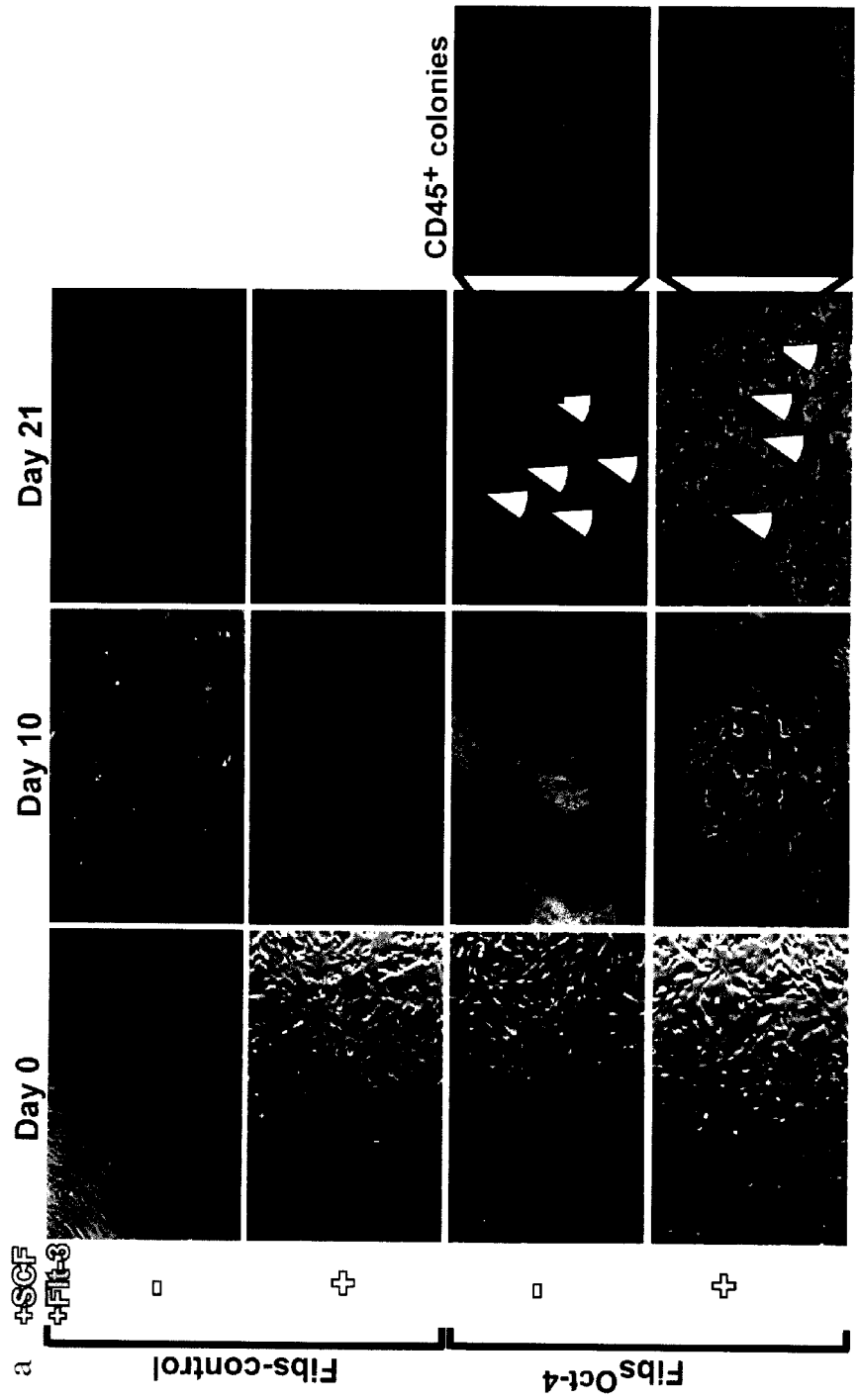

FIG. 11 shows CD45 positive colonies emerged from Oct-4 transduced cell between day 14-to-21 post transduction. a. Representative bright field images of human Fibs and hFibs$^{Oct-4}$ plus/minus SCF and Flt3 over the time line of colony emergence (white arrows) (day 0-21) (n=6). Enlarged box represents live CD45 stained colonies at day 21.

Figure 12:
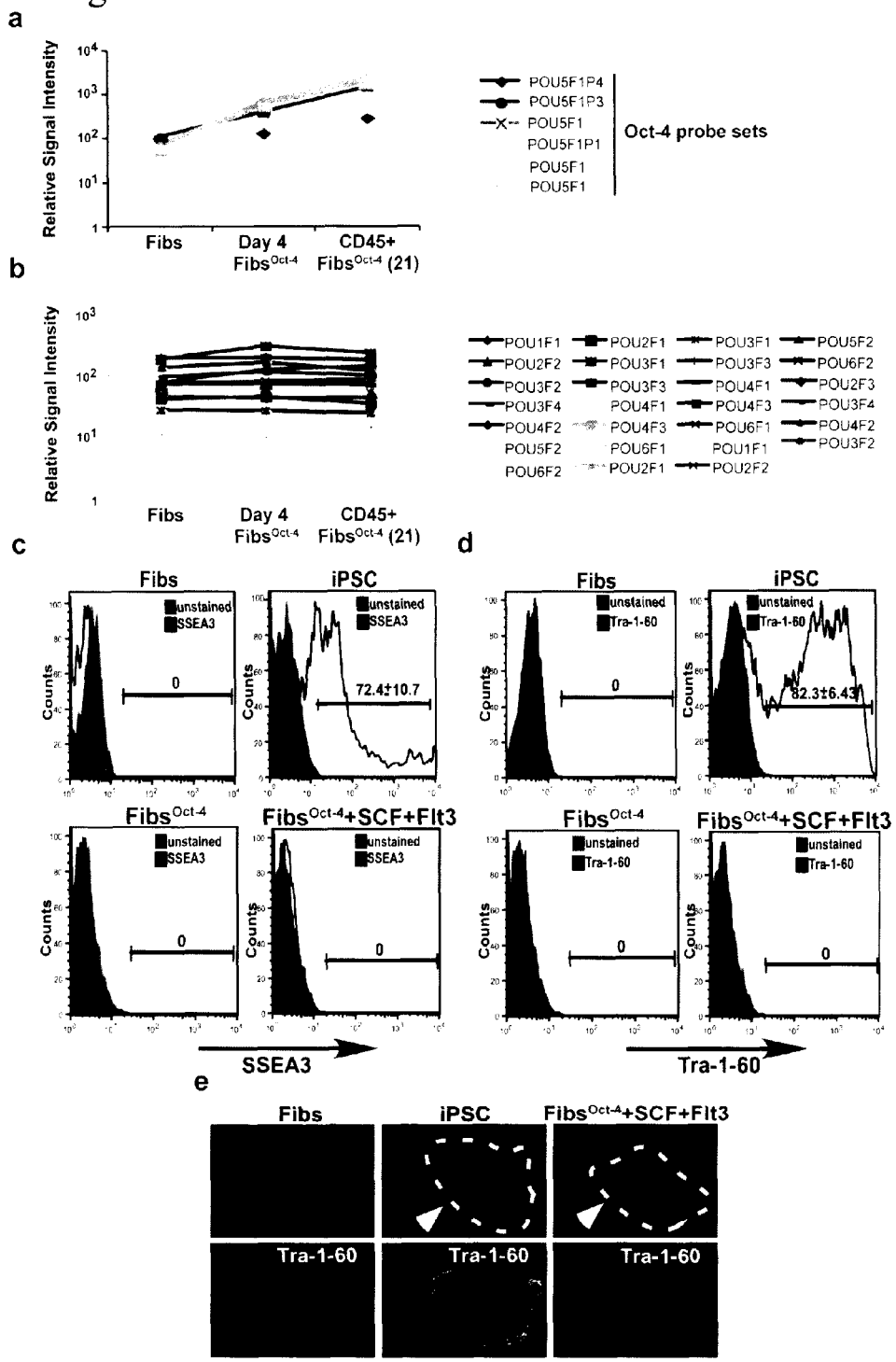

FIG. 12 shows Oct-4 transduced CD45 positive colonies do not acquire a pluripotent phenotype. a. Gene expression profile of Oct (POU) family members differentially regulated. Oct-4 (POU5F1) was the only POU family member differentially regulated over the time course of CD45$^{+ve}$ cell emergence; i.e. in Fibs (D0), Day 4 Fibs$^{Oct-4}$ (D4) and CD45$^+$ Fibs$^{Oct-4}$ (D21). b. Gene expression profile of POU family of genes that were not differentially regulated (excluding Oct-4) over the time course of CD45$^{+ve}$ cell emergence; i.e. in Fibs (D0), Day 4 Fibs$^{Oct-4}$ (D4) and CD45$^+$ Fibs$^{Oct-4}$ (D21). c. Representative FACS histogram of SSEA3 positive population frequency in untransduced Fibs and Fibs$^{Oct-4}$ plus/minus SCF and Flt3 and iPSC (n=6). d. Representative FACS histogram of Tra-1-60 positive population frequency in untransduced Fibs, Fibs$^{Oct-4}$ plus/minus SCF and Flt3 and iPSC (n=6). e. Live staining for Tra-1-60 positive colonies (arrows and dashed lines) in untransduced-Fibs, Fibs$^{Oct-4}$ plus SCF and Flt3 and iPSCs.

Figure 13:
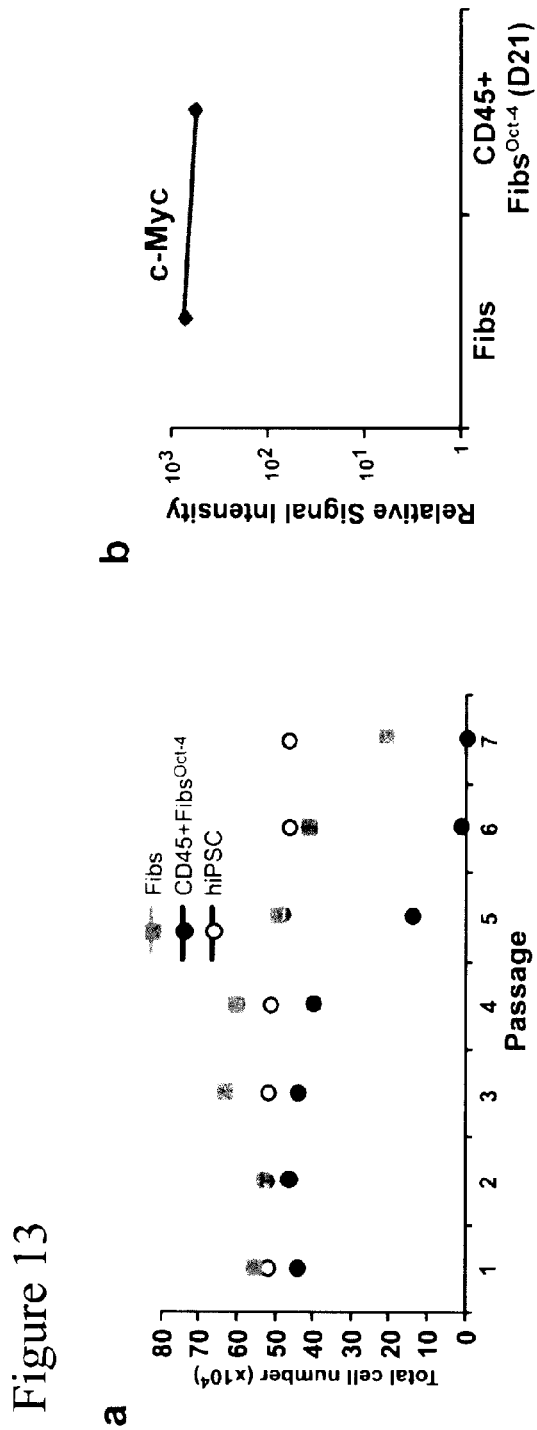

FIG. 13 shows growth dynamics and c-Myc expression over the time course of CD45$^{+ve}$ cell emergence. a. Growth/expansion dynamics of Fibs, CD45$^+$ Fibs$^{Oct-4}$ cells and human iPSCs (hiPSC) over 7 passages (n=9). b. Gene expression profile of c-Myc over the time course of CD45$^{+ve}$ cell emergence; i.e. in Fibs versus CD45$^+$ Fibs$^{Oct-4}$ (day 21—D21).

Figure 14:
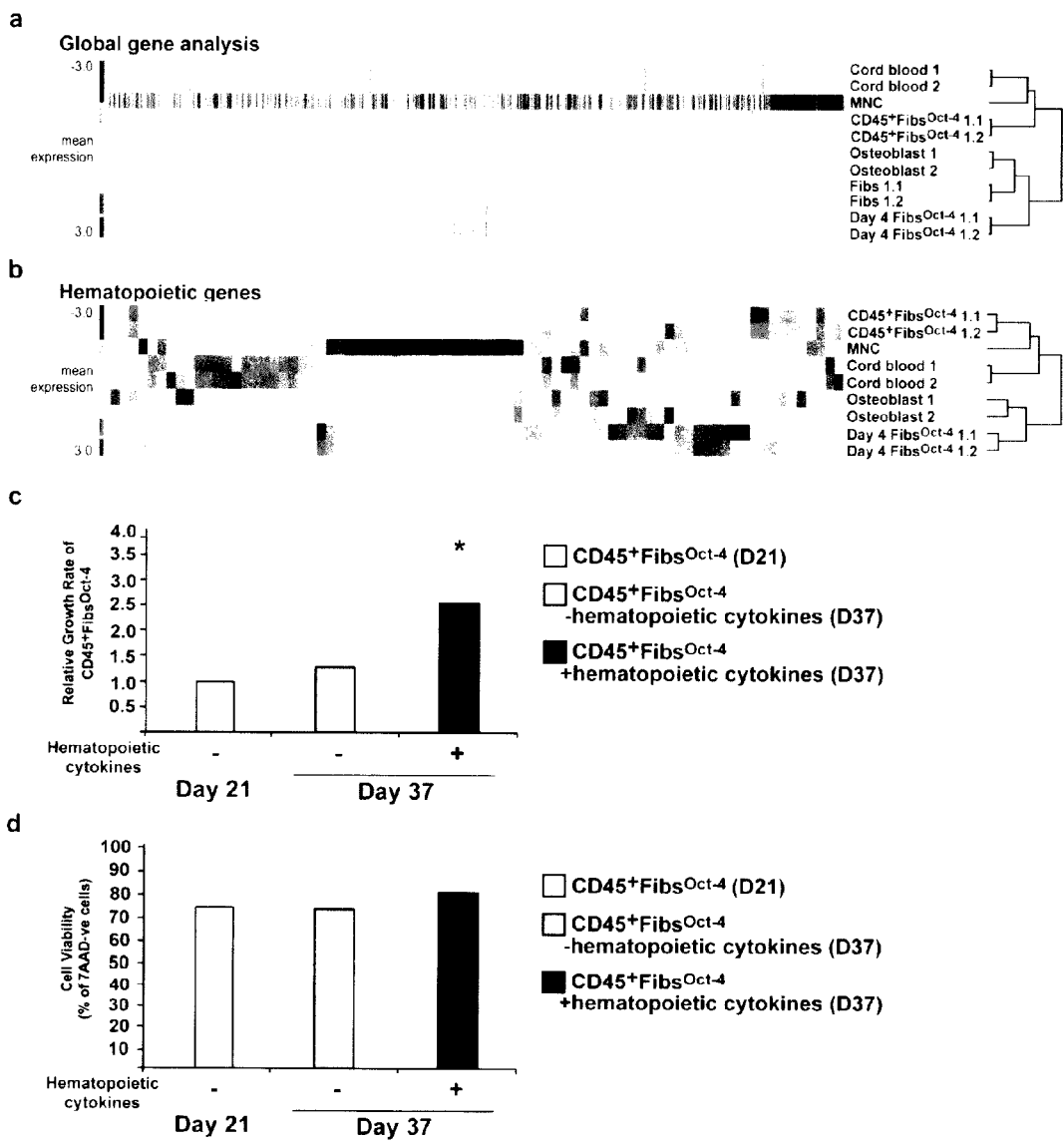

FIG. 14 shows global gene signatures cluster mononuclear cells with Oct4 positive CD45$^{+ve}$ cells and cord blood derived progenitors with day 4 Oct-4 transduced Fibs. a. Global gene cluster analysis of mononuclear cells (MNC), cord blood derived hematopoietic progenitors (UCB), Fibs, osteoblasts, Day 4 Fibs$^{Oct-4}$ and CD45$^+$ Fibs$^{Oct-4}$. b. Hematopoietic gene analysis of MNCs, UCB cells, Fibs, osteoblasts, Day 4 Fibs$^{Oct-4}$ and CD45$^+$ Fibs$^{Oct-4}$. c. CD45$^+$Fibs$^{Oct-4}$ treated with hematopoietic cytokines over an additional 16 days (day 37—D37) had enhanced proliferation capacity versus CD45$^+$ Fibs$^{Oct-4}$ before cytokine treatment (day 21—D21) and untreated CD45$^+$Fibs$^{Oct-4}$ at day 37 (D37) (n=6; *p<0.001). d. Cell viability of CD45$^+$Fibs$^{Oct-4}$ cells with and without hematopoietic cytokine treatment at day 37 (D37) and CD45$^+$ Fibs$^{Oct-4}$ cells at day 21 (D21) (n=6).

Figure 15:
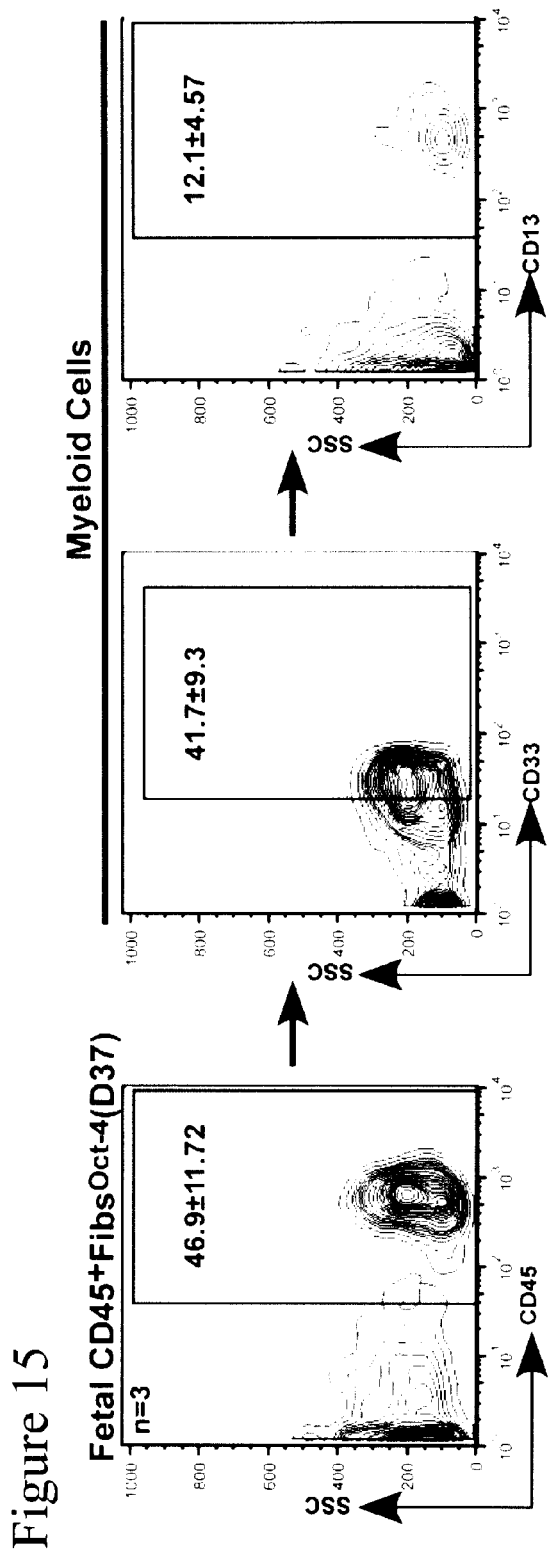

FIG. 15 shows in vitro reconstitution of the myeloid cells by hematopoietic cytokine treated Oct-4 transduced CD45 positive fetal foreskin derived Fibs at day 37. FACS analysis of myeloid cells (CD45$^+$CD13$^+$ and CD13$^+$CD33$^+$ cells) derived from Fetal CD45$^+$Fibs$^{Oct-4}$ at day 37 (D37) (n=3).

Figure 16:
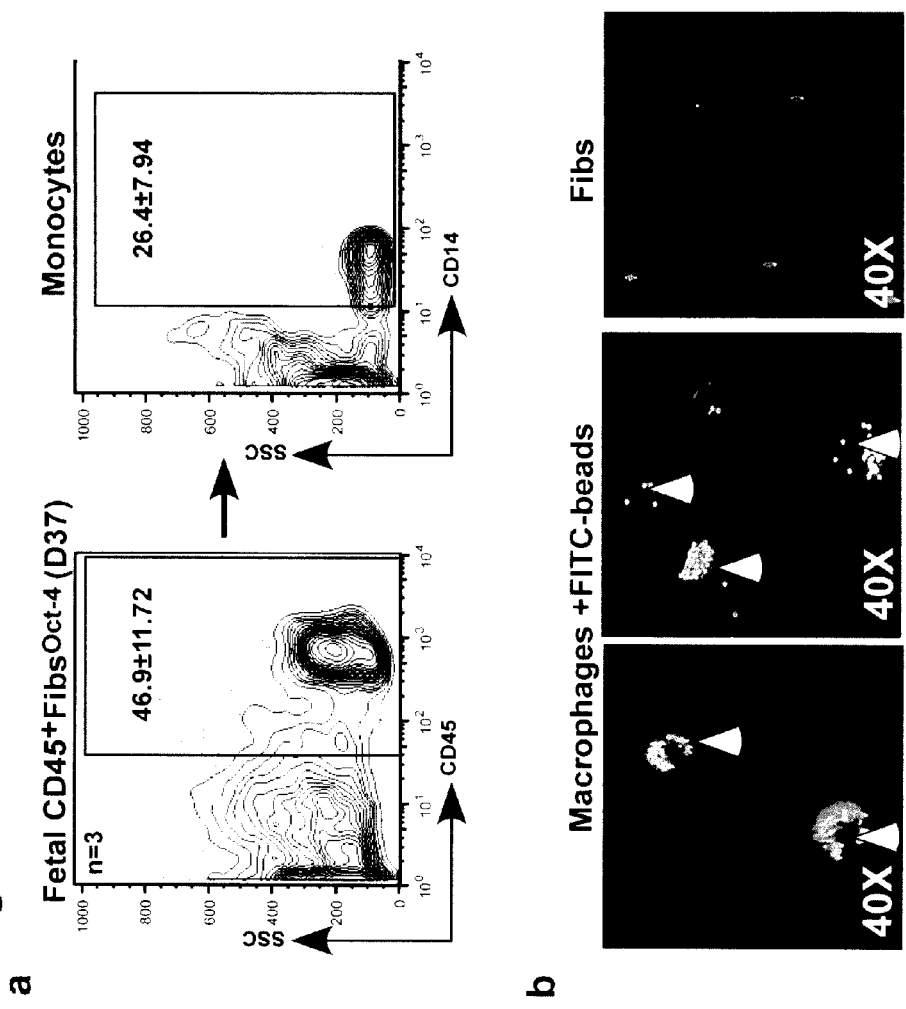

FIG. 16 shows in vitro reconstitution of the monocyte lineage by hematopoietic cytokine treated Oct-4 transduced CD45 positive Fetal and adult Fibs at day 37. a. Representative FACS plots of monocytes at day 37 (D37) (CD45$^+$CD14$^+$ cells; n=3). b. FITC-labeled beads uptake by CD45$^+$ Fibs$^{Oct-4}$ derived macrophages (40x) compared with untransduced Fibs (white arrows-cells containing beads).

Figure 17:
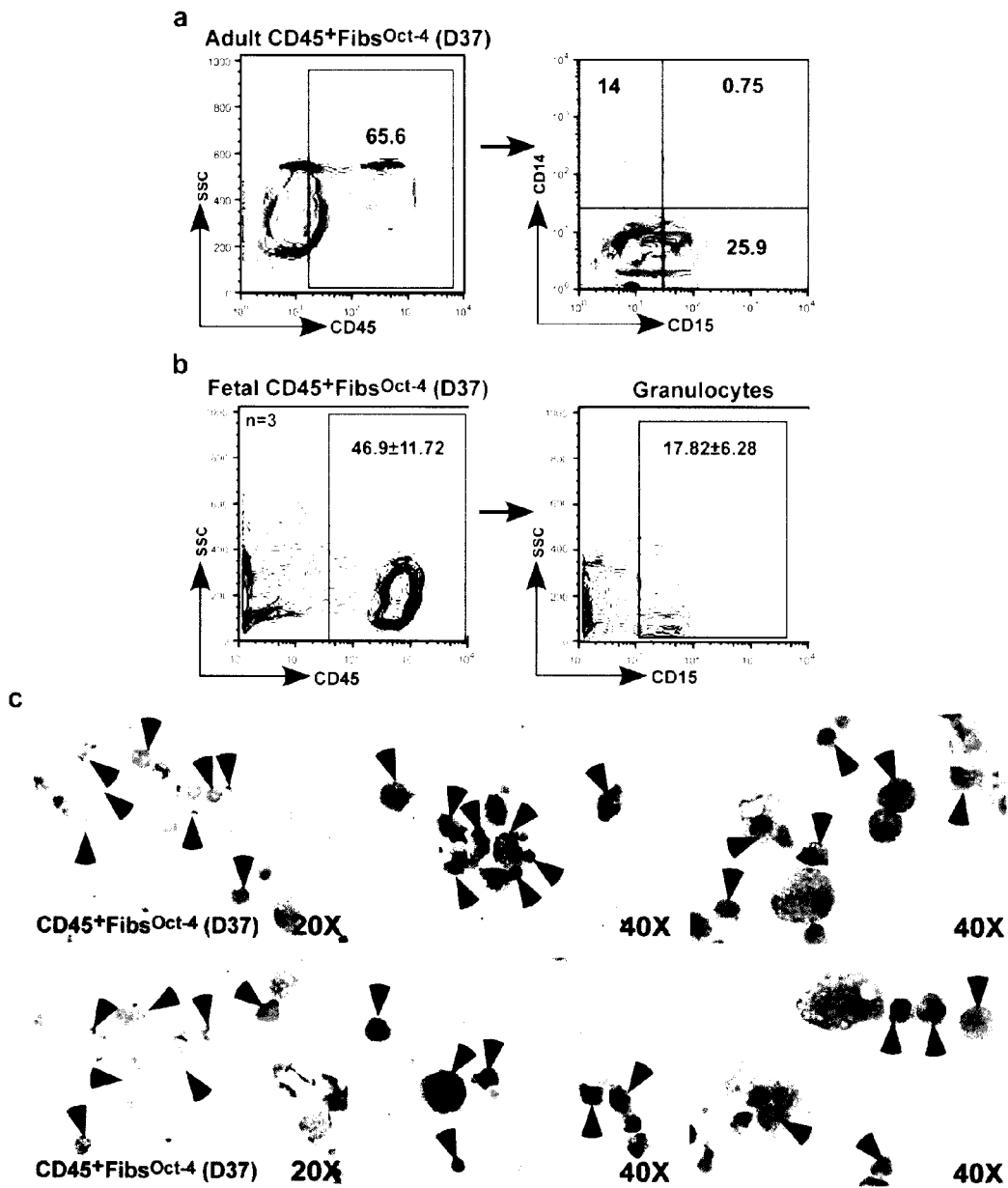

FIG. 17 shows in vitro reconstitution of the myeloid lineage by hematopoietic cytokine treated Oct-4 transduced CD45 positive Fibs at day 37. a. Representative FACS analysis of CD45+ Fibs$^{Oct-4}$ cells triple-stained with CD45, CD14 and CD15, showing lack of CD14 and CD15 co-expression at day 37 (D37) (n=3). b. Representative FACS plot of granulocytes (CD45+CD15+ cells) derived from Fetal CD45+Fibs$^{Oct-4}$ at day 37 (D37) (n=3). c. Representative bulk images of Giemsa Wright stained CD45+Fibs$^{Oct-4}$ cells treated with cytokines at day 37 (D37) (20× and 40×; n=6) (arrows-hematopoietic cells).

Figure 18:
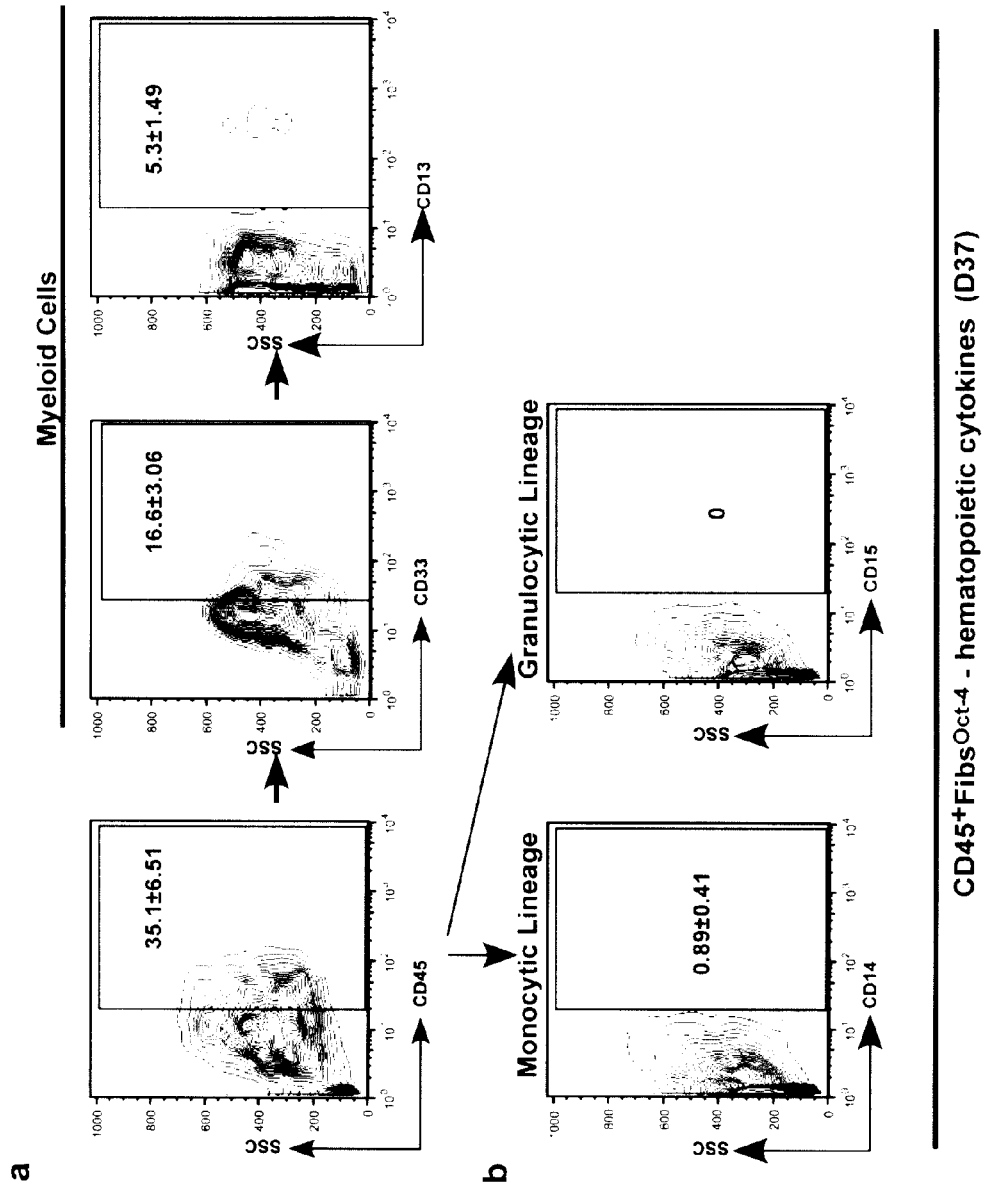

FIG. 18 shows in vitro reconstitution of the myeloid lineage in the absence of hematopoietic cytokine treatment in Oct-4 transduced CD45 positive Fibs at day 37. a. FACS analysis of myeloid cells (CD45+CD13+ and CD13+CD33+ cells) in the absence of hematopoietic cytokine in CD45+ Fibs$^{Oct-4}$ at day 37 (D37) (n=6). b. Representative FACS plots of monocytes (CD45+CD14+ cells) and granulocytes (CD45+ CD15+ cells) in the absence of hematopoietic cytokine in CD45+Fibs$^{Oct-4}$ at day 37 (D37) (n=6).

Figure 19:
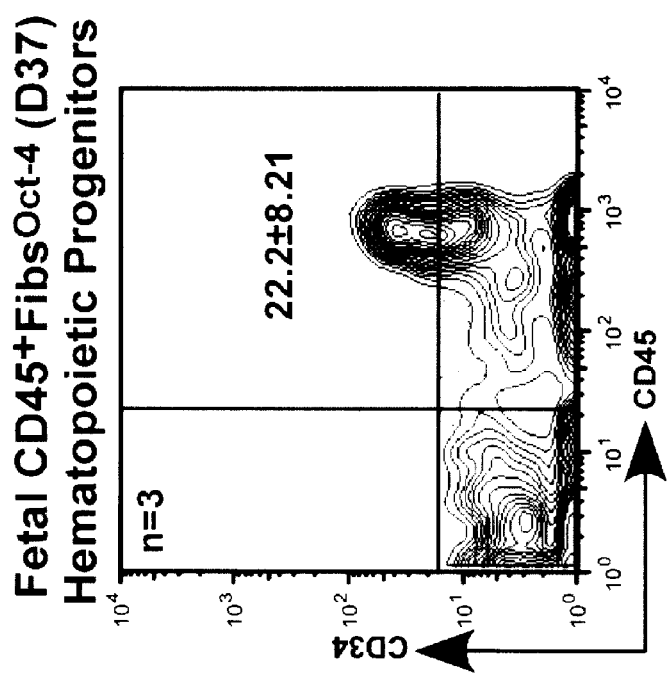

FIG. 19 shows in vitro reconstitution of the myeloid lineage by hematopoietic cytokine treated Oct-4 transduced CD45 positive fetal foreskin derived Fibs. Hematopoietic cytokine treated Fetal CD45+Fibs$^{Oct-4}$ cells give rise to hematopoietic progenitors (CD45+CD34+ cells) at day 37 (D37) (n=3).

Figure 20:
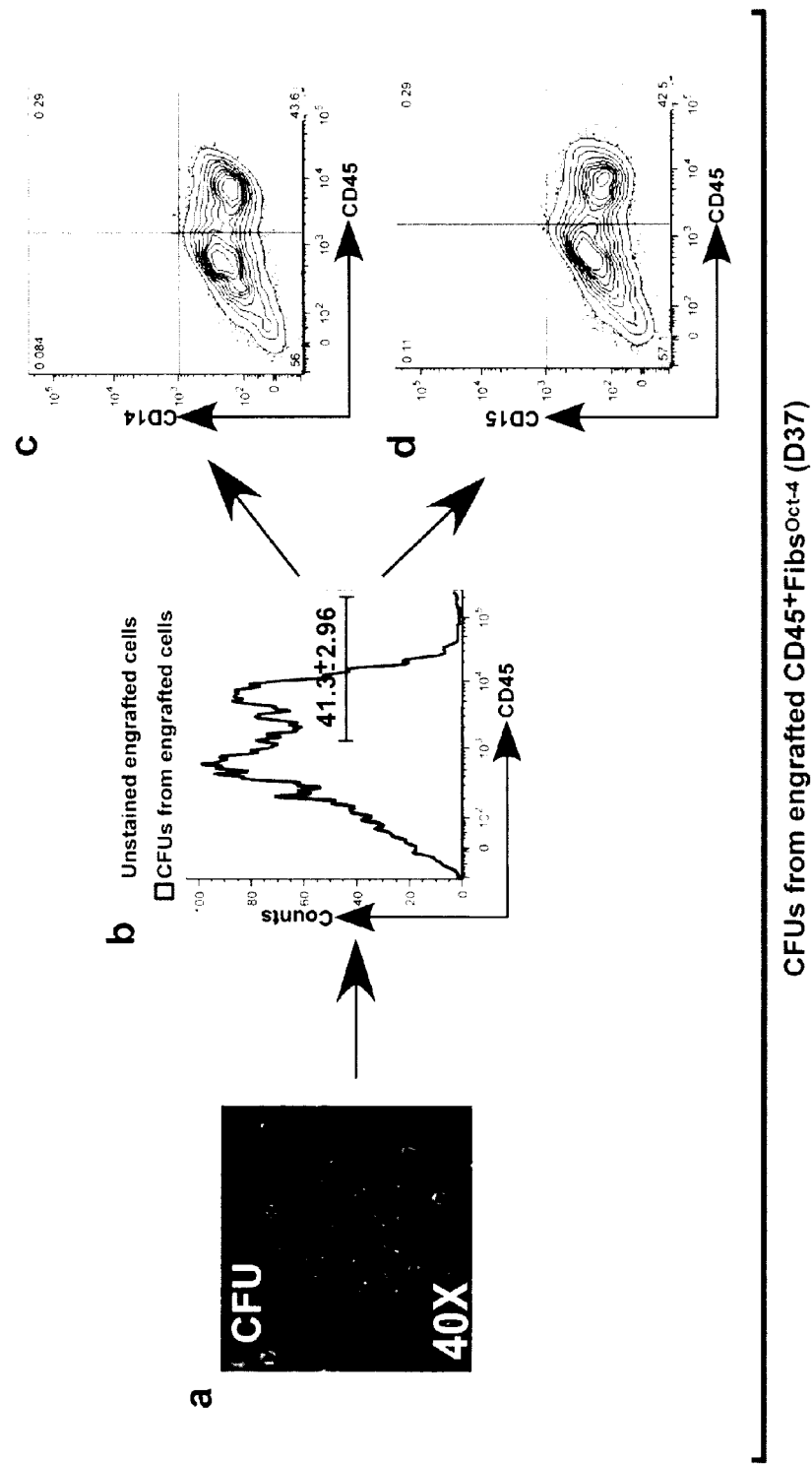

FIG. 20 shows colony forming units derived from immunodeficient mice engrafted CD45+Fibs$^{Oct-4}$ cells maintained CD45 expression. a. Bright field image of CFUs derived from engrafted CD45+Fibs$^{Oct-4}$ cells (n=3). b. Representative FACS histogram indicating CD45 expression in CFUs derived from engrafted CD45+Fibs$^{Oct-4}$ (n=3). c. Representative FACS plots indicating CD45 versus CD14 expression in CFUs derived from engrafted CD45+Fibs$^{Oct-4}$ (n=3). d. Representative FACS plots indicating CD45 versus CD15 expression in CFUs derived from engrafted CD45+Fibs$^{Oct-4}$ (n=3).

Figure 21:
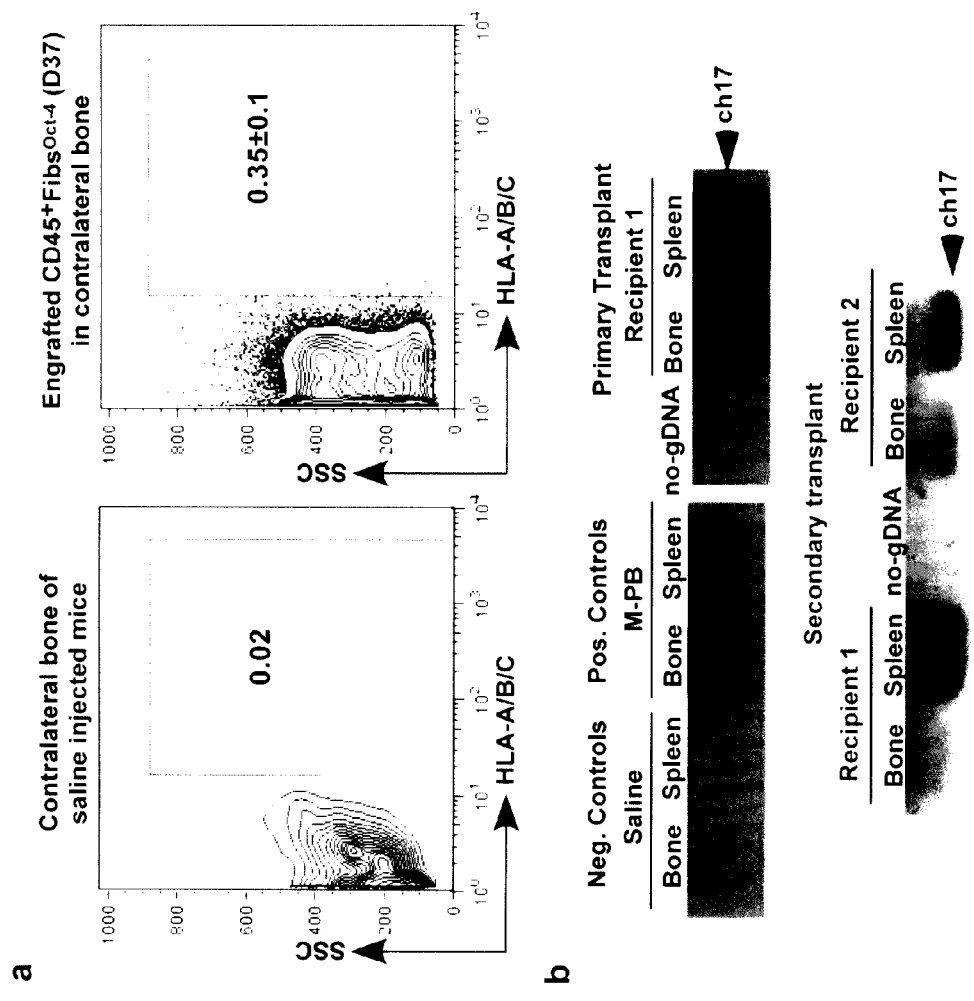

FIG. 21 shows in vivo reconstitution of the Oct-4 transduced CD45 positive cells derived Fibs. a. Representative FACS plot showing engraftment of CD45+Fibs$^{Oct-4}$ (D37) cells in contralateral bone of injected immunodeficient (NSG) mice compared with saline injected counterparts (n=8; p<0.01) b. Primary and secondary reconstitution capacity of the engrafted CD45+Fibs$^{Oct-4}$ cells. Human chimerism in bone and spleen of recipient NSG mice was analyzed via the presence of human chromosome 17. Positive control—mobilized peripheral blood (M-PB); Negative control-spleen and bones from saline injected mice; Control—no genomic DNA—no gDNA.

Figure 22:
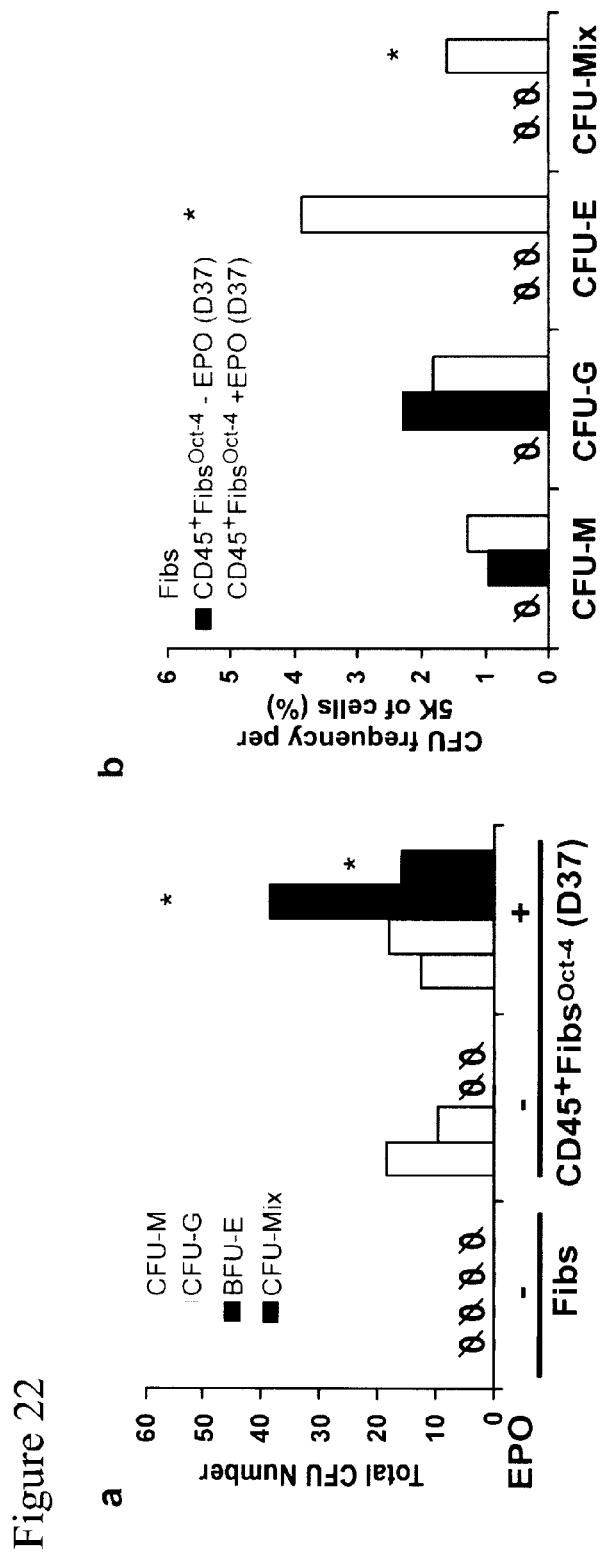

FIG. 22 shows EPO treatment resulted in erythroid colony forming units formation. a. Quantification of colony forming units derived from Fibs, CD45+Fibs$^{Oct-4}$ with or without EPO treatment (n=3; *p<0.001). b. Bar graph representing the frequency of colony (CFU) formation per 5,000 cells plated (n=3; *p<0.001). (monocytic-CFU-M; granulocytic-CFU-G, erythroid-BFU-E; mixed colonies containing erythroid, granulocytic, monocytic—CFU-Mix).

Figure 23:
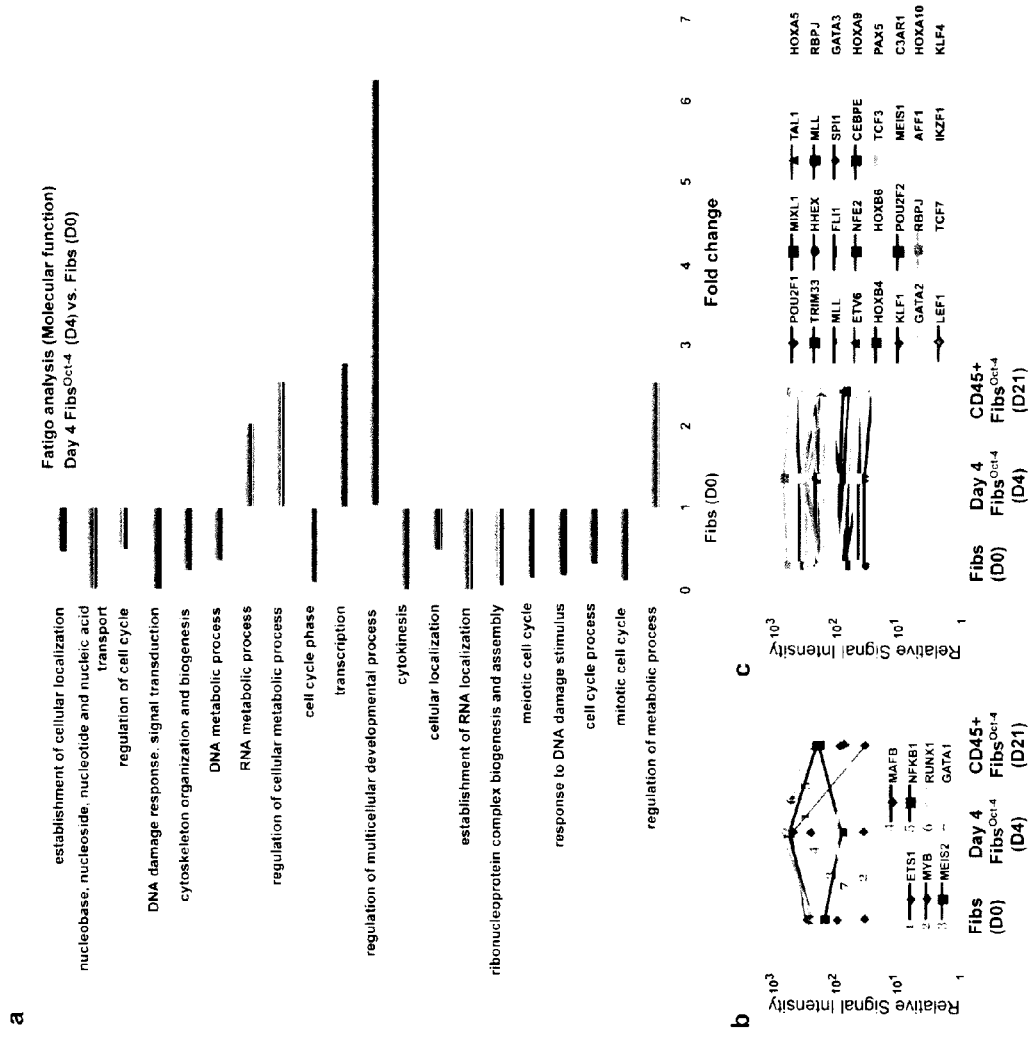

FIG. 23 shows Oct-4 induced changes over the time course of CD45+ve cell emergence. a. Fatigo analysis of molecular/functional pathways in adult dermal Fibs versus Fibs at day 4 post Oct-4 transduction (threshold set at 2-fold; p<0.001). b. Gene expression profile of hematopoietic genes showing significant transcriptional regulation (p<0.001) and c. showing the absence of transcriptional regulation over the time course of CD45+ve cell emergence; i.e. in Fibs (day 0—D0), puromycin selected Day 4 Fibs$^{Oct-4}$ (day 4—D4) and sorted CD45+ Fibs$^{Oct-4}$ (day 21—D21).

Figure 24:
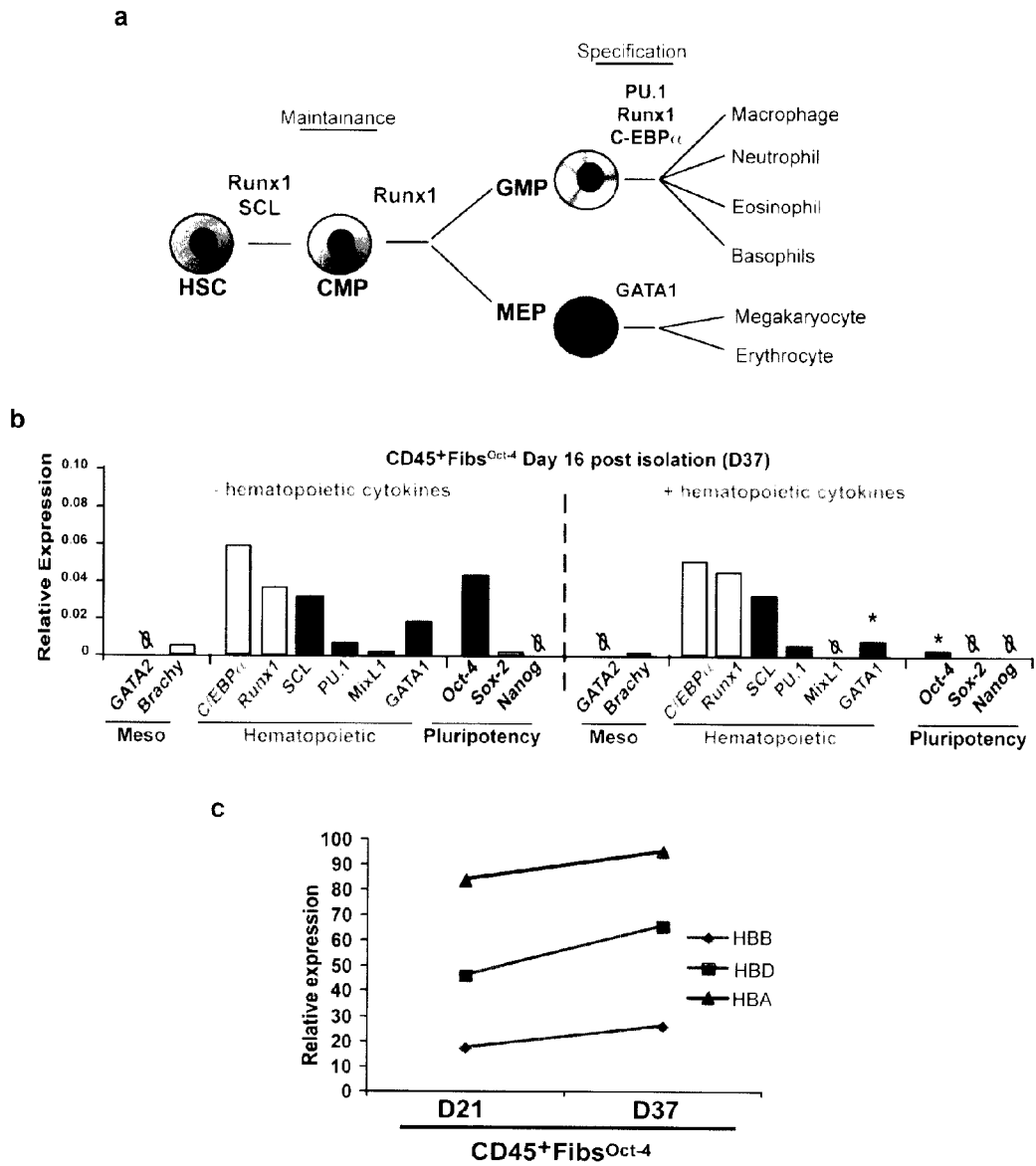

FIG. 24 shows hematopoietic gene expression during maturation of Oct4 transduced CD45+ve cells. a. Schematic representation of the hematopoietic genes shown to be involved in hematopoietic specification (Runx1, SCL) and maturation (PU.1, Runx1, C/EBPα and GATA1). b. Relative mRNA expression analysis of mesodermal genes (GATA2, Brachyury), hematopoietic specific genes (SCL, MixL1, Runx1, GATA1, PU.1 and C/EBPα) and pluripotency genes (Oct-4, Sox-2 and Nanog) in CD45+ Fibs$^{Oct-4}$ with or without hematopoietic cytokine cocktail treatment (Flt-3, G-CSF, SCF, IL6, IL3, BMP-4) at day 37 (D37) (n=3, *p<0.001). c. Adult hemoglobin (beta, alpha and delta) expression at day 21 (D21) and day 37 (D37) following Oct-4 transduction in CD45+Fibs$^{Oct-4}$ cells. (HBB—β-hemoglobin; HBA—α-hemoglobin; HBD—δ-hemoglobin).

Figure 25:
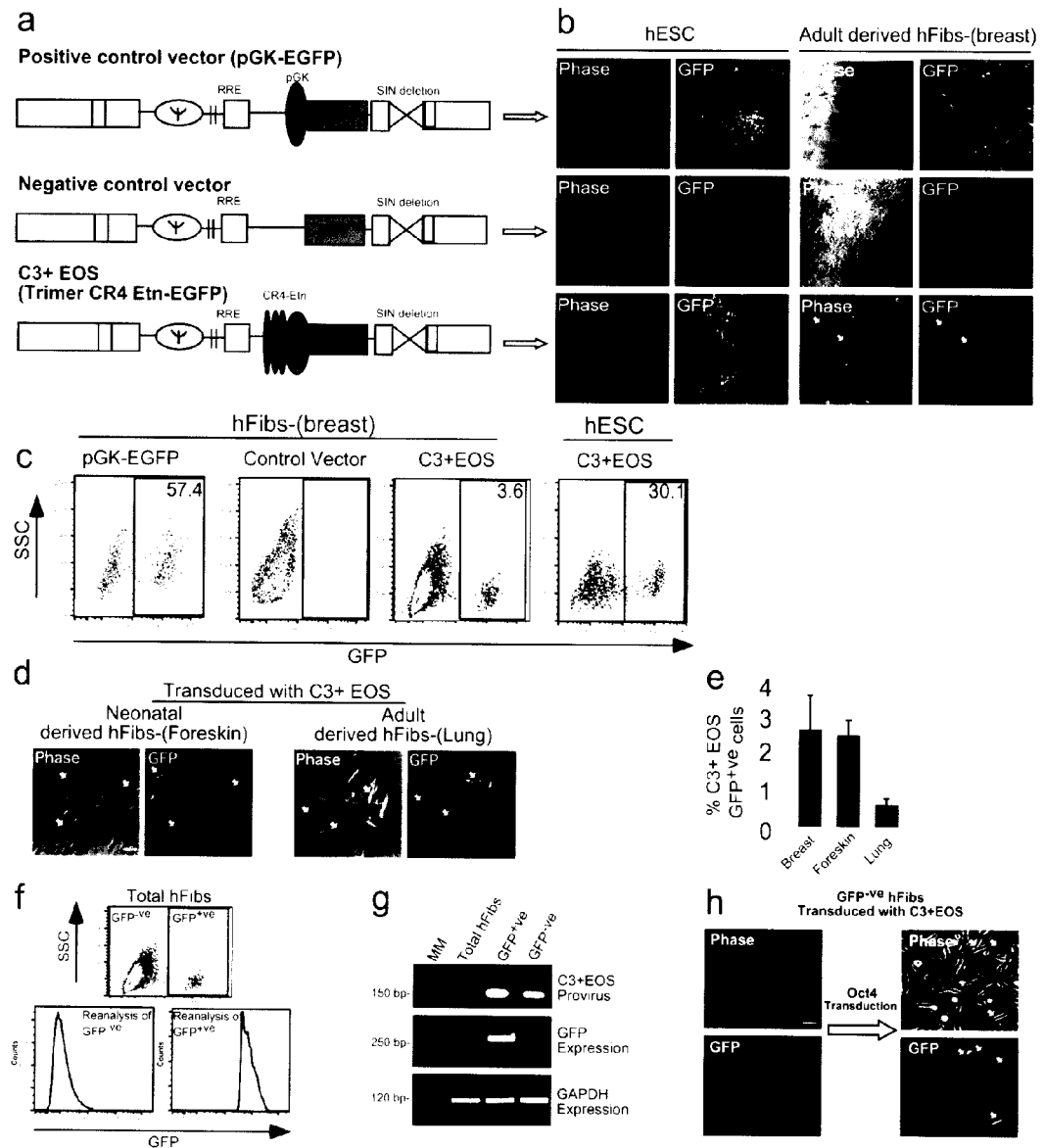

FIG. 25 shows Oct enhancer driven GFP expression in unique subset of cells derived from fibroblast cultures. (a) Schematic representation of PGK-EGFP (positive control), promoter-less EGFP (negative control) vector, C3+EOS EGFP IRES Puro vector. (b) Representative phase and fluorescence microscopy images of hESC and human dermal adult fibroblasts (hFibs) transduced with PGK-EGFP, negative control and C3+ EOS GFP IRES Puro vectors. GFP positive (GFP+ve) from C3+EOS vector are indicated with arrows. (c) Representative FACS plots of GFP+ve cell frequency upon C3+EOS transduction in breast derived hFibs and positive control hESC. (d) Representative phase and fluorescence microscopy images of foreskin and lung derived fibroblasts (hFibs) transduced with C3+ EOS GFP vector. GFP positive (GFP+ve) from C3+EOS vector are indicated with arrows. (e) Frequency of GFP+ve cells in Breast (n=5), foreskin (n=3) and lung derived fibroblasts (n=3) upon C3+EOS transduction was studied using flow cytometry. (f) Schematic representation of the strategy used for sorting GFP+ve and GFP−ve hFibs from total hFibs transduced with C3+ EOS lentivirus and subsequent analysis of the sorted subfractions. (g) Representative provirus integration and GFP expression profile was studied in sorted cells. (h) Phase and fluorescence microscopy images of GFP−ve fibroblast fraction that was transduced with pSIN Oct4 lentivirus. Arrows indicate GFP cells that are observed after Oct4 overexpression.

Figure 26:
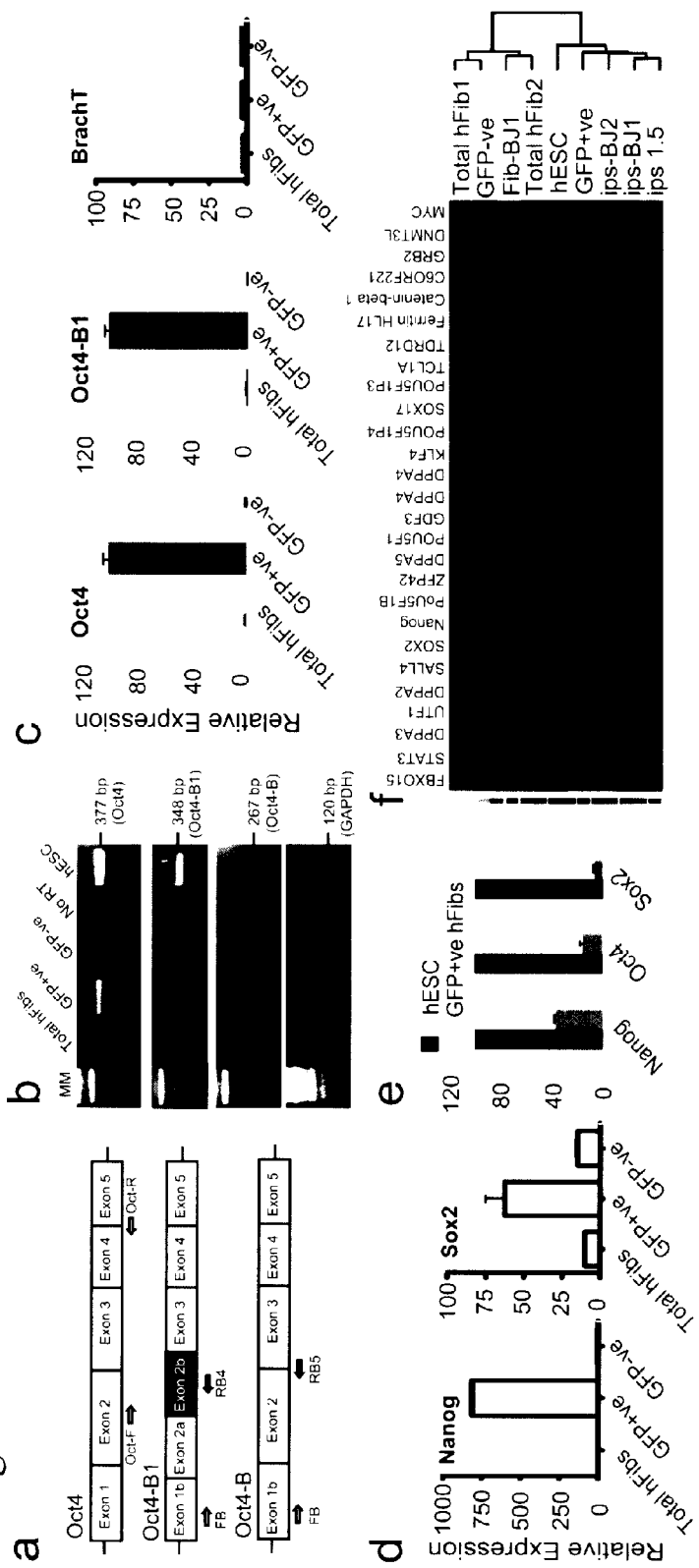
Figure 26:
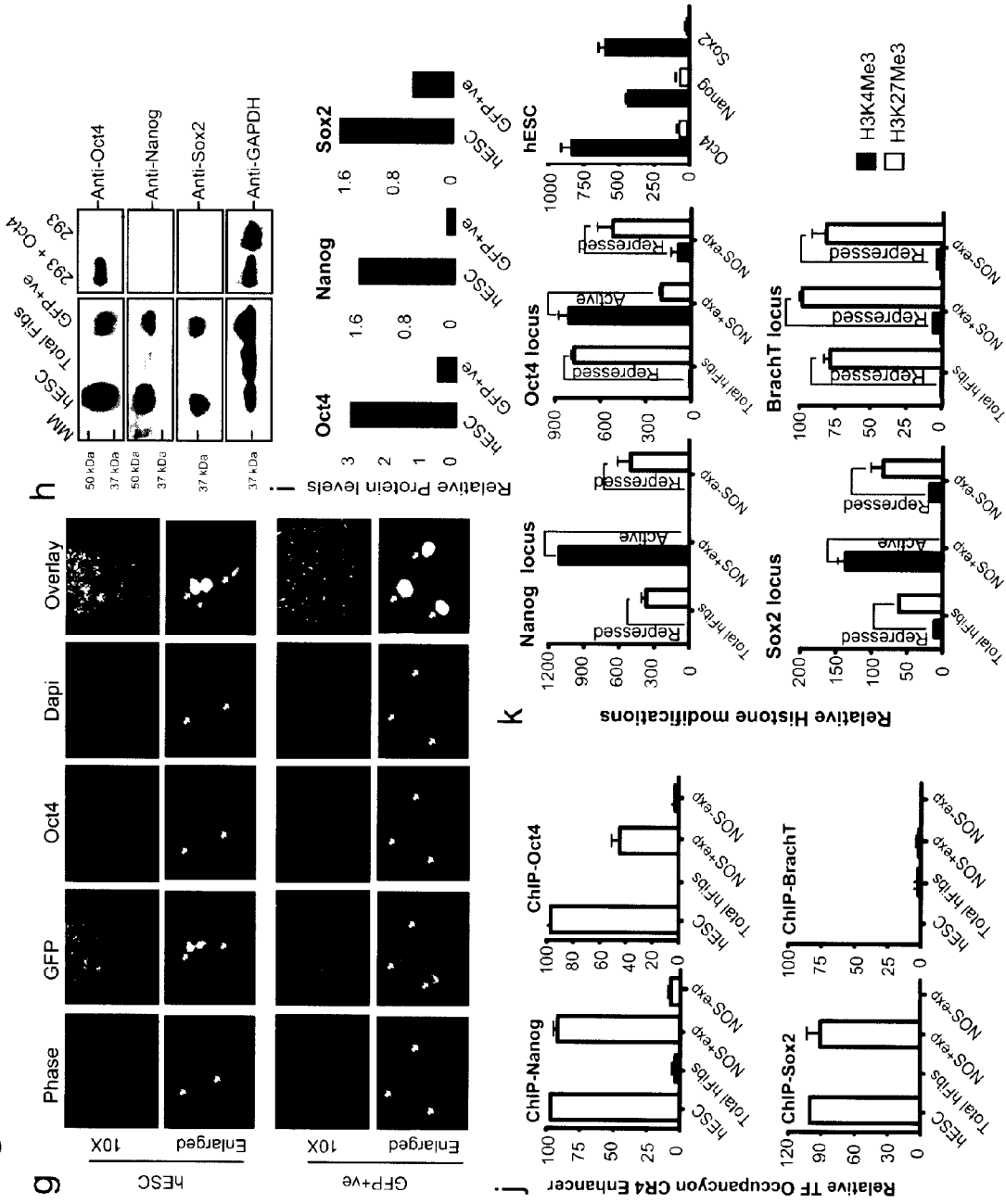

FIG. 26 shows EOS+ve fibroblasts cells express pluripotency genes. (a) Schematic representation of Oct4 locus and primers spanning various exons on the loci. (b and c) Expression of Oct4 isoforms in semi quantitative and quantitative PCR analysis. (d) Relative expression of key pluripotency genes Nanog, Sox2 and Brachyury (BrachT) in various subfractions of fibroblasts. (e) Expression of Oct4, Nanog, and Sox2 from GFP+ve hFibs was compared to hESCs by quantitative RT-PCR analysis. (f) Hierarchical clustering of total hFibs, NOS+exp fibroblasts, NOS−exp fibroblasts, hESC, iPSC NOS+exp fibroblasts and iPS from public data sets (Fib-BJ1, iPS BJ1 ans iPS BJ2). Expression profiles are based on genes enriched in mouse ESCs (Takahashi et al. 2007), human ESCs and adult fibroblast markers (Yu et al. 2007). (g) Representative images (10×) and enlarged images for immunostaining of Oct4 in control hESC and GFP+ve cells using specific antibody. (h) Expression of Oct4, Nanog, and Sox2 in total hFibs, GFP+ve hFibs, 293, 293 overexpressing Oct4 and control hESCs by western blotting. (l) Occupancy of Oct4, Nanog, and Sox2 on Oct4 Enhancer (CR4) of C3+ EOS GFP IRES Puro vector was studied using ChIP assay. (j) Epigenetic state of Oct4, Nanog, and Sox2 loci in control hESC, NOS+exp, NOS−exp and total hFib cells was analyzed using ChIP to identify H3K4Me3 (black bars) and H3K27Me3 (white bars) marks.

Figure 27:
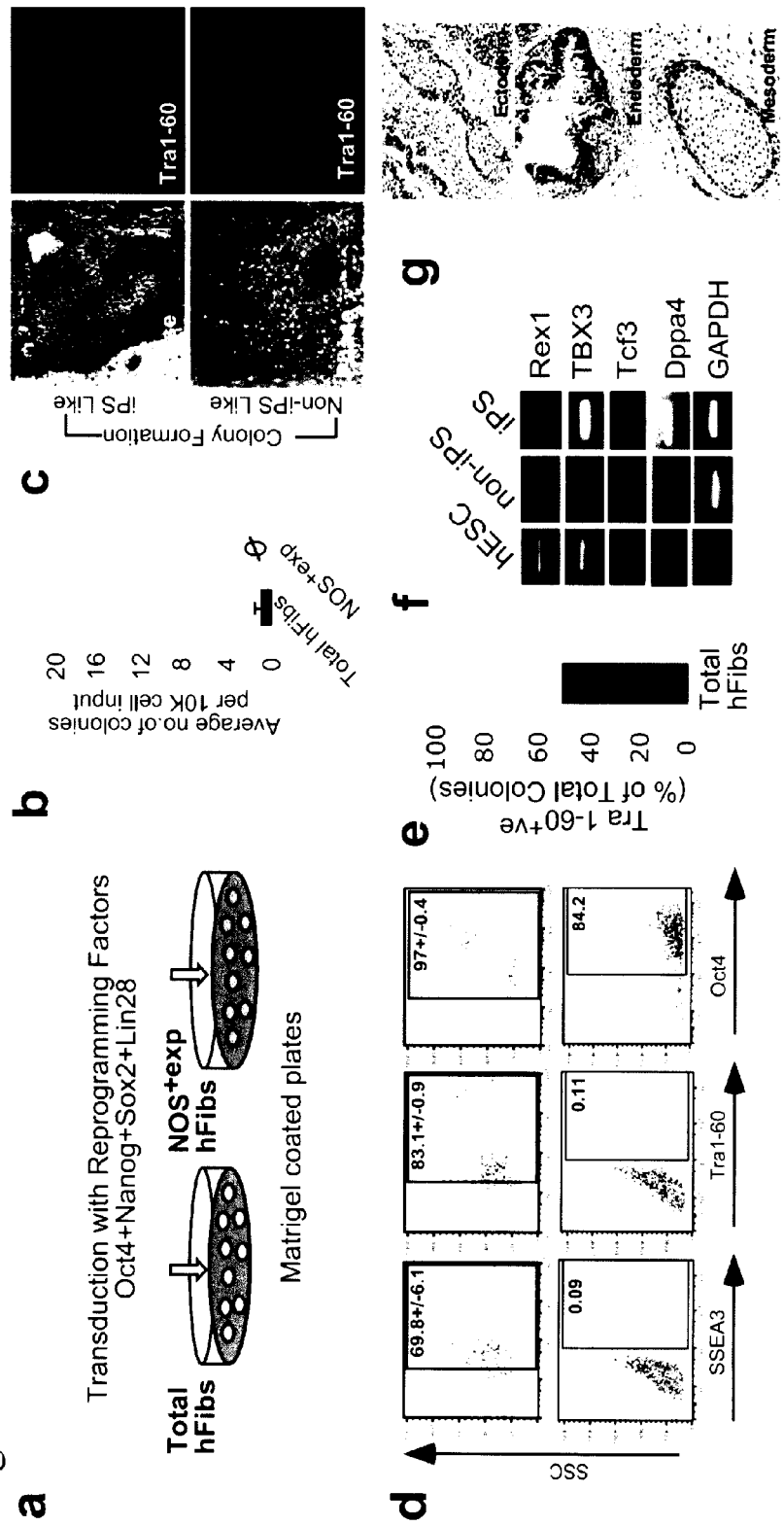

FIG. 27 shows NOS+exp cells separated from total fibroblast cultures exhibit reduced reprogramming efficiency. (a)

Schematic representation of protocol used for reprogramming human Fibs and its subfraction NOS$^{+exp}$ on matrigel. (b) iPSC derivation from 10,000 total fibroblasts or NOS$^{+exp}$ cells on matrigel. Reprogramming of total fibroblast was performed 9 times and NOS$^{+exp}$ for n=6, using three different viral titers. (c) Representative phase images of iPSC and non-iPSC like colonies derived total fibroblasts. Fluorescence microscopy images show live staining of Tra 1-60 in both the colonies. (d) Expression of pluripotency markers SSEA3, Tra 1-60 and Oct4 staining was verified in iPSC and non-iPSC like colonies by flow cytometry. (e) Average number of Tra 1-60$^{+ve}$ colonies derived from total hFibs. (f) Semi-quantitative PCRs showing expression of key ES specific markers in iPSC and non-iPSC colonies obtained from total hFib reprogramming. (g) Hematoxylin and eosin staining of teratoma derived from iPS cells showing mesoderm, endoderm, and ectoderm differentiation. (h) NOS$^{+exp}$ hFibs were mixed with total hFibs in the indicated ratio, Lentivirus encoding Oct4, Sox2, Nanog, and Lin28 were transduced 24 hrs post plating. Graph represents quantification of number of colonies three-week post transduction. Data represented is from three biological replicates performed in duplicates using three different viral titers. (i) Representative phase and fluorescence images 1K+9K mixtures (1:9), GFP$^{+ve}$ colonies were contributed by NOS$^{+exp}$ (EOS$^{+ve}$) cells which was further confirmed by EOS provirus integration. EOS$^{-ve}$ colonies were contributed by total hFibs. To differentiate between fully versus partially reprogrammed colonies Tra 1-60 live staining was performed. (j) Semi quantitative PCRs of pluripotency genes to study reactivation of ES specific genes in reprogrammed colonies from mixture experiments. (asterisks indicate these colonies were selected for further flow cytometry analysis). (k) Flow cytometry analysis for reprogrammed colonies derived from NOS$^{+exp}$ and total hFibs in mixture experiments. (i) NOS$^{+exp}$ hFib derived iPSC cells was injected into mouse testicle for teratoma formation. Hematoxylin and eosin staining of teratoma showing differentiation of all three germ layers (mesoderm, endoderm, and ectoderm).

Figure 28:
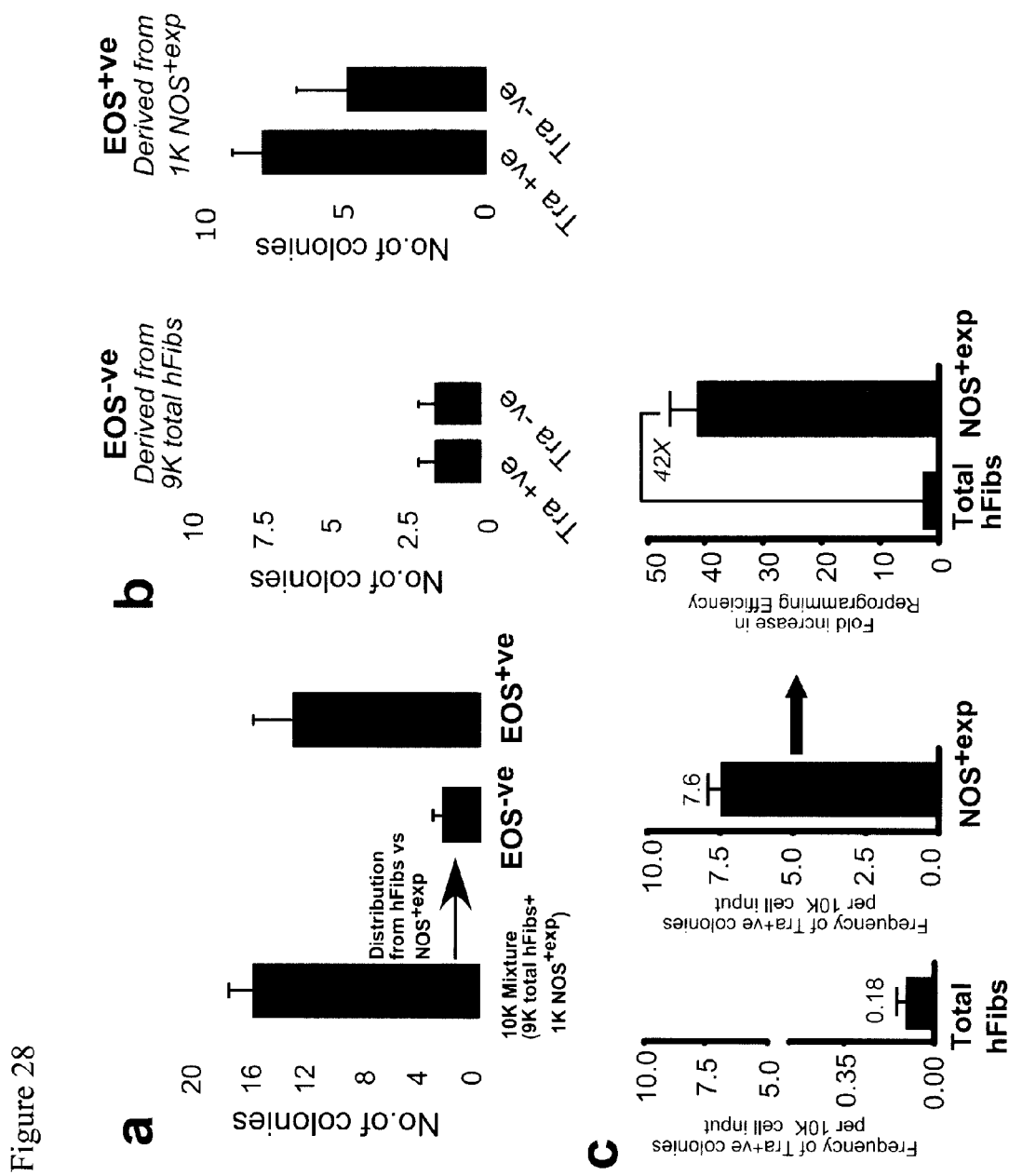

FIG. 28 shows NOS$^{+exp}$ cells are predisposed for reprogramming. (a) hFibs were transduced with C3+ EOS GFP vector, NOS$^{+exp}$ cells were sorted on matrigel and combined with total fibroblast in 1:9 ratio (1000 NOS$^{+exp}$ cells plus 9000 total hFibs) or 10000 total fibroblasts cells and plated on matrigel. Lentivirus encoding Oct4, Sox2, Nanog, and Lin28 were transduced 24 hrs post plating. Right panel represents quantification of colony number derived from 1K to 9K mixture experiments. Left panel represents colony contribution from EOS$^{-ve}$ and EOS$^{+ve}$ cells. (b) Tra 1-60 live staining was performed to study the complete reprogramming in colonies derived from NOS$^{+exp}$ (EOS$^{+ve}$ derived from 1K) or total hFibs (EOS$^{-ve}$ derived from 9K) in mixture experiment. (c) Frequency of complete reprogramming (Tra 1-60$^{+ve}$ colonies) was studied in a mixture experiment by dividing number of Tra 1-60$^{+ve}$ colonies from each compartment to its input cell count [no. of Tra 1-60$^{+ve}$ (EOS$^{-ve}$)/9000 or no. of Tra 1-60$^{+ve}$ (EOS$^{+ve}$)/1000].

Figure 29:
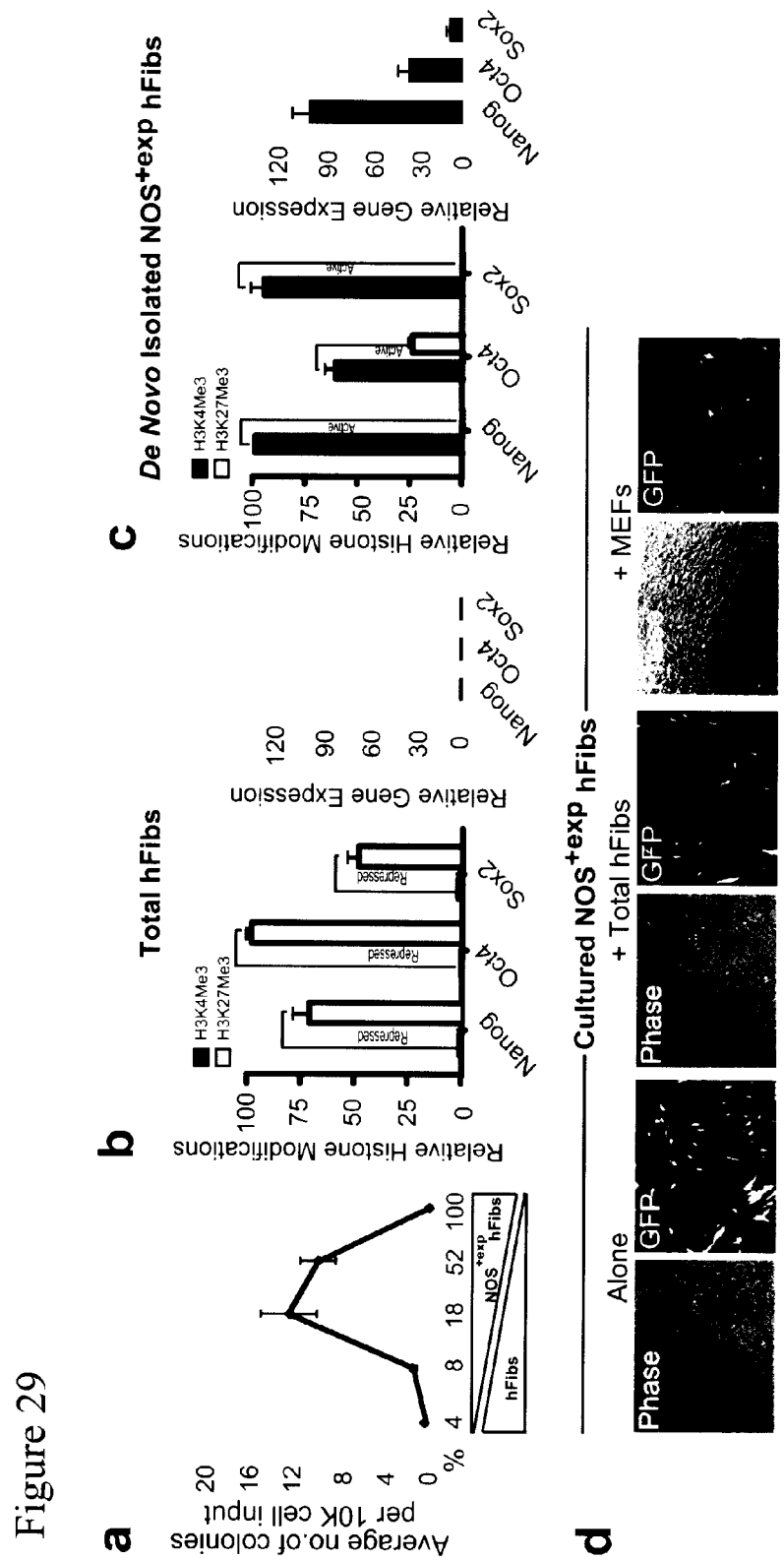
Figure 29:
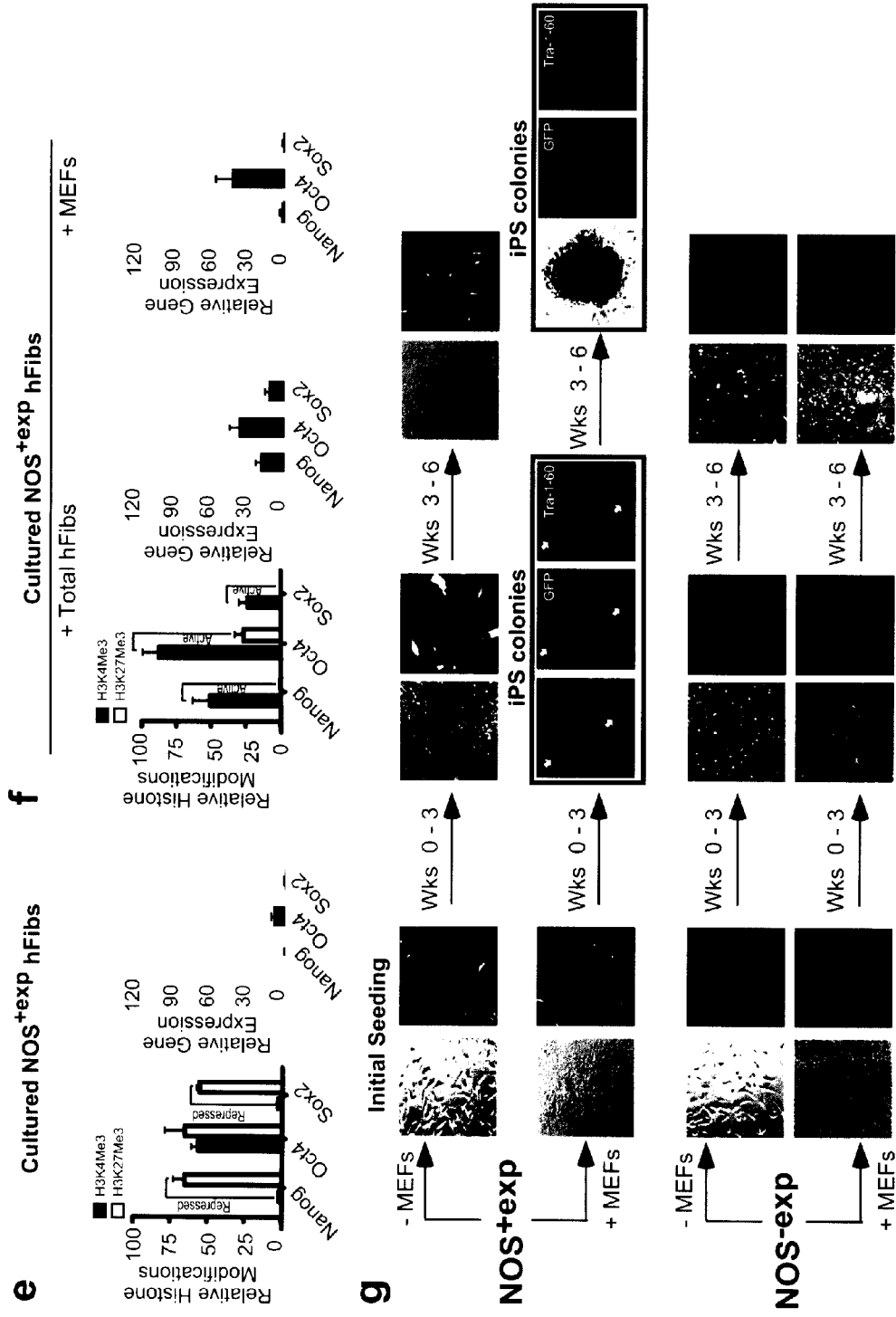

FIG. 29 shows molecular state of NOS$^{+exp}$ can be regulated by microenvironment for cellular reprogramming competency. (a) Ten thousand cells containing indicated densities of the NOS$^{+exp}$ were seeded on matrigel coated plates. Lentivirus encoding Oct4, Sox2, Nanog, and Lin28 were transduced 24 hrs post plating. Number of colonies were counted three weeks post transduction and average numbers of colonies are represented. (b-c) Total hFibs and de novo isolated NOS$^{+exp}$ hFibs were analyzed by ChIP assays to assess the endogenous chromatin state followed by gene expression analysis of key pluripotency genes. (d) Representative phase and fluorescence images of NOS$^{+exp}$ hFibs cultured alone, or co-cultured with total hFibs and MEFs from left to right respectively. (e) ChIP assay performed in cultured NOS$^{+exp}$ hFibs indicated bivalency at Oct4 loci while Nanog and Sox2 promoter loci were repressed. Quantitative PCR analysis indicated reduced expression of Oct4 in cultured NOS$^{+exp}$ compared to de novo isolated cells. (f) NOS$^{+exp}$ hFibs were cocultured with total hFibs or mouse embryonic fibroblasts in 50-50 ratios. Cocultured NOS$^{+exp}$ (GFP$^{+ve}$) were isolated directly from co-cultures purified population analyzed for histone modifications and gene expression. ChIP assay from co-cultured NOS$^{+exp}$ on total hFibs indicated active marks on endogenous pluripotency genes. Quantitative PCR of cocultured NOS$^{+exp}$ analysis indicated regained expression of Nanog, Oct4 and Sox2 compared to that of cultured NOS$^{+exp}$. (g) Reprogramming potential of NOS$^{+exp}$ and NOS$^{-exp}$ cells was tested on MEFs. Left panel—Phase and fluorescence images of NOS$^{+exp/-exp}$ cells on MEFs or without MEFs (matrigel). Right panel—Phase and fluorescence images of three-five week post reprogramming. Induced pluripotent colonies were only observed when NOS$^{+exp}$ cells were reprogrammed on MEFs. Observed colonies were GFP$^{+ve}$ and Tra 1-60$^{+ve}$.

Figure 30:
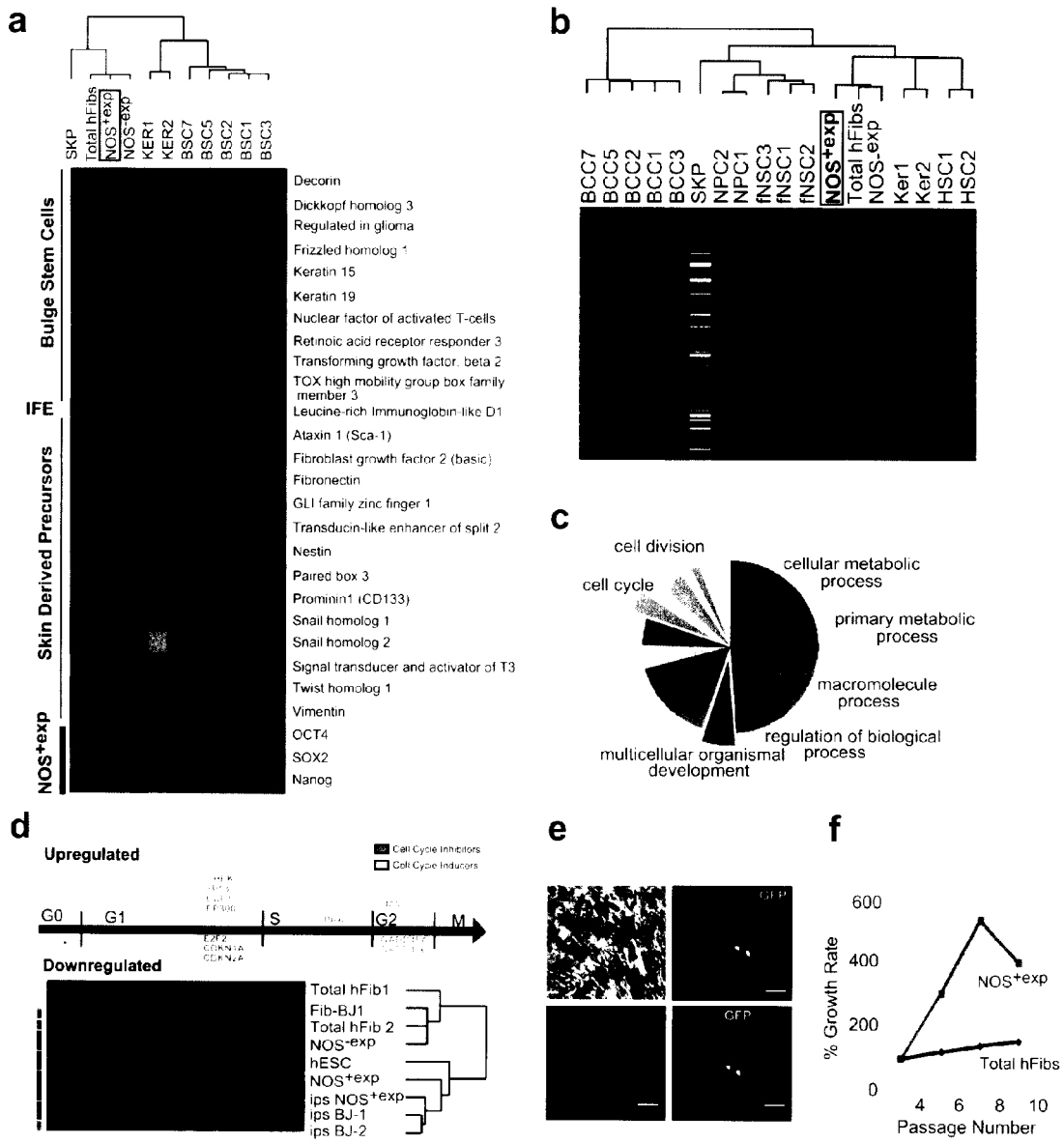

FIG. 30 shows unique NOS$^{+exp}$ population identified in hFibs exhibits distinct molecular state and cell cycle properties. (a) Hierarchical clustering of total hFibs, NOS$^{+exp}$ hFibs, NOS$^{-exp}$ hFibs, Skin derived precursors (SKPs), keratinocytes and bulge stem cells (BSC) gene expression signature of fibroblasts and molecular markers specific to individual skin stem/progenitor. (b) Global Cluster analysis of adult stem/progenitor cells. (c) Pie chart for the genes differentially upregulated in NOS$^{+exp}$ over total population. Genes were filtered based on 3-fold cutoff and were 100% present across NOS$^{+exp}$ replicate samples. (d) Hierarchical clustering of gene expression profiles based on cell cycle pathway (http://www.genome.jp/kegg/) expression in control hESC, Total hFibs, NOS$^{+exp}$, NOS$^{-exp}$, iPS NOS$^{+exp}$ cells and public data set Fib BJ1, iPS BJ1,2. Featured cell cycle genes are upregulated/downregulated in NOS$^{+exp}$ fibroblasts/iPS cells compared to total hFibs are indicated. (e) HMMR (CD168) staining was performed in hFibs transduced with EOS vector. HMMR localization was observed in the nuclei of dividing NOS$^{+exp}$ hFibs. (f) hFibs were transduced with EOS vector and growth of NOS$^{+exp}$ and total fibroblasts cells were measured at every passage by flow cytometry.

Figure 31:
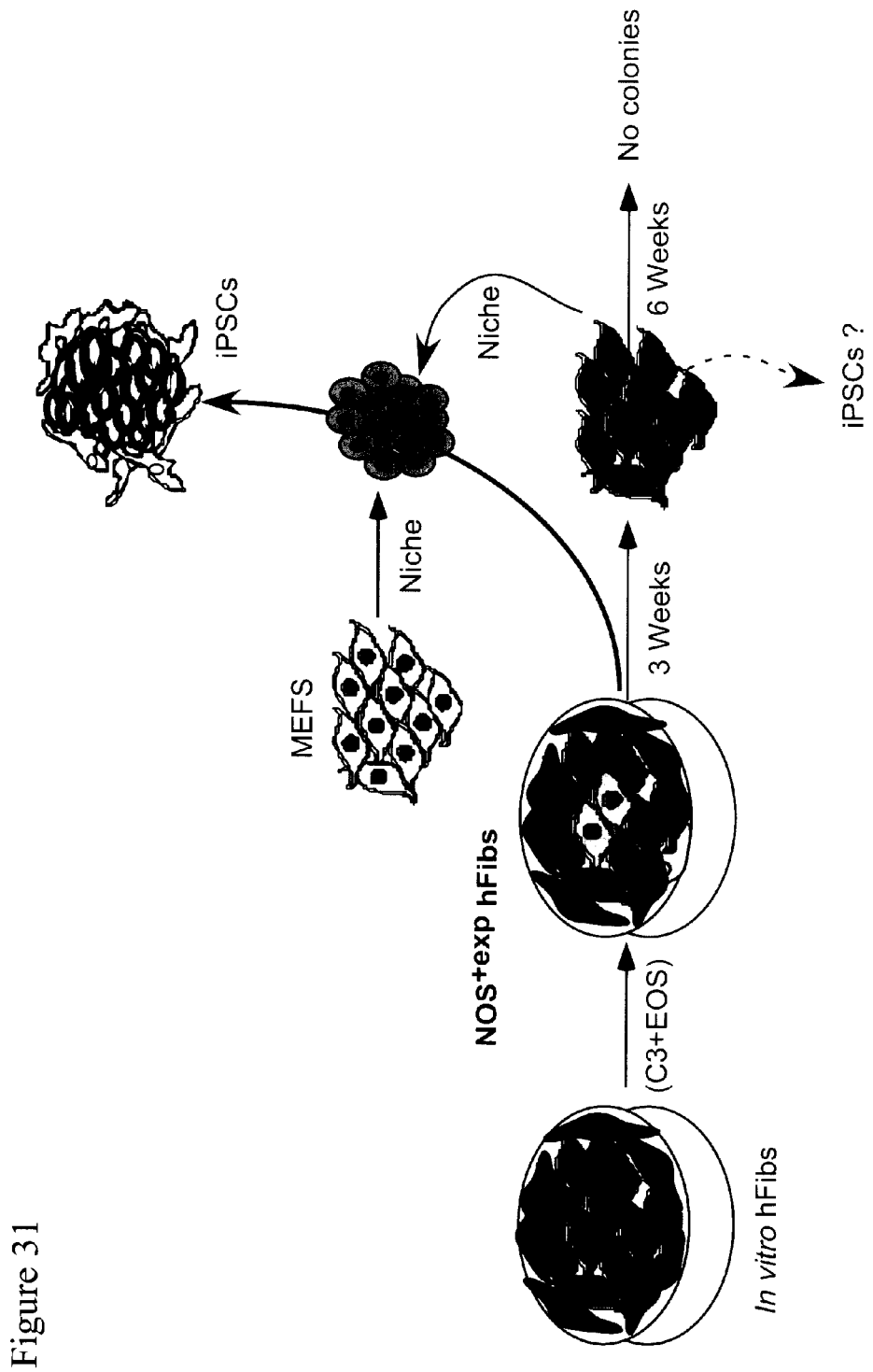

FIG. 31 shows a proposed model for the role of predisposed NOS$^{+exp}$ hFibs towards pluripotent reprogramming.

Figure 32:
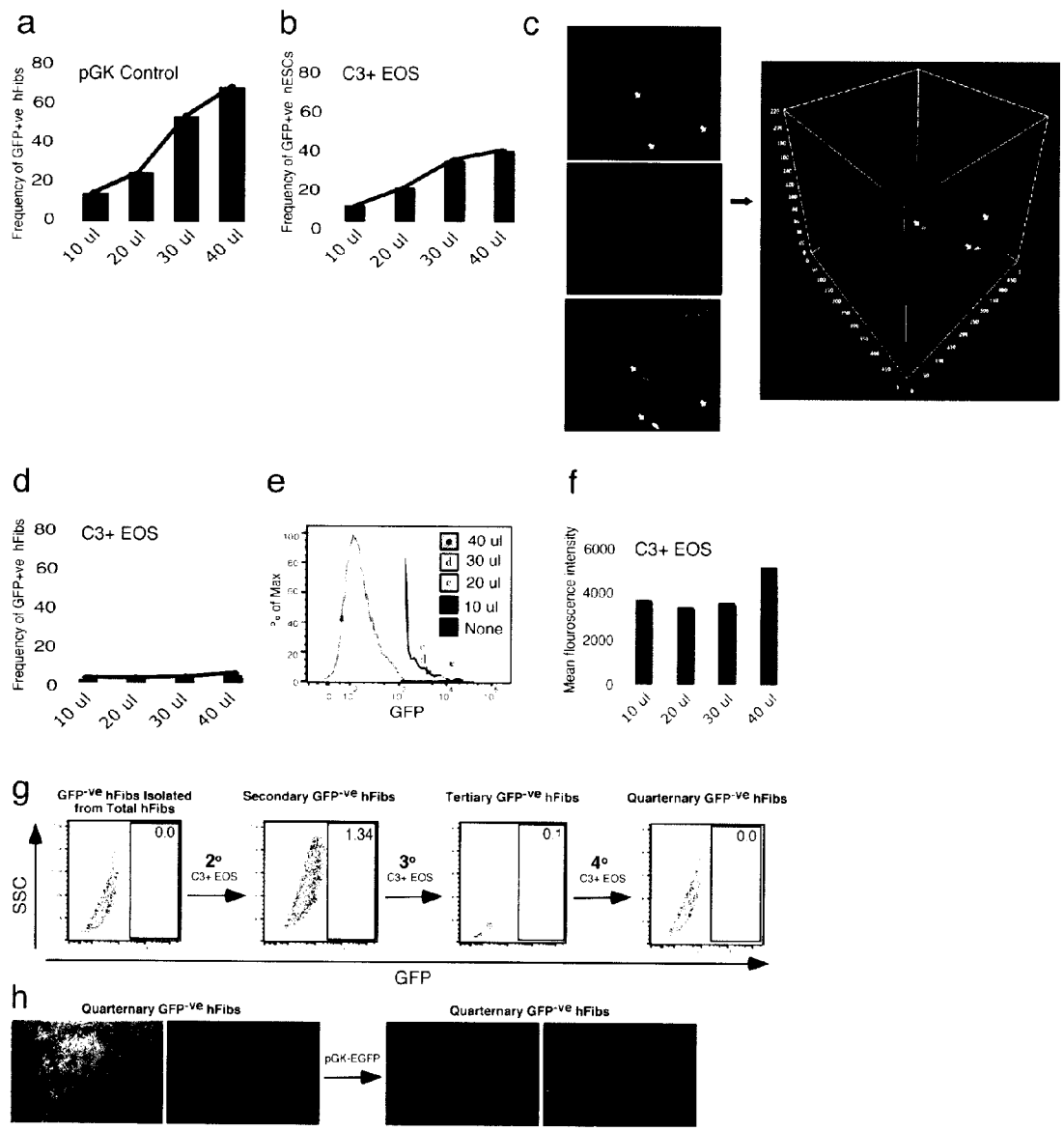

FIG. 32 shows GFP+ve cells are unique in total hFib cultures. (a) Total hFibs were transduced with pGK-EGFP and number of GFP+ve cells were estimated by flow cytometry analysis. (b) Transduction of C3+ EOS lentivirus in control hESC followed by flow cytometry demonstrated consistent increase in GFP$^{+ve}$ cells. (c) Representative phase and immunofluorescence and 3D Z-stack images of hFibs transduced with EOS vector. Arrows indicate EOS transduced GFP$^{+ve}$ cells in the different plane than total hFibs. (d-f) Total hFibs were transduced with C3+ EOS lentivirus. Percentage of GFP$^{-ve}$ cells and mean florescence intensities calculated by flow cytometry analysis indicated constant 3-4% GFP$^{+ve}$ cells upon EOS C3+ transduction irrespective of viral dilution suggesting these cells are not the artifact due to high copy viral integration. (g) To demonstrate the GFP$^{+ve}$ cells are not the artifacts of high copy viral integration GFP$^{-ve}$ cells were sorted from total hFibs and secondary EOS C3+ transductions were performed. GFP$^{-ve}$ cells from secondary infections were further sorted to perform tertiary infections. An increase in GFP$^{+ve}$ cells was not observed with tertiary and quaternary infections due to the increasing viral copy number. (h) Emergence of green cells upon PGK-EGFP transduction in quaternary-infected cells suggested lack of GFP$^{+ve}$ cells upon EOS C3+ transduction was not due to problems associated with viral uptake.

Figure 33:
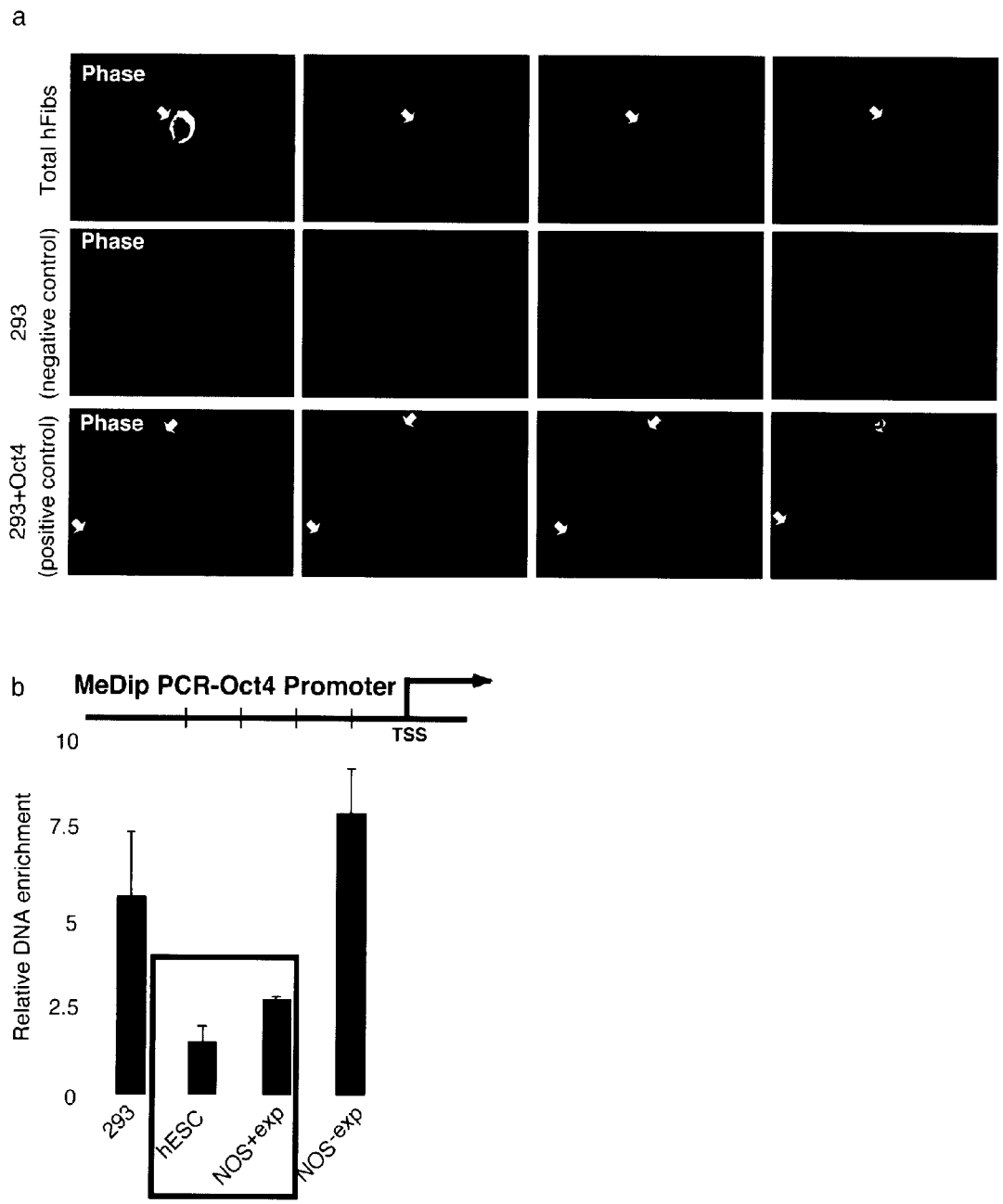

FIG. 33 shows unique cells in fibroblasts cultures express pluripotency gene Oct4. (a) Immunostaining of Oct4 in total hFib cultures, 293 cells and 293 cells overexpressing Oct4 transgene. Arrows indicate Oct4 staining colocalizing with DAPI in the nucleus. (b) MeDIP ChIP was performed in total hFib cultures, 293 cells, hESC, NOS$^{+exp}$ (GFP$^{+ve}$) cells. The graph shows specific enrichment of Oct4 promoter methylation in 293 and total fibroblasts compared to that hESC and NOS$^{+exp}$ (GFP$^{+ve}$) cells.

Figure 34:
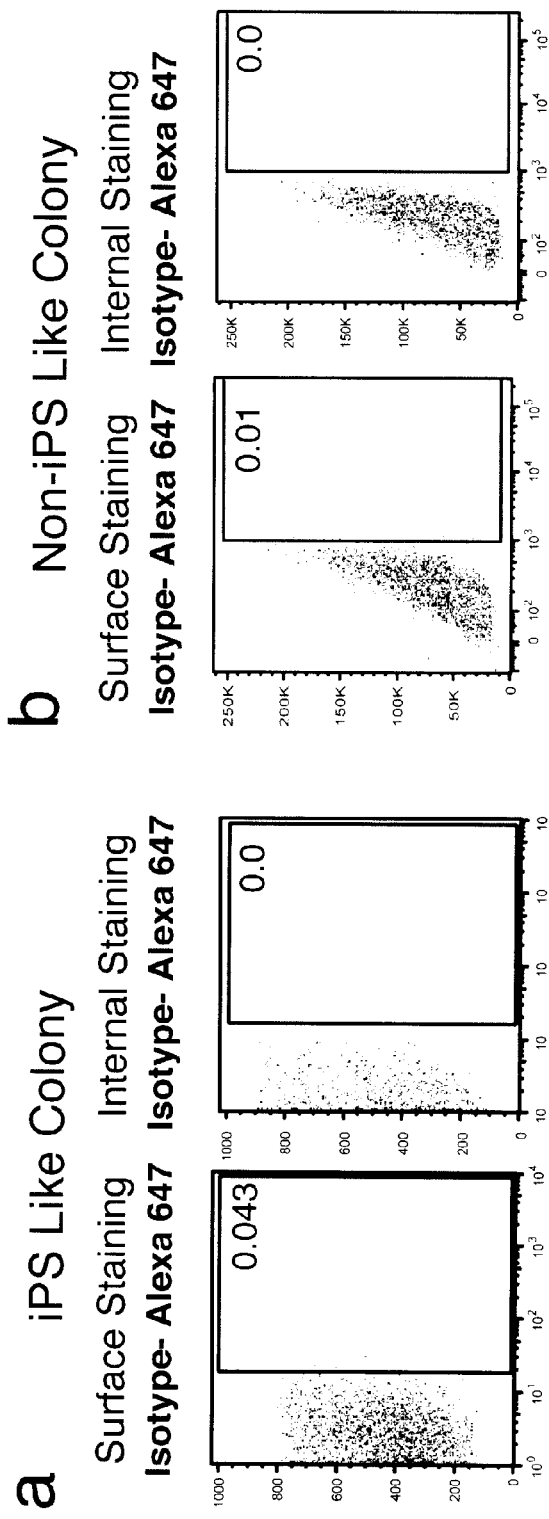

FIG. 34 shows isotype staining for the reprogrammed colonies from total Fibroblast cells. (a) Flow cytometry analysis for surface isotype staining (control for SSEA3 surface staining) and internal isotype staining (control for Oct4 staining) in iPS like colony derived from total hFibs (b) Flow cytometry analysis for surface isotype staining (control for SSEA3 surface staining) and internal isotype staining (control for Oct4 staining) in non-iPSC colony derived from total hFibs.

Figure 35:
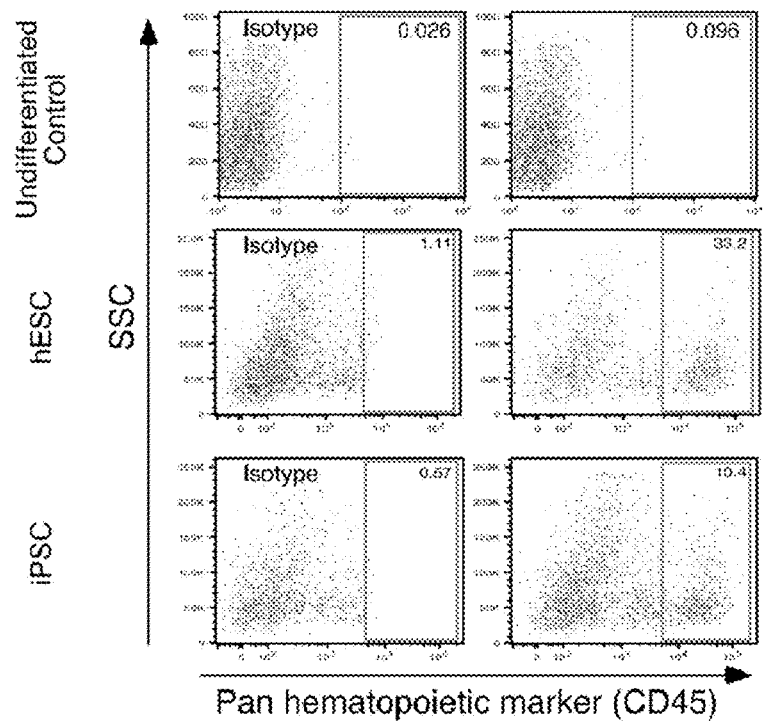
Figure 35:
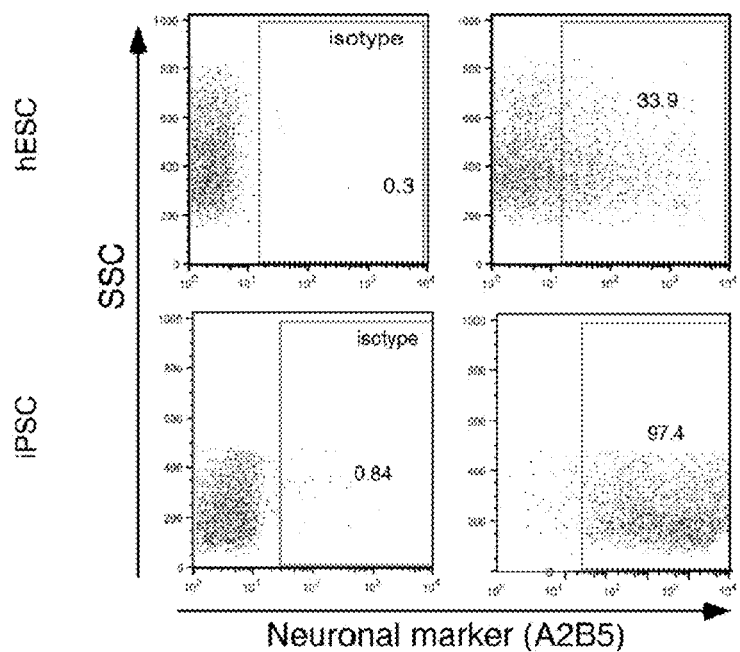

FIG. 35 shows induced Pluripotent cells generated from NOS$^{+exp}$ cells can be differentiated into various lineages. (a) In vitro EB differentiation of human ES and iPS cells derived from NOS$^{+exp}$ Fibs towards the hematopoietic lineage as shown by CD45 pan hematopoietic factor staining. (b) Human ES cells and iPSC cells derived from NOS$^{+exp}$ hFibs differentiate towards the neuronal lineage as shown by A2B5 staining.

Figure 36:
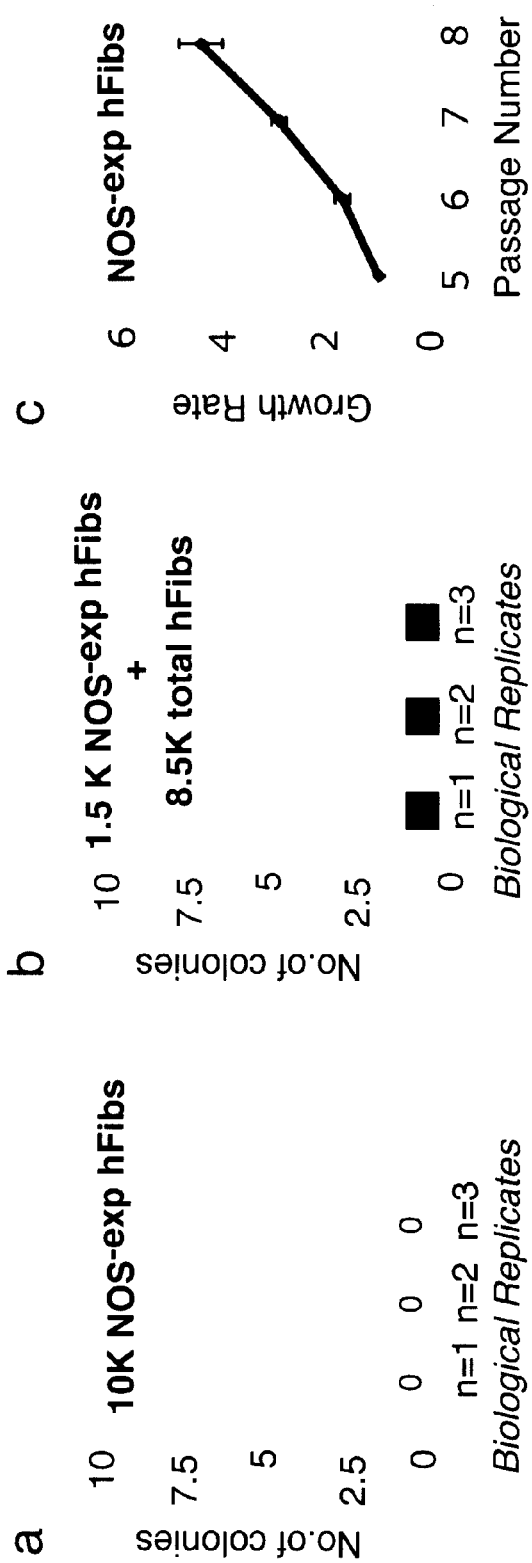

FIG. 36 shows NOS$^{-exp}$ hFibs are slow growing and do not contribute to reprogramming. (a) Purified NOS$^{-exp}$ hFibs were transduced with lentivirus containing Oct4, Nanog, Sox2, and Lin28. Cultures were monitored for 6 weeks, NOS$^{-exp}$ hFibs did not generate iPSC colonies. (b) NOS$^{-exp}$ were mixed with heterogeneous hFibs at a ratio indicated, and transduced with lentivirus containing Oct4, Nanog, Sox2, and Lin28. Between 2-6 weeks, only one colony was detected in any experiment. (c) Fifty thousand NOS$^{-exp}$ were seeded and growth rate was monitored by cell counting over serial passages indicated.

Figure 37:
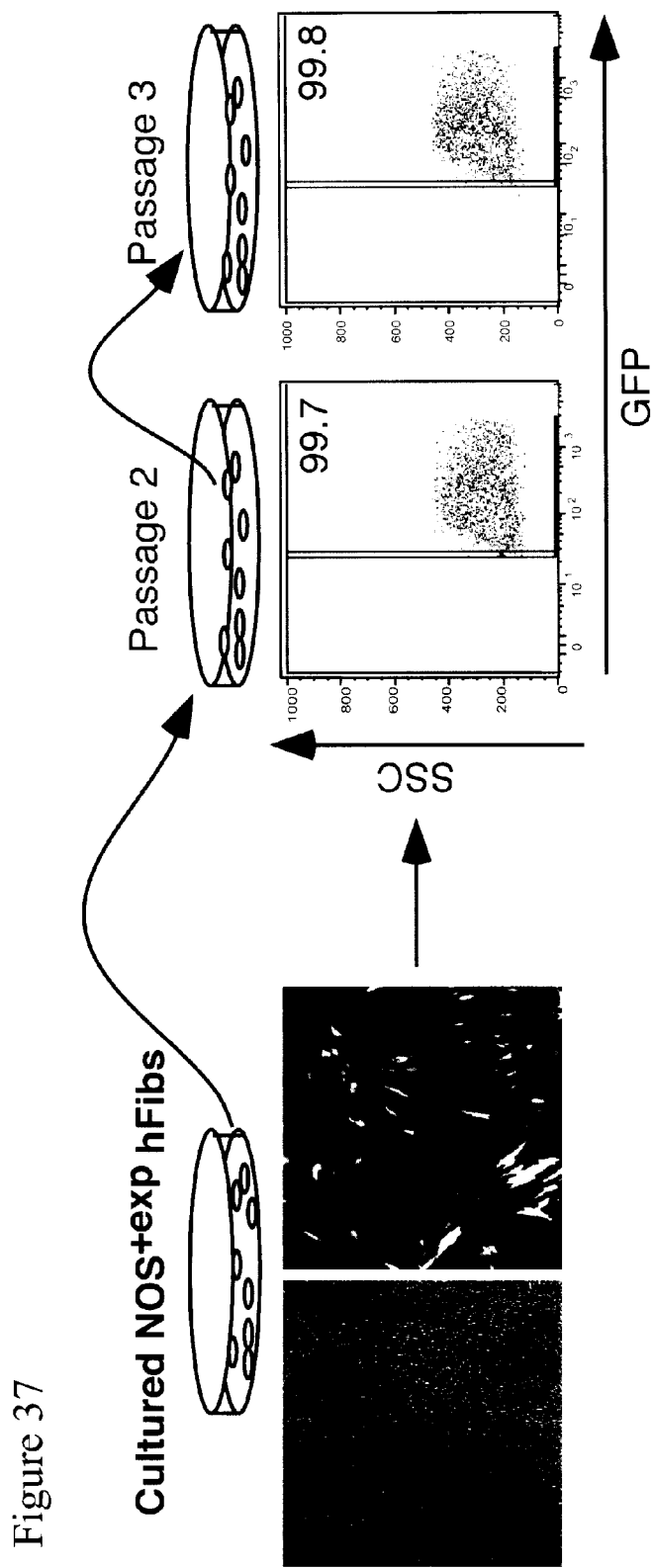

FIG. 37 shows hFibs were transduced with C3+ EOS Lentivirus and NOS$^{+exp}$ hFibs were sorted and maintained for indicated passages. At every passage GFP expression was measured by flow cytometry.

Figure 38:
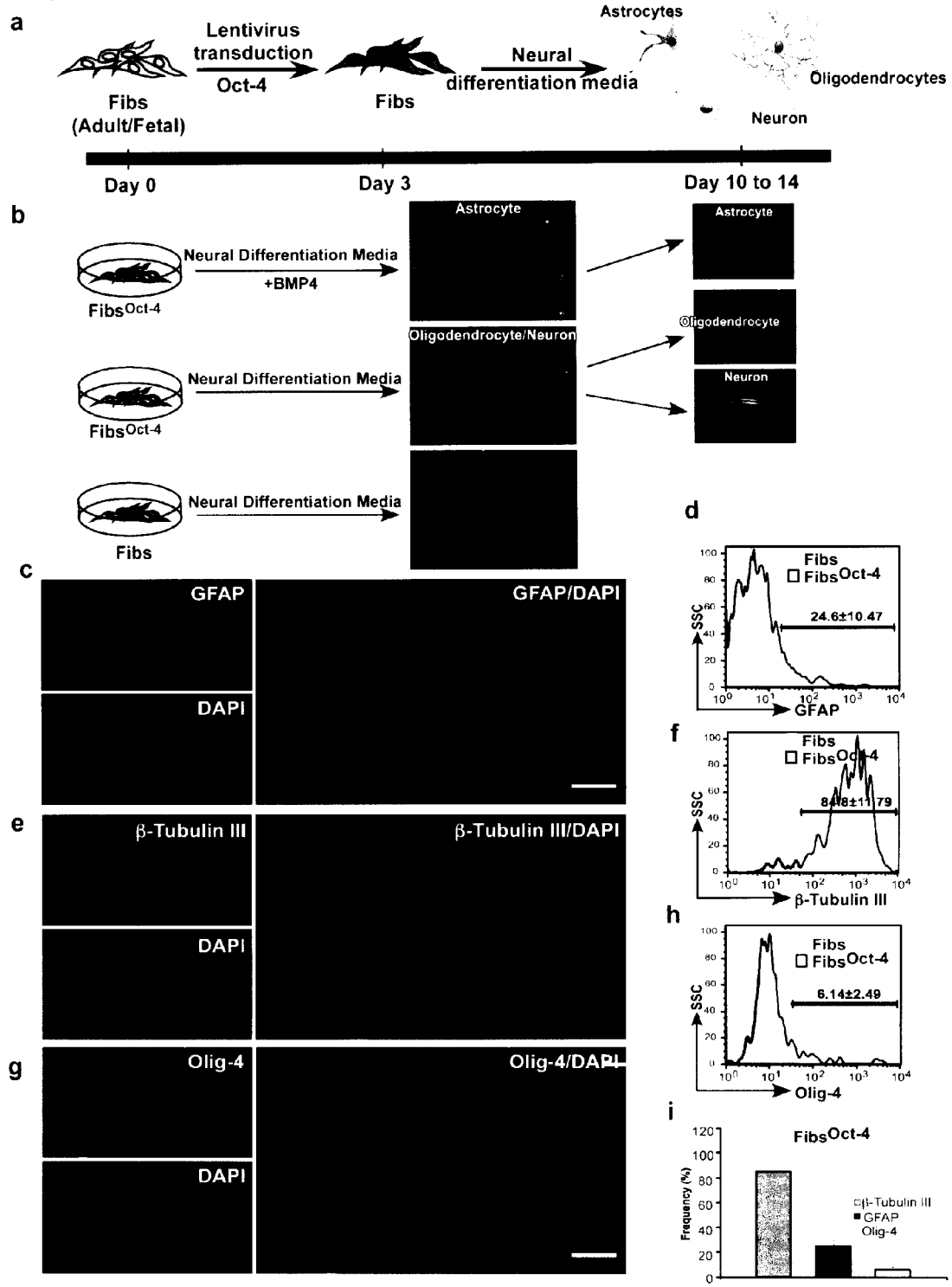

FIG. 38 shows Oct-4 transduced human fibroblasts give rise to astrocytes, oligodendrocytes and neurons. a. Schema presenting neural lineage specification time line upon Oct-4 transduction. b. Representative bright field images of untransduced fibroblasts and Oct-4-transduced fibroblast that gave rise to astrocytes, oligodendrocytes and neurons (n=3). c. Representative immunofluorescence image of astrocytes stained with GFAP (n=3). d. Representative FACS plot of GFAP levels in fibroblasts (Fibs) and Oct-4 transduced fibroblasts (Fibs$^{Oct-4}$) (n=3; p<0.01). e. Representative immunofluorescence image of neurons stained with beta-Tubulin III (n=3). f. Representative FACS plot of beta-Tubulin III levels in fibroblasts (Fibs) and Oct-4 transduced fibroblasts (Fibs$^{Oct-4}$) (n=3; p<0.01). g. Representative immunofluorescence image of oligodendrocytes stained with Olig-4 (n=3). h. Representative FACS plot of Olig-4 levels in fibroblasts (Fibs) and Oct-4 transduced fibroblasts (Fibs$^{Oct-4}$) (n=3; p<0.01). i. Frequency of GFAP, Olig-4 and beta-Tubulin III levels in Oct-4 transduced fibroblasts (n=3).

Figure 39:
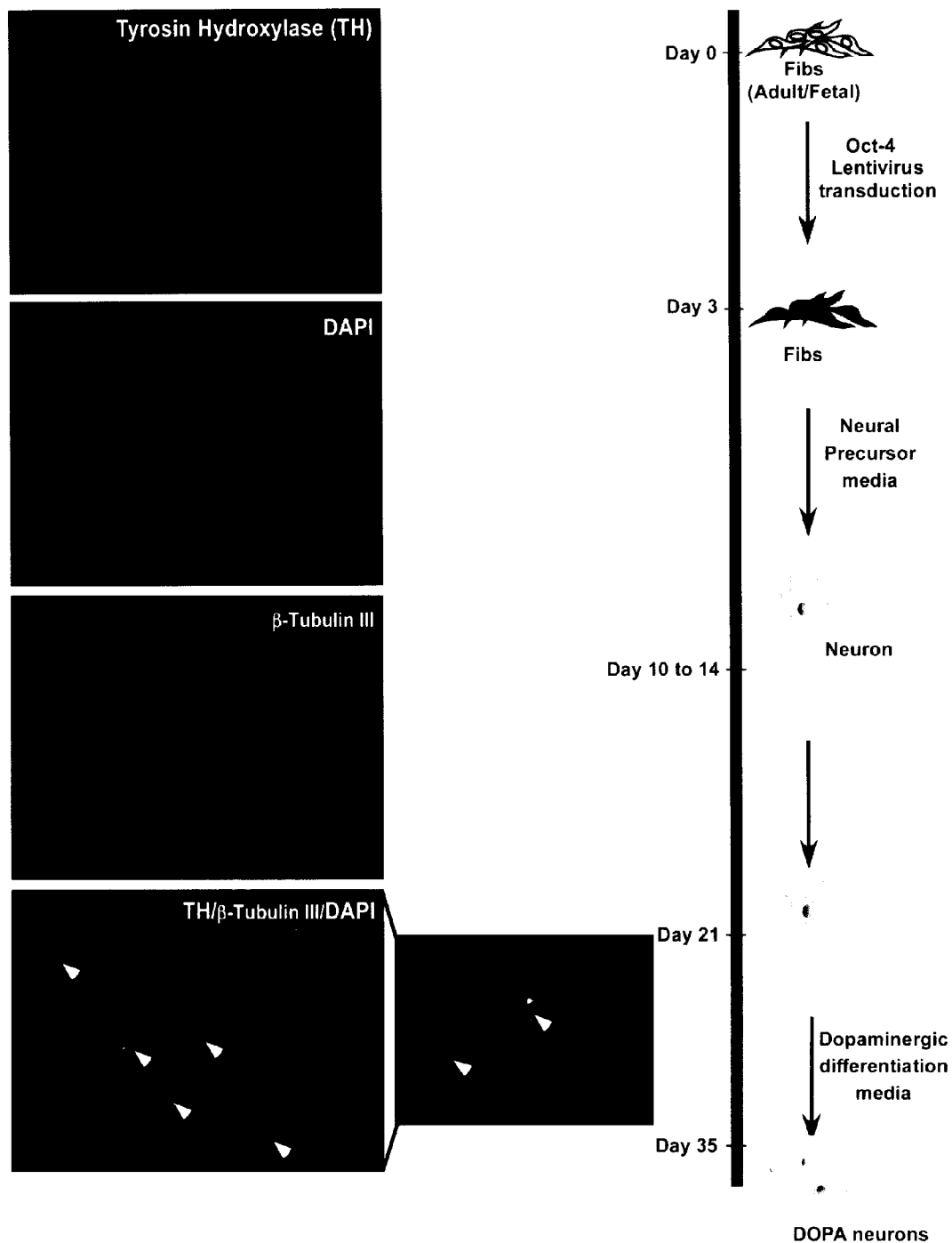

FIG. 39 shows Oct-4 transduced human fibroblasts give rise to mature neurons with a dopaminergic phenotype. Schema presenting dopamenergic neuron derivation time line (right panel) and dopaminergic neural immunofluorescence staining beta-Tubulin III and Tyrosine Hydroxylase.

Figure 40:
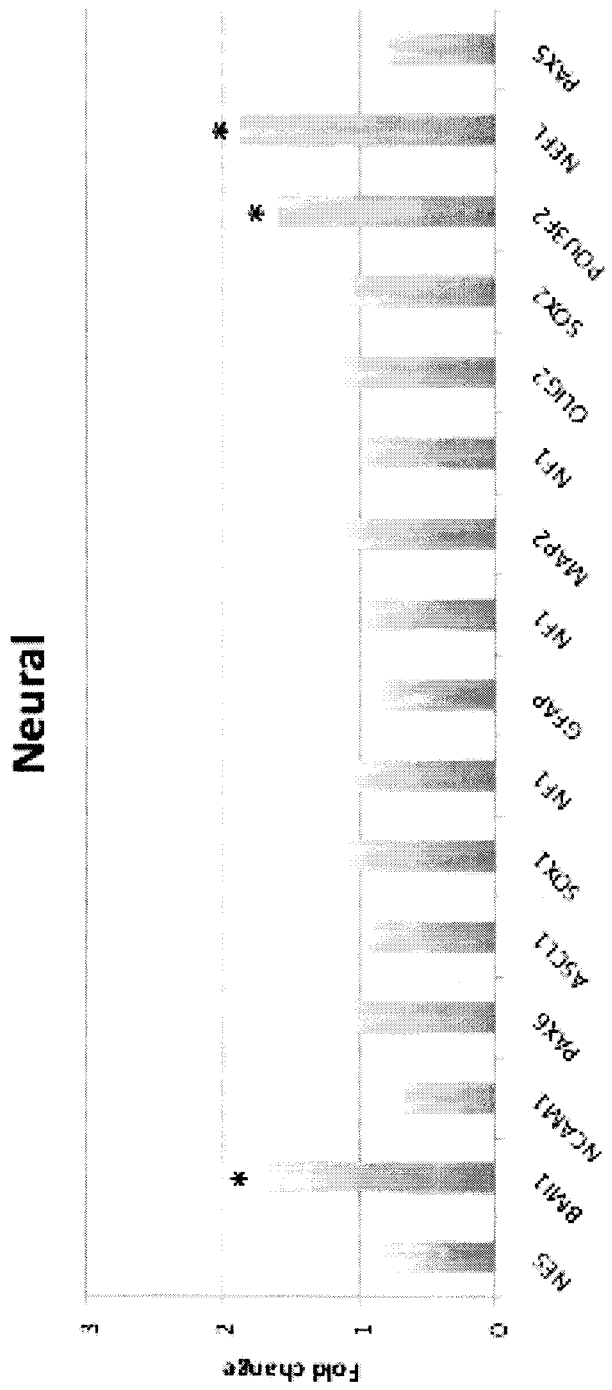

FIG. 40 shows transduction of fibroblasts with Oct4 induces the expression of genes associated with neural progenitor development. Gene expression patterns obtained by affymetrix array hybridization of samples derived from fibroblasts and fibroblasts transduced with Oct4 after 4 days. Gene expression patterns were compared in silico and are differences are depicted as fold change of fibroblasts+OCT4/fibroblasts. Statistical significance testing was performed using Student's t-test.

DETAILED DESCRIPTION OF THE DISCLOSURE

A. Direct Conversion of Fibroblasts to Progenitor and Differentiated Cells

The present inventors have shown that Oct-4 transduced dermal fibroblasts give rise to hematopoietic and neural progenitor cells. The inventors further showed that the hematopoietic progenitor cells had the capacity to fully reconstitute the myeloid lineage.

Accordingly, the present disclosure provides a method of generating progenitor cells from fibroblasts comprising:
 a) providing fibroblasts that express or are treated with the POU domain containing gene or protein; and
 b) culturing the cells of step (a) under conditions to allow production of progenitor cells without traversing the pluripotent state.

The term "POU domain containing gene or protein" as used herein refers to a gene or protein containing a POU domain that binds to Octamer DNA binding sequences as shown in FIG. 7 or SEQ ID NOs:1 or 2. In one embodiment, the POU domain containing gene or protein is an Oct gene or protein, including without limitation, the Oct-1, -2, -4, or -11. In a particular embodiment, the Oct gene or protein is Oct-4.

The term "progenitor cell" as used herein refers to a less specialized cell that has the ability to differentiate into a more specialized cell. Types of progenitor cells include, without limitation, cells that give rise to neural and hematopoietic lineages. In one embodiment, the progenitor cell is a hematopoietic progenitor cell. In another embodiment, the progenitor cell is a neural progenitor cell.

The phrase "without traversing the pluripotent state" as used herein refers to the direct conversion of the fibroblast to the progenitor cell, for example, the produced cells lack pluripotent stem cell properties, such as Tra-1-60 or SSEA3.

The term "hematopoietic progenitor cell" as used herein refers to a cell that gives rise to blood cells and includes, without limitation, CD45+ cells. Accordingly, in an embodiment, the cells of (b) are sorted to purify CD34 or CD45 positive cells.

The term "neural progenitor cell" as used herein refers to a cell that gives rise to cells of the neural lineage, including, without limitation, neurons and glial cells, for example, astrocytes and oligodendrocytes. Neural progenitor markers include, without limitation, A2B5, nestin, GFAP, betta tubulin III, oligo-4 and tyrosin Hydroxylase. In an optional embodiment, the neural cells are sorted using these markers.

The term "fibroblast" as used herein refers to a type of cell encountered in many tissues of the body including connective tissue and that can be derived using standard cell culture methods. For example, fibroblasts can be generated from adult and fetal tissues including blood, bone marrow, cord blood and placenta. In one embodiment, the fibroblast is a dermal fibroblast. The term "dermal fibroblast" as used herein refers to fibroblasts isolated from skin of any animal, such as a human. In one embodiment, the animal is an adult. In another embodiment, the fibroblast has been cryopreserved. In an alternative embodiment, cells expressing POU domain containing genes other than fibroblasts can be used in step (a).

The term "Oct-4" as used herein refers to the gene product of the Oct-4 gene and includes Oct-4 from any species or source and includes analogs and fragments or portions of Oct-4 that retain enhancing activity. The Oct-4 protein may have any of the known published sequences for Oct-4 which can be obtained from public sources such as Genbank. An example of such a sequence includes, but is not limited to, NM_002701. OCT-4 also referred to as POU5-F1 or MGC22487 or OCT3 or OCT4 or OTF3 or OTF4.

The term "Oct-1" as used herein refers to the gene product of the Oct-1 gene and includes Oct-1 from any species or source and includes analogs and fragments or portions of Oct-1 that retain enhancing activity. The Oct-1 protein may have any of the known published sequences for Oct-1 which can be obtained from public sources such as Genbank. An example of such a sequence includes, but is not limited to, NM_002697.2. Oct-1 also referred to as POU2-F1 or OCT1 or OTF1.

The term "Oct-2" as used herein refers to the gene product of the Oct-2 gene and includes Oct-2 from any species or source and includes analogs and fragments or portions of Oct-2 that retain enhancing activity. The Oct-2 protein may have any of the known published sequences for Oct-2 which can be obtained from public sources such as Genbank. An example of such a sequence includes, but is not limited to, NM_002698.2. Oct-2 is also referred to as POU2-F2 or OTF2.

The term "Oct-11" as used herein refers to the gene product of the Oct-11 gene and includes Oct-11 from any species or source and includes analogs and fragments or portions of Oct-11 that retain enhancing activity. The Oct-11 protein may have any of the known published sequences for Oct-11 which can be obtained from public sources such as Genbank. An example of such a sequence includes, but is not limited to, NM_014352.2. Oct-11 is also referred to as POU2F3.

In one embodiment, fibroblasts that express a POU domain containing gene or protein, such as Oct-1, -2, -4 or -11, include overexpression of the endogenous POU domain containing gene or ectopic expression of the POU domain containing gene or protein. In an embodiment, the fibroblasts do not additionally overexpress or ectopically express or are not treated with Nanog or Sox-2.

Fibroblasts that express a POU domain containing protein or gene, such as Oct-1, -2, -4 or -11, can be obtained by various methods known in the art, including, without limitation, by overexpressing endogenous POU domain containing gene, or by introducing a POU domain containing protein or gene into the cells to produce transformed, transfected or transduced cells. The terms "transformed", "transfected" or "transduced" are intended to encompass introduction of a nucleic acid (e.g. a vector) into a cell by one of many possible techniques known in the art. For example, nucleic acid can be introduced into mammalian cells via conventional techniques such as calcium phosphate or calcium chloride co-precipitation, DEAE-dextran mediated transfection, lipofectamine, electroporation or microinjection or via viral transduction or transfection. Suitable methods for transforming, transducing and transfecting cells can be found in Sambrook et al. (Molecular Cloning: A Laboratory Manual, 3rd Edition, Cold Spring Harbor Laboratory Press, 2001), and other laboratory textbooks. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)) and pMT2PC (Kaufman et al., EMBO J. 6:187-195 (1987)).

In one embodiment, fibroblasts that express a POU domain containing gene or protein are produced by lentiviral transduction. In another embodiment, the fibroblasts that are treated with a POU domain containing gene or protein include addition of exogenous POU domain containing protein or functional variants or fragments thereof or peptide mimetics thereof. In another embodiment, the fibroblasts that are treated with a POU domain containing gene or protein include addition of a chemical replacer that can be used that induces a POU domain containing gene or protein expression.

The POU domain containing proteins may also contain or be used to obtain or design "peptide mimetics". For example, a peptide mimetic may be made to mimic the function of a POU domain containing protein. "Peptide mimetics" are structures which serve as substitutes for peptides in interactions between molecules (See Morgan et al (1989), *Ann. Reports Med. Chem.* 24:243-252 for a review). Peptide mimetics include synthetic structures which may or may not contain amino acids and/or peptide bonds but retain the structural and functional features. Peptide mimetics also include molecules incorporating peptides into larger molecules with other functional elements (e.g., as described in WO 99/25044). Peptide mimetics also include peptoids, oligopeptoids (Simon et al (1972) *Proc. Natl. Acad, Sci USA* 89:9367) and peptide libraries containing peptides of a designed length representing all possible sequences of amino acids corresponding to a POU domain containing peptide.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of the secondary structures of the proteins described herein. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

The term "variant" as used herein includes modifications, substitutions, additions, derivatives, analogs, fragments or chemical equivalents of the POU domain containing proteins that perform substantially the same function in substantially the same way. For instance, the variants of the POU domain containing proteins would have the same function of being useful in binding the Octamer sequences shown in FIG. 7.

Conditions that allow production of progenitor cells are readily known in the art. For example, colony formation is a standard method known in the art for culturing progenitor cells. The cell culture medium can be any medium that can support the growth of cells including, without limitation, a semi-solid medium. In one embodiment, the conditions comprise a culture period from 14-31 days, optionally 21 days.

In another embodiment, the cells are cultured in any medium that can support the growth of cells and then, for example, after at least 3 days, are placed in differentiation media, such as hematopoietic medium, or neural medium, under conditions to allow production of differentiated cells, such as hematopoietic and neural cells.

The term "differentiation" or "differentiated" as used herein refers to the process by which a less specialized cell, such as a stem cell, becomes a more specialized cell type, such that it is committed to a specific lineage.

The term "hematopoietic medium" as used herein refers to cell culture media that supports growth and/or differentiation of hematopoietic cells. In one embodiment, the hematopoietic medium comprises at least one hematopoietic cytokine, such as Flt3, SCF or EPO. In an embodiment, the cytokine is Flt3 or SCF. In one embodiment, the differentiated hematopoietic cell is of the myeloblast lineage, such as a monocyte or granulocyte. In another embodiment, the hematopoietic cytokine is EPO and the differentiated hematopoietic cell is of the erythroid or megakaryocytic lineage.

The term "neural medium" as used herein refers to cell culture media that supports growth and/or differentiation of neural cells. In one embodiment, the neural medium comprises neural basal media supplemented with fibroblast growth factor, epidermal growth factor or bone morphogenetic factor 4 (BMP-4), bFGF (10 ng/ml), the N-terminal active fragment of human SHH (200 ng/ml), FGF8 (100 ng/ml; R&D), GDNF (20 ng/ml), BDNF (20 ng/ml) and/or fetal bovine serum. In an embodiment, the differentiated neural cell is a neuron or a glial cell such as an astrocyte, and/or oligodendrocyte.

In another aspect, the present disclosure provides isolated progenitor or differentiated cells generated by the methods described herein. Such cells do not express a number of pluripotency markers, such as TRA-1-60 or SSEA-3. In addition, during development such cells lose the expression of the Oct-4 pluripotency marker and thus represent a new source of safe alternatives for progenitor cells.

In yet another aspect, the disclosure provides use of the cells described herein for engraftment or cell replacement. In another embodiment, the disclosure provides the cells described herein for use in engraftment or cell replacement. Further provided herein is use of the cells described herein in the manufacture of a medicament for engraftment or cell replacement. "Engraftment" as used herein refers to the transfer of the hematopoietic cells produced by the methods described herein to a subject in need thereof. The graft may be allogeneic, where the cells from one subject are transferred to another subject; xenogeneic, where the cells from a foreign species are transferred to a subject; syngeneic, where the cells are from a genetically identical donor or an autograft, where the cells are transferred from one site to another site on the same subject. Accordingly, also provided herein is a method of engraftment or cell replacement comprising transferring the cells described herein to a subject in need thereof. The term "cell replacement" as used herein refers to replacing cells of a subject, such as red blood cells or platelets, or neurons or glial cells or hematopoietic progenitors. In yet another embodiment, cells for engraftment or cell replacement may be modified genetically or otherwise for the correction of disease. Fibroblasts before or after transfection or transduction with a POU domain containing gene may be genetically modified to overexpress a gene of interest capable of correcting an abnormal phenotype, cells would be then selected and transplanted into a subject. In another aspect, fibroblasts or POU domain containing gene-expressing fibroblasts overexpressing or lacking complete expression of a gene that is characteristic of a certain disease would produce progenitor or differentiated cells for disease modeling, for example drug screening.

The term "subject" includes all members of the animal kingdom, including human. In one embodiment, the subject is an animal. In another embodiment, the subject is a human.

In one embodiment, the engraftment or cell replacement described herein is for autologous or non-autologous transplantation. The term "autologous transplantation" as used herein refers to providing fibroblasts from a subject, generating progenitor or differentiated cells from the isolated fibroblasts by the methods described herein and transferring the generated progenitor or differentiated cells back into the same subject. The term "non-autologous transplantation" refers to providing fibroblasts from a subject, generating progenitor or differentiated cells from the isolated fibroblasts by the methods described herein and transferring the generated progenitor or differentiated cells back into a different subject.

In yet another aspect, the disclosure provides use of the cells described herein as a source of blood, cellular or acellular blood components, blood products, hematopoietic stem cells and neural cells. Such sources can be used for replacement, research and/or drug discovery.

The methods and cells described herein may be used for the study of the cellular and molecular biology of progenitor cell development, for the discovery of genes, growth factors, and differentiation factors that play a role in differentiation and for drug discovery. Accordingly, in another aspect, the disclosure provides a method of screening progenitor or differentiated cells comprising
  a) preparing a culture of progenitor or differentiated cells by the methods described herein;
  b) treating the progenitor or differentiated cells with a test agent or agents; and
  c) subjecting the treated progenitor or differentiated cells to analysis.

In one embodiment, the test agent is a chemical or other substance, such as a drug, being tested for its effect on the differentiation of the cells into specific cell types. In such an embodiment, the analysis may comprise detecting markers of differentiated cell types. For example: CD45, CD13, CD33, CD14, CD15, CD71, CD235a (Glycophorin A), CD133, CD38, CD127, CD41a, beta-globin, HLA-DR, HLA-A,B,C, CD34, A2B5, nestin, GFAP, beta tubulin III, oligo-4 and tyrosin Hydroxylase. In another embodiment, the test agent is a chemical or drug and the screening is used as a primary or secondary screen to assess the efficacy and safety of the agent. Such analysis can include measuring cell proliferation or death or cellular specific features such as mast cell degranulation, phagocytosis, oxygen exchange, neural signaling, presence of action potential, secretion of certain proteins, activation of specific genes or proteins, activation or inhibition of certain signaling cascades.

B. Reprogramming Fibroblasts into Induced Pluripotent Stem Cells

Given the unknown origins of human fibroblasts that form the foundation for cellular reprogramming toward human iPSCs, the present inventors sought to characterize adult dermal fibroblasts in the context of the cellular reprogramming process. The present inventors have identified and characterized a subpopulation of adult human dermal fibroblasts responsible for the generation of reprogrammed cells.

Accordingly, the present disclosure provides a method of isolating a subpopulation of fibroblasts with increased reprogramming potential comprising
  a) providing fibroblasts that express an Oct-4-reporter; and
  b) isolating cells positive for the reporter.

Definitions from part A that are relevant to this section apply to this section as well.

Fibroblasts that express an Oct-4-reporter can be produced by various methods known in the art, including, without limitation, introduction of a nucleic acid construct or vector by transformation, transfection or transduction as herein defined. In one embodiment, the Oct-4-reporter gene is introduced by lentiviral transduction.

The term "reprogramming potential" as used herein refers to the potential of the cells to regain progenitor or stem cell capacity or pluripotent state. The term "increased reprogramming potential" as used herein means that the reprogramming potential is greater than the potential for a mixed population of fibroblasts that have not been selected or isolated.

The term "Oct-4-reporter" as used herein refers to DNA sequences that are bound by Oct-4 upstream of a reporter that allow or enhance transcription of the downstream sequences of the reporter. Oct-4 reporters are known in the art. For example, an Oct-4 reporter is described in Hotta et al. 2009 and Okumura-Nakanishi et al. 2005 incorporated herein by reference in its entirety.

The term "reporter gene" and "reporter" as used herein refers to any gene that encodes a protein that is identifiable. Reporter genes and reporter products are readily identified by a skilled person. In an embodiment, more than one reporter gene/reporter is used. In one embodiment, the reporter gene comprises a fluorescent protein (such as green fluorescent protein, GFP) and the cells are isolated in step (b) by detection of the fluorescent protein under fluorescence. In another embodiment, the reporter gene encodes a gene conferring antibiotic resistance, such as to puromycin, and the cells are isolated by survival in the presence of the antibiotic. In one embodiment, the fibroblasts are dermal fibroblasts. The reporter gene could also encode a tag and the cells can be isolated based on immuno separation (http://www.miltenyibiotec.com/en/PG_167_501_MACSelect_Vectors_and_Tag_Vector_Sets.aspx).

The disclosure also provides a method of generating reprogrammed fibroblast-derived induced pluripotent stem (iPS) cells comprising
  a) providing (i) a population of fibroblasts with increased expression of Oct-4 and (ii) a mixed population of fibroblasts or a population of Oct-4 negative fibroblasts;
  b) treating the fibroblasts of a) with Oct-4, Sox-2, Nanog and Lin-28; and
  c) culturing the cells of (b) under conditions that allow the production of iPS cells.

In one embodiment, the fibroblasts in b) are treated with Oct-4, Sox-2, Nanog and Lin-28 by introducing the respective genes by viral transduction, such as lentiviral transduction.

The term "stem cell" as used herein refers to a cell that has the ability for self-renewal. In one embodiment, the stem cell is a pluripotent stem cell. The term "pluripotent" as used herein refers to an undifferentiated cell that maintains the ability to allow differentiation into various cell types. The term "induced pluripotent stem cell" refers to a pluripotent stem cell that has been artificially derived from a non-pluripotent stem cell.

The term "Sox-2" as used herein refers to the gene product of the Sox-2 gene and includes Sox-2 from any species or source and includes variants, analogs and fragments or portion of Sox-2 that retain activity. The Sox-2 protein may have any of the known published sequences for Sox-2, which can be obtained from public sources such as GenBank. An example of such a sequence includes, but is not limited to, NM_003106.

The term "Nanog" as used herein refers to the gene product of the Nanog gene and includes Nanog from any species or source and includes variants, analogs and fragments or portion of Nanog that retain activity. The Nanog protein may have any of the known published sequences for Nanog, which can be obtained from public sources such as GenBank. An example of such a sequence includes, but is not limited to, NM_024865.

The term "Lin-28" as used herein refers to the gene product of the Lin-28 gene and includes Lin-28 from any species or source and includes variants, analogs and fragments or portions of Lin-28 that retain activity. The Lin-28 protein may have any of the known published sequences for Lin 28, which can be obtained from public sources such as GenBank. An example of such a sequence includes, but is not limited to, BC028566.2. Lin-28 also called CSDD1 or ZCCHC1 or Lin28A.

The term "mixed population" as used herein refers to a mixed population of fibroblasts derived from an animal as opposed to a selected subpopulation. The term bulk population may also be used interchangeably in this disclosure. The mixed population contains cells that express varying levels of Oct-4, Sox-2 and/or Nanog.

In another embodiment, the method further comprises analyzing and selecting cells that express a marker of undifferentiated stem cells, such as TRA-1-60, SSEA-3, Sox2, Nanog, SSEA4, TRA-1-81, IGF1 receptor, connexin 43, E-cadherin, Alkaline phosphatase, REX1, CRIPTO, CD24, CD90, CD29, CD9 and CD49f. In one embodiment, the cells are selected for expression of TRA-1-60 and/or SSEA-3.

The term "TRA-1-60" as used herein refers to the gene product of the TRA-1-60 gene and includes TRA-1-60 from any species or source and includes analogs and fragments or portion of TRA-1-60 that retain activity. The TRA-1-60 protein may have any of the known published sequences for TRA-1-60, which can be obtained from public sources such as GenBank. Examples of such sequences include, but are not limited to, NM_001018111 and NM_005397.

The term "SSEA-3" as used herein refers to the gene product of the SSEA-3 gene and includes SSEA-3 from any species or source and includes analogs and fragments or portion of SSEA-3 that retain activity. The SSEA-3 protein may have any of the known published sequences for SSEA-3 which can be obtained from public sources such as GenBank. Examples of such sequences include, but are not limited to NM_001122993.

In an embodiment, the population of fibroblasts with increased expression of Oct-4 are produced by the method described herein for isolating a subpopulation of fibroblasts with reprogramming potential. In an embodiment, the population of fibroblasts expressing Oct-4 comprise expression of Oct-4 or its isoform B1 but not its cytoplasmic isoform Oct4B.

In one embodiment, the fibroblasts are dermal fibroblasts. Dermal fibroblasts may be derived, for example, from the skin of an animal.

In one embodiment, the ratio of cells in step (a) (i) to cells in step (a) (ii) is 50:50 to 10:90. In an embodiment, the ratio of cells in step (a) (i) to cells in step (a) (ii) is 50:50. In another embodiment, the ratio of cells in step (a) (i) to cells in step (a) (ii) is 10:90. In yet another embodiment, the ratio of cells in step (a) (i) to cells in step (a) (ii) is 25:75.

Conditions that allow the production of iPS cells are readily known in the art and include, without limitation, colony forming assays for a culture period from 2 to 3 weeks.

The present disclosure further provides isolated induced pluripotent stem (iPS) cells generated by the method described herein and cells differentiated therefrom.

In yet another aspect, the disclosure provides use of the iPS cells described herein or cells differentiated therefrom for engraftment. The disclosure also provides the iPS cells described herein or cells differentiated therefrom for use in engraftment. Further provided is the use of the iPS cells described herein in the preparation of a medicament for engraftment. "Engraftment" as used herein refers to the transfer of the cells produced by the methods described herein to a subject in need thereof. The graft may be allogeneic, where the cells from one subject are transferred to another subject; xenogeneic, where the cells from a foreign species are transferred to a subject; syngeneic, where the cells are from a genetically identical donor or an autograft, where the cells are transferred from one site to another site on the same subject. Accordingly, also provided herein is a method of engraftment comprising transferring the iPS cells described herein or cells differentiated therefrom to a subject in need thereof.

The term "subject" includes all members of the animal kingdom, including human. In one embodiment, the subject is an animal. In another embodiment, the subject is a human.

In one embodiment, the engraftment described herein is for autologous or non-autologous transplantation. The term "autologous transplantation" as used herein refers to providing fibroblasts from a subject, generating iPS cells from the isolated fibroblasts by the methods described herein and transferring the generated iPS cells or cells differentiated therefrom back into the same subject. The term "non-autologous transplantation" refers to providing fibroblasts from a subject, generating iPS cells from the isolated fibroblasts by the methods described herein and transferring the generated iPS cells or cells differentiated therefrom back into a different subject. For cells differentiated from the iPS cells, the iPS cells are first differentiated in vitro and then transferred into the subject.

In yet another aspect, the disclosure provides use of the cells described herein as a source of iPS cells or differentiated cells therefrom.

The methods and cells described herein may be used for the study of the cellular and molecular biology of stem cell development, for the discovery of genes, growth factors, and differentiation factors that play a role in stem cell differentiation and for drug discovery. Accordingly, in another aspect, the disclosure provides a method of screening iPS cells or cells differentiated therefrom comprising
a) preparing a culture of iPS cells by the methods described herein or cells differentiated therefrom;
b) treating the cells with a test agent or agents; and
c) subjecting the treated cells to analysis.

In one embodiment, the test agent is a chemical or other substance, such as a drug, being tested for its effect on the differentiation of the iPS cells into specific cell types. In such an embodiment, the analysis may comprise detecting markers of differentiated cell types. For example, CD45, CD13, CD33, CD14, CD15, CD71, CD235a (Glycophorin A), CD133, CD38, CD127, CD41a, beta-globin, HLA-DR, HLA-A,B,C, and CD34, A2B5, nestin, GFAP, beta tubulin III, oligo-4 and tyrosin Hydroxylase. In another embodiment, the test agent is a chemical or drug and the screening is used as a primary or secondary screen to assess the efficacy and safety of the agent. In an embodiment, the analysis comprises analyzing cell proliferation or cell death or cell differentiation, or generation of progenitors or differentiated cells of interest.

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Direct Conversion from Dermal Fibroblasts to Blood

Results
Emergence of a $CD45^{+ve}$ Population from hFibs Transduced with Oct-4

Reprogramming towards pluripotency requires a cascade of events that encompasses generation of various intermediate cells among a rare subset of stable induced pluripotent stem cells (iPSCs) capable of teratoma formation (Takahashi et al., 2007; Takahashi and Yamanaka, 2006) (FIGS. 8a-c). A portion of these intermediates form colonies that possess round cellular morphology resembling hematopoietic cells (FIG. 9a) and express the human pan-hematopoietic marker CD45 ($CD45^{+ve}$), but lack co-expression of the pluripotency marker Tra-1-60 (Chan et al., 2009), indicative of iPSCs (FIGS. 9b-c). These human fibroblast (hFib)-derived $CD45^{+ve}$ cells could be isolated by FACS and shown to preferentially express ectopic Oct-4 whilst demonstrating low levels of Sox-2 and Nanog (FIGS. 9d-e). These findings indicate that, unlike the fully reprogrammed iPSCs, hFib-derived intermediates could acquire distinct lineage-specific phenotype, as exemplified by the acquisition of the human hematopoietic marker CD45.

Figure 1:
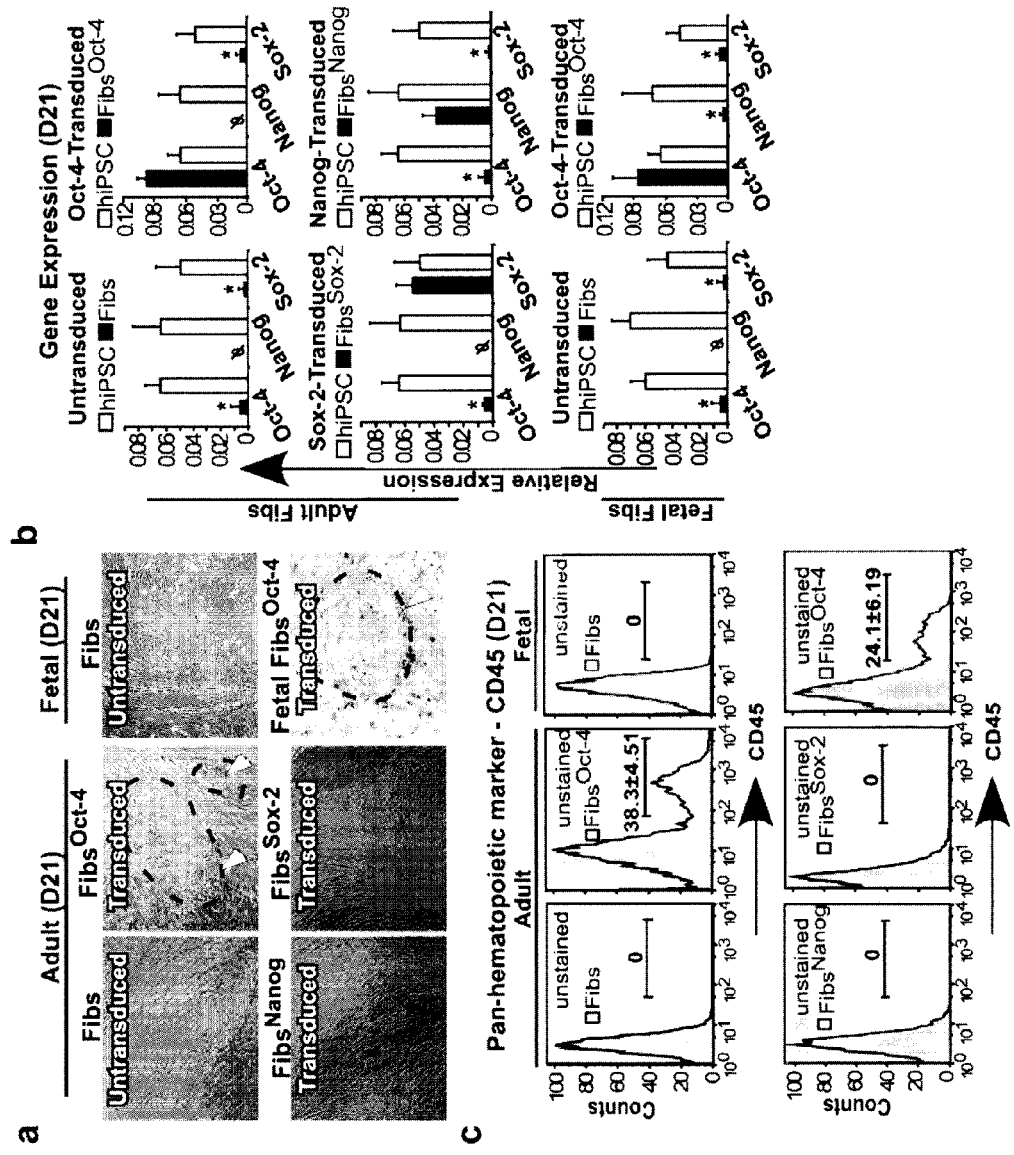
FIG. 1 shows Oct-4 transduced human adult dermal fibroblasts and fetal fibroblasts give rise to $CD45^{+ve}$ colonies. a. Representative bright field images of untransduced (Fibs) and Oct-4-($Fibs^{Oct-4}$), Sox-2-($Fibs^{Sox-2}$) or Nanog-($Fibs^{Nanog}$)

Based on the acquisition of CD45, together with higher levels of Oct-4 vs Nanog or Sox-2, the role of Oct-4 during colony emergence from two independent sources of adult dermal and fetal (foreskin) hFibs was compared with that of Nanog or Sox-2 alone (FIG. 1a). Transduced and untransduced hFibs were examined for colony formation between 14-21 days post-transduction (illustrated in FIG. 10). Unlike untransduced, or hFibs transduced with Sox-2 ($hFibs^{Sox-2}$) or Nanog ($hFibs^{Nanog}$), hFibs expressing Oct-4 ($hFib^{Oct-4}$) gave rise to colonies (FIG. 1a and FIG. 10b) and exhibited Oct-4 expression similar to the levels detected in established iPSCs (FIG. 1b). Only the $hFibs^{Oct-4}$ gave rise to hematopoietic-like $CD45^{+ve}$ cells (FIG. 1c; adult hFibs~38%; fetal hFibs~24%). Furthermore, $CD45^{+ve}$ cells ($CD45^+hFibs^{Oct-4}$ (day 21)) showed an increase in Oct-4 expression using multiple probe sets (FIG. 9c) with a concomitant decrease in the fibroblast specific gene expression (Yu et al., 2007) (FIG. 2a), demonstrating the acquisition of a distinct gene signature. Approximately 1000 genes were downregulated and an equal number upregulated by day 4 post-transduction resulting in the observed shift from a fibroblast phenotype towards a $CD45^{+ve}$ phenotype (Table 3). Collectively, these data indicate that Oct-4 is uniquely sufficient to initiate the $CD45^{+ve}$ cell emergence from multiple sources of human dermal fibroblasts.

To better characterize emerging $CD45^{+ve}$ hFibs, it was aimed to enhance $CD45^{+ve}$ colony formation using Flt3 (FMS-like tyrosine kinase 3) ligand and SCF (stem cell factor), representing inductive growth factors essential for early hematopoiesis (Gabbianelli et al., 1995; Hassan and Zander, 1996; Lyman et al., 1993). Treatment with Flt3L and SCF increased the frequency of CD45$^{+ve}$ colony emergence from both fetal and adult hFibs$^{Oct-4}$ by 4- and 6-fold respectively, compared with untreated hFib$^{Oct-4}$ counterparts (FIGS. 2b-c), while no effect was detectable in the control hFibs (FIGS. 2b-c and FIG. 11). These results indicated that CD45$^{+ve}$ cells derived from Oct-4-transduced hFibs are responsive to early hematopoietic growth factors.

CD45$^{+ve}$ Cell Derivation from hFibs does not Traverse the Pluripotent State

Ectopic expression of Oct-4 alone has been shown to result in pluripotent reprogramming of neural progenitors that endogenously express Sox-2 (Kim et al., 2009). Accordingly, the expression of a panel of genes known to be essential for induction and maintenance of pluripotency (Takahashi and Yamanaka, 2006) was examined during Oct-4-induced emergence of CD45$^{+ve}$ hFibs. Apart from upregulation of Oct-4 (POU5F1) (FIG. 12a), Oct-4 transduction did not alter the pluripotency gene expression profile of the hFibs (FIG. 2d). Furthermore, related POU family members Oct-2 (POU2F2) and Oct-1 (POU2F1) remained unaffected (FIG. 12b). In addition, established markers of fully reprogrammed iPSCs such as SSEA3 and Tra-1-60 levels were examined during Oct-4-induced CD45$^{+ve}$ colony emergence vs iPSC derivation from hFibs transduced with complete set of reprogramming factors (Oct-4, Sox-2, Nanog, and Lin-28) (Yu et al., 2007). Upon ectopic expression of Oct-4 alone, neither SSEA3 nor Tra-1-60 was detectable between days 0 to 31 in hFibs$^{Oct-4}$, whereas SSEA3 and Tra-1-60 levels gradually increased during establishment of pluripotent iPSCs (FIGS. 3a-b, FIGS. 12c-e). Unlike the fully reprogrammed iPSCs that are able to give rise to endoderm, mesoderm, and ectoderm germ layers, injection of an equal number of Oct-4-transduced hFibs into immunodeficient mice failed to give rise to teratomas (FIG. 2c and Table 1). Unlike iPSCs, neither hFibs nor CD45$^{+ve}$hFibs$^{Oct-4}$ were immortalized, but could be maintained for approximately 7 passages (FIG. 13a), without elevation of oncogenic-transforming factor c-Myc (Lebofsky and Walter, 2007) (FIG. 13b). Accordingly, the results indicate that the hFib$^{Oct-4}$ cells manifest a cell fate decision conducive to hematopoietic fate selection without the detectable phenotype or functional properties of transformed or pluripotent cells.

CD45$^{+ve}$hFibs$^{Oct-4}$ Possess In Vitro and In Vivo Hematopoietic Progenitor Capacity Global gene expression analysis indicated that the CD45$^{+ve}$hFibs$^{Oct-4}$ cluster with mononuclear cells (MNCs) derived from mobilized peripheral blood (M-PB)- and umbilical cord blood (UCB)-derived hematopoietic progenitors (CD34$^{+ve}$ cells) (FIGS. 14a-b). This suggests that CD45$^{+ve}$hFibs$^{Oct-4}$ may possess functional hematopoietic potential of multiple blood cell types. To define functional human hematopoietic capacity, both adult and fetal CD45$^{+ve}$hFibs$^{Oct-4}$ were physically isolated and subsequently cultured with a cytokine cocktail known to support human adult hematopoietic progenitor development (Wang et al., 2005) (FIG. 4a), which allowed subsequent expansion of CD45$^{+ve}$hFibs$^{Oct-4}$ (FIGS. 14c-d). The resulting progeny retained CD45 expression and acquired myeloid-specific markers CD33 and CD13 (FIG. 4b and FIG. 15). A subfraction of CD45$^{+ve}$hFibs$^{Oct-4}$ progeny included monocytes expressing CD14 (FIGS. 4c-d and FIG. 16a) that could be further stimulated by responsiveness to M-CSF and IL-4 to functionally mature into macrophages capable of phagocytosis (Silverstein et al., 1977). CD45$^{+ve}$hFibs$^{Oct-4}$-derived monocytes were able to engulf FITC-labeled latex beads, as indicated by FACS (FIG. 4e) and immunofluorescence analysis (FIG. 4f and FIG. 16b), while untransduced cytokine treated hFibs were devoid of this unique property (FIG. 4e). Hematopoietic cytokine-treated CD45$^{+ve}$hFibs$^{Oct-4}$ derived from multiple sources of hFibs (adult and fetal) could also give rise to granulocytic cell types distinct from the monocytic cells (FIG. 17a), as indicated by expression of granulocyte marker CD15 (FIG. 4g and FIG. 17b) and by characteristic cellular and polynuclear morphologies that are associated with granulocytic subtypes including neutrophils, eosinophils, and basophils (FIG. 4h and FIG. 17c). Without cytokines, CD45$^{+ve}$hFibs$^{Oct-4}$ cells retained CD45 expression, however, myeloid-specific markers were significantly reduced and monocytic and granulocytic lineages were absent (FIGS. 18a-b). These results indicate that cytokine stimulation is necessary for hematopoietic expansion and maturation from CD45$^{+ve}$hFibs$^{Oct-4}$.

Approximately ¼ of the cytokine-stimulated CD45$^{+ve}$hFibs$^{Oct-4}$ from either adult or fetal dermal sources co-expressed CD34 and CD45, suggestive of hematopoietic progenitor potential (FIG. 4i and FIG. 19). Clonal proliferative and developmental potential to the granulocytic and monocytic hematopoietic lineages were measured by standard colony forming unit (CFU) assays (FIGS. 4j-k). Similar to somatic UCB-derived hematopoietic progenitors, CD45$^{+ve}$hFibs$^{Oct-4}$ were able to give rise to CFUs at relatively equal capacity (FIGS. 4k-l). Collectively, the data indicates that the CD45$^{+ve}$hFibs$^{Oct-4}$ have the ability to give rise to functional hematopoietic progenitor-like cells that are able to mature into human myeloid lineages in vitro.

Based on the primitive myeloid capacity detected in vitro, CD45$^{+ve}$hFibs$^{Oct-4}$ progeny (day 37 post transduction) were transplanted into immunodeficient NOD/SCID IL2Rγc-null (NSG) mice by intrafemoral injection to characterize their in vivo reconstitution potential (FIG. 5a). CD45$^{+ve}$hFibs$^{Oct-4}$-derived cells engrafted all transplanted NSG recipients up to levels of 20%, as indicated by presence of human cells (HLA-A/B/C$^{+ve}$) (FIG. 5b), while injection of adult hFibs or saline did not give rise to a graft in NSG mice (FIG. 5c). The levels of engraftment of CD45$^{+ve}$hFibs$^{Oct-4}$ were comparable to those observed for the engrafted UCB-derived progenitors and M-PB (FIG. 5d). The cells that primarily reconstituted the NSG recipients exhibited a predominantly myeloid phenotype (~41%—CD45$^+$CD14$^+$) (FIG. 5c), compared with UCB- and M-PB-derived engrafted cells (FIG. 5e). After 10 weeks of in vivo hematopoietic engraftment (FIG. 5a), the human cells were isolated from recipients and analyzed for their ability to form CFUs in vitro as a measure of sustained progenitor capacity. A proportion of the engrafted cells retained CFU initiation potential similar to hematopoietic engrafted cells derived from human UCB (FIG. 5f), which was verified by flow cytometry analysis (FIGS. 20a-d). The ability to generate human hematopoietic progenitors after 10 weeks of engraftment and the presence of engraftment, albeit at low levels, in the contralateral bones of the primary NSG recipients (FIG. 21a) further supports the in vivo functional capacity of CD45$^{+ve}$hFibs$^{Oct-4}$-derived cells. Engrafted CD45$^{+ve}$ cells possessed limited secondary grafts in recipient NSG mice, (FIG. 21b) indicating they do not possess transformed leukemic stem cell properties (Hope et al., 2004), thus representing safer alternatives as hematopoietic transplantation products in comparison to hPSC-derived cells that retain tumor potential (Amariglio et al., 2009; Roy et al., 2006).

EPO Induces Erythroid and Megakaryocytic Capacity from CD45$^{+ve}$ hFibs

Despite the ability to derive all myeloid lineages from CD45$^{+ve}$hFibs$^{Oct-4}$, erythroid cells were not detected. Erythropoietin (EPO) has been shown to induce early erythroid differentiation (Fried, 2009), thus it was chosen to induce erythroid cell derivation from CD45$^{+ve}$hFibs$^{Oct-4}$. Upon Oct-4 transduction, hFibs expressed the erythroblast marker CD71 at a frequency of nearly 40% (FIG. 6a), which increased 2-fold following EPO induction. In addition, expressions of Glycophorin-A (critical membrane protein required for erythrocyte function) (FIG. 6b), and expression of human adult β-globin protein (uniquely required for oxygen transport by red blood cells) (FIG. 6c), were also induced upon EPO treatment. Untransduced hFibs (FIG. 6c) and hematopoietic cells derived from hPSCs (FIG. 6c inset) lacked β-globin protein levels. In the absence of EPO, only β-globin transcript was expressed in the CD45$^{+ve}$hFibs$^{Oct-4}$ (FIG. 5d), while β-globin protein was undetectable (FIG. 6c). In contrast, and unlike hematopoietic cells derived from hPSCs (Cerdan et al., 2004; Perlingeiro et al., 2001), hematopoietic cells derived from CD45$^{+ve}$hFibs$^{Oct-4}$ lacked embryonic (zeta) globin expression and only expressed modest levels of fetal (epsilon) globin (FIG. 6d). EPO-treated CD45$^{+ve}$hFibs$^{Oct-4}$ exhibited both primitive and mature erythrocyte (enucleated) morphologies (FIG. 6e) and allowed for erythroid progenitor emergence, detected by colony formation (BFU-E) and CFU-Mixed colonies (CFU-Mix; dual myeloid and erythroid capacity), similar to that observed for UCB, without reduction in monocytic or granulocytic progenitor capacity (FIGS. 6f-g, FIGS. 22a-b). Based on BFU-E potential and the presence of both adult β-globin protein and enucleated red cells, EPO-treated CD45$^{+ve}$hFibs$^{Oct-4}$ may utilize definitive (adult) and not primitive (embryonic) hematopoietic programs (Orkin and Zon, 2002) during conversion of hFibs to hematopoietic fate.

Studies have indicated that erythroid and megakaryocytic lineage commitment occurs together and potentially arises from a common precursor population (Debili et al., 1996; Klimchenko et al., 2009). Accordingly, the emergence of megakaryocytic lineage following EPO stimulation of CD45$^{+ve}$hFibs$^{Oct-4}$ was tested using an in vitro assay available for detection of Megakaryocytic (Mk)-CFUs that serves as a surrogate measure for predicting megakaryocytic recovery in patients (Strodtbeck et al., 2005). Treatment of the CD45$^{+ve}$hFibs$^{Oct-4}$ with EPO resulted in the emergence of megakaryocytes (CFU-Mk), as indicated by the presence of Mk-specific antigen GPIIb/IIIa (CD41) positive colonies (FIG. 6h—right panel and FIG. 6i), while this hematopoietic progenitor type was absent (non-CFU-Mk devoid of GPIIb/IIIa) in CD45$^{+ve}$hFibs$^{Oct-4}$ not stimulated with EPO (FIG. 6h—middle panel, FIG. 6i) or control hFibs (FIG. 6h—left panel and FIG. 6i). These data indicate that CD45$^{+ve}$hFibs$^{Oct-4}$ possess both erythroid and megakaryocytic potential. Based on the ability of EPO to reveal additional hematopoietic lineage capacities, CD45$^{+ve}$hFibs$^{Oct-4}$ may possess physiological competency and responsiveness to growth factors similar to hematopoietic progenitors derived from the human adult bone marrow compartment (Wojchowski et al., 2006).

Role of Oct-4 During Hematopoietic Program Activation in hFibs

To develop a broader understanding of the role of POU domain containing protein Oct-4 during hematopoietic conversion of hFibs, gene expression profiles and Oct-4 promoter occupancy of hematopoietic, non-hematopoietic and pluripotency factors were examined over the time course of CD45$^{+ve}$ cell emergence and maturation (FIG. 7a). Global gene expression analysis indicated several changes in both transcriptional activation and repression. As early as day 4 post Oct-4 transduction, significant changes occur in numerous molecular pathways including metabolic and developmental processes (FIG. 23a). Furthermore, global gene expression of the hFibs taken at three time points over the course of CD45$^{+ve}$ cell emergence (hFibs (day 0), CD45$^{+ve}$hFibs$^{Oct-4}$ (day 4) and CD45$^{+ve}$hFibs$^{Oct-4}$ (day 21)) indicated a decrease in fibroblast-specific gene expression (Yu et al., 2007) (FIG. 7b), without pluripotency gene induction, excluding the predictable increase in Oct-4 (POU5F1-specific probe sets) (FIG. 7c). Oct-4-transduced hFibs immediately demonstrated an upregulation of a number of hematopoietic cytokine receptors required for responsiveness to cytokines, including Flt3 and c-kit receptors of FLT3L and SCF respectively (FIG. 7d). In addition, transcription factors associated with early human hematopoietic development were also upregulated (FIG. 7e and FIGS. 23b-c). These data indicate that Oct-4 induces a cascade of molecular changes in hFibs that orchestrate the hematopoietic fate conversion.

Ground state bulk populations of hFibs possess nearly undetectable levels of genes associated with pluripotency, such as Nanog and Sox-2, or hematopoietic specification, such as SCL/Tal-1 (T-cell acute lymphocytic leukemia protein 1), Runx1 (Runt-related transcription factor 1), C/EBPα (CCAAT/enhancer-binding protein alpha), GATA1 (GATA binding factor 1) or PU.1/Spi-1 (Feng et al., 2008; Friedman, 2007; Ichikawa et al., 2004; Shivdasani et al., 1995) (FIG. 7f and FIG. 24a). However, transduction with Oct-4 was accompanied by a substantial increase of specific hematopoietic genes including SCL, C/EBPα, GATA1, and Runx1 (FIG. 7f). Interestingly, hematopoietic-associated genes PU.1 and MixL1, which were previously shown to regulate primitive blood development (Feng et al., 2008; Koschmieder et al., 2005; Ng et al., 2005), were not differentially regulated (FIGS. 7e-f and FIGS. 23 and 24b-c), suggesting these genes may not be essential for the conversion to blood fate from hFibs. Expression of genes associated with mesodermal transition from the pluripotent state, such as Brachyury and GATA2, were absent in both untransduced hFibs and CD45$^{+ve}$hFibs$^{Oct-4}$ (FIG. 7f), indicating that hematopoietic specification from hFibs does not involve embryonic programs akin to mesodermal specification from hPSCs (Tsai et al., 1994; Vijayaragavan et al., 2009). Molecular analysis of CD45$^{+ve}$hFibs$^{Oct-4}$ following cytokine treatment (D37) that resulted in hematopoietic maturation also reduced Oct-4 levels, but maintained levels of Runx1, SCL, and C/EBPα (FIG. 24b), whereas expression of all adult globins was induced, including hemoglobin-alpha, beta, and delta (FIG. 24c and FIG. 6d).

Similar to Oct-4, POU domain containing proteins Oct-1 and -2 are also able to regulate hematopoietic-specific genes implicated in specification and maturation of blood cells (Table 2) (Boyer et al., 2005; Ghozi et al., 1996; Kistler et al., 1995; Rodda et al., 2005; Sridharan et al., 2009). Accordingly, gene expression profile of POU domain containing proteins was evaluated in emergence of CD45$^{+ve}$ hFibs. While the expression of Oct-4 (POU5F1) increased during CD45$^{+ve}$ cell emergence, followed by a significant reduction upon cytokine treatment, the expression levels of Oct-2 (POU2F2) and Oct-1 (POU2F1) remained unchanged (FIG. 7g), suggesting that Oct-4 does not target other Oct family members. Nevertheless, Oct-1, -2 and -4 have the potential to bind the same octamer (POU) binding sequences in a cell context specific manner, thereby raising the possibility that Oct-4 has the capacity to bind and potentially regulate similar gene targets of Oct-1 and -2 (Boyer et al., 2005; Kistler et al., 1995; Rodda et al., 2005; Sridharan et al., 2009) (FIG. 7h and Table 2). Thus, to obtain more insight into the possible mechanism by which Oct-4 induces hematopoietic conversion, Oct-4 occupancy of hematopoietic, non-hematopoietic, and pluripotency genes that contain shared Oct 1, 2 or 4 binding sequences in their putative promoters/enhancers was examined (FIG. 7h, Table 2). Consistent with changes in gene expression (FIG. 7f), Runx1, SCL, and GATA1 displayed substantial Oct-4 occupancy (FIG. 7i), a phenomenon previously reported in partially reprogrammed mouse iPSCs and in mouse fibroblasts expressing Oct-4 alone (Sridharan et al., 2009). In addition, the CD45$^{+ve}$hFibs$^{Oct-4}$ also showed an increase in Oct-4 occupancy at the CD45 promoter (FIG. 7i). To assess the specificity of Oct-4 occupancy of hematopoietic targets during CD45$^{+ve}$ cells emergence, non-hematopoietic associated promoters previously shown to bind Oct-1 or -2, thus possessing the capacity to bind Oct-4 were also examined. Consistent with global gene expression data (FIG. 14a), housekeeping genes Gadd45a and Pol2ra exhibited an increase in Oct-4 occupancy at their respective promoters, while non-hematopoietic genes Myf5 and Nkx2.5, associated with mesodermal development did not demonstrate significant Oct-4 occupancy in either Oct-4 transduced hFibs or CD45$^{+ve}$ cells (FIG. 7j). However, Oct-4 uniquely occupied a network of promoters in human pluripotent stem cells (hPSCs) such as Nanog, c-Myc, and Tbx3 (FIG. 7k), which were not bound by Oct-4 in the CD45$^{+ve}$hFibs$^{Oct-4}$, further supporting the idea that Oct-4 DNA occupancy is cell context-dependent. While Oct-4 binds its own promoter (FIG. 7k), it does not bind the Oct-2 promoter (FIG. 7i), consistent with the gene expression profile of Oct-2 (FIGS. 12a-b). Despite these analyses, due to the conserved octamer binding sequences among Oct-1, -2 and -4 (Table 2), it remains plausible that ectopic expression of Oct-4 could act as a surrogate for Oct-1 or -2 during this process. Collectively, temporal gene expression analyses along with Oct-4 occupancy studies shown here demonstrate that ectopic Oct-4 expression results in induction of a hematopoietic program in hFibs that supports blood fate conversion.

Discussion

The present Example demonstrates the ability of human adult dermal and fetal foreskin fibroblasts to be directly converted to multipotent hematopoietic cells of the myeloid, erythroid, and megakaryocytic blood fates via Oct-4-dependent cellular programming without traversing the pluripotent state or activation of mesodermal pathways (Tsai et al., 1994; Vijayaragavan et al., 2009). Furthermore, given that transition from primitive to definitive hematopoiesis is delineated by the shift from embryonic to adult hemoglobin expression (Orkin and Zon, 2002), it is demonstrated that CD45$^{+ve}$ fibroblasts, unlike hPSC-derived hematopoietic cells (Chang et al., 2006), acquire an exclusive adult-globin protein and hematopoietic gene profile which indicates that definitive hematopoietic programs were being recruited during this conversion process.

Although recent reports demonstrate conversion of mouse fibroblasts to neural, cardiac, and macrophage-like cells from mouse fibroblasts (Feng et al., 2008; Ieda et al., 2010; Vierbuchen et al., 2010), the present Example uniquely demonstrates the ability to generate multipotent vs unipotent cell types from human fibroblasts, hence establishing a future clinical application for these multipotent blood cells. Clinical transplantation studies have estimated that a minimum of 1.5×10$^8$ CD34$^{+ve}$ blood cells (enriched for hematopoietic progenitors) are required to achieve rapid engraftment in an average 60 kg patient for recovery of neutrophils, red blood cells, and megakaryocyte after myeloablative therapies (Bender et al., 1992; Feugier et al., 2003). Taking into account the yield, expansion capacity and clinical feasibility using this direct conversion approach to hematopoietic fate (Table 4), the present method could provide a reasonable basis for autologous cell replacement therapies.

The present Example reveals a previously unknown role for Oct-4 that permitted the fibroblasts to acquire a hematopoietic phenotype via upregulation of hematopoiesis-specific cytokine receptors and transcription factors. The acquisition of this phenotype is linked to the direct binding of Oct-4 to the regulatory loci of hematopoietic-specific genes (i.e. SCL, Runx1, CD45, and GATA1) (Boyer et al., 2005; Ghozi et al., 1996; Kwon et al., 2006; Sridharan et al., 2009). While Oct-1 and Oct-2 have been shown to play a role in adult lymphopoiesis (Brunner et al., 2003; Emslie et al., 2008; Pfisterer et al., 1996), Oct-4 has not been previously implicated in blood development. Given the high conservation between the native or predicted octamer binding sequences among Oct-1, -2 and -4, it is predicted that POU domains shared among Oct proteins have a redundant role in human fibroblast conversion to hematopoietic fate. However, while Oct-4 converts fibroblasts to myeloid and erythroid progenitors, lymphoid hematopoietic fate was absent. Nonetheless, it is predicted that ectopic expression of Oct-4, -1 and -2, coupled with specific culture conditions that support B-cell and T-cell development, may support lymphoid conversion from fibroblasts.

Thus, the present inventors have demonstrated that adult human dermal fibroblasts can be directly converted into CD45+ hematopoietic cells by transduction with Oct-4 alone that have hematopoietic reconstitution capacity. The CD45+ Oct-4 transduced cells under the right stimuli are able to give rise to hematopoietic progenitors as well as mature blood cells, such macrophages, basophils, neutrophils, eosinophils, megakaryocytes and erythroid cells, without traversing the pluripotent or mesodermal progenitor state. Furthermore, the presence of beta-globin in EPO treated CD45+ Oct-4 transduced cells provide the hallmark that the cells are utilizing definitive hematopoiesis versus primitive hematopoiesis that is observed for iPSCs and hESC. The present study uncovers a novel method for derivation of hematopoietic cells. Such cells can provide a quicker, cheaper and safer alternative for example, for autologous transplantation, due to both their in vitro and in vivo competence.

Methods

Cell Culture

Primary human dermal adult fibroblasts were derived from breast dermal tissue and the fetal fibroblasts were derived form foreskin tissue and were initially maintained in fibroblast medium (DMEM (Gibco) supplemented with 10% v/v FBS (Fetal Bovine Serum, HyClone), 1 mM L-glutamine (Gibco), 1% v/v non essential amino acids (NEAA; Gibco) before transduction with Oct-4 lentivirus-vector. Human dermal fibroblasts transduced with Oct-4 were maintained on matrigel-coated dishes in complete F12 media (F12 DMEM; Gibco) supplemented with 10% knockout serum replacement (Gibco), 1% nonessential amino acids (Gibco), 1 mM L-glutamine (Gibco), and 0.1 mM β-mercaptoethanol) containing 16 ng/ml bFGF (BD Biosciences) and 30 ng/ml IGFII (Millipore) or complete F12 medium containing 16 ng/ml bFGF and 30 ng/ml IGFII and supplemented with 300 ng/ml Flt-3 (R&D Systems) and 300 ng/ml stem cell factor (SCF; R&D Systems) for 21 days. The arising CD45$^{+ve}$ Oct-transduced cells were transferred onto low attachment 24-well plates in hematopoietic medium consisting of 80% knockout DMEM (KO-DMEM) (Gibco), 20% v/v non-heat inactivated fetal calf serum (FCS) (HyClone), 1% v/v nonessential amino acids, 1 mM L-glutamine, and 0.1 mM β-mercaptoethanol (Sigma) for 16 days. Cultures were replaced with hematopoietic differentiation medium with cytokines (SCF, G-CSF, Flt3, IL-3, IL-6 and BMP-4; R&D Systems) or for erythroid/megakaryocytic differentiation the media was supplemented with hematopoietic cytokines plus 3 U/ml EPO and changed every 4 days, followed by collection for molecular and functional analysis.

Lentivirus Production

Lentiviral vectors (pSIN) containing cDNAs of Oct-4, Nanog, Sox-2 and Lin-28 were obtained from Addgene. These vectors were transfected with virapower in 293-FT packaging cells line. Viral supernatants were harvested 48 h post transfection and ultracentrifuged to concentrate the virus. Equal amount of each virus was used for fibroblast transduction in presence of 8 µg/ml polybrene.

Lentivirus Transduction

For generation of cells containing single transcription factors, human adult dermal fibroblasts (Fibs) (derived from breast skin; age between 30-40 yrs.) or fetal foreskin Fibs were seeded at the density of 10,000 cells/well on matrigel coated 12-well plates. Twenty-four hours post seeding, Fibs were infected with lentivirus expressing either Oct-4 or Nanog or Sox-2 (Nanog and Sox-2 transduction was only performed for adult dermal Fibs). Transduced fibroblasts were then grown in complete F12 medium media containing 16 ng/ml bFGF and 30 ng/ml IGFII supplemented with 300 ng/ml Flt-3 and 300 ng/ml SCF or complete F12 media containing 16 ng/ml bFGF and 30 ng/ml IGFII alone for up to 21 days. Emerging CD45$^{+ve}$ colonies were counted 14 to 21 days post infections. Colonies were picked manually and maintained on matrigel-coated wells. Molecular analysis was done on purified untransduced Fibs (D0), Oct-4 transduced Fibs at day 4 (D4), CD45$^{+ve}$ Fibs at day 21 (D21) and hematopoietic cytokine treated or untreated CD45$^{+ve}$ Fibs at day 37 (D37). Day 4 post Oct-4 transduction was chosen as the early event time point based on a number of criteria: a, optimal time for recovery following transduction; b, visible morphological changes within the culture; and c, resumption of normal cell cycle kinetics. The day 4 Oct-4 transduced Fibs (D4) were isolated by puromycin selection overnight (Oct-4 vector contains puromycin resistance cassette), purity of sample was validated by staining for Oct-4 followed by Oct-4 expression analysis using flow cytometry; samples used for molecular analysis exhibited 99% Oct-4 levels. The day 21 (D21) and day 37 (D37) CD45$^{+ve}$Fibs$^{Oct-4}$ were isolated based on their CD45 expression. D21 and D37 cells were stained with CD45-APC antibody (BD Biosciences) and sorted using FACSAria II (Becton-Dickinson); samples used for molecular analysis exhibited 99% CD45 levels.

Induction of Reprogramming

For generation of reprogrammed cells from fibroblasts; cells were seeded at the density of 10,000 cells/well on matrigel coated 12-well plates. Twenty-four hours post seeding, fibroblasts were transduced with lentivirus expressing Oct-4/Nanog/Sox-2/Lin-28 (Yu et al. 2007). Transduced fibroblasts were then grown in F12 media supplemented with 30 ng/ml IGFII and 16 ng/ml bFGF. Reprogrammed iPSC colonies were counted four weeks post infections. Colonies were picked manually and maintained on matrigel-coated wells.

Live Staining

For live staining sterile Tra-1-60 antibody (Millipore) was preconjugated with sterile Alexa Fluor-647 at room temperature. Reprogrammed colonies were washed once with F12 medium and incubated with Tra-1-60-Alexa 647 antibodies for 30 mins. at room temperature. Cultures were then washed twice to remove unbound antibody. Cells were visualized by Olympus IX81 fluorescence microscope.

Flow Cytometry

For pluripotency marker expression, cells were treated with collagenase IV, and then placed in cell dissociation buffer for 10 minutes at 37° C. (Gibco). Cell suspensions were stained with SSEA3 antibody (1:100) (Developmental Studies Hybridoma Bank, mAB clone MC-631, University of Iowa, Iowa City, Iowa) or Tra-1-60-PE (1:100) antibody (BD Biosciences). For SSEA3 staining Alexa Fluor-647 goat anti-rat IgM (1:1000) (Molecular Probes, Invitrogen) was used as the secondary antibody. Live cells were identified by 7-Amino Actinomycin (7AAD) exclusion and then analyzed for cell surface marker expression using the FACSCalibur (Becton-Dickinson). Collected events were analyzed using FlowJo 8.8.6 Software (Tree Star Inc.).

Cells from the hematopoietic differentiation medium were disassociated with TrypLE (Gibco) at day 16 and analyzed for expression of hematopoietic progenitor and mature hematopoietic markers. Hematopoietic cells were identified by staining single cells with fluorochrome-conjugated monoclonal antibodies (mAb): CD34-FITC and APC- or FITC-labelled anti-human CD45 (BD Biosciences), FITC-anti-CD33 (BD Pharmingen), PE-anti-CD13 (BD Pharmingen), PE- or FITC-anti-CD71 (BD Pharmingen), FITC-anti-HLA-A/B/C (BD Pharmingen), PE-anti-CD15 (BD Pharmingen), PE-anti-CD15 (BD Pharmingen); PE anti-CD14 (BD Pharmingen), FITC- or PE-anti-GlyA (BD Pharmingen), and APC- or PE-anti-beta-globin (SantaCruz Biotech). The mAb and their corresponding isotypes were used at 1-2 mg/ml, optimal working dilutions were determined for individual antibodies. Frequencies of cells possessing the hemogenic and hematopoietic phenotypes were determined on live cells by 7AAD (Immunotech) exclusion, using FACSCalibur (Beckman Coulter), and analysis was performed using the FlowJo 8.8.6 Software.

RT-PCRs and q-PCRs

Total RNA was isolated using Norgen RNA isolation kit. RNA was then subjected to cDNA synthesis using superscript III (Invitrogen). Quantitative PCR (qPCR) was performed using Platinum SYBR Green-UDP mix (Invitrogen). For the analysis of the sample, the threshold was set to the detection of Gus-B (beta-glucuronidase) (Oschima et al. 1987) and then normalized to internal control GAPDH. The base line for the experiment was set to the gene expression levels observed in fibroblasts. Given the expression of some of the genes within this starting population of fibroblasts, the gene expression pattern for these cells was included. Hence, the data is represented as delta cycle threshold ($\Delta C(t)$) versus delta $\Delta C(t)$ ($\Delta\Delta C(t)$). (qPCR primer sequences are provided in Table 5).

Genomic DNA was isolated using ALL IN ONE isolation kit (Norgen). For integration studies 150 ng genomic DNA was used per PCR reaction. PCR reactions were performed using 2×PCR Master Mix (Fermentas).

Affymetrix Analysis

Total RNA was extracted from human dermal fibroblasts (2 replicates), puromycin selected day 4 Oct-4 transduced fibroblasts (2 replicates) and sorted CD45$^{+ve}$ cells (2 replicates) using the Total RNA Purification Kit (Norgen). RNA integrity was assessed using the Bioanalyzer (Agilent Technologies, Santa Clara, Calif., USA). Sample labeling and hybridization to Human Gene 1.0 ST arrays (Affymetrix) were performed by the Ottawa Health Research Institute Microarray Core Facility (OHRI; Ottawa, Canada). Affymetrix data were extracted, normalized, and summarized with the robust multi-average (RMA) method implemented in the Affymetrix Expression Console. CEL files were imported into dChIP software (Li and Wong 2001) for data normalization, extraction of signal intensities and probe-level analysis.

Chromatin Immunoprecipitation

ChIP was performed as described previously (Rampalli et al. 2007). Briefly, human pluripotent cells (H9 and iPSC1.2), human dermal fibroblast cells, puromycin selected day 4

Oct-4 transduced cells, sorted day 21 CD45$^{+ve}$ cells were cross-linked using 1% formaldehyde. Chromatin was digested in buffer containing 0.1% SDS to obtain fragments of approximately of 1000 bp length. Sonicated DNA was subjected to immunoprecipitation using anti-Oct4 (ChIP quality antibody; Cell Signaling Technology) and anti rabbit IgG antibodies (Santacruz Biotechnology). Immunoprecipitated DNA was further reverse cross-linked, purified and subjected to qPCR analysis using UDG-Platinium Syber Green mix (Invitrogen). The promoter specific ChIP primers are listed in Table 6. To calculate the relative enrichment, signals observed in control antibody were subtracted from signals detected from the specific antibody; the resulting differences were divided by signals observed from $\frac{1}{50}^{th}$ ChIP input material.

Megakaryocyte Assay

To detect human megakaryocytes MegaCult™-C Complete Kit with Cytokines (Stem Cell Technologies) was used. The derivation of megakaryocytes was done according to instruction included with the kit. The kit includes pre-screened components for optimal growth of megakaryocyte CFUs, such as thrombopoietin (TPO), Interleukin-3 (IL-3), IL-6, IL-11 and SCF, chamber slides for growth and antibodies for subsequent immunocytochemical staining. In short 10,000 CD45$^{+ve}$ EPO treated cells were plated in the Mega-Cult medium containing cocktail of growth factors stated above. The human CFU-Mks were detectable by day 10 to 15 and were subsequently fixed and stained according to protocol. Mk-specific antigen GPIIb/IIIa (CD41) linked to a secondary biotinylated antibody-alkaline phosphatase avidin conjugated detection system was used, where Mk-CFUs were red/pink in colour.

Cytospin

1000 CD45$^{+ve}$ Oct-4 transduced cells were washed twice in cold 2% FBS in PBS and dilute in 500 µl of cold 1% FBS in PBS. The samples were loaded into the appropriate wells of the Cytospin. The samples were spun at 500 rpm for 5 minutes to allow adherence to the slides. The slides were fixed with methanol for 1 min. and allowed to dry for 30 min. Then slides were stained with Giemsa-Wright stain for 3 min followed by 10 min. in PBS and a quick wash in distilled water. The slides were allowed to dry overnight and mounted with mounting medium (Dako). Slides were viewed by Olympus IX81 microscope.

Macrophage Phagocytosis Assay

Fluorescein (FITC) conjugated-latex beads (Sigma) were used as particle tracers to analyze phagocytosis by monocytes derived from CD45$^+$Fibs$^{Oct-4}$ cells treated with IL-4 and M-CSF. To measure phagocytosis, 10 µl of packed beads suspended in 3% FBS in PBS was added to $10^6$ cells in Teflon tubes. After incubation for 90 min at either 37° C., cells were washed three times with cold PBS containing 3% FBS and 0.1% EDTA to remove free beads. The cells were then labeled to detect expression of CD45 (APC-conjugated CD45 mAb) together with FITC-bead uptake, and analyzed by flow cytometry using FACSCalibur (BD) or visualized by cytospinning 1000 cells onto tissue culture quality slides (VWR) and viewed by Olympus IX81 fluorescence microscope.

Methylcellulose Colony-Forming Assay

Cells were plated at 1,000 FACSAria II sorted (Becton-Dickinson) CD45$^+$CD34$^+$ cells or 5000 total cell (EPO treatment) in 1 ml Methocult GF H4434 (Stem Cell Technologies, Vancouver, BC). Colonies were scored after 14 days of culture using standard morphological criteria and analyzed using the FACSCalibur (Becton-Dickinson) for hematopoietic surface markers. Collected events were analyzed using FlowJo 8.8.6 Software (Tree Star Inc.). For colony derivation from xenotransplant derived engrafted cells, the cells were first sorted based on HLA-A/B/C (BD Biosciences) followed by CD45 expression using a human specific anti-CD45 (BD Biosciences). The HLA-A/B/C and CD45 double positive cells were then plated at a density of 1000 cell/ml in Methocult GF H4434. The colonies derived from engrafted cells were further analyzed for hematopoietic surface markers using FACSAria II (Becton-Dickinson). Collected events were analyzed using FlowJo 8.8.6 Software (Tree Star Inc.).

Xenotransplant Assays

NOD/SCID IL2Rγc null adult mice (NSG) were sublethally irradiated with 325 rads 24 hours before transplantation. $5.0 \times 10^5$ CD45$^{+ve}$ Oct-transduced (D37) or human dermal fibroblasts or human mobilized peripheral blood or human umbilical cord blood lineage depleted cells were transplanted by intrafemoral injection. After 10 weeks, animals were culled, and bone marrow (BM) from injected femur, contralateral bones and spleen were analyzed for the presence of human cells by flow cytometry (FACSCalibur, Becton-Dickinson), followed by data analysis using FlowJo 8.8.6 Software (Tree Star Inc.). Cells positive for HLA-A/B/C and CD45 were analyzed for the expression of hematopoietic lineage specific markers such as CD14. For secondary transplants, total engrafted bone marrow cells were transplanted intravenously (IV injection) in adult irradiated NSG mice as described for primary transplants. Genomic DNA from engrafted cells were then analyzed using conventional PCR by primers specific for α-satellite of human chromosome 17:
forward-5'-GGGATAATTTCAGCTGACTAAACAG-3'
(SEQ ID NO:3) and reverse-5'-TTCCGTTTAGTTAGGTG-CAGTTATC-3' (SEQ ID NO:4).

Teratoma Assay

The McMaster University Animal Care Council approved all procedures and protocols. Adult dermal fibroblasts, fetal dermal (foreskin) fibroblasts, CD45$^{+ve}$ Oct-4 transduced adult dermal fibroblasts, CD45$^{+ve}$ Oct-4 transduced fetal fibroblasts and iPSC 1.1 to 1.4 were treated with collagenase IV for 5-10 min followed by collection and washing 2× with saline and resuspended in saline. 500,000 cells per sample were injected intratesticularly into male NOD-SCID mice. Mice were killed 10-12 weeks after initial injection. Teratomas were extracted, embedded in paraffin and sectioned in 5 µm intervals followed by deparafinization in xylene and processing through a graded series of alcohol concentrations. Samples were stained with Hematoxylin and eosin or Oct4 followed by dehydration and xylene treatment. Slides were mounted using Permount and imaged by scanning slides using Aperio Scan Scope and images were captured using Image Scope v9.0.19.1516. software. Tissue was also collected from a variety of organs including lung, spleen, liver, brain and kidney to investigate the presence of metastatic cells. Tissue typing was performed based on stringent histological and morphological criteria specific for each germ layer subtype. Mesoderm lineages, such as bone were identified using presence of osteocytes and bone spicules; cartilage was identified by the presence of chondrocytes and specific staining of the extra cellular matrix. Endoderm lineages, such as intestinal lumens were identified by the presence of goblet cells in the lumen epithelium. Ectoderm lineages, such as skin were identified based on distinguishing cell layer morphologies (i.e. stratified); brain or neural tube was identified based on specific histological criteria. The presence of the germ layers and tissue typing was confirmed by McMaster Pathology.

Statistical Analysis

All tests were performed using InStat Version 3.0a statistical software (GraphPad Software). Descriptive statistics including mean and s.e.m. along with one-way ANOSAs, independent sample two-tailed t-tests were used to determine significant differences. p<0.01 was considered significant.

Example 2

Reprogramming Dermal Fibroblasts into Induced Pluripotent Stem Cells

Results

Human Dermal Fibroblasts Contain a Rare Subpopulation

Transcription factors Oct4 and Sox2 share common DNA binding motifs, and regulate enhancer and promoter regions of genes implicated in the pluripotency network (Loh et al. 2006; Kim et al. 2008). Human embryonic stem cells (hESCs) and human fibroblasts (hFibs) were transduced with a recently reported EOS lentiviral vector containing trimerized (C3+) Oct4 enhancer elements, (FIG. 25a) (Hotta et al. 2009). Using positive control vector where GFP expression is controlled by the pGK promoter, GFP expressing (GFP$^{+ve}$) cells were readily detectable by microscopy (FIG. 25b) and had an overall lentiviral transduction efficiency into hFibs or hESCs of 50-60%, quantitated by flow cytometry (FIG. 25c and FIG. 32a). Using a negative control vector devoid of promoter elements, GFP expression was not detectable in either hFibs or hESCs using microscopy (FIG. 25b) or flow cytometric analysis (FIG. 25c). As expected, a high frequency of GFP$^{+ve}$ hESCs transduced with C3+EOS vector was observed (FIG. 25b,c and FIG. 32b). However, C3+EOS transduction into adult breast-derived hFibs revealed a rare population of dermal fibroblasts expressing GFP (FIG. 25b, c). Confocal Z-stack imaging of hFib cultures transduced with C3+EOS indicated rare GFP$^{+ve}$ hFibs are morphologically and spatially distinct from other hFibs residing in the culture (FIG. 32c). Detection of this subpopulation of hFibs was not due to high copy integrations in individual cells, as transduction of hFibs using different concentrations of EOS lentivirus did not alter frequencies of GFP$^{+ve}$ hFibs, whereas individual GFP$^{+ve}$ hFibs expressed an indistinguishable level of GFP on a per cell basis irrespective of viral concentration (FIG. 32d-f). Given that the composition of in vitro cultured fibroblasts varies depending on the tissue from which they are derived, unique sources of human neonatal foreskin- and adult lung-derived fibroblasts, both devoid of hair follicles that contain tissue-specific dermal stem cell populations, were examined (Terunuma et al. 2008). Similar to adult breast-derived dermal hFibs, foreskin and lung fibroblasts transduced with C3+EOS vector contained GFP$^{+ve}$ subsets at a frequency of 0.5-4%, indicating that the presence of the GFP$^{+ve}$ subset is not dependent on human fibroblast source (FIG. 25d,e).

To rule out the potential bias in viral uptake among hFibs, hFibs were serially infected with C3+EOS lentivirus starting with primary GFP$^{-ve}$ hFib subfraction (FIG. 32g). As a result of secondary EOS lentivirus transduction of primary GFP$^{-ve}$ hFibs, 1.34% GFP$^{+ve}$ emerging was observed (FIG. 32g), indicating a small frequency of these unique cells was not detected due to initial limits of 50% overall transduction efficiency (FIG. 25c). FACS isolation of secondary GFP$^{-ve}$ hFibs, followed by subsequent transduction with C3+EOS lentivirus, demonstrated a frequency of <0.1% GFP$^{+ve}$ cells, whereas tertiary and quaternary transductions with C3+EOS lentivirus were unable to show any increase in GFP Oct reporter expression (FIG. 32g); indicating all hFibs competent for C3+EOS expression had been saturated. To ensure sequentially transduced GFP$^{-ve}$ hFibs were not simply resistant to lentiviral infection, quaternary GFP$^{-ve}$ hFibs were transduced with positive control vector pGK-EGFP that gave rise to robust GFP$^{+ve}$ hFibs, thus confirming these cells were competent for lentiviral infection (FIG. 32h). These studies demonstrate that observed GFP$^{+ve}$ subpopulation of hFibs was not due to high copy integrations in individual cells, or to differences in infection rate between subpopulations.

To molecularly validate C3+EOS reporter expression and presence of integrated provirus, GFP$^{+ve}$ and GFP$^{-ve}$ hFibs transduced with EOS vector were prospectively isolated at 99.99% purity (FIG. 25f). Using isolated populations, provirus was shown to be present in both fractions, whereas GFP transcript expression was present only in GFP$^{+ve}$ hFibs, and absent in GFP$^{-ve}$ hFibs (FIG. 25g). To ensure GFP$^{-ve}$ hFibs containing integrated C3+EOS vector were not silenced, these hFibs with Oct4 expressing lentivirus were transduced. Upon ectopic expression of Oct4, GFP$^{-ve}$ cells could be induced to express GFP (FIG. 25h), demonstrating the integrated proviral vector was functional in these cells.

Collectively, these results indicate that human fibroblasts cultured in vitro are heterogeneous by revealing a unique subset that permits expression of the Oct4 reporter EOS vector independent of ontogenic source or anatomical location from which hFibs were derived.

Rare Subset of hFibs Possesses Molecular Features of Pluripotent Cells

Aside from pluripotent stem cells (PSCs), Oct4 expression has also been reported in multiple somatic tissues including dermis, multipotent stem cells, and cancer cells (Li et al.; Jiang et al. 2002; Goolsby et al. 2003; Dyce et al. 2004; Johnson et al. 2005; Moriscot et al. 2005; Zhang et al. 2005; D'Ippolito et al. 2006; Dyce et al. 2006; Izadpanah et al. 2006; Nayernia et al. 2006; Reno et al. 2006; Yu et al. 2006; Izadpanah et al. 2008), while the surrogacy and function of Oct4 in non-PSCs remains elusive (Lengner et al. 2007; Lengner et al. 2008). Given that activation of the C3+EOS vector is based on the presence of Oct4, the expression of Oct4 was carefully examined in total hFibs and GFP$^{+ve}$ vs. GFP$^{-ve}$ hFib subsets. Several Oct4 isoforms and pseudogenes have sequence similarity (Atlasi et al. 2008), making interpretation of transcript detection complex and potentially leading to false positives. As such, Oct4 transcripts were identified in hFibs using multiple primer sets recently characterized (Atlasi et al. 2008) that faithfully recognize: 1. Oct4; 2. Oct4B1 embryonic-specific Oct4 isoforms; and 3. Oct4B cytoplasmic variants (FIG. 26a). GFP$^{+ve}$ hFibs were enriched for expression of Oct4 and its isoform B1, but lacked expression of cytoplasmic isoform Oct4B similar to that of hESC controls (FIG. 26b,c), whereas total and GFP$^{-ve}$ hFibs did not express any form of Oct transcript (FIG. 26b,c). The mesodermal gene Brachyury used as a control for lineage-specific gene expression was not differentially expressed (FIG. 26c). The possibility that GFP$^{+ve}$ hFibs expressed other genes associated with Oct4 and pluripotency was next examined. In addition to Oct4 (FIG. 26b,c), quantitative gene expression analysis demonstrated expression of Nanog and Sox2 in GFP$^{-ve}$ hFibs (FIG. 26d), albeit at lower levels compared to hESCs (FIG. 25e). Whole genome expression profiles from total hFibs vs. GFP$^{+ve}$ and GFP$^{-ve}$ hFibs were compared to hESC, iPSC lines using 3' oligonucleotide arrays and evaluated for expression of genes specific to human and mouse ESCs vs. genes associated with heterogeneous fibroblast cultures (Takahashi et al. 2007; Yu et al. 2007). GFP$^{-ve}$ hFibs strongly clustered with multiple sources of heterogeneous human dermal fibroblasts, whereas GFP$^{+ve}$ hFibs did not cluster with total hFibs from which they were derived, but instead with pluirpotent hESC and iPSC lines (FIG. 26f).

As transcript expression is not a determinant of protein, protein expression of Oct4 was examined using Oct4-specific antibodies. Oct4 intracellular localization was examined using immunofluorescent staining analysis. In GFP$^{+ve}$ hFibs, Oct4 co-localized with DAPI stained nuclei similar to that observed in hESCs that served as a positive control (FIG. 26g), and 293 cells transduced with Oct4 transgene (FIG. 33a). Oct4 staining was not detected in untransduced 293 cells that served as a negative control, while rare Oct4 positive cells were seen in total hFib cultures, consistent with the frequency of GFP$^{+ve}$ cells detected by the EOS vector (0.5-4%) (FIG. 33a). Using western analysis, in addition to Oct4, protein levels of both Nanog and Sox2 were differentially expressed in GFP$^{+ve}$ hFibs (FIG. 26h,i), where hESCs and Oct4-transduced and untransduced 293 cells served as positive and negative controls (FIG. 26h). Based on these analyses, these subsets of hFibs were termed as Nanog, Oct4, and Sox2 expressing hFibs, or NOS$^{+exp}$ hFibs, vs. majority of hFibs that were GFP$^{-ve}$ hFibs, and as such termed NOS$^{-exp}$ hFibs.

To better understand the molecular nature of rare NOS$^{+exp}$ hFibs, chromatin precipitation (ChIP) was performed using specific antibodies against Oct4, Nanog, Sox2, and Brachyury proteins in hESCs, total hFibs, NOS$^{+exp}$ and NOS$^{-exp}$ hFib subsets for binding to CR4 enhancer motifs within the EOS vector. Occupancy of these pluripotent factors to CR4 motif was highly enriched in NOS$^{+exp}$ hFibs, whereas negative control Brachyury was not bound (FIG. 26j). Comparison of active (H3K4Me3) and repressive (H3K27Me3) histone modification marks at the endogenous promotor loci revealed that NOS$^{+exp}$ hFibs possessed active marks for Oct4, Nanog, and Sox2 similar to that of hESC positive controls, whereas total unselected hFibs and NOS$^{-exp}$ loci were repressed (FIG. 26k). As demethylation of Oct4 loci associated with gene activation is extensively studied in PSCs (Simonsson and Gurdon 2004), MeDIP ChIP assays were performed. Reduced methylation of Oct4 promoter was similarly detected in hESCs and NOS$^{+exp}$ hFibs, in contrast to 293 cells and NOS$^{-exp}$ hFibs (FIG. 33b). These results further confirm Oct4 loci is activated in NOS$^{+exp}$ hFibs.

The role of Oct4 and other pluripotent-associated factors in somatic compartment has been met with skepticism due to inappropriate controls for transcript and protein expression detection, and absence of any functional evidence for the role of these cells or factors expressed (Lengner et al. 2007). The present results have extended characterization of such cells beyond simple PCR transcript detection of a single gene such as Oct4, and has analyzed chromatin, protein, subcellular localization, and global gene expression cluster analysis for Oct4, Nanog, and Sox2, together with positive (hESCs) and negative controls (293 cells) for each factor. Collectively, these data provide the foundation for the existence of NOS$^{+exp}$ hFibs that represent a unique and rare subset within human fibroblasts that shares common molecular features with human PSCs. The ability to isolate these subsets of NOS$^{+exp}$ and NOS$^{-exp}$ hFibs provides the unprecedented opportunity to perform functional analysis and define the biological significance of these shared features with PSCs.

Heterogeneous Total hFibs, in Contrast to Purified NOS$^{+exp}$ Subsets, can be Reprogrammed Under Feeder-Free Conditions Since NOS$^{+exp}$ hFibs share hallmark features of gene expression with fully reprogrammed iPSCs, their capacity for functional reprogramming compared to total hFibs was examined. The majority of iPSC lines are derived using heterogeneous hFibs and use mouse embryonic fibroblast (MEF) feeder layers to support iPSC generation (Park et al. 2008). However, clinical applications of iPSCs will require xeno-free conditions and methods that allow for rapid and simple isolation and separation of human iPSCs from supportive cells such as MEFs. To specifically address this application-based limitation, human iPSCs were derived on matrigel using feeder-free conditions as schematically illustrated in FIG. 27a. Total and NOS$^{+exp}$ hFibs were transduced with previously defined reprogramming factors (Hotta et al. 2009), and cultures were examined by both phase contrast and live fluorescence microscopy to characterize morphological changes, identify colony formation, and identify subfraction of colonies expressing Tra1-60. Consistent with previously reported frequencies for human iPSC generation (Utikal et al. 2009; Aasen et al. 2008; Meissner et al. 2007), total hFibs exhibited approximately 0.9% colony formation efficiency (per 10,000 input cells), whereas the same number of highly purified NOS$^{+exp}$ hFibs isolated failed to generate any colonies (FIG. 27b). This result was consistently observed in 6 independent experimental replicates, indicating that from over 60,000 NOS$^{+exp}$ hFibs (6×10,000) analyzed, formation of proliferating colonies towards iPSC generation could not be derived using this purified subset.

Although colony formation is the initial requirement for iPSC generation, colony formation alone does not denote fully reprogrammed cells. As such, Tra1-60 expression colonies were quantitatively identified using recently established live staining methods (FIG. 27c) that faithfully identify reprogrammed iPSCs from non-iPSC-like colonies (Chan et al. 2009) using total hFibs that generated colonies in the absence of feeders (FIG. 27b). In addition, these colonies were also assessed for expression of SSEA3 and Oct4 by flow cytometry and compared to Tra1-60 acquisition. Both Tra1-60$^{+ve}$ and Tra1-60$^{-ve}$ colonies expressed high levels of Oct4, but only Tra1-60$^{+ve}$ colonies expressed pluripotency marker SSEA3, while Tra1-60$^{-ve}$ colonies lacked SSEA3 expression (FIG. 27d). Overall, the Tra1-60$^{+ve}$ colonies represented 50% of total number of colonies generated (FIG. 27e). These two types of colonies (Tra1-60$^{+ve}$ and Tra1-60$^{-ve}$) were further examined using a subset of genes strongly associated with pluripotency (Rex1, Tbx3, TcF3, and Dppa4), and indicated that only Tra1-60$^{+ve}$ colony acquired a pluripotent gene expression signature (FIG. 27f). Finally, in vivo differentiation potential of Tra1-60$^{+ve}$ colonies was tested by teratoma formation assay demonstrating that these colonies have potential to give rise to all three germ layers (FIG. 27g). Using these collective criteria, starting with colony formation and subsequent Tra1-60, Oct4 and SSEA3 expression analysis, together with pluripotent gene expression analysis and ability to form pluripotent teratomas, independent measures are provided to define iPSC generation, thereby establishing that, in contrast to purified NOS$^{+exp}$ hFibs, total heterogeneous hFibs can be reprogrammed under feeder-free conditions.

NOS$^{+exp}$ hFibs Represent the Major Contributor to Pluripotent Reprogramming

Purified NOS$^{+exp}$ hFibs failed to generate reprogrammed colonies upon isolation from heterogeneous cultures of total hFibs (FIG. 27b). Given the well established effects of the niche on the regulation of stem cell properties (Bendall et al. 2007), it was hypothesized that the reprogramming potential of the NOS$^{+exp}$ subpopulation may be dependent on complex microenvironmental cues that prevented iPSC emergence from highly purified NOS$^{+exp}$ hFibs. Since NOS$^{+exp}$ hFibs are transduced with the EOS vector, GFP and provirus integration provide a fluorescent and molecular marker of NOS$^{+exp}$ cells that can be used to distinguish the contribution of NOS$^{+exp}$ hFibs upon co-culture with heterogeneous fibroblasts. NOS$^{+exp}$ hFibs were mixed with total hFibs in a ratio of 1:9 in a competitive assay to measure reprogramming ability and contribution to iPSC generation using established criteria (FIG. 27b-g).

Consistent with previous observations (Yamanaka 2009), total hFibs (10,000 input cells) exhibited an expected low frequency of colony formation, while co-cultures of NOS$^{+exp}$ hFibs (total input of 10,000 cells comprising 1,000 NOS$^{+exp}$ hFibs together with 9,000 total hFibs=1:9 ratio) remarkably garnered a 14-fold increase in colony formation (FIG. 27h). To quantitatively assess the contribution of NOS$^{+exp}$ vs. total hFibs towards reprogramming, colonies identified for iPSC-like morphology by phase contrast were enumerated and further scrutinized by live fluorescence microscopy for Tra1-60 expression, and the presence or absence of GFP expression and EOS proviral integration. A representative experiment using this approach is shown in FIG. 27i displaying detailed analysis on individual colonies identified. Combined results from 6 independent mixture experiments demonstrated that 90% of the Tra1-60$^{+ve}$ colonies were positive for GFP and EOS provirus, while the remaining 10% were contributed by total hFibs (FIG. 27i). Tra1-60$^{+ve}$ and $^{-ve}$ colonies derived from NOS$^{+exp}$ and total hFibs were isolated and examined for activation of pluripotency factors and SSEA3 expression to ascertain and quantitate the number of complete reprogrammed iPSCs. Representative analysis from EOS$^{+ve}$ colonies that could only be derived from NOS$^{+exp}$ hFibs (C2 and C9) that were positive (C2) and negative (C9) for Tra1-60 expression vs. EOS$^{-ve}$ colonies (C11 and C12) positive (C11) and negative (C12) for Tra1-60 expression are shown (FIG. 27j,k). Tra1-60 provided a strong surrogate marker for colonies capable of pluripotent gene activation (FIG. 27j) and SSEA3 expression (FIG. 27k), independent of NOS$^{+exp}$ or total hFib origins. Fully reprogrammed colonies derived from NOS$^{+exp}$ hFibs were capable of teratoma formation comprising all three germ layers (FIG. 27i), and possessed in vitro differentiation capacity towards the mesodermal (hematopoietic, FIG. 35a) and ectodermal (neuronal, FIG. 35b) lineages similar to pluripotent hESCs shown as a positive control for lineage development (FIG. 35a-b). Since NOS$^{+exp}$ hFibs were capable of reprogramming and generating iPSCs upon co-culture, reprogramming potential of remaining NOS$^{-exp}$ hFibs derived from heterogeneous hFib cultures were similarly examined. Direct analysis for reprogramming ability demonstrated that highly purified NOS$^{-exp}$ hFibs cultured in feeder-free conditions were completely devoid of colony generation (FIG. 29a), and co-culture of NOS$^{-exp}$ hFibs with total hFibs resulted in a biologically insignificant colony frequency of <0.01% (FIG. 36a-b). This represents a single colony per 10,000 input cells in 3 independent experiments (FIG. 36b) that is likely derived from total hFibs that do contain NOS$^{+exp}$ hFibs unmarked by C3+EOS transduction.

To quantitatively determine the precise contribution of NOS$^{+exp}$ hFibs to generation of iPSCs in co-cultures with total hFibs, the overall data set from 6 independent mixture experiments was analyzed. Firstly, identification of iPSC-like colony formation enumerated by microscopy indicated an average of 12 colonies could be generated from an input of 10,000 cells comprising 9K of total hFibs and 1K of NOS$^{+exp}$ hFibs (FIG. 28a). Despite a 9-fold greater proportion of total hFib input cells (GFP$^{-ve}$, EOS$^{-ve}$), the contribution of NOS$^{+exp}$ hFibs (GFP$^{+ve}$, EOS$^{+ve}$) colony formation was 4-fold higher, based on definitive criteria of GFP expression, and the presence of EOS proviral integration (FIG. 28a). Quantitative analysis of Tra1-60 expression among EOS$^{-ve}$ colonies (derived from 9,000 total hFibs) vs. EOS$^{+ve}$ colonies (derived from 1,000 NOS$^{+exp}$ hFibs) indicated that an equal proportion of Tra$^{+ve}$ vs. Tra$^{-ve}$ colonies arise from total hFibs, whereas colonies derived from NOS$^{+exp}$ hFibs enriches for Tra1-60$^{+ve}$ fully reprogrammed colonies (FIG. 28b). On a per 10,000 cell input basis, direct comparative analysis indicates that the overall reprogramming efficiency of unselected total hFibs was 0.18 vs. an average of 7.6 arising from NOS$^{+exp}$ hFibs (FIG. 28c). Accounting for the 9-fold difference in the input cells, these results demonstrate a 42-fold increase in reprogramming efficiency using NOS$^{+exp}$ hFib isolation and enrichment (n=6, FIG. 28c).

Although NOS$^{+exp}$ hFibs are incapable of cell-autonomous reprogramming in purified cultures, these results reveal that this unique, but rare subset of hFibs is the major contributor of cells to reprogrammed iPSCs, but requires co-culture with heterogeneous hFibs. These functional studies suggest that NOS$^{+exp}$ hFibs possess a predisposition to cellular reprogramming induction due to their unique molecular and epigenetic state (FIG. 26) that is already akin to pluripotent cells prior to induced reprogramming.

Molecular State of NOS$^{+exp}$ hFibs can be Modulated by Microenvironment for Pluripotent Reprogramming Competency In the presence of microenvironment provided by total heterogeneous hFibs, purified NOS$^{+exp}$ hFibs generated iPSC colonies in co-cultures containing 10% NOS$^{+exp}$ hFibs and 90% total hFibs (FIG. 28). Accordingly, whether microenvironment composition could influence the reprogramming frequency of predisposed population as a product of NOS$^{+exp}$ hFib relative cellular densities was explored. Using a range of relative enrichment densities of NOS$^{+exp}$ hFibs vs. total hFibs, reprogramming capacity was examined by colony formation and NOS$^{+exp}$ hFib contribution was distinguished by GFP expression. Increase in the densities of NOS$^{+exp}$ hFibs towards 50% demonstrated a plateau for reprogramming efficiency (FIG. 29a). Beyond this plateau, the reprogramming capacity of NOS$^{+exp}$ hFibs decreased as supportive total hFib proportion decreased, eventually demonstrating the complete absence of colony formation once supportive total hFibs were absent (FIG. 29a). Decreasing the density of NOS$^{+exp}$ hFibs to <2.5% in the mixtures resulted in reduced colony generation (FIG. 30a), reminiscent of the low frequency of iPSC generation derived from total hFibs (FIG. 27a-g) These results suggested that the reprogramming capacity of NOS$^{+exp}$ hFIbs is dependent on specific densities relative to microenvironment or supportive niche cells.

To better understand the molecular basis for the requirement of supportive heterogenous hFibs to NOS$^{+exp}$ hFib reprogramming, gene expression and epigenetic status of total hFibs and purified NOS$^{+exp}$ hFibs before (de novo isolated) and after co-culture were evaluated. In contrast to total hFibs (FIG. 29b), de novo prospectively isolated NOS$^{+exp}$ hFibs demonstrated detectable expression of pluripotent factors and active marks on gene loci (FIG. 29c). De novo isolated NOS$^{+exp}$ hFibs cultured multiple passages retained stable GFP expression (FIG. 37). Next, chromatin state at the endogenous loci of Oct4, Nanog, and Sox2, and transcript expression for these genes in NOS$^{+exp}$ hFibs cultured alone, and then in the presence of hFibs or co-cultured with MEFs was compared (FIG. 29d). Cultured NOS$^{+exp}$ hFibs alone induced a bivalent state at Oct4 loci and a loss of active histone marks for Nanog and Sox2 loci (FIG. 30f) that were corroborated with reduced gene expression for Oct4 and complete absence of Nanog and Sox2 transcripts (FIG. 30e). These molecular changes correlated to the inability to reprogram NOS$^{+exp}$ hFibs cultured alone in feeder-free conditions (FIG. 27b). However, NOS$^{+exp}$ hFibs subsequently co-cultured with total hFibs or with MEFs were able to re-acquire active chromatin marks on Oct4, Nanog, and Sox2 loci (FIG. 30g), and gene expression upon co-culturing with total hFibs or with MEFs (FIG. 30g).

Role of microenvironment in derivation and maintenance of pluripotent stem cells has been reported (Schnerch et al.; Bendall et al. 2007; Stewart et al. 2008), and is consistent with the inferred requirement of MEFs as iPSC derivation protocols include the use of MEF feeders (Takahashi and Yamanaka 2006; Takahashi et al. 2007; Wernig et al. 2007; Yu et al. 2007; Aasen et al. 2008; Hanna et al. 2008; Lowry et al. 2008; Park et al. 2008; Woltjen et al. 2009). To determine whether co-culture-induced modulation of epigenetic state of NOS$^{+exp}$ hFibs affects reprogramming competency, NOS$^{+exp}$ hFibs and NOS$^{-exp}$ hFibs were cultured in the presence or absence of MEFs and hFib fractions were exposed to lentivirus-expressing reprogramming factors. A total of 10,000 NOS$^{+exp}$ or NOS$^{-exp}$ hFibs were transduced with reprogramming factors, and cultures were examined 3 and 6 weeks post-infection for colony formation, GFP expression, and colonies expressing Tra1-60. Consistent with the previous results (FIG. 27b and FIG. 36a-b), NOS$^{+exp}$ or NOS$^{-exp}$ hFibs did not generate colonies in the absence of co-cultured cells at either 3-week or extended 6-week cultures (FIG. 29h). Similarly iPSC generation was not detectable from the NOS$^{-exp}$ hFibs, even upon co-culture with MEFs (FIG. 29h). However, NOS$^{+exp}$ hFibs co-cultured on MEFs produced detectable colonies at 3-weeks post transduction and continued to demonstrate complete reprogrammed iPSCs at 6-weeks of MEF co-culture (FIG. 29h). Colonies generated expressed GFP and the pluripotency marker Tra1-60, indicative of complete reprogramming (Chan et al. 2009) (FIG. 29h).

Collectively, comparative molecular analysis of de novo isolated NOS$^{+exp}$ hFibs vs. absence and presence of co-cultured heterogeneous hFibs or MEFS revealed that NOS$^{+exp}$ hFibs respond and modulate their epigenetic state and gene expression through currently unknown signaling mechanisms that are provided by microenvironmental cues. Molecular changes induced by co-culture microenvironment are restricted to NOS$^{+exp}$ hFib subfraction, and are required to maintain predisposed state and competency for pluripotent reprogramming.

NOS$^{+exp}$ hFibs are Molecularly Exclusive from Other Human Stem/Progenitor Cells and Possess Unique Cell Cycle Properties Previous studies have demonstrated isolation of multipotent stem cells from various regions of the skin including bulge region of hair follicle (Bulge Stem Cells), interfollicular epidermis (IFE stem cells), and the dermal papillae (SKPs) (Manabu Ohyama 2006; Biernaskie et al. 2009; Jensen et al. 2009). In order to assess the potential similarity between NOS$^{+exp}$ hFibs and previously described multipotent stem/progenitor cells isolated from skin, this unique population of hFibs was further examined based on global genome expression profiles. Hierarchical clustering of total hFibs, NOS$^{+exp}$ hFibs, and NOS$^{-exp}$ hFibs; compared to Bulge Stem Cells, Keratinocytes, and SKPs (Toma et al. 2005; Manabu Ohyama 2006; Jensen et al. 2009), using fibroblast gene signature and molecular markers specific to individual skin stem/progenitors (FIG. 30a) revealed that NOS$^{+exp}$ hFibs are distinct from pre-existing skin stem/progenitors and are further distinguished by their expression of the pluripotency transcriptional network that includes Nanog, Oct4, and Sox2 (FIG. 30a). In addition to dermal-derived stem/progenitor cells, neural, hematopoietic, and keratinocyte progenitors have been shown to possess enhanced reprogramming capacities (Aasen et al. 2008; Eminli et al. 2009). As such, the global molecular phenotype of NOS$^{+exp}$ hFibs to these lineage-specific adult stem cells was compared which indicated that NOS$^{+exp}$ hFibs did not cluster with these stem cell types (FIG. 29b). Collectively, these analyses indicate that NOS$^{exp}$ hFibs are distinct from stem/progenitor cells previously associated with dermal skin derivatives or tissue-specific progenitors reported to undergo enhanced reprogramming (FIG. 29b).

Next, global gene expression differences between NOS$^{+exp}$ hFibs and total hFibs were evaluated towards identification of additional features, other than those shared with human PSCs that may distinguish NOS$^{+exp}$ hFibs from bulk total hFibs. Gene ontology analysis of the list of differentially expressed genes revealed several categories that were enriched in NOS$^{exp}$ hFibs vs. total heterogeneous hFib cultures. These predominantly included gene products involved in development, cell cycle, and cell division (FIG. 30c). Of these ontologies, genes involved in cell cycle progression were most prevalently differentially expressed (17.48%, p<0.000003). Further in-depth analysis of cell cycle-associated genes revealed higher expression of genes associated with replication and mitotic processing in NOS$^{+exp}$ hFibs that were also co-expressed uniquely in hESCs and fibroblast-derived iPSCs (FIG. 30d). Of these genes, a non-integral cell surface receptor CD168 [also called Hyaluronan-mediated motility receptor (HMMR)] found in the nucleus and associated with cells in the developing human embryo (Choudhary et al. 2007; Manning and Compton 2008) was co-expressed with GFP expressing NOS$^{+exp}$ hFibs amongst heterogeneous hFibs transduced with EOS vector (FIG. 30e). Consistent with unique cell cycle regulation of NOS$^{+exp}$ hFibs, direct comparison of growth rates between NOS$^{+exp}$ hFibs to total hFibs indicated NOS$^{+exp}$ hFibs proliferate at a higher rate (FIG. 30f), thereby functionally validating the unique proliferative properties of NOS$^{+exp\ hFibs}$.

Taken together, these data provide further comparative characterization of these previously unidentified NOS$^{+exp}$ hFibs predisposed for cellular reprogramming that is best defined by unprecedented expression of genes associated with pluripotency and proliferation.

Discussion

Using human dermal fibroblasts as a clinically relevant model system for understanding and enhancing pluripotent reprogramming, evidence is provided for the existence of a predisposed cell population with molecular similarities to pluripotent cells and inherent cell cycle status that is conducive towards pluripotent reprogramming and without wishing to be bound by theory, a model is proposed for the role of these cells in the reprogramming process (FIG. 31). These predisposed human dermal fibroblasts possess unique cell cycle properties including enhanced expression of cell cycle activators (such as CCNB1/2, PCNA, MCM 2-7, and ANAPC1) and are identified and distinguished by expression of Nanog, Oct4, and Sox2, therefore termed NOS$^{+exp}$ hFibs (FIG. 31). The unique molecular and epigenetic ground state of NOS$^{+exp}$ hFibs are distinct from heterogeneous cultures of fibroblasts or previously reported stem/progenitor populations capable of enhanced reprogramming, and are similar to human iPSCs and ESCs. The remaining hFibs (NOS$^{-exp}$) do not participate in reprogramming to iPSCs, despite co-culture with supportive niche, or prolonged culture periods (FIG. 31). Nevertheless, the possibility that some unique conditions may allow induced pluripotency, such as introduction of oncogenes or perturbation of cell cycle regulators is not excluded (FIG. 31). Since both stem/progenitor and enhanced proliferation state positively influence iPSC generation, a cell type similar to NOS$^{+exp}$ hFibs identified here that has intrinsic cell cycle properties is amenable for efficient and enhanced reprogramming. Consistent with this notion, a recent study published by Smith et al (Smith et al. 2010) provides evidence that the small and fast-dividing subfraction of MEFs contributes to iPSC colony formation, however, no further characterization has been done, likely due to the current inability to define and isolate these unique cell types among MEFs. Since reprogramming is thought to remove existing epigenetic states or cellular "memory" of target cells required to establish a new pluripotent state, given the similar molecular phenotype and epigenetic status of NOS$^{+exp}$ hFibs to hPSCs the extent to which reprogramming converts terminally differentiated fibroblasts vs. overcoming limiting commitment steps essential to achieve pluripotency warrants further conceptual and experimental examination. These results support an elite stochastic model to describe reprogramming induction at the cellular level, where an elite subset of predisposed cells is uniquely capable of responding to inductive molecular changes required to establish pluripotent state.

These results identify a predisposed cell population that exclusively contributes to reprogramming in a niche-dependent manner that can be supplied by either heterogeneous hFibs or MEFs (FIG. 31). As such, a previously unappreciated role of microenvironment in iPSC derivation from human dermal fibroblasts has been uncovered. Although the results indicate that the fibroblasts are not equipotent for reprogramming, it does not discount the possibility that other subfractions among heterogeneous human fibroblasts could be induced to reprogram under uniquely designed conditions. This is similar to recent reports that suggest that the reprogramming of mouse B-cells might be a stochastic event by demonstrating that almost every donor cell can be reprogrammed to the pluripotent state by continuous and prolonged expression of reprogramming factors for extended periods (Hanna et al. 2009). Interestingly, 3-5% of colonies emerged after only two weeks of reprogramming and may represent predisposed cell types similar to NOS$^{+exp}$ hFibs identified here, while the appearance of remaining iPSC colonies emerging over the subsequent 4-5 months with continued doxycyclin induction of reprogramming factors may be a result of the specific selective conditions utilized that include the use of drug-induced gene expression involving the oncogene c-myc. Such experiments in non-predisposed fractions of human hFibs (NOS$^{-exp}$ cells) could provide more insights into prerequisite of oncogenic processes for pluripotent reprogramming.

Similar to all current reports of pluripotent reprogramming, the relevance of predisposed NOS$^{+exp}$ hFibs pertains to in vitro processes of somatic cell reprogramming and the use of derived cells once reprogrammed in vitro. To date, no reports have indicated that cells can be reprogrammed to the pluripotent state in vivo. While plasticity of fibroblast cells in invertebrates has recently been documented (Kragl et al. 2009), such plasticity is not fully explored in mammals (Sánchez Alvarado 2009), thus existence of predisposed hFibs and its in vivo function is intriguing, but its role in normal in vivo physiology is merely speculative at this point, and is likely limited to in vitro phenomenon. Nevertheless, NOS$^{+exp}$ hFibs can easily be derived from a variety of human tissue, and represent the most rapid and robust contributor to human iPSC generation reported to date. These properties underscore the clinical utility of NOS$^{+exp}$ hFibs where immediate isolation and characterization of fully reprogrammed iPSCs from patients is required for rapid drug and genetic screening or cell transplantation upon differentiation induction.

Methods

Cell Culture

Adult Human dermal fibroblasts were derived from breast skin (obtained passage 1; recommended expansion—15 population doubling), neonatal dermal fibroblasts derived from foreskin (obtained passage 1; recommended expansion—15 population doubling), and lung fibroblasts were derived from lung tissue (obtained passage 10; recommended expansion—24 population doubling) [Sciencell] and maintained in fibroblast medium (DMEM (Gibco) supplemented with 10% FBS (HyClone), L-glutamine (Gibco), nonessential amino acids (NEAA; Gibco). All the experiments were conducted using breast derived dermal fibroblasts unless mentioned otherwise. Human iPS cells were maintained on matrigel-coated dishes in iPS media (F12 DMEM (Gibco) supplemented with 20% knockout serum replacement (Gibco), L-glutamine (Gibco), NEAA, beta-mercaptoethanol supplemented with 16 ng/ml bFGF (BD Biosciences). hESCs were maintained on matrigel coated dishes in MEF-condition media supplemented with 8 ng/ml bFGF. Pluripotent cells were transduced with different concentrations of EOS C3+ lentivirus on day 2 following passage. 293 cells were cultured in DMEM containing 10% fetal bovine serum, essential amino acids and L-glutamine. 293 cells were seeded in chamber slides prior to transfection. One microgram pSIN-Oct4 vector was transfected using lipofectamine 2000 reagent (Invitrogen). Experiments were performed 36 hr post transfection. For generation of cultured NOS$^{+exp}$ hFibs, adult dermal fibroblast cells were transduced with EOS C3+ Oct4 lentiviral vector, NOS$^{+exp}$ cells were sorted and cultured for at least 5 passages in fibroblasts media.

Lentivirus Production

Lentiviral pSIN-EGFP, pSIN-PGK-EGFP and pSIN-C3+ EOS vectors were synthesized and described by Hotta et al 2008. Lentiviral vectors (pSIN) containing cDNAs of Oct4, Nanog, Sox2, and Lin28 were obtained from Addgene. These vectors were co-transfected with virapower in 293-FT packaging cells line. Viral supernatants were harvested 48 h post transfection and ultracentrifuged to concentrate the virus. To confirm the transduction efficiency of positive control pGK EGFP lentivirus was transduced in fibroblasts at indicated dilution. Equal amount of each virus was used for fibroblast transduction in presence of 8 ng/ml polybrene.

Human Adult Fibroblast Sorting

Fibroblast cells were transduced at passage three with C3+ EOS vector and maintained for three passages. Cells were trypsinized and live cells were identified using 7AAD exclusion. Fibroblasts were sorted based on GFP expression on FACS Ariall (BD). For qRT-PCR assays and chromatin immunoprecipitation (ChIP) assays 50,000 GFP$^{+ve}$ (NOS$^{+exp}$) and GFP$^{-ve}$ (NOS$^{-exp}$) cells were sorted into the tubes containing 0.5% FBS in PBS (v/v). Cells were either collected by centrifugation for RNA extraction or cross-linked using 1% Formaldehyde for ChIP studies.

Induction of Reprogramming—On matrigel

For generation of reprogrammed cells from total hFibs, GFP$^{+ve}$ cells (referred to as 10,000 NOS$^{+exp}$ cells) and 10,000 GFP$^{-ve}$ cells (referred to as 10,000 NOS$^{-exp}$ cells), cells were seeded at the density of 10,000 cells/well on matrigel coated 12-well plates. For mixture experiments NOS$^{+exp}$ cultured cells were mixed in 1:9 ratio (1000 NOS$^{+exp}$ cultured+9000 total hFibs) or in 1:1 ratio (5000 NOS$^{+exp}$ cultured+5000 total hFibs). For the experiments pertaining to demonstration of predisposition, 1000 NOS$^{+exp}$ cells were sorted from total hFib cultures and combined with 9000 total hFibs onto matrigel-coated dishes. 24 hrs post seeding, fibroblasts were transduced with lentiviruses expressing Oct4, Nanog, Sox2, and Lin28. Transduced fibroblasts were then grown in iPSC media. Reprogrammed colonies were counted three to 6 weeks post infections. Colonies were picked manually and maintained on matrigel-coated wells. On MEFs: 10,000 NOS$^{+exp}$ or NOS$^{-exp}$ cells were seeded in 12-well dish in triplicates. 24 hrs post seeding, hFibs were transduced with lentiviruses expressing Oct4, Nanog, Sox2, and Lin28. 36 hrs post transduction, hFibs were collected by trypsinization and transferred on to plates containing irradiated MEFs. Reprogrammed colonies were counted 3 to 6 weeks post infections. Colonies were picked manually and maintained on MEFs.

Hematopoietic and Neuronal Differentiation Assays

Human ES cells or iPSC cells derived on matrigel were grown until 80% confluence and EBs were made as described previously (Chadwick et al. 2003). Cells were transferred to low attachment 6-well plates in differentiation medium consisting of 80% knockout DMEM (KO-DMEM) (Gibco), 20% non-heat inactivated fetal Bovine serum (FBS) (HyClone), 1% nonessential amino acids, 1 mM L-glutamine, and 0.1 mM β-merchaptoethanol. Cultures were replaced with fresh differentiation medium or medium supplemented with 50 ng/ml BMP-4 (R&D Systems), 300 ng/ml stem cell factor (SCF) (Amgen), and 300 ng/ml Flt-3 ligand (R&D Systems). EBs were maintained for 15 days, and medium was changed every 4 days. For neural precursor differentiation, EBs were cultured in EB medium alone for 4 days. After the initial 4 days the EBs were transferred to 12-well plates coated with poly-L-lysine/fibronectin and maintained in neural proliferation medium consisting of DMEM/F12 with B27 and N2 supplements (Gibco), 10 ng/ml bFGF, 10 ng/ml human epidermal growth factor (hEGF), 1 ng/ml human platelet derived growth factor-AA (PDGF-AA) (R&D Systems), and 1 ng/ml human insulin-like growth factor-1 (hIGF-1) (R&D systems). Cultures were allowed to adhere to the plates and expand as a monolayer over 4 days.

RT-PCRs and PCRs

Total RNA was isolated using Norgen total RNA isolation kit. RNA was then subjected to cDNA synthesis using superscript III (Invitrogen). Quantitative PCRs were performed using Platinium SYBR Green-UDP mix (Invitrogen). Genomic DNA was isolated using ALL IN ONE isolation kit (Norgen). For EOS provirus integration studies 150 ng genomic DNA was used for amplification of GFP in PCR reactions. PCR reactions were performed using 2×PCR Master Mix (Fermentas). Products were resolved on 1.2% agarose gels. Primer sequences are provided in Table 7.

Western Blotting

Cell extracts were prepared in lysis buffer [50 mM Tris (pH 8.0), 150 mM NaCl, 1% (v/v) Nonidet P-40, 0.1% (w/v) SDS, 0.5% (v/v) sodium deoxycholate and Complete protease inhibitors (GE Healthcare)] from hESC, total fibroblasts, 293, 293 overexpressing Oct4, GFP$^{+ve}$ ((NOS$^{+exp}$) and total hFibs. Approximately 60 μg of protein was loaded for western blotting with indicated antibodies.

Chromatin Immunoprecipitations

Chromatin IPs were performed as described previously (Rampalli et al. 2007). In brief cells were crosslinked using 1% formaldehyde and chromatin was digested in buffer containing 0.1% SDS to obtain fragments of approximately 400 bp length. Sonicated DNA was subjected to immunoprecipitation using ChIP grade antibodies (anti-trimethyl H3K4 (Abcam), anti trimethyl-H3K27 (Abcam), anti Oct4 (Cell Signaling), anti Nanog (Cell Signaling), anti Sox2 (Cell Signaling), anti BrachuryT (Abcam), anti rabbit IgG and anti mouse IgG antibodies). Immunoprecipitated DNA was further reverse crosslinked, purified and subjected to qPCR analysis using Platinium Syber Green-UDP mix. To calculate relative enrichment, control-IP signals were subtracted from specific ones and the resulting difference was divided by signal observed from $\frac{1}{50}^{th}$ of input material.

MeDip ChIP assay was performed as described previously. Briefly genomic DNA was extracted from 293, hESC, total hFibs and NOS$^{+exp}$ (GFP$^{+ve}$) cells by overnight Proteinase K treatment, phenol-chloroform extraction, ethanol precipitation and RNase digestion. Before carrying out MeDIP, genomic DNA was sonicated to produce random fragments ranging in size from 300 to 1,000 bp. Immunopurified DNA was subjected to qPCR analysis using Platinium Sybr Green-UDP mix. To calculate relative enrichment, control-IP signals were subtracted from specific ones and the resulting difference was divided by signal of input material. Primers for quantitative PCR analysis are provided in Table 7.

Live Staining

For live staining sterile Tra-1-60 antibody (Millipore) was preconjugated with sterile Alexa Fluor 647 goat anti-mouse IgM (Molecular Probes, Invitrogen) at room temperature. Reprogrammed colonies were washed once with iPSC medium and incubated with Tra-1-60-Alexa 647 antibodies for 30 mins at room temperature. Cultures were then washed twice to remove unbound antibody. Cells were visualized using the Olympus fluorescence microscope.

Flow Cytometry

Induced pluripotent cells were treated with collagenase IV (Gibco), and then placed in cell dissociation buffer (Gibco) for minutes at 37° C. Cell suspensions were stained with SSEA-3 (Developmental Studies Hybridoma Bank, mAB clone MC-631, University of Iowa, Iowa City, Iowa). Cells were visualized with Alexa Fluor 647 goat anti-rat IgM (Molecular Probes, Invitrogen). Appropriate negative controls were utilized. Live cells were identified by 7-Amino Actinomycin (7AAD) exclusion and then analyzed for cell surface marker expression using the FACS Calibur (BDIS). Collected events were analyzed using FlowJo 6.4.1 Software (Tree Star Inc.). EBs generated from iPSC cells were disassociated with 0.4 U/ml Collagenase B (Roche Diagnostics, Laval, QC, Canada) at day 15 and analyzed for expression of hemogenic and hematopoietic markers. Hematopoietic cells (CD45+) were identified by staining single cells (2-5×10$^5$ cells/ml) with fluorochrome-conjugated monoclonal antibodies (mAb) pan-leukocyte marker CD45-APC (Milteny Biotech, Germany). The mAb and their corresponding isotype was used at 1-2 mg/ml. Frequencies of cells possessing the hematopoietic phenotypes were determined on live cells by 7AAD (Immunotech) exclusion, using FACS Calibur, and analysis was performed using the FlowJo software (Tree Star). EBs in neural proliferation medium were trypsinized after 4 d in culture and stained with the cell surface marker A2B5 (R&D Systems). Cells were visualized using Alexa Fluor 647 goat-anti-mouse IgM (Molecular Probes, Invitrogen). Frequencies of cells expressing A2B5 were determined on live cells by 7AAD (Immunotech) exclusion, using FACS Calibur, and analysis was performed using the FlowJo software (Tree Star).

Immunocytochemistry

Total fibroblasts, 293, 293 transfected with pSIN-Oct4 vector and sorted NOS$^{+exp}$ cells were seeded on chamber slides. hESC transduced with EOS C3+ were grown on matrigel coated 12-well dishes. Cells fixed in paraformaldehyde and permeabilized in Triton X-100 prior to staining for human Oct4 (Rat anti-Human Oct3/4 monoclonal antibody clone 240408) (R&D systems). Cells were then stained with secondary antibody Alexa Fluor 647 anti-Rat IgG (Molecular Probes). Chamber slides were mounted and counterstained with Vectashield Mounting Medium containing DAPI (Vector Labs). For HMMR staining adult dermal fibroblast cells were transduced with EOS C3+ lentivirus and CD168 (HMMR) (ab 67003) staining was performed as described above. Cells were visualized using the Olympus IX81 fluorescence microscope.

Teratoma Assay

The McMaster University Animal Care Council approved all procedures and protocols. Induced pluripotent stem cell cultures were treated with collagenase IV for 5-10 min followed by collection and washing 2× with saline and resuspended in saline. 500,000 cells per sample were injected intratesticularly into male NOD-SCID mice. Mice were killed 10-12 weeks after initial injection. Teratomas were extracted, embedded in paraffin and sectioned in 5 µm intervals followed by deparaffinization in xylene and processing through a graded series of alcohol concentrations. Samples were stained with hematoxylin and eosin or Oct4 followed by dehydration and xylene treatment. Slides were mounted using Permount and imaged by scanning slides using Aperio Scan Scope and images were captured using Image Scope v9.0.19.1516. software. Tissue typing was performed based on stringent histological and morphological criteria specific for each germ layer subtype. Mesoderm lineages, such as bone were identified using presence of osteocytes and bone spicules; cartilage was identified by the presence chondrocytes and specific staining of the extra cellular matrix. Endoderm lineages, such as intestinal lumens were identified by the presence of goblet cells in the lumen epithelium. Ectoderm lineages, such as skin were identified based on distinguishing cell layer morphologies (i.e. stratified); brain or neural tube was identified based on specific histological criteria. The presence of the germ layers and tissue typing was confirmed by McMaster Pathology.

3-D Reconstitution/Z-Stacking

Adult dermal fibroblasts transduced with EOS vector were seeded in chamber slides. Cells were washed with PBS and fixed with 4% paraformaldehyde/PBS for 10 minutes, followed by permeabilization in Triton X-100. Slides were mounted and counterstained using VECTASHIELD HardSet Mounting Medium with DAPI (Vector Labs). Cells were visualized using the Olympus IX81 microscope and z-stacks (30 sections per field) were captured with a Photometrix Cool Snap HQ2 camera using In Vivo version 3.1.2 (Photometrix) software. Z-sections/image stacks were pseudo-coloured and 3-D mapped using ImageJ software.

Microarray Analysis

Total RNA was isolated from adult dermal fibroblasts (total), NOS$^{+exp}$ (GFP$^{+ve}$), NOS$^{-exp}$ (GFP$^{-ve}$) cells, iPS NOS$^{+ve}$ and hESC using total RNA purification kit (Norgen) according to the manufacturer's instructions. RNA amplification, GeneChip 3' oligonucleotide microarray hybridization and processing was performed by the OGIC, Ottawa Health Research Institute, Ottawa, Ontario according to the manufacturer's protocols (Affymetrix). For each sample, 200 ng of single-stranded DNA was labeled and hybridized to the Affymetrix HG-U133 Plus 2.0 chips. Expression signals were scanned on an Affymetrix GeneChip Scanner and data extraction was performed using Affymetrix AGCC software. Data normalization and analysis was performed using Dchip software (Li and Wong 2001 PNAS). Hierarchical clustering using Pearson correlation coefficients was performed on the normalized data. Differentially upregulated genes were analyzed using D-ChIP. Gene Ontology (GO) analysis was performed using FATIGO (http://babelomics.bioinfo.cipf.es).

Example 3

Direct Neural Conversion from Human Dermal Fibroblasts

Results and Discussion

Oct-4 (POU5F1) together with neuronal cytokines (bFGF, EGF) was used to promote neuronal conversion from human dermal fibroblasts. While, Vierbuchen and colleagues (Vierbuchen et al., 2010) have shown mouse fibroblast conversion to single neuronal cell-type, namely neurons, the present example demonstrates the conversion of human fibroblasts to oligodendrocytes, astrocytes and neurons while bypassing a pluripotent state (FIG. 38). Human dermal fibroblasts transduced with POU domain binding protein Oct-4 were plated for standard neural, oligodendrocyte and astrocyte differentiation assays used in the filed using human laminin coated dishes and cultured in neural/oligodendrocyte or astrocyte differentiation medium supplemented with bFGF, EGF and BMP-4 (FIG. 38a). Unlike untransduced/control fibroblasts, human dermal fibroblasts transduced with Oct-4 gave rise to all three neural lineages (neurons, astrocytes and oligodendrocyte), as demonstrated by acquisition of neural lineage specific morphologies (FIG. 38b). The Oct-4 transduced fibroblasts were further analyzed for expression of neural lineage specific marker expression, such as astrocyte specific marker GFAP (Glial fibrillary acidic protein), oligodendrocyte specific marker Olig-4 (oligodendrocyte transcription factor 4) and neuron specific marker (TUBB3) beta-Tubulin III. Human dermal fibroblasts transduced with Oct-4 expressed GFAP, TUBB3 and Olig-4, as demonstrated by immunofluorescence imaging (FIG. 38c, e, g) and FACS analysis (FIG. 38d, f, h, i) indicative of astrocyte, neuron and oligodendrocyte emergence.

To demonstrate that the neurons are able to give rise to mature and functional dopaminergic neurons, the human dermal fibroblasts were further differentiated as described by Roy and colleagues (2006). The human dermal fibroblasts transduced with Oct-4 gave rise to dopaminergic neurons as indicated by co-expression of TUBB3 and Tyrosine Hydroxylase (markers of dopaminergic neurons) (FIG. 39). Collectively, these results indicate that human dermal fibroblasts ectopically expressing Oct-4 in conjunction with neural linage inductive conditions are able to give rise to astrocyte, neuron and oligodendrocyte, as well as functional and mature neurons with dopaminergic phenotypes.

Further gene expression comparisons between untransduced and Oct4 transduced fibroblasts at day 4 after treatment evidenced a significant increase in the expression of certain genes associated with neural development such as BMI1, POU3F2, and NEFL between 1.6 and 1.8 fold (p<0.009; FIG. 40). These data support the activation of neural differentiation programs in progenitors derived from dermal fibroblasts transduced with Oct-4.

Methods

Neural Precursor Differentiation

Adapted from (Pollard et al., 2009; Reubinoff et al., 2001; Roy et al., 2006). Adult dermal and fetal dermal fibroblasts were cultured in F12-DMEM media supplemented with 20% FBS, IGFII and bFGF. Fibroblasts were transduced with Oct-4 lentivirus and cultured in the media described above. Further neuronal differentiation was carried out in neural precursor medium consisting of DMEM/F12 with B27 and N2 supplements (Gibco), 20 ng/ml bFGF and 20 ng/ml human epidermal growth factor (hEGF), (R&D systems) (Carpenter et al., 2001). Cells were allowed to adhere to the plates and expand as a monolayer over 14 days. Medium was replaced every 3 days, and cells were passed on day 7 by dissociation into a single cell suspension using Accutase (Sigma) for 5 minutes.

Dopaminergic Progenitor Induction

For dopaminergic progenitor differentiation cultures were prepared as previously described (Roy et al., 2006), Briefly, neural precursor cultures were dissociated in Accutase for 5 minutes, and then transferred to new laminin-coated plates (BD Biosciences) in midbrain neuron media consisting of DMEM/F12 supplemented with N2 (Gibco), bFGF (10 ng/ml), the N-terminal active fragment of human SHH (200 ng/ml), and FGF8 (100 ng/ml; R&D). Medium was replaced every 3 days. After 7 days, dopaminergic neuron differentiation was induced by withdrawing SHH and the FGFs, and replacing with DMEM/F12 media supplemented with N2, GDNF (20 ng/ml), BDNF (20 ng/ml) and 0.5% FBS. Cultures were maintained for 14 days in these conditions and then fixed for staining (ie. Tyrosine Hydroxylase, βIII Tubulin for dopaminergic neurons).

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLES

TABLE 1

| Samples | Biological Replicates (n) | Mesoderm (layer/biological replicate) | Ectoderm (layer/biological replicate) | Endoderm (layer/biological replicate) |
|---|---|---|---|---|
| Fibs | 3 | 0/3 | 0/3 | 0/3 |
| Fibs$^{Oct-4}$ | 3 | 0/3 | 0/3 | 0/3 |
| hiPSC | 8 | 8/8 | 8/8 | 8/8 |

TABLE 2

| Genes | Promoter/ Enhancer | Oct Binding Sequence | Oct-1/Oct-2/ Oct-4 Binding Reported | References |
|---|---|---|---|---|
| Runx1 | Promoter | ATGCAAAN | Oct-2/Oct-1 | (Sridharan et al 2009, Cell) (Ghozi et al, 1996, PNAS) |
| SCL | Enhancer | NTGCAANN | Oct-2/Oct-1 | (Boyer et al 2005, Cell) |
| PU.1 | Promoter | ATGCAAAN | Oct-2/Oct-1 | (Kistler et al 1995, Oncogene) |
| GATA1 | 5'side | ATGCANNN | Oct-1/Oct-4 | (Sridharan et al 2009, Cell) |
| CD45 | Promoter | TTTGCAT | Oct-1/Oct-4 predicted | (Kwon et al, 2006, BBRC) (Boyer et al 2005, Cell) |
| Oct-2 | 5'side | None | ND | (Boyer et al 2005, Cell) |
| MixL1 | 5'side | None | ND | None |
| Oct-4 | 5'side | ATGCATNN | Oct-4 | (Boyer et al 2005, Cell) |
| Nanog | Promoter | TTTGCAT | Oct-4 | (Boyer et al 2005, Cell) (Rodda et al ,2005 JBC) |
| Tbx3 | Promoter | NTGCAAAT | Oct-4 | (Boyer et al 2005, Cell) |
| c-Myc | 5'side | ATGCAAAT | Oct-4 | (Sridharan et al 2009, Cell) |
| Myf5 | Promoter | NTGCAAAT | Oct-2 | (Robertson et al 2006, Nucleic Acid Res.) |
| Nkx2.5 | Promoter | ATGCANAN | Oct-2 | (Robertson et al 2006, Nucleic Acid Res.) |
| Gadd45a | Promoter | TTTGCAT | Oct-2/Oct-1 | (Kang et al 2009, Trends Biochem Sci.) |
| Pol2ra | Promoter | NTGCANAT | Oct-2/Oct-1 | (Kang et al 2009, Trends Biochem Sci.) |

TABLE 3

Global gene expression profile of hFibs vs. Oct-4 transduced hFibs at Day 4

| GENES | Accession | Fold change | p-value |
|---|---|---|---|
| IL1A: interleukin 1, alpha | NM_000575 | 25.87 | 0.001934644 |
| BIRC3: baculoviral IAP repeat-containing 3 | NM_001165 | 21.8 | 0.010578005 |
| HIST1H3E: histone cluster 1, H3e | NM_003532 | 19.5 | 0.013600383 |
| TNFAIP3: tumor necrosis factor, alpha-induced protein 3 | NM_006290 | 18.76 | 0.012982616 |
| BHLHB3: basic helix-loop-helix domain containing, class B, 3 | NM_030762 | 18.02 | 0.005532449 |
| ZNF670: zinc finger protein 670 | NM_033213 | 17.48 | 0.008794967 |
| HDAC9: histone deacetylase 9 | NM_178423 | 15.41 | 0.000236429 |
| RRAD: Ras-related associated with diabetes | NM_001128850 | 15.18 | 0.013434877 |
| C1orf51: chromosome 1 open reading frame 51 | BC027999 | 13.56 | 0.000739754 |
| TUFT1: tuftelin 1 | NM_020127 | 13.4 | 0.018978702 |
| CYP1A1: cytochrome P450, family 1, subfamily A, polypeptide 1 | NM_000499 | 13.04 | 0.031138196 |
| HIST2H4A: histone cluster 2, H4a | NM_003548 | 12.84 | 0.008543485 |
| HIST2H4A: histone cluster 2, H4a | NM_003548 | 12.84 | 0.008543485 |
| AXUD1: AXIN1 up-regulated 1 | NM_033027 | 12.13 | 0.025799785 |
| IFIT2: interferon-induced protein with tetratricopeptide repeats 2 | NM_001547 | 11.69 | 0.019285607 |
| EGR2: early growth response 2 (Krox-20 homolog, *Drosophila*) | NM_000399 | 11.49 | 0.010572069 |
| DDIT3: DNA-damage-inducible transcript 3 | NM_004083 | 11.16 | 0.04497724 |
| ATF3: activating transcription factor 3 | NM_001040619 | 11.12 | 0.02030641 |
| ZNF844: zinc finger protein 844 | BC125186 | 10.89 | 0.024129158 |
| NUAK1: NUAK family, SNF1-like kinase, 1 | NM_014840 | 10.64 | 0.034088258 |
| ICAM1: intercellular adhesion molecule 1 | NM_000201 | 10.39 | 0.003127828 |
| HLF: hepatic leukemia factor | NM_002126 | 10.13 | 0.009535536 |
| POU5F1: POU class 5 homeobox 1 | NM_002701 | 10 | 0.008557916 |
| SLC25A25: solute carrier family 25 | NM_052901 | 9.84 | 0.00211957 |
| KLF10: Kruppel-like factor 10 | NM_005655 | 9.62 | 0.006678425 |
| RYBP: RING1 and YY1 binding protein | NM_012234 | 9.4 | 0.018976746 |
| IRF1: interferon regulatory factor 1 | NM_002198 | 9.23 | 0.026074286 |
| GADD45B: growth arrest and DNA-damage-inducible, beta | NM_015675 | 9.03 | 0.02123219 |
| POU5F1: POU class 5 homeobox 1 | NM_002701 | 8.99 | 0.008153649 |
| POU5F1: POU class 5 homeobox 1 | NM_002701 | 8.99 | 0.008153649 |
| CCRN4L: CCR4 carbon catabolite repression 4-like (*S. cerevisiae*) | NM_012118 | 8.85 | 0.043078237 |
| ZNF763: zinc finger protein 763 | NM_001012753 | 8.85 | 0.037261964 |
| CD83: CD83 molecule | NM_004233 | 8.44 | 0.017160482 |
| ARL5B: ADP-ribosylation factor-like 5B | NM_178815 | 8.41 | 0.014951415 |
| HIST4H4: histone cluster 4, H4 | NM_175054 | 8.22 | 0.009968564 |
| ZNF699: zinc finger protein 699 | NM_198535 | 8.2 | 0.002752974 |
| BDKRB1: bradykinin receptor B1 | NM_000710 | 8.16 | 0.000257582 |
| HIST1H3H: histone cluster 1, H3h | NM_003536 | 8.05 | 0.044438878 |
| FILIP1L: filamin A interacting protein 1-like | NM_182909 | 7.99 | 0.011930597 |
| C7orf53: chromosome 7 open reading frame 53 | BC031976 | 7.89 | 0.028087424 |
| ZNF140: zinc finger protein 140 | NM_003440 | 7.84 | 0.031209015 |
| GADD45A: growth arrest and DNA-damage-inducible, alpha | NM_001924 | 7.79 | 0.025929534 |
| LIF: leukemia inhibitory factor (cholinergic differentiation factor) | NM_002309 | 7.75 | 0.037199994 |
| HOXB9: homeobox B9 | NM_024017 | 7.67 | 0.03720824 |
| NR1D1: nuclear receptor subfamily 1, group D, member 1 | NM_021724 | 7.64 | 0.025254369 |
| RIT1: Ras-like without CAAX 1 | NM_006912 | 7.61 | 0.035367727 |
| HIST1H4H: histone cluster 1, H4h | NM_003543 | 7.53 | 0.00172024 |
| EFCAB7: EF-hand calcium binding domain 7 | NM_032437 | 7.52 | 0.039529612 |
| ZNF596: zinc finger protein 596 | NM_001042416 | 7.48 | 0.041548238 |
| NFKBIA | NM_020529 | 7.44 | 0.027269255 |
| DKFZp686O24166: hypothetical protein DKFZp686O24166 | BC136797 | 7.39 | 0.013762938 |
| ZNF441: zinc finger protein 441 | NM_152355 | 7.31 | 0.033410843 |
| EGR1: early growth response 1 | NM_001964 | 7.3 | 0.002499187 |
| PPP1R15A: protein phosphatase 1, regulatory subunit 15A | NM_014330 | 7.28 | 0.031859194 |
| LOC253724: hypothetical LOC253724 | BC064342 | 7.17 | 0.04832593 |
| GNPDA1: glucosamine-6-phosphate deaminase 1 | NM_005471 | 7.16 | 0.027064994 |
| HSPC159: galectin-related protein | NM_014181 | 7.14 | 0.028997946 |
| PMAIP1: phorbol-12-myristate-13-acetate-induced protein 1 | NM_021127 | 7.02 | 0.020362551 |
| SETDB2: SET domain, bifurcated 2 | NM_031915 | 7.01 | 0.00928835 |
| ZBTB2: zinc finger and BTB domain containing 2 | NM_020861 | 6.92 | 0.012078835 |
| FOSB: FBJ murine osteosarcoma viral oncogene homolog B | NM_006732 | 6.85 | 0.005383006 |
| PLD6: phospholipase D family, member 6 | BC031263 | 6.81 | 0.021517786 |
| DLX2: distal-less homeobox 2 | NM_004405 | 6.73 | 0.036189927 |
| HEY1: hairy/enhancer-of-split related with YRPW motif 1 | NM_012258 | 6.69 | 0.016580802 |
| HIST2H2BE: histone cluster 2, H2be | NM_003528 | 6.68 | 0.038129201 |
| HHLA3: HERV-H LTR-associating 3 | NM_001036645 | 6.68 | 0.011341273 |
| ZNF331: zinc finger protein 331 | NM_018555 | 6.59 | 0.001392362 |
| SYT14: synaptotagmin XIV | NM_153262 | 6.56 | 0.045681189 |
| CLCN6: chloride channel 6 | NM_001286 | 6.53 | 0.008634214 |

TABLE 3-continued

Global gene expression profile of hFibs vs. Oct-4 transduced hFibs at Day 4

| GENES | Accession | Fold change | p-value |
|---|---|---|---|
| TNFSF4: tumor necrosis factor (ligand) superfamily, member 4 | NM_003326 | 6.46 | 0.040253375 |
| PMEPA1: prostate transmembrane protein, androgen induced 1 | NM_020182 | 6.38 | 0.002028046 |
| BAMBI: BMP and activin membrane-bound inhibitor homolog | NM_012342 | 6.38 | 0.034502411 |
| ZC3H12C: zinc finger CCCH-type containing 12C | NM_033390 | 6.24 | 0.019105365 |
| ADNP2: ADNP homeobox 2 | NM_014913 | 6.23 | 0.014858499 |
| DRAM: damage-regulated autophagy modulator | NM_018370 | 6.17 | 0.028646178 |
| CHRM4: cholinergic receptor, muscarinic 4 | NM_000741 | 6.15 | 0.010244254 |
| GCNT4: glucosaminyl (N-acetyl) transferase 4, core 2 | NM_016591 | 6.14 | 0.018575818 |
| GDF15: growth differentiation factor 15 | NM_004864 | 6.14 | 0.027566627 |
| HSD17B14: hydroxysteroid (17-beta) dehydrogenase 14 | NM_016246 | 6.12 | 0.028923662 |
| MAFF: v-maf musculoaponeurotic fibrosarcoma oncogene F | NM_012323 | 6.07 | 0.011992298 |
| POU5F1P1: POU class 5 homeobox 1 pseudogene 1 | NR_002304 | 6.05 | 0.007397716 |
| BCOR: BCL6 co-repressor | NM_001123385 | 6 | 0.030250342 |
| RBM24: RNA binding motif protein 24 | NM_153020 | 6 | 0.008244762 |
| MAFG: v-maf musculoaponeurotic fibrosarcoma oncogene G | NM_002359 | 5.98 | 0.035148933 |
| SCG2: secretogranin II (chromogranin C) | NM_003469 | 5.98 | 0.037412393 |
| IL8: interleukin 8 | NM_000584 | 5.96 | 0.02865206 |
| CPEB4: cytoplasmic polyadenylation element binding protein 4 | NM_030627 | 5.93 | 0.016746602 |
| KCNH1: potassium voltage-gated channel, subfamily H member 1 | NM_172362 | 5.93 | 0.01547663 |
| SCYL1BP1: SCY1-like 1 binding protein 1 | NM_152281 | 5.88 | 0.012966029 |
| ZNF317: zinc finger protein 317 | NM_020933 | 5.84 | 0.022725415 |
| TIFA: TRAF-interacting protein with forkhead-associated domain | NM_052864 | 5.84 | 0.033569825 |
| ZNF79: zinc finger protein 79 | NM_007135 | 5.74 | 0.007742455 |
| C3orf34: chromosome 3 open reading frame 34 | NM_032898 | 5.73 | 0.026236354 |
| ZNF155: zinc finger protein 155 | NM_003445 | 5.73 | 0.005506844 |
| HIST1H2BK: histone cluster 1, H2bk | NM_080593 | 5.71 | 0.015294734 |
| ZNF14: zinc finger protein 14 | NM_021030 | 5.7 | 0.03687599 |
| CCL2: chemokine (C-C motif) ligand 2 | NM_002982 | 5.7 | 0.008538229 |
| TP53INP1: tumor protein p53 inducible nuclear protein 1 | NM_033285 | 5.69 | 0.006633605 |
| C8orf46: chromosome 8 open reading frame 46 | BC028400 | 5.68 | 0.026344262 |
| VDR: vitamin D (1,25-dihydroxyvitamin D3) receptor | NM_001017535 | 5.67 | 0.013902566 |
| ZNF461: zinc finger protein 461 | NM_153257 | 5.65 | 0.025400068 |
| HES1: hairy and enhancer of split 1, (Drosophila) | NM_005524 | 5.64 | 0.038166108 |
| CDKN1A: cyclin-dependent kinase inhibitor 1A (p21, Cip1) | NM_078467 | 5.62 | 0.028474475 |
| HIST3H2A: histone cluster 3, H2a | NM_003445 | 5.59 | 0.008403117 |
| TXNIP: thioredoxin interacting protein | NM_006472 | 5.56 | 0.010732189 |
| RAB9A: RAB9A, member RAS oncogene family | NM_004251 | 5.55 | 0.02698267 |
| KCNC1: potassium voltage-gated channel 1 | L00621 | 5.52 | 0.005713574 |
| C21orf91: chromosome 21 open reading frame 91 | NM_001100420 | 5.49 | 0.005266017 |
| KCTD11: potassium channel tetramerisation domain containing 11 | NM_001002914 | 5.45 | 0.036695369 |
| ZNF436: zinc finger protein 436 | NM_001077195 | 5.44 | 0.025014862 |
| KLF11: Kruppel-like factor 11 | NM_003597 | 5.42 | 0.020441303 |
| ZNF790: zinc finger protein 790 | NM_206894 | 5.4 | 0.006140836 |
| PER1: period homolog 1 (Drosophila) | NM_002616 | 5.37 | 0.008493001 |
| ZHX2: zinc fingers and homeoboxes 2 | NM_014943 | 5.36 | 0.023595819 |
| SPATA18: spermatogenesis associated 18 homolog (rat) | NM_145263 | 5.32 | 0.033684731 |
| NR4A3: nuclear receptor subfamily 4, group A, member 3 | NM_173198 | 5.31 | 0.026475332 |
| CYP1B1: cytochrome P450, family 1, subfamily B, polypeptide 1 | NM_000104 | 5.29 | 0.01942686 |
| TSC22D3: TSC22 domain family, member 3 | NM_198057 | 5.29 | 0.012500308 |
| ZBTB1: zinc finger and BTB domain containing 1 | NM_001123329 | 5.29 | 0.024341909 |
| ZNF442: zinc finger protein 442 | NM_030824 | 5.27 | 0.004701685 |
| CDKN2AIP: CDKN2A interacting protein | NM_017632 | 5.26 | 0.002961744 |
| TNFRSF9: tumor necrosis factor receptor superfamily, member 9 | NM_001561 | 5.26 | 0.012292344 |
| RASL11B: RAS-like, family 11, member B | NM_023940 | 5.25 | 0.045697479 |
| KIAA1370: KIAA1370 | NM_019600 | 5.2 | 0.030797805 |
| LYPLAL1: lysophospholipase-like 1 | NM_138794 | 5.2 | 0.011640207 |
| STX3: syntaxin 3 | NM_004177 | 5.13 | 0.041739703 |
| CPEB2: cytoplasmic polyadenylation element binding protein 2 | NM_182485 | 5.09 | 0.006967805 |
| FAM83G: family with sequence similarity 83, member G | NM_001039999 | 5.09 | 0.014589212 |
| PLK2: polo-like kinase 2 (Drosophila) | NM_006622 | 5.08 | 0.006770249 |
| HSPA4L: heat shock 70 kDa protein 4-like | NM_014278 | 5.02 | 0.010568433 |
| ZNF585A: zinc finger protein 585A | NM_152655 | 4.98 | 0.026304196 |
| HS3ST2: heparan sulfate (glucosamine) 3-O-sulfotransferase 2 | NM_006043 | 4.98 | 0.04000135 |
| MAFG: v-maf musculoaponeurotic fibrosarcoma oncogene G | NM_032711 | 4.95 | 0.025633084 |

TABLE 3-continued

Global gene expression profile of hFibs vs. Oct-4 transduced hFibs at Day 4

| GENES | Accession | Fold change | p-value |
|---|---|---|---|
| TNF: tumor necrosis factor (TNF superfamily, member 2) | NM_000594 | 4.95 | 0.012786232 |
| TNF: tumor necrosis factor (TNF superfamily, member 2) | NM_000594 | 4.95 | 0.012786232 |
| TNF: tumor necrosis factor (TNF superfamily, member 2) | NM_000594 | 4.95 | 0.012786232 |
| ZNF433: zinc finger protein 433 | NM_001080411 | 4.91 | 0.008982418 |
| HBEGF: heparin-binding EGF-like growth factor | NM_001945 | 4.88 | 0.008424841 |
| ZNF354A: zinc finger protein 354A | NM_005649 | 4.87 | 0.023629804 |
| ZNF425: zinc finger protein 425 | NM_001001661 | 4.86 | 0.024180798 |
| JUNB: jun B proto-oncogene | NM_002229 | 4.86 | 0.021099531 |
| HIVEP1 | NM_002114 | 4.83 | 0.004781069 |
| GEM: GTP binding protein overexpressed in skeletal muscle | NM_005261 | 4.83 | 0.016619793 |
| SOD2: superoxide dismutase 2, mitochondrial | NM_001024465 | 4.82 | 0.004130069 |
| EGR3: early growth response 3 | NM_004430 | 4.81 | 0.011683548 |
| ZNF44: zinc finger protein 44 | NM_016264 | 4.78 | 0.028861556 |
| TLE4: transducin-like enhancer of split 4 | NM_007005 | 4.77 | 0.033194396 |
| FLJ27255: hypothetical LOC401281 | AK130765 | 4.76 | 0.04371683 |
| ZNF383: zinc finger protein 383 | NM_152604 | 4.75 | 0.046317321 |
| IFIT3: interferon-induced protein with tetratricopeptide repeats 3 | NM_001031683 | 4.75 | 0.019581114 |
| NFKBIE | NM_004556 | 4.74 | 0.029597747 |
| SMCR8: Smith-Magenis syndrome chromosome region, candidate 8 | NM_144775 | 4.72 | 0.01311253 |
| PLA2G4C: phospholipase A2, group IVC | NM_003706 | 4.7 | 0.002438767 |
| EDA2R: ectodysplasin A2 receptor | NM_021783 | 4.69 | 0.008321597 |
| TGFB2: transforming growth factor, beta 2 | NM_003238 | 4.68 | 0.040921831 |
| RASSF9: Ras association (RalGDS/AF-6) domain family member 9 | NM_005447 | 4.63 | 0.00865133 |
| LRRC32: leucine rich repeat containing 32 | NM_001128922 | 4.62 | 0.012902013 |
| NPY1R: neuropeptide Y receptor Y1 | NM_000909 | 4.61 | 0.029391154 |
| IL6: interleukin 6 (interferon, beta 2) | NM_000600 | 4.6 | 0.005204195 |
| TNFRSF10B: tumor necrosis factor receptor 10b | NM_003842 | 4.59 | 0.021271781 |
| FICD: FIC domain containing | NM_007076 | 4.57 | 0.005031673 |
| SC5DL: sterol-C5-desaturase-like | NM_006918 | 4.57 | 0.023382119 |
| RGS5: regulator of G-protein signaling 5 | NM_003617 | 4.57 | 0.003674002 |
| AEN: apoptosis enhancing nuclease | NM_022767 | 4.56 | 0.009974851 |
| ZNF627: zinc finger protein 627 | NM_145295 | 4.54 | 0.010467624 |
| MARCH3: membrane-associated ring finger (C3HC4) 3 | NM_178450 | 4.53 | 0.023826056 |
| BEST3: bestrophin 3 | NM_032735 | 4.47 | 0.010248807 |
| KCTD11: potassium channel tetramerisation domain containing 11 | NM_001002914 | 4.45 | 0.036728406 |
| LOC729127: hypothetical protein LOC729127 | AK092418 | 4.44 | 0.036166195 |
| DKK2: dickkopf homolog 2 (Xenopus laevis) | NM_014421 | 4.43 | 0.036152444 |
| ZNF222: zinc finger protein 222 | NM_013360 | 4.43 | 0.023199269 |
| FRS2: fibroblast growth factor receptor substrate 2 | NM_006654 | 4.4 | 0.009574668 |
| ZNF214: zinc finger protein 214 | NM_013249 | 4.39 | 0.005325101 |
| CDC14A: CDC14 cell division cycle 14 homolog A (S. cerevisiae) | NM_003672 | 4.38 | 0.024062032 |
| USP38: ubiquitin specific peptidase 38 | NM_032557 | 4.37 | 0.026290174 |
| PPP1R3B: protein phosphatase 1, regulatory (inhibitor) subunit 3B | NM_024607 | 4.35 | 0.023942719 |
| OSGIN1: oxidative stress induced growth inhibitor 1 | NM_013370 | 4.35 | 0.005808394 |
| ZNF542: zinc finger protein 542 | NR_003127 | 4.32 | 0.003693601 |
| NUAK2: NUAK family, SNF1-like kinase, 2 | NM_030952 | 4.32 | 0.004657622 |
| LOC440350: similar to nuclear pore complex interacting protein | NM_001018122 | 4.31 | 0.036134208 |
| ZNF10: zinc finger protein 10 | NM_015394 | 4.31 | 0.037020672 |
| C16orf87: chromosome 16 open reading frame 87 | BC056676 | 4.3 | 0.004525228 |
| GPR85: G protein-coupled receptor 85 | NM_018970 | 4.3 | 0.009011067 |
| ZBTB25: zinc finger and BTB domain containing 25 | NM_006977 | 4.3 | 0.032110574 |
| C1orf162: chromosome 1 open reading frame 162 | BC017973 | 4.29 | 0.02127661 |
| TDH: L-threonine dehydrogenase | NR_001578 | 4.29 | 0.030003012 |
| FNDC7: fibronectin type III domain containing 7 | NM_173532 | 4.26 | 0.014980274 |
| OSGIN2: oxidative stress induced growth inhibitor family member 2 | NM_004337 | 4.26 | 0.040290355 |
| PLEKHF2: pleckstrin homology domain containing, family F2 | NM_024613 | 4.26 | 0.019367416 |
| BTG2: BTG family, member 2 | NM_006763 | 4.26 | 0.000755183 |
| LY96: lymphocyte antigen 96 | NM_015364 | 4.26 | 0.045357606 |
| C3: complement component 3 | NM_000064 | 4.23 | 0.010904555 |
| SERTAD2: SERTA domain containing 2 | NM_014755 | 4.23 | 0.011727345 |
| DPY19L2P2: dpy-19-like 2 pseudogene 2 (C. elegans) | NR_003561 | 4.23 | 0.031876595 |
| FLVCR2: feline leukemia virus subgroup C cellular receptor 2 | NM_017791 | 4.21 | 0.044393143 |
| SQSTM1: sequestosome 1 | NM_003900 | 4.2 | 0.013064954 |
| ATXN7L1: ataxin 7-like 1 | NM_020725 | 4.19 | 0.011799405 |
| ICAM4: intercellular adhesion molecule 4 | NM_022377 | 4.18 | 0.029920502 |

TABLE 3-continued

Global gene expression profile of hFibs vs. Oct-4 transduced hFibs at Day 4

| GENES | Accession | Fold change | p-value |
|---|---|---|---|
| DYRK3: dual-specificity tyrosine-phosphorylation regulated kinase 3 | NM_001004023 | 4.18 | 0.002489408 |
| C12orf5: chromosome 12 open reading frame 5 | NM_020375 | 4.17 | 0.020099505 |
| NFE2L2: nuclear factor (erythroid-derived 2)-like 2 | NM_006164 | 4.15 | 0.013322293 |
| HIVEP2 | NM_006734 | 4.14 | 0.011002788 |
| RNF144B: ring finger 144B | NM_182757 | 4.12 | 0.047696251 |
| RELB: v-rel reticuloendotheliosis viral oncogene homolog B | NM_006509 | 4.12 | 0.024916205 |
| DNAJC6: DnaJ (Hsp40) homolog, subfamily C, member 6 | NM_014787 | 4.12 | 0.010416437 |
| BBS10: Bardet-Biedl syndrome 10 | NM_024685 | 4.11 | 0.024438054 |
| TIPARP: TCDD-inducible poly(ADP-ribose) polymerase | NM_015508 | 4.11 | 0.015065546 |
| ZFP112: zinc finger protein 112 homolog (mouse) | NM_001083335 | 4.11 | 0.02449417 |
| TMEM88: transmembrane protein 88 | NM_203411 | 4.1 | 0.021458994 |
| ZNF671: zinc finger protein 671 | NM_024833 | 4.1 | 0.012782651 |
| ENO3: enolase 3 (beta, muscle) | NM_001976 | 4.1 | 0.0448664 |
| RAD9B: RAD9 homolog B (S. cerevisiae) | NM_152442 | 4.09 | 0.00224161 |
| IER2: immediate early response 2 | NM_004907 | 4.09 | 0.027072343 |
| C5orf41: chromosome 5 open reading frame 41 | NM_153607 | 4.08 | 0.019814333 |
| MAMDC2: MAM domain containing 2 | NM_153267 | 4.08 | 0.034539195 |
| AVIL: advillin | NM_006576 | 4.08 | 0.00885929 |
| CLK4: CDC-like kinase 4 | NM_020666 | 4.06 | 0.041643886 |
| THAP1: THAP domain containing, apoptosis associated protein 1 | NM_018105 | 4.05 | 0.021316751 |
| IL11: interleukin 11 | NM_000641 | 4.04 | 0.028630107 |
| RND3: Rho family GTPase 3 | NM_005168 | 4.01 | 0.015595845 |
| FOXN2: forkhead box N2 | NM_002158 | 4.01 | 0.030011565 |
| CCNL1: cyclin L1 | NM_020307 | 4.01 | 0.017383657 |
| MAP2K1IP1 | NM_021970 | 4 | 0.036777936 |
| RNF146: ring finger protein 146 | NM_030963 | 4 | 0.036079701 |
| PCF11: PCF11, cleavage and polyadenylation factor subunit, homolog | NM_015885 | 3.99 | 0.007519478 |
| TIGD2: tigger transposable element derived 2 | NM_145715 | 3.99 | 0.018863445 |
| RAB30: RAB30, member RAS oncogene family | NM_014488 | 3.97 | 0.044990829 |
| ZNF566: zinc finger protein 566 | NM_032838 | 3.96 | 0.001066628 |
| SCAND3: SCAN domain containing 3 | NM_052923 | 3.95 | 0.008246658 |
| ZNF462: zinc finger protein 462 | NM_021224 | 3.95 | 0.022005711 |
| STX11: syntaxin 11 | NM_003764 | 3.93 | 0.030873581 |
| GBAP: glucosidase, beta; acid, pseudogene | NR_002188 | 3.93 | 0.00106888 |
| C10orf26: chromosome 10 open reading frame 26 | NM_017787 | 3.93 | 0.030090004 |
| DDB2: damage-specific DNA binding protein 2, 48 kDa | NM_000107 | 3.91 | 0.024058092 |
| ALKBH1: alkB, alkylation repair homolog 1 (E. coli) | NM_006020 | 3.91 | 0.022505275 |
| ARRDC4: arrestin domain containing 4 | NM_183376 | 3.9 | 0.002706984 |
| ZBTB6: zinc finger and BTB domain containing 6 | NM_006626 | 3.9 | 0.013105076 |
| ATXN7L1: ataxin 7-like 1 | NM_020725 | 3.89 | 0.038026386 |
| RASSF2: Ras association (RalGDS/AF-6) domain family member 2 | NM_014737 | 3.89 | 0.018647804 |
| ZNF563: zinc finger protein 563 | NM_145276 | 3.89 | 0.046559742 |
| C4orf18: chromosome 4 open reading frame 18 | NM_001128424 | 3.88 | 0.012934484 |
| TET3: tet oncogene family member 3 | NM_144993 | 3.87 | 0.015687232 |
| MGC42105: hypothetical protein MGC42105 | BC036422 | 3.87 | 0.045569556 |
| BLOC1S2: biogenesis of lysosomal organelles complex-1, subunit 2 | NM_001001342 | 3.86 | 0.005921207 |
| PELI1: pellino homolog 1 (Drosophila) | NM_020651 | 3.85 | 0.030042055 |
| ZNF160: zinc finger protein 160 | NM_001102603 | 3.85 | 0.028974443 |
| ZSWIM6: zinc finger, SWIM-type containing 6 | ENST00000252744 | 3.84 | 0.010331935 |
| C3orf59: chromosome 3 open reading frame 59 | BC036194 | 3.83 | 0.013149717 |
| HIST1H2AI: histone cluster 1, H2ai | NM_003509 | 3.82 | 0.026727634 |
| BCL6: B-cell CLL/lymphoma 6 | NM_001706 | 3.81 | 0.013140439 |
| ZNF669: zinc finger protein 669 | NM_024804 | 3.81 | 0.003810158 |
| C20orf111: chromosome 20 open reading frame 111 | NM_016470 | 3.81 | 0.000917602 |
| THAP6: THAP domain containing 6 | NM_144721 | 3.8 | 0.012056405 |
| THNSL1: threonine synthase-like 1 (S. cerevisiae) | NM_024838 | 3.79 | 0.039689189 |
| ZNF175: zinc finger protein 175 | NM_007147 | 3.78 | 0.014604301 |
| NFKB2 | NM_002502 | 3.77 | 0.0001512 |
| ZNF772: zinc finger protein 772 | NM_001024596 | 3.77 | 0.038266151 |
| BHLHB2: basic helix-loop-helix domain containing, class B, 2 | NM_003670 | 3.77 | 0.024753871 |
| C6orf58: chromosome 6 open reading frame 58 | AK303850 | 3.77 | 0.046923923 |
| ZNF211: zinc finger protein 211 | NM_006385 | 3.75 | 0.024268097 |
| C2orf67: chromosome 2 open reading frame 67 | NM_152519 | 3.73 | 0.009819026 |
| ERRFI1: ERBB receptor feedback inhibitor 1 | NM_018948 | 3.73 | 0.007138312 |
| HIST1H2AC: histone cluster 1, H2ac | NM_003512 | 3.73 | 0.025902603 |
| TMEM55B: transmembrane protein 55B | NM_001100814 | 3.72 | 0.028182102 |
| ZNF438: zinc finger protein 438 | NM_182755 | 3.7 | 0.020090563 |
| UAP1L1: UDP-N-acetylglucosamine pyrophosphorylase 1-like 1 | NM_207309 | 3.7 | 0.009016598 |
| ZNF506: zinc finger protein 506 | NM_001099269 | 3.7 | 0.019918406 |

TABLE 3-continued

Global gene expression profile of hFibs vs. Oct-4 transduced hFibs at Day 4

| GENES | Accession | Fold change | p-value |
|---|---|---|---|
| MAML2: mastermind-like 2 (Drosophila) | NM_032427 | 3.66 | 0.004011896 |
| IKZF3: IKAROS family zinc finger 3 (Aiolos) | NM_012481 | 3.65 | 0.049454019 |
| C3AR1: complement component 3a receptor 1 | U62027 | 3.65 | 0.027935192 |
| SLC9A8: solute carrier family 9, member 8 | NM_015266 | 3.64 | 0.035070108 |
| DCUN1D3: DCN1, defective in cullin neddylation 1 | NM_173475 | 3.63 | 0.020185386 |
| TNFRSF10C | NM_003841 | 3.63 | 0.022792614 |
| EAF1: ELL associated factor 1 | NM_033083 | 3.62 | 0.041518282 |
| TGFB3: transforming growth factor, beta 3 | NM_003239 | 3.61 | 0.042467987 |
| PLEKHO2: pleckstrin homology domain containing, family O 2 | NM_025201 | 3.61 | 0.00613281 |
| THAP2: THAP domain containing, apoptosis associated protein 2 | NM_031435 | 3.59 | 0.041850864 |
| CHMP2B: chromatin modifying protein 2B | NM_014043 | 3.58 | 0.019964868 |
| IFRD1: interferon-related developmental regulator 1 | NM_001550 | 3.57 | 0.005756425 |
| ACYP2: acylphosphatase 2, muscle type | NM_138448 | 3.57 | 0.044815679 |
| GAD1: glutamate decarboxylase 1 (brain, 67 kDa) | NM_000817 | 3.57 | 0.018872615 |
| ASH1L: ash1 (absent, small, or homeotic)-like (Drosophila) | NM_018489 | 3.56 | 0.024275028 |
| ZNF616: zinc finger protein 616 | NM_178523 | 3.55 | 0.016285018 |
| LUZP1: leucine zipper protein 1 | NM_033631 | 3.55 | 0.011709365 |
| NFKBIZ | NM_031419 | 3.55 | 0.020202803 |
| TRIM22: tripartite motif-containing 22 | NM_006074 | 3.55 | 0.024275441 |
| ZNF267: zinc finger protein 267 | NM_003414 | 3.55 | 0.015002939 |
| EXPH5: exophilin 5 | NM_015065 | 3.54 | 0.019518872 |
| ZNF226: zinc finger protein 226 | NM_001032372 | 3.54 | 0.040615764 |
| LOC400657: hypothetical LOC400657 | BC036588 | 3.53 | 0.005361606 |
| SLC7A8: solute carrier family 7, member 8 | NM_012244 | 3.52 | 0.044718749 |
| THUMPD2: THUMP domain containing 2 | NM_025264 | 3.52 | 0.020267196 |
| TLR4: toll-like receptor 4 | NM_138554 | 3.51 | 0.003298925 |
| C3orf38: chromosome 3 open reading frame 38 | BC024188 | 3.51 | 0.035632083 |
| FLJ31715: hypothetical protein FLJ31715 | BC022164 | 3.5 | 0.00661263 |
| RNF6: ring finger protein (C3H2C3 type) 6 | NM_005977 | 3.5 | 0.014090742 |
| ZSCAN12: zinc finger and SCAN domain containing 12 | BC041661 | 3.49 | 0.001409015 |
| MFAP4: microfibrillar-associated protein 4 | NM_002404 | 3.49 | 0.029486476 |
| CLEC2B: C-type lectin domain family 2, member B | NM_005127 | 3.49 | 0.016272762 |
| PPM1D: protein phosphatase 1D magnesium-dependent delta isoform | NM_003620 | 3.48 | 0.02416687 |
| IL1B: interleukin 1, beta | NM_000576 | 3.48 | 0.049947548 |
| ZNF284: zinc finger protein 284 | NM_001037813 | 3.48 | 0.019269189 |
| ZNF557: zinc finger protein 557 | NM_024341 | 3.47 | 0.041288469 |
| ZFP3: zinc finger protein 3 homolog (mouse) | NM_153018 | 3.47 | 0.008143118 |
| URG4: up-regulated gene 4 | NM_017920 | 3.45 | 0.004558363 |
| AVPI1: arginine vasopressin-induced 1 | NM_021732 | 3.45 | 0.0091021 |
| DUSP14: dual specificity phosphatase 14 | NM_007026 | 3.44 | 0.030281982 |
| FSTL3: follistatin-like 3 (secreted glycoprotein) | NM_005860 | 3.44 | 0.021558861 |
| FNIP1: folliculin interacting protein 1 | NM_133372 | 3.44 | 0.012239205 |
| ZNF416: zinc finger protein 416 | NM_017879 | 3.44 | 0.02687115 |
| LOC492311: similar to bovine IgA regulatory protein | NM_001007189 | 3.44 | 0.019195652 |
| RND1: Rho family GTPase 1 | NM_014470 | 3.44 | 0.010032455 |
| ZC3H6: zinc finger CCCH-type containing 6 | NM_198581 | 3.43 | 0.007049425 |
| TNFAIP6: tumor necrosis factor, alpha-induced protein 6 | NM_007115 | 3.43 | 0.037415638 |
| ZNF721: zinc finger protein 721 | NM_133474 | 3.43 | 0.014598811 |
| SLC16A6: solute carrier family 16, member 6 | NM_004694 | 3.43 | 0.036215977 |
| ZNF223: zinc finger protein 223 | NM_013361 | 3.43 | 0.011281453 |
| ZNF701: zinc finger protein 701 | NM_018260 | 3.43 | 0.041557926 |
| IL32: interleukin 32 | NM_001012631 | 3.43 | 0.043847422 |
| HIST2H2BF: histone cluster 2, H2bf | NM_001024599 | 3.42 | 0.009584114 |
| DBP: D site of albumin promoter (albumin D-box) binding protein | NM_001352 | 3.42 | 6.58E−05 |
| TGIF2: TGFB-induced factor homeobox 2 | NM_021809 | 3.41 | 0.007219969 |
| ZNF597: zinc finger protein 597 | NM_152457 | 3.41 | 0.016631685 |
| PAN2: PAN2 polyA specific ribonuclease subunit homolog | NM_014871 | 3.39 | 0.006176653 |
| FLRT2: fibronectin leucine rich transmembrane protein 2 | NM_013231 | 3.38 | 0.020458934 |
| BAZ2B: bromodomain adjacent to zinc finger domain, 2B | NM_013450 | 3.38 | 0.018290813 |
| FLCN: folliculin | NM_144997 | 3.38 | 0.008266513 |
| SLC30A1: solute carrier family 30 (zinc transporter), member 1 | NM_021194 | 3.37 | 0.015710802 |
| CSF1: colony stimulating factor 1 (macrophage) | NM_000757 | 3.37 | 0.021787205 |
| PRDM2: PR domain containing 2, with ZNF domain | NM_012231 | 3.37 | 0.041976521 |
| REPIN1: replication initiator 1 | NM_013400 | 3.36 | 0.033000065 |
| ENC1: ectodermal-neural cortex (with BTB-like domain) | NM_003633 | 3.36 | 0.015099205 |
| RPS27L: ribosomal protein S27-like | NM_015920 | 3.36 | 0.013107109 |
| NFKBIB | NM_002503 | 3.35 | 0.013479872 |
| MAP1LC3B2: microtubule-associated protein 1 light chain 3 beta 2 | NM_001085481 | 3.35 | 0.003838611 |

TABLE 3-continued

Global gene expression profile of hFibs vs. Oct-4 transduced hFibs at Day 4

| GENES | Accession | Fold change | p-value |
|---|---|---|---|
| MXD1: MAX dimerization protein 1 | NM_002357 | 3.34 | 0.00553368 |
| CAMKK1: calcium/calmodulin-dependent protein kinase kinase 1A | NM_032294 | 3.33 | 0.022850782 |
| FLJ42627: hypothetical LOC645644 | ENST00000382337 | 3.32 | 0.04630049 |
| ZNF292: zinc finger protein 292 | NM_015021 | 3.31 | 0.030126048 |
| PFKFB4: 6-phosphofructo-2-kinase/fructose-2,6-biphosphatase 4 | NM_004567 | 3.31 | 0.029334584 |
| RRAGD: Ras-related GTP binding D | NM_021244 | 3.31 | 0.04135844 |
| ZNF654: zinc finger protein 654 | NM_018293 | 3.3 | 0.000395798 |
| C2orf60: chromosome 2 open reading frame 60 | NR_004862 | 3.3 | 0.008611094 |
| CAP2: CAP, adenylate cyclase-associated protein, 2 (yeast) | NM_006366 | 3.29 | 0.000904472 |
| UVRAG: UV radiation resistance associated gene | NM_003369 | 3.26 | 0.010565147 |
| ZNF136: zinc finger protein 136 | NM_003437 | 3.26 | 0.035578432 |
| WDR63: WD repeat domain 63 | NM_145172 | 3.25 | 0.015959866 |
| ZNF329: zinc finger protein 329 | NM_024620 | 3.25 | 0.035125919 |
| CABLES1: Cdk5 and Abl enzyme substrate 1 | NM_138375 | 3.24 | 0.012237888 |
| ZFP37: zinc finger protein 37 homolog (mouse) | NM_003408 | 3.24 | 0.025496593 |
| GLIS2: GLIS family zinc finger 2 | NM_032575 | 3.23 | 0.00664897 |
| C1orf103: chromosome 1 open reading frame 103 | NM_018372 | 3.22 | 0.004213356 |
| CBLL1: Cas-Br-Mecotropic retroviral transforming sequence-like 1 | NM_024814 | 3.22 | 0.011303935 |
| RNASE7: ribonuclease, RNase A family, 7 | NM_032572 | 3.22 | 0.015976655 |
| C13orf31: chromosome 13 open reading frame 31 | NM_153218 | 3.22 | 0.041718086 |
| NSUN6: NOL1/NOP2/Sun domain family, member 6 | NM_182543 | 3.21 | 0.016203766 |
| EPC1: enhancer of polycomb homolog 1 (Drosophila) | NM_025209 | 3.21 | 0.015101279 |
| RNF185: ring finger protein 185 | NM_152267 | 3.21 | 0.015893453 |
| KCNRG: potassium channel regulator | NM_173605 | 3.21 | 0.024829485 |
| FAM179B: family with sequence similarity 179, member B | NM_015091 | 3.2 | 0.001910819 |
| HRH1: histamine receptor H1 | NM_001098213 | 3.2 | 0.014195297 |
| ZNF630: zinc finger protein 630 | NM_001037735 | 3.2 | 0.026240946 |
| TOPORS: topoisomerase I binding, arginine/serine-rich | NM_005802 | 3.19 | 0.004180115 |
| ZNF23: zinc finger protein 23 (KOX 16) | NM_145911 | 3.19 | 0.002448662 |
| MOSPD1: motile sperm domain containing 1 | NM_019556 | 3.19 | 0.020052342 |
| AMY2B: amylase, alpha 2B (pancreatic) | NM_020978 | 3.19 | 0.048103763 |
| HMGCL: 3-hydroxymethyl-3-methylglutaryl-Coenzyme A lyase | NM_000191 | 3.18 | 0.042673921 |
| FIGN: fidgetin | NM_018086 | 3.18 | 0.018511553 |
| TRAF1: TNF receptor-associated factor 1 | NM_005658 | 3.18 | 0.048973251 |
| ANKRA2: ankyrin repeat, family A (RFXANK-like), 2 | NM_023039 | 3.18 | 0.004596453 |
| CCDC126: coiled-coil domain containing 126 | NM_138771 | 3.17 | 0.042950357 |
| ZNF304: zinc finger protein 304 | NM_020657 | 3.16 | 0.029694616 |
| DUSP3: dual specificity phosphatase 3 | NM_004090 | 3.16 | 0.01052187 |
| FLJ32065: hypothetical protein FLJ32065 | BC073870 | 3.16 | 0.014638913 |
| GABARAPL2: GABA(A) receptor-associated protein-like 2 | NM_007285 | 3.15 | 0.02820069 |
| LOC441734: similar to hypothetical protein DKFZp434I1020 | XM_001715597 | 3.15 | 0.01559399 |
| C15orf51: chromosome 15 open reading frame 51 | AK125787 | 3.15 | 0.01559399 |
| KBTBD8: kelch repeat and BTB (POZ) domain containing 8 | NM_032505 | 3.15 | 0.032068177 |
| H1F0: H1 histone family, member 0 | NM_005318 | 3.15 | 0.022241211 |
| CRYM: crystallin, mu | NM_001888 | 3.15 | 0.016699474 |
| C6orf145: chromosome 6 open reading frame 145 | NM_183373 | 3.15 | 0.01871981 |
| ZNF408: zinc finger protein 408 | NM_024741 | 3.15 | 0.003167884 |
| BHLHB9: basic helix-loop-helix domain containing, class B, 9 | NM_030639 | 3.14 | 0.028051035 |
| ZNF555: zinc finger protein 555 | NM_152791 | 3.14 | 0.014099323 |
| YTHDF3: YTH domain family, member 3 | NM_152758 | 3.14 | 0.023192339 |
| SH3BGRL2: SH3 domain binding glutamic acid-rich protein like 2 | NM_031469 | 3.14 | 0.033107675 |
| DNAH12L: dynein, axonemal, heavy chain 12-like | NM_198564 | 3.14 | 0.037105609 |
| CTSS: cathepsin S | NM_004079 | 3.13 | 0.006028636 |
| JMJD1C: jumonji domain containing 1C | NM_004241 | 3.11 | 0.042616374 |
| PIWIL4: piwi-like 4 (Drosophila) | NM_152431 | 3.11 | 0.03192624 |
| SLC4A5: solute carrier family 4, sodium bicarbonate cotransporter 5 | NM_133478 | 3.11 | 0.004520157 |
| C1orf163: chromosome 1 open reading frame 163 | BC015313 | 3.1 | 0.017034213 |
| MFAP3L: microfibrillar-associated protein 3-like | NM_021647 | 3.1 | 0.010916007 |
| TMEM159: transmembrane protein 159 | NM_020422 | 3.1 | 0.043872113 |
| GABARAPL1: GABA(A) receptor-associated protein like 1 | NM_031412 | 3.1 | 0.041833295 |
| ZNF776: zinc finger protein 776 | NM_173632 | 3.1 | 0.003902668 |
| HIST1H2BG: histone cluster 1, H2bg | NM_003518 | 3.08 | 0.000239016 |
| FGF1: fibroblast growth factor 1 (acidic) | NM_000800 | 3.08 | 0.005135439 |
| BDNF: brain-derived neurotrophic factor | NM_170732 | 3.07 | 0.024437494 |
| LACTB2: lactamase, beta 2 | NM_016027 | 3.07 | 0.011861108 |
| LCP1: lymphocyte cytosolic protein 1 (L-plastin) | NM_002298 | 3.06 | 0.044037562 |
| MAFG: v-maf musculoaponeurotic fibrosarcoma oncogene G | NM_032711 | 3.06 | 0.023114742 |

TABLE 3-continued

Global gene expression profile of hFibs vs. Oct-4 transduced hFibs at Day 4

| GENES | Accession | Fold change | p-value |
|---|---|---|---|
| ZNF440: zinc finger protein 440 | NM_152357 | 3.06 | 0.010892152 |
| SLC31A2: solute carrier family 31 (copper transporters), member 2 | NM_001860 | 3.05 | 0.037146585 |
| CREB5: cAMP responsive element binding protein 5 | NM_182898 | 3.05 | 0.012201181 |
| PDRG1: p53 and DNA damage regulated 1 | NM_030815 | 3.05 | 0.032943493 |
| ERF: Ets2 repressor factor | NM_006494 | 3.05 | 0.004730393 |
| C5orf51: chromosome 5 open reading frame 51 | NM_175921 | 3.04 | 0.013194106 |
| ZNF137: zinc finger protein 137 | NR_023311 | 3.04 | 0.000792801 |
| RRAGC: Ras-related GTP binding C | NM_022157 | 3.03 | 0.024892917 |
| STAT2: signal transducer and activator of transcription 2, 113 kDa | NM_005419 | 3.03 | 0.028210059 |
| ZNF644: zinc finger protein 644 | NM_201269 | 3.02 | 0.000924768 |
| CAPS2: calcyphosine 2 | NM_032606 | 3.02 | 0.044140399 |
| ZNF546: zinc finger protein 546 | NM_178544 | 3.02 | 0.026749932 |
| TMEM69: transmembrane protein 69 | NM_016486 | 3.02 | 0.021783875 |
| HCCS: holocytochrome c synthase (cytochrome c heme-lyase) | NM_005333 | 3.01 | 0.019281137 |
| WBP2: WW domain binding protein 2 | NM_012478 | 3.01 | 0.046388537 |
| PIM3: pim-3 oncogene | NM_001001852 | 3.01 | 0.033321055 |
| EGR4: early growth response 4 | NM_001965 | 3.01 | 0.012383011 |
| PFKFB2: 6-phosphofructo-2-kinase/fructose-2,6-biphosphatase 2 | NM_006212 | 3.01 | 0.025738676 |
| ZNF235: zinc finger protein 235 | NM_004234 | 3.01 | 0.015058937 |
| ZNF658: zinc finger protein 658 | NM_033160 | 3 | 0.001825251 |
| LOC440348: similar to nuclear pore complex interacting protein | NM_001018059 | 3 | 0.023855828 |
| SOX4: SRY (sex determining region Y)-box 4 | NM_003107 | 3 | 0.033282073 |
| LINS1: lines homolog 1 (Drosophila) | NM_018148 | 3 | 0.014275826 |
| TRIM13: tripartite motif-containing 13 | NM_213590 | 3 | 0.002170186 |
| IDI1: isopentenyl-diphosphate delta isomerase 1 | NM_004508 | 3 | 0.021553025 |
| ZNF658: zinc finger protein 658 | NM_033160 | 2.99 | 0.002099728 |
| CHIC2: cysteine-rich hydrophobic domain 2 | NM_012110 | 2.99 | 0.036687396 |
| HIST3H2BB: histone cluster 3, H2bb | NM_175055 | 2.99 | 0.006331769 |
| CCR4: chemokine (C-C motif) receptor 4 | NM_005508 | 2.99 | 0.004204277 |
| ANKRD10: ankyrin repeat domain 10 | NM_017664 | 2.98 | 0.022670758 |
| ZNF132: zinc finger protein 132 | NM_003433 | 2.98 | 0.039673318 |
| PPIF: peptidylprolyl isomerase F (cyclophilin F) | NM_005729 | 2.98 | 0.033443052 |
| HEL308: DNA helicase HEL308 | NM_133636 | 2.98 | 0.041633691 |
| PAG1: phosphoprotein associated glycosphingolipid microdomains 1 | NM_018440 | 2.97 | 0.006118738 |
| LRRC37B: leucine rich repeat containing 37B | NM_052888 | 2.97 | 0.014791612 |
| TSC22D2: TSC22 domain family, member 2 | NM_014779 | 2.96 | 0.025805661 |
| MITD1: MIT domain containing 1 | NM_138798 | 2.96 | 0.02073231 |
| KCNAB1: potassium voltage-gated channel, beta member 1 | NM_003471 | 2.95 | 0.020186746 |
| ZNF253: zinc finger protein 253 | NM_021047 | 2.95 | 0.022609189 |
| AOC2: amine oxidase, copper containing 2 (retina-specific) | NM_009590 | 2.94 | 0.029979527 |
| ZNF503: zinc finger protein 503 | NM_032772 | 2.94 | 0.010841563 |
| LHX4: LIM homeobox 4 | NM_033343 | 2.94 | 0.019586398 |
| ZNF26: zinc finger protein 26 | NM_019591 | 2.93 | 0.012211671 |
| ZNF502: zinc finger protein 502 | NM_033210 | 2.93 | 0.037008738 |
| CHMP1B: chromatin modifying protein 1B | NM_020412 | 2.92 | 0.026047526 |
| RUNX1: runt-related transcription factor 1 | NM_001001890 | 2.91 | 0.033938878 |
| H2AFJ: H2A histone family, member J | NM_177925 | 2.91 | 0.022343125 |
| ATP6V1G1: ATPase, H+ transporting, V1 subunit G1 | NM_004888 | 2.9 | 0.019366028 |
| GZF1: GDNF-inducible zinc finger protein 1 | NM_022482 | 2.9 | 0.017043271 |
| CCDC122: coiled-coil domain containing 122 | NM_144974 | 2.89 | 0.014344725 |
| FAM53C: family with sequence similarity 53, member C | AF251040 | 2.88 | 0.013675061 |
| HSD17B7: hydroxysteroid (17-beta) dehydrogenase 7 | NM_016371 | 2.88 | 0.010531032 |
| KLF7: Kruppel-like factor 7 (ubiquitous) | NM_003709 | 2.88 | 0.021964801 |
| C9orf85: chromosome 9 open reading frame 85 | NM_182505 | 2.88 | 0.00686446 |
| ABHD4: abhydrolase domain containing 4 | NM_022060 | 2.87 | 0.026745454 |
| ZNF330: zinc finger protein 330 | NM_014487 | 2.87 | 0.046210196 |
| KIAA0415: KIAA0415 | NM_014855 | 2.87 | 0.00640548 |
| GCA: grancalcin, EF-hand calcium binding protein | NM_012198 | 2.87 | 0.0486402 |
| SGIP1: SH3-domain GRB2-like (endophilin) interacting protein 1 | NM_032291 | 2.87 | 0.022835814 |
| TMEM144: transmembrane protein 144 | NM_018342 | 2.87 | 0.045265032 |
| FBXW7: F-box and WD repeat domain containing 7 | NM_033632 | 2.87 | 0.004759001 |
| RAB7L1: RAB7, member RAS oncogene family-like 1 | NM_003929 | 2.86 | 0.046141351 |
| C2orf76: chromosome 2 open reading frame 76 | BC126397 | 2.86 | 0.004536406 |
| ASPN: asporin | NM_017680 | 2.86 | 0.019873462 |
| ATP13A3: ATPase type 13A3 | NM_024524 | 2.85 | 0.007598924 |
| HRASLS3: HRAS-like suppressor 3 | NM_007069 | 2.85 | 0.043777915 |

TABLE 3-continued

Global gene expression profile of hFibs vs. Oct-4 transduced hFibs at Day 4

| GENES | Accession | Fold change | p-value |
|---|---|---|---|
| CHCHD7: coiled-coil-helix-coiled-coil-helix domain containing 7 | NM_001011667 | 2.85 | 0.023108464 |
| NUFIP2 | NM_020772 | 2.84 | 0.010392776 |
| C6orf199: chromosome 6 open reading frame 199 | NM_145025 | 2.84 | 0.026233691 |
| HEXIM1: hexamethylene bis-acetamide inducible 1 | NM_006460 | 2.84 | 0.038002092 |
| GCH1: GTP cyclohydrolase 1 | NM_000161 | 2.84 | 0.042076474 |
| FAM21C: family with sequence similarity 21, member C | BC006456 | 2.83 | 0.01912708 |
| ANKRD1: ankyrin repeat domain 1 (cardiac muscle) | NM_014391 | 2.82 | 0.036347211 |
| NOG: noggin | NM_005450 | 2.82 | 0.038775993 |
| ZNF564: zinc finger protein 564 | NM_144976 | 2.82 | 0.020106104 |
| USP50: ubiquitin specific peptidase 50 | NM_203494 | 2.82 | 0.028093525 |
| C17orf91: chromosome 17 open reading frame 91 | NM_032895 | 2.82 | 0.021603548 |
| KLF15: Kruppel-like factor 15 | NM_014079 | 2.82 | 0.025628131 |
| RNF169: ring finger protein 169 | NM_001098638 | 2.81 | 0.033029936 |
| PER3: period homolog 3 (*Drosophila*) | NM_016831 | 2.81 | 0.006609059 |
| ZNF658: zinc finger protein 658 | NM_033160 | 2.8 | 0.011159824 |
| ZNF717: zinc finger protein 717 | NM_001128223 | 2.8 | 0.049503262 |
| ZBTB4: zinc finger and BTB domain containing 4 | NM_020899 | 2.8 | 0.00983032 |
| HEATR2: HEAT repeat containing 2 | NM_017802 | 2.8 | 0.037293252 |
| ZNF24: zinc finger protein 24 | NM_006965 | 2.8 | 0.011006306 |
| ZNF828: zinc finger protein 828 | NM_032436 | 2.8 | 0.003323432 |
| IKZF5: IKAROS family zinc finger 5 (Pegasus) | NM_022466 | 2.79 | 0.032055423 |
| ZNF91: zinc finger protein 91 | NM_003430 | 2.79 | 0.045198612 |
| MRAS: muscle RAS oncogene homolog | NM_012219 | 2.78 | 0.045059597 |
| NAP1L3: nucleosome assembly protein 1-like 3 | NM_004538 | 2.78 | 0.041693897 |
| C7orf38: chromosome 7 open reading frame 38 | NM_145111 | 2.78 | 0.03911549 |
| YOD1: YOD1 OTU deubiquinating enzyme 1 homolog (*S. cerevisiae*) | NM_018566 | 2.77 | 0.019176899 |
| MGC21874: transcriptional adaptor 2 (ADA2 homolog, yeast)-beta | NM_152293 | 2.77 | 0.025006478 |
| LBA1: lupus brain antigen 1 | NM_014831 | 2.77 | 0.007283661 |
| KLHL28: kelch-like 28 (*Drosophila*) | NM_017658 | 2.77 | 0.031353233 |
| ZNF256: zinc finger protein 256 | NM_005773 | 2.77 | 0.04807829 |
| ACTA2: actin, alpha 2, smooth muscle, aorta | NM_001613 | 2.76 | 0.024924217 |
| TMEM217: transmembrane protein 217 | ENST00000336655 | 2.76 | 0.010262657 |
| LOC554203: hypothetical LOC554203 | BC029480 | 2.76 | 0.026347446 |
| CYLD: cylindromatosis (turban tumor syndrome) | NM_015247 | 2.76 | 0.018718919 |
| BRF2 | NM_018310 | 2.75 | 0.046389996 |
| C2orf58: chromosome 2 open reading frame 58 | BC031410 | 2.75 | 0.029184398 |
| LGALS8: lectin, galactoside-binding, soluble, 8 | NM_006499 | 2.75 | 0.014605358 |
| ZMAT3: zinc finger, matrin type 3 | NM_022470 | 2.74 | 0.012078936 |
| ZBTB43: zinc finger and BTB domain containing 43 | NM_014007 | 2.74 | 0.004556569 |
| DACT1: dapper, antagonist of beta-catenin, homolog 1 | NM_016651 | 2.74 | 0.03256625 |
| ZNF16: zinc finger protein 16 | NM_001029976 | 2.74 | 0.001098076 |
| ZNF548: zinc finger protein 548 | NM_152909 | 2.73 | 0.025890232 |
| PLEKHM1: pleckstrin homology domain containing, family M 1 | NM_014798 | 2.73 | 0.034581207 |
| PLEKHA7: pleckstrin homology domain containing, family A7 | NM_175058 | 2.73 | 0.006939973 |
| SNAPC1: small nuclear RNA activating complex, polypeptide 1 | NM_003082 | 2.73 | 0.004723659 |
| ZNF791: zinc finger protein 791 | NM_153358 | 2.72 | 0.02484794 |
| ABCA5: ATP-binding cassette, sub-family A (ABC1), member 5 | NM_018672 | 2.72 | 0.049190357 |
| ZNF264: zinc finger protein 264 | NM_003417 | 2.72 | 0.006854892 |
| SERPINB8: serpin peptidase inhibitor, Clade B, member 8 | NM_002640 | 2.72 | 0.002638449 |
| SNX16: sorting nexin 16 | NM_022133 | 2.72 | 0.017835039 |
| SLFN12: schlafen family member 12 | NM_018042 | 2.72 | 0.008484158 |
| ZNF510: zinc finger protein 510 | NM_014930 | 2.72 | 0.005467203 |
| NKAPL: NFKB activating protein-like | NM_001007531 | 2.72 | 0.049874159 |
| BEX1: brain expressed, X-linked 1 | NM_018476 | 2.72 | 0.011962857 |
| CXCL1: chemokine (C—X—C motif) ligand 1 | NM_001511 | 2.71 | 0.036675901 |
| FAM21B: family with sequence similarity 21, member B | NM_018232 | 2.71 | 0.018369561 |
| JAG1: jagged 1 (Alagille syndrome) | NM_000214 | 2.71 | 0.018840282 |
| TPP1: tripeptidyl peptidase I | NM_000391 | 2.71 | 0.002388114 |
| ZBTB20: zinc finger and BTB domain containing 20 | NM_015642 | 2.71 | 0.007968807 |
| CLN5: ceroid-lipofuscinosis, neuronal 5 | NM_006493 | 2.71 | 0.015628021 |
| CNOT6L: CCR4-NOT transcription complex, subunit 6-like | uc003hkt.1 | 2.7 | 0.023687729 |
| FAM21A: family with sequence similarity 21, member A | NM_001005751 | 2.7 | 0.017431301 |
| ZNF827: zinc finger protein 827 | NM_178835 | 2.7 | 0.049900335 |
| ZNF532: zinc finger protein 532 | NM_018181 | 2.7 | 0.007489661 |
| MAFK: v-maf musculoaponeurotic fibrosarcoma oncogene homolog K | NM_002360 | 2.7 | 0.002017768 |
| PHLDA3: pleckstrin homology-like domain, family A, member 3 | NM_012396 | 2.7 | 0.024222899 |

TABLE 3-continued

Global gene expression profile of hFibs vs. Oct-4 transduced hFibs at Day 4

| GENES | Accession | Fold change | p-value |
|---|---|---|---|
| MAFB: v-maf musculoaponeurotic fibrosarcoma oncogene homolog B | NM_005461 | 2.7 | 0.015500473 |
| FAM21C: family with sequence similarity 21, member C | NM_015262 | 2.69 | 0.019375457 |
| ZNF350: zinc finger protein 350 | NM_021632 | 2.69 | 0.008588347 |
| SLC19A2: solute carrier family 19 (thiamine transporter), member 2 | NM_006996 | 2.69 | 0.043004634 |
| TMEM199: transmembrane protein 199 | NM_152464 | 2.68 | 0.014440283 |
| CPEB1: cytoplasmic polyadenylation element binding protein 1 | NM_030594 | 2.68 | 0.02172188 |
| PRICKLE2: prickle homolog 2 (Drosophila) | NM_198859 | 2.68 | 0.037670176 |
| ATP6V0A1: ATPase, H+ transporting, lysosomal V0 subunit a1 | NM_005177 | 2.68 | 0.032523311 |
| RRM2B: ribonucleotide reductase M2 B (TP53 inducible) | NM_015713 | 2.68 | 0.046469533 |
| CHD2: chromodomain helicase DNA binding protein 2 | NM_001271 | 2.67 | 0.007327301 |
| CLN8: ceroid-lipofuscinosis, neuronal 8 | NM_018941 | 2.67 | 0.035461042 |
| NEDD4L | NM_015277 | 2.67 | 0.028872166 |
| ZNF337: zinc finger protein 337 | NM_015655 | 2.67 | 0.003300715 |
| CD24: CD24 molecule | NM_013230 | 2.67 | 0.020529003 |
| PGF: placental growth factor | NM_002632 | 2.66 | 0.005902837 |
| ARID5A: AT rich interactive domain 5A (MRF1-like) | NM_212481 | 2.66 | 0.017133097 |
| ZNF567: zinc finger protein 567 | NM_152603 | 2.66 | 0.020423909 |
| NRIP1: nuclear receptor interacting protein 1 | NM_003489 | 2.65 | 0.004930566 |
| CYFIP2: cytoplasmic FMR1 interacting protein 2 | NM_001037332 | 2.65 | 0.008498776 |
| TXNL4B: thioredoxin-like 4B | NM_017853 | 2.65 | 0.002878021 |
| ZNF625: zinc finger protein 625 | NM_145233 | 2.65 | 0.005918898 |
| REV3L: REV3-like, catalytic subunit of DNA polymerase zeta (yeast) | NM_002912 | 2.64 | 0.004548281 |
| ZNF75A: zinc finger protein 75a | NM_153028 | 2.64 | 0.01291228 |
| BCDIN3D: BCDIN3 domain containing | NM_181708 | 2.64 | 0.006288708 |
| SNORD74: small nucleolar RNA, C/D box 74 | NR_002579 | 2.63 | 0.033620987 |
| MRC1: mannose receptor, C type 1 | NM_002438 | 2.63 | 0.039469245 |
| MRC1: mannose receptor, C type 1 | NM_002438 | 2.63 | 0.039469245 |
| TCEAL1: transcription elongation factor A (SII)-like 1 | NM_004780 | 2.63 | 0.049397508 |
| ATXN7L1: ataxin 7-like 1 | NM_020725 | 2.63 | 0.000802799 |
| FRMPD4: FERM and PDZ domain containing 4 | NM_014728 | 2.62 | 0.017275209 |
| NEK10: NIMA (never in mitosis gene a)-related kinase 10 | NM_001031741 | 2.62 | 0.029767874 |
| SERINC4: serine incorporator 4 | NM_001033517 | 2.62 | 0.018049001 |
| LYRM1: LYR motif containing 1 | NM_001128301 | 2.62 | 0.027769738 |
| BBS12: Bardet-Biedl syndrome 12 | NM_152618 | 2.62 | 0.008328017 |
| ZNF682: zinc finger protein 682 | NM_033196 | 2.62 | 0.026858035 |
| ZNF134: zinc finger protein 134 | NM_003435 | 2.62 | 0.011255455 |
| PLEKHM1: pleckstrin homology domain containing, family M 1 | NM_014798 | 2.61 | 0.002848361 |
| ZNF778: zinc finger protein 778 | AK295122 | 2.61 | 0.024163823 |
| PARP6: poly (ADP-ribose) polymerase family, member 6 | NM_020214 | 2.61 | 0.007097119 |
| C1orf71: chromosome 1 open reading frame 71 | BC036200 | 2.61 | 0.019765437 |
| CTGLF1: centaurin, gamma-like family, member 1 | NM_133446 | 2.61 | 0.001608268 |
| NKIRAS1: NFKB inhibitor interacting Ras-like 1 | NM_020345 | 2.61 | 0.00450932 |
| LIN52: lin-52 homolog (C. elegans) | NM_001024674 | 2.61 | 0.036814203 |
| ZNF570: zinc finger protein 570 | NM_144694 | 2.61 | 0.03229297 |
| RUSC2: RUN and SH3 domain containing 2 | NM_014806 | 2.6 | 0.03546014 |
| SOCS2: suppressor of cytokine signaling 2 | NM_003877 | 2.6 | 0.033684386 |
| SECTM1: secreted and transmembrane 1 | NM_003004 | 2.6 | 0.023641895 |
| ZNF700: zinc finger protein 700 | NM_144566 | 2.6 | 0.012243042 |
| SPRY1: sprouty homolog 1, antagonist of FGF signaling (Drosophila) | NM_005841 | 2.59 | 0.041400742 |
| SOX30: SRY (sex determining region Y)-box 30 | NM_178424 | 2.59 | 0.037951891 |
| IPMK: inositol polyphosphate multikinase | NM_152230 | 2.59 | 0.019722475 |
| CFLAR: CASP8 and FADD-like apoptosis regulator | NM_003879 | 2.59 | 0.026917209 |
| ZNF521: zinc finger protein 521 | NM_015461 | 2.58 | 0.007436907 |
| AKAP5: A kinase (PRKA) anchor protein 5 | NM_004857 | 2.58 | 0.044644534 |
| ZNF782: zinc finger protein 782 | NM_001001662 | 2.58 | 0.012649402 |
| PGBD4: piggyBac transposable element derived 4 | NM_152595 | 2.57 | 0.017883939 |
| ZNF606: zinc finger protein 606 | NM_025027 | 2.57 | 0.026449335 |
| ZIK1: zinc finger protein interacting with K protein 1 homolog | NM_001010879 | 2.57 | 0.020046311 |
| CYP2U1: cytochrome P450, family 2, subfamily U, polypeptide 1 | NM_183075 | 2.57 | 0.038943828 |
| ZFP82: zinc finger protein 82 homolog (mouse) | NM_133466 | 2.57 | 0.004413068 |
| RAPH1: Ras association and pleckstrin homology domains 1 | NM_213589 | 2.57 | 0.041700053 |
| SERTAD1: SERTA domain containing 1 | NM_013376 | 2.57 | 0.004734306 |
| ZFAND3: zinc finger, AN1-type domain 3 | NM_021943 | 2.56 | 0.015371302 |
| IL23A: interleukin 23, alpha subunit p19 | NM_016584 | 2.56 | 0.005208438 |
| HSPBAP1: HSPB (heat shock 27 kDa) associated protein 1 | NM_024610 | 2.56 | 0.036345288 |
| GPR175: G protein-coupled receptor 175 | NM_016372 | 2.56 | 0.031915764 |

TABLE 3-continued

Global gene expression profile of hFibs vs. Oct-4 transduced hFibs at Day 4

| GENES | Accession | Fold change | p-value |
|---|---|---|---|
| SULF2: sulfatase 2 | NM_018837 | 2.56 | 0.01434201 |
| LRP12: low density lipoprotein-related protein 12 | NM_013437 | 2.55 | 0.043058142 |
| CCNT1: cyclin T1 | NM_001240 | 2.55 | 0.015958873 |
| SH2D5: SH2 domain containing 5 | NM_001103161 | 2.55 | 0.04569523 |
| ZRSR1: zinc finger, RNA-binding motif and serine/arginine rich 1 | BC104811 | 2.55 | 0.037279199 |
| EPM2AIP1: EPM2A (laforin) interacting protein 1 | NM_014805 | 2.55 | 0.031524174 |
| ZNF397OS: zinc finger protein 397 opposite strand | NM_001112734 | 2.55 | 0.024817293 |
| ZNF154: zinc finger protein 154 | NM_001085384 | 2.54 | 0.012185399 |
| RNF114: ring finger protein 114 | NM_018683 | 2.54 | 0.043374183 |
| IHPK1: inositol hexaphosphate kinase 1 | NM_153273 | 2.54 | 0.022995342 |
| HOXC8: homeobox C8 | NM_022658 | 2.54 | 0.047486075 |
| TNFRSF14: tumor necrosis factor receptor superfamily, member 14 | NM_003820 | 2.54 | 0.032832484 |
| ZNF84: zinc finger protein 84 | NM_003428 | 2.54 | 0.004189893 |
| YAF2: YY1 associated factor 2 | NM_005748 | 2.54 | 0.036728538 |
| CAMSAP1L1: calmodulin regulated spectrin-assoc protein 1-like 1 | NM_203459 | 2.53 | 0.006181221 |
| UBE2W: ubiquitin-conjugating enzyme E2W (putative) | NM_001001481 | 2.53 | 0.019177154 |
| MAP3K14: mitogen-activated protein kinase kinase kinase 14 | NM_003954 | 2.52 | 0.009347849 |
| JUN: jun oncogene | NM_002228 | 2.52 | 0.025787819 |
| STARD10: StAR-related lipid transfer (START) domain containing 10 | NM_006645 | 2.52 | 0.016934182 |
| ZNF295: zinc finger protein 295 | NM_001098402 | 2.52 | 0.035475391 |
| UTP23: UTP23, small subunit processome component, homolog | NM_032334 | 2.52 | 0.023322121 |
| HSPA2: heat shock 70 kDa protein 2 | NM_021979 | 2.52 | 0.006220521 |
| VPS18: vacuolar protein sorting 18 homolog (S. cerevisiae) | NM_020857 | 2.51 | 0.01913541 |
| C18orf1: chromosome 18 open reading frame 1 | NM_181481 | 2.51 | 0.048450596 |
| LOC100129391 | XR_039731 | 2.51 | 0.045691432 |
| TBC1D3F: TBC1 domain family, member 3F | NM_001123391 | 2.5 | 0.002900422 |
| ZFP36L2: zinc finger protein 36, C3H type-like 2 | NM_006887 | 2.5 | 0.000712886 |
| FAM111A: family with sequence similarity 111, member A | NM_022074 | 2.5 | 0.031234434 |
| ZNF468: zinc finger protein 468 | NM_199132 | 2.5 | 0.018361656 |
| TULP4: tubby like protein 4 | NM_020245 | 2.5 | 0.02789447 |
| ZNF225: zinc finger protein 225 | NM_013362 | 2.5 | 0.024727473 |
| ANAPC13: anaphase promoting complex subunit 13 | NM_015391 | 2.49 | 0.036719162 |
| SNORD60: small nucleolar RNA, C/D box 60 | NR_002736 | 2.49 | 0.03197453 |
| CCDC121: coiled-coil domain containing 121 | NM_024584 | 2.49 | 0.004406989 |
| TANC1 | NM_033394 | 2.48 | 0.02900901 |
| PPP3CC: protein phosphatase 3, catalytic subunit, gamma isoform | NM_005605 | 2.48 | 0.01663471 |
| RGS2: regulator of G-protein signaling 2, 24 kDa | NM_002923 | 2.48 | 0.037062472 |
| KIAA0241: KIAA0241 | BC027724 | 2.48 | 0.002515659 |
| MR1: major histocompatibility complex, class I-related | NM_001531 | 2.48 | 0.029696928 |
| AADACL1: arylacetamide deacetylase-like 1 | NM_020792 | 2.48 | 0.041042532 |
| BACH1 | NM_001011545 | 2.48 | 0.004227532 |
| PPP1R10: protein phosphatase 1, regulatory (inhibitor) subunit 10 | NM_002714 | 2.48 | 0.035152814 |
| PPP1R10: protein phosphatase 1, regulatory (inhibitor) subunit 10 | NM_002714 | 2.48 | 0.035152814 |
| PPP1R10: protein phosphatase 1, regulatory (inhibitor) subunit 10 | NM_002714 | 2.48 | 0.035152814 |
| C10orf11: chromosome 10 open reading frame 11 | NM_032024 | 2.48 | 0.003430419 |
| PRKAB1: protein kinase, AMP-activated, beta 1 non-catalytic subunit | NM_006253 | 2.47 | 0.034879309 |
| ZSCAN21: zinc finger and SCAN domain containing 21 | NM_145914 | 2.47 | 0.005947306 |
| NFIL3: nuclear factor, interleukin 3 regulated | NM_005384 | 2.47 | 0.044021278 |
| LOC134466: hypothetical protein LOC134466 | BC117490 | 2.47 | 0.027151542 |
| DHRS2: dehydrogenase/reductase (SDR family) member 2 | NM_182908 | 2.46 | 0.016509992 |
| ZBTB38: zinc finger and BTB domain containing 38 | NM_001080412 | 2.46 | 0.013776215 |
| SPHK1: sphingosine kinase 1 | NM_182965 | 2.46 | 0.027427305 |
| TAF7: TAF7 RNA polymerase II | NM_005642 | 2.46 | 0.023230123 |
| OSTM1: osteopetrosis associated transmembrane protein 1 | NM_014028 | 2.46 | 0.033109621 |
| RBM18: RNA binding motif protein 18 | NM_033117 | 2.45 | 0.008237294 |
| JMJD3: jumonji domain containing 3, histone lysine demethylase | NM_001080424 | 2.45 | 0.024600464 |
| REST: RE1-silencing transcription factor | NM_005612 | 2.45 | 0.00552277 |
| RP4-692D3.1: hypothetical protein LOC728621 | NM_001080850 | 2.45 | 0.02107732 |
| ZNF124: zinc finger protein 124 | NM_003431 | 2.45 | 0.043244159 |
| GRIA3: glutamate receptor, ionotrophic, AMPA 3 | NM_007325 | 2.45 | 0.028388193 |
| FAM117A: family with sequence similarity 117, member A | NM_030802 | 2.45 | 0.010742758 |
| XG: Xg blood group | NM_175569 | 2.44 | 0.011411205 |
| YTHDF1: YTH domain family, member 1 | NM_017798 | 2.44 | 0.020105104 |

TABLE 3-continued

Global gene expression profile of hFibs vs. Oct-4 transduced hFibs at Day 4

| GENES | Accession | Fold change | p-value |
|---|---|---|---|
| CTGLF1: centaurin, gamma-like family, member 1 | NM_133446 | 2.44 | 0.004400434 |
| TIMM8B: translocase of inner mitochondrial membrane 8 homolog B | NM_012459 | 2.44 | 0.007086815 |
| BTLA: B and T lymphocyte associated | NM_181780 | 2.43 | 0.019285607 |
| IER5: immediate early response 5 | NM_016545 | 2.43 | 0.018710829 |
| CBX4: chromobox homolog 4 (Pc class homolog, *Drosophila*) | NM_003655 | 2.43 | 0.043713256 |
| C14orf4: chromosome 14 open reading frame 4 | NM_024496 | 2.43 | 0.015055592 |
| C1orf156: chromosome 1 open reading frame 156 | NM_033418 | 2.43 | 0.003402752 |
| ZNF182: zinc finger protein 182 | NM_006962 | 2.41 | 0.026539813 |
| MRFAP1L1: Morf4 family associated protein 1-like 1 | NM_152301 | 2.41 | 0.010913873 |
| ZNF562: zinc finger protein 562 | NM_017656 | 2.41 | 0.015210224 |
| SIAH1: seven in absentia homolog 1 (*Drosophila*) | NM_001006610 | 2.41 | 0.047668015 |
| SAMD4A: sterile alpha motif domain containing 4A | NM_015589 | 2.41 | 0.043929127 |
| LYSMD3: LysM, putative peptidoglycan-binding, domain containing 3 | NM_198273 | 2.4 | 0.013244322 |
| RAB32: RAB32, member RAS oncogene family | NM_006834 | 2.4 | 0.042963641 |
| ADHFE1: alcohol dehydrogenase, iron containing, 1 | NM_144650 | 2.4 | 0.007977862 |
| ZFX: zinc finger protein, X-linked | NM_003410 | 2.39 | 0.035056766 |
| DKFZp547E087: hypothetical gene LOC283846 | BC061522 | 2.39 | 0.000146979 |
| FBXO28: F-box protein 28 | NM_015176 | 2.39 | 0.006737537 |
| DKFZp547E087: hypothetical gene LOC283846 | BC061522 | 2.39 | 0.005521916 |
| ZFHX4: zinc finger homeobox 4 | NM_024721 | 2.39 | 0.035823484 |
| SAT2: spermidine/spermine N1-acetyltransferase family member 2 | NM_133491 | 2.39 | 0.045021804 |
| ZEB2: zinc finger E-box binding homeobox 2 | NM_014795 | 2.39 | 0.042396204 |
| F2RL2: coagulation factor II (thrombin) receptor-like 2 | NM_004101 | 2.39 | 0.033316614 |
| GABARAPL3: GABA(A) receptors associated protein like 3 | AF180519 | 2.39 | 0.031729422 |
| DKFZp547E087: hypothetical gene LOC283846 | BC061522 | 2.38 | 0.002440052 |
| NFKB1 | NM_003998 | 2.38 | 0.03972863 |
| MOCS3: molybdenum cofactor synthesis 3 | NM_014484 | 2.38 | 0.013561043 |
| ZNF641: zinc finger protein 641 | NM_152320 | 2.38 | 0.038163805 |
| RCHY1: ring finger and CHY zinc finger domain containing 1 | NM_015436 | 2.38 | 0.008242317 |
| DKFZp547E087: hypothetical gene LOC283846 | BC061522 | 2.37 | 0.000838747 |
| PEA15: phosphoprotein enriched in astrocytes 15 | NM_003768 | 2.37 | 0.030845268 |
| PLCXD2 | NM_153268 | 2.37 | 0.013924114 |
| ZNF592: zinc finger protein 592 | NM_014630 | 2.37 | 0.005080807 |
| HECW2: HECT, C2 and WW domain containing E3 ubiquitin ligase 2 | NM_020760 | 2.37 | 0.029247963 |
| VAMP2: vesicle-associated membrane protein 2 (synaptobrevin 2) | NM_014232 | 2.37 | 0.034921211 |
| C1GALT1 | NM_020156 | 2.37 | 0.028333801 |
| C17orf48: chromosome 17 open reading frame 48 | NM_020233 | 2.37 | 0.02702369 |
| GTPBP5: GTP binding protein 5 (putative) | NM_015666 | 2.36 | 0.001790962 |
| CTGLF1: centaurin, gamma-like family, member 1 | NM_133446 | 2.36 | 0.043433614 |
| SLC28A3: solute carrier family 28, member 3 | NM_022127 | 2.36 | 0.019740539 |
| ARMCX5: armadillo repeat containing, X-linked 5 | NM_022838 | 2.36 | 0.025899942 |
| SGK269: NKF3 kinase family member | NM_024776 | 2.36 | 0.008093168 |
| LUM: lumican | NM_002345 | 2.36 | 0.019014071 |
| LOC729603: calcium binding protein P22 pseudogene | NR_003288 | 2.36 | 0.044173561 |
| C15orf51: chromosome 15 open reading frame 51 | NR_003260 | 2.36 | 0.003680433 |
| CTGLF1: centaurin, gamma-like family, member 1 | NM_133446 | 2.35 | 0.031666883 |
| SNORD75: small nucleolar RNA, C/D box 75 | NR_003941 | 2.35 | 0.012471427 |
| SCML1: sex comb on midleg-like 1 (*Drosophila*) | NM_001037540 | 2.35 | 0.01599555 |
| TYW1B: tRNA-yW synthesizing protein 1 homolog B | BC068520 | 2.35 | 0.026615484 |
| MGC9913: hypothetical protein MGC9913 | BC008651 | 2.35 | 0.004951854 |
| SLC22A4: solute carrier family 22, member 4 | NM_003059 | 2.35 | 0.021487551 |
| TBC1D3H: TBC1 domain family, member 3H | NM_001123390 | 2.34 | 0.018398902 |
| HKR1: GLI-Kruppel family member HKR1 | NM_181786 | 2.34 | 0.001351111 |
| GCC1: GRIP and coiled-coil domain containing 1 | NM_024523 | 2.34 | 0.043089449 |
| LMCD1: LIM and cysteine-rich domains 1 | NM_014583 | 2.34 | 0.017154824 |
| DNAL4: dynein, axonemal, light chain 4 | NM_005740 | 2.34 | 0.036540012 |
| ASXL1: additional sex combs like 1 (*Drosophila*) | NM_015338 | 2.34 | 0.021137736 |
| RBM4: RNA binding motif protein 4 | NM_002896 | 2.34 | 0.00685358 |
| ZFP2: zinc finger protein 2 homolog (mouse) | NM_030613 | 2.34 | 0.027334262 |
| TOM1: target of myb1 (chicken) | NM_005488 | 2.33 | 0.010051619 |
| STBD1: starch binding domain 1 | NM_003943 | 2.33 | 0.0273185 |
| GTF2H1: general transcription factor IIH, polypeptide 1, 62 kDa | NM_005316 | 2.32 | 0.016760443 |
| STX6: syntaxin 6 | NM_005819 | 2.32 | 0.004825179 |
| HOXA7: homeobox A7 | NM_006896 | 2.32 | 0.040591193 |
| ZNF536: zinc finger protein 536 | NM_014717 | 2.32 | 0.014519843 |
| FLJ45055: 60S ribosomal pseudogene | NR_003572 | 2.32 | 0.02278277 |
| GPATCH8: G patch domain containing 8 | NM_001002909 | 2.31 | 0.049195173 |
| FAM122A: family with sequence similarity 122A | NM_138333 | 2.31 | 0.014751406 |

TABLE 3-continued

Global gene expression profile of hFibs vs. Oct-4 transduced hFibs at Day 4

| GENES | Accession | Fold change | p-value |
|---|---|---|---|
| TMEM38B: transmembrane protein 38B | NM_018112 | 2.31 | 0.033460216 |
| ORAOV1: oral cancer overexpressed 1 | NM_153451 | 2.31 | 0.003921467 |
| ETV3: ets variant gene 3 | NM_005240 | 2.31 | 0.011561176 |
| C5orf32: chromosome 5 open reading frame 32 | NM_032412 | 2.31 | 0.01562417 |
| TET2: tet oncogene family member 2 | NM_017628 | 2.31 | 0.016009216 |
| ZNF623: zinc finger protein 623 | NM_014789 | 2.3 | 0.002635741 |
| ZNF841: zinc finger protein 841 | ENST00000389534 | 2.3 | 0.031050605 |
| LOC390345: similar to ribosomal protein L10 | XR_038919 | 2.3 | 0.042624979 |
| MTHFR: 5,10-methylenetetrahydrofolate reductase (NADPH) | NM_005957 | 2.3 | 0.027666267 |
| FAM107B: family with sequence similarity 107, member B | BC072452 | 2.3 | 0.035505938 |
| TOB1: transducer of ERBB2, 1 | NM_005749 | 2.3 | 0.000638521 |
| TBC1D3H: TBC1 domain family, member 3H | NM_001123390 | 2.29 | 0.019105827 |
| TNFRSF10D | NM_003840 | 2.29 | 0.032854214 |
| TBPL1: TBP-like 1 | NM_004865 | 2.29 | 0.02543063 |
| SLC3A2: solute carrier family 3, member 2 | NM_001012661 | 2.29 | 0.035914016 |
| C2orf44: chromosome 2 open reading frame 44 | BC035698 | 2.29 | 0.001060836 |
| EFNB2: ephrin-B2 | NM_004093 | 2.29 | 0.037832677 |
| ZNF620: zinc finger protein 620 | NM_175888 | 2.29 | 0.019178544 |
| CTNS: cystinosis, nephropathic | NM_004937 | 2.28 | 0.041128076 |
| PEX12: peroxisomal biogenesis factor 12 | NM_000286 | 2.28 | 0.029545005 |
| UTP3: UTP3, small subunit (SSU) processome component, homolog | NM_020368 | 2.28 | 0.008952567 |
| ZNF480: zinc finger protein 480 | NM_144684 | 2.28 | 0.000597071 |
| NSAP11: nervous system abundant protein 11 | AY176665 | 2.28 | 0.047460746 |
| PRRX2: paired related homeobox 2 | NM_016307 | 2.28 | 0.009883097 |
| NCK1: NCK adaptor protein 1 | NM_006153 | 2.28 | 0.003976377 |
| SNORD13: small nucleolar RNA, C/D box 13 | NR_003041 | 2.28 | 0.00715273 |
| SLC7A2: solute carrier family 7, member 2 | NM_003046 | 2.28 | 0.036939634 |
| ZNF221: zinc finger protein 221 | NM_013359 | 2.28 | 0.01463236 |
| JUB: jub, ajuba homolog (Xenopus laevis) | NM_032876 | 2.28 | 0.012182893 |
| DNAJB2: DnaJ (Hsp40) homolog, subfamily B, member 2 | NM_006736 | 2.27 | 0.001863914 |
| CTGLF1: centaurin, gamma-like family, member 1 | NM_133446 | 2.27 | 0.034047944 |
| CD163L1: CD163 molecule-like 1 | NM_174941 | 2.27 | 0.034502847 |
| SELPLG: selectin P ligand | NM_003006 | 2.27 | 0.015033026 |
| IL10RA: interleukin 10 receptor, alpha | NM_001558 | 2.27 | 0.018951415 |
| CTTNBP2NL: CTTNBP2 N-terminal like | NM_018704 | 2.27 | 0.000446979 |
| LST1: leukocyte specific transcript 1 | NM_007161 | 2.27 | 0.045494412 |
| LST1: leukocyte specific transcript 1 | NM_007161 | 2.27 | 0.045494412 |
| LST1: leukocyte specific transcript 1 | NM_007161 | 2.27 | 0.045494412 |
| TBC1D3B: TBC1 domain family, member 3B | NM_001001417 | 2.26 | 0.026085055 |
| PIK3CD: phosphoinositide-3-kinase, catalytic, delta polypeptide | NM_005026 | 2.26 | 0.030888266 |
| ZNF420: zinc finger protein 420 | NM_144689 | 2.26 | 0.020865305 |
| NEU1: sialidase 1 (lysosomal sialidase) | NM_000434 | 2.26 | 0.04598836 |
| NEU1: sialidase 1 (lysosomal sialidase) | NM_000434 | 2.26 | 0.04598836 |
| CCDC51: coiled-coil domain containing 51 | NM_024661 | 2.26 | 0.024648852 |
| MAD2L1BP: MAD2L1 binding protein | NM_014628 | 2.26 | 0.008340159 |
| NDFIP2: Nedd4 family interacting protein 2 | NM_019080 | 2.26 | 0.049184707 |
| ITGB7: integrin, beta 7 | NM_000889 | 2.26 | 0.023533165 |
| ZNF419: zinc finger protein 419 | NM_001098491 | 2.26 | 0.025633549 |
| ARL8B: ADP-ribosylation factor-like 8B | NM_018184 | 2.26 | 0.010645741 |
| TBC1D3G: TBC1 domain family, member 3G | NM_001040282 | 2.25 | 0.022105211 |
| TBC1D3G: TBC1 domain family, member 3G | NM_001040282 | 2.25 | 0.020994337 |
| TBC1D3G: TBC1 domain family, member 3G | NM_001040282 | 2.25 | 0.021690129 |
| TBC1D3B: TBC1 domain family, member 3B | NM_001001417 | 2.25 | 0.025275374 |
| RIOK3: RIO kinase 3 (yeast) | NM_003831 | 2.25 | 0.000909778 |
| NEK6: NIMA (never in mitosis gene a)-related kinase 6 | NM_014397 | 2.25 | 0.047213211 |
| OVGP1: oviductal glycoprotein 1, 120 kDa | NM_002557 | 2.25 | 0.049797511 |
| TRAPPC6B: trafficking protein particle complex 6B | NM_001079537 | 2.25 | 0.022724473 |
| LIG4: ligase IV, DNA, ATP-dependent | NM_002312 | 2.25 | 0.03833795 |
| RBM7: RNA binding motif protein 7 | NM_016090 | 2.25 | 0.0173952 |
| MGAM: maltase-glucoamylase (alpha-glucosidase) | NM_004668 | 2.24 | 0.049693307 |
| CTGLF1: centaurin, gamma-like family, member 1 | NM_133446 | 2.24 | 0.024637266 |
| CTGLF1: centaurin, gamma-like family, member 1 | NM_133446 | 2.24 | 0.045669873 |
| CTGLF1: centaurin, gamma-like family, member 1 | NM_133446 | 2.24 | 0.045669873 |
| SLC37A2: solute carrier family 37, member 2 | NM_198277 | 2.24 | 0.011116625 |
| RLF: rearranged L-myc fusion | NM_012421 | 2.24 | 0.006274162 |
| SETD4: SET domain containing 4 | NM_017438 | 2.24 | 0.00606507 |
| OTUD1: OTU domain containing 1 | ENST00000376495 | 2.24 | 0.039753725 |
| CCRK: cell cycle related kinase | NM_178432 | 2.24 | 0.023654088 |
| ADNP: activity-dependent neuroprotector homeobox | NM_015339 | 2.24 | 0.007766557 |
| PPTC7: PTC7 protein phosphatase homolog (S. cerevisiae) | NM_139283 | 2.24 | 0.020090711 |
| PDZK1IP1: PDZK1 interacting protein 1 | NM_005764 | 2.24 | 0.049444656 |
| HEXA: hexosaminidase A (alpha polypeptide) | NM_000520 | 2.23 | 0.043347876 |

TABLE 3-continued

Global gene expression profile of hFibs vs. Oct-4 transduced hFibs at Day 4

| GENES | Accession | Fold change | p-value |
|---|---|---|---|
| HDX: highly divergent homeobox | NM_144657 | 2.23 | 0.035404144 |
| BPTF: bromodomain PHD finger transcription factor | NM_004459 | 2.23 | 0.003086138 |
| KIAA1324: KIAA1324 | NM_020775 | 2.23 | 0.004572609 |
| C18orf25: chromosome 18 open reading frame 25 | NM_145055 | 2.23 | 0.047968856 |
| LOC340274: similar to argininosuccinate synthase | XR_038613 | 2.23 | 0.005252661 |
| ZBTB38: zinc finger and BTB domain containing 38 | NM_001080412 | 2.22 | 0.014947978 |
| ATXN7L1: ataxin 7-like 1 | NM_020725 | 2.22 | 0.047619805 |
| C21orf7: chromosome 21 open reading frame 7 | NM_020152 | 2.22 | 0.017864402 |
| ZNF501: zinc finger protein 501 | NM_145044 | 2.22 | 0.048426676 |
| NR1D2: nuclear receptor subfamily 1, group D, member 2 | NM_005126 | 2.22 | 0.011555262 |
| TRIM69: tripartite motif-containing 69 | NM_182985 | 2.22 | 0.038319911 |
| C7orf60: chromosome 7 open reading frame 60 | NM_152556 | 2.22 | 0.02513105 |
| SLC25A30: solute carrier family 25, member 30 | NM_001010875 | 2.22 | 0.010174334 |
| ZNF28: zinc finger protein 28 | NM_006969 | 2.22 | 0.014935025 |
| FAM134B: family with sequence similarity 134, member B | NM_001034850 | 2.22 | 0.039897781 |
| KRCC1: lysine-rich coiled-coil 1 | NM_016618 | 2.22 | 0.003277617 |
| ZNF92: zinc finger protein 92 | NM_152626 | 2.22 | 0.017665102 |
| SMAD1: SMAD family member 1 | NM_005900 | 2.22 | 0.028548345 |
| C20orf69: chromosome 20 open reading frame 69 | BC118988 | 2.22 | 0.030576011 |
| C20orf69: chromosome 20 open reading frame 69 | BC118988 | 2.22 | 0.030576011 |
| ZNF181: zinc finger protein 181 | NM_001029997 | 2.22 | 0.010848955 |
| PSTPIP2: proline-serine-threonine phosphatase interacting protein 2 | NM_024430 | 2.21 | 0.030210117 |
| CTGLF4: centaurin, gamma-like family, member 4 | NM_001077685 | 2.21 | 0.016193644 |
| SLC41A2: solute carrier family 41, member 2 | NM_032148 | 2.21 | 0.046639512 |
| ALS2: amyotrophic lateral sclerosis 2 (juvenile) | NM_020919 | 2.21 | 0.012239445 |
| COX19: COX19 cytochrome c oxidase assembly homolog | NM_001031617 | 2.21 | 0.023602673 |
| MX1: myxovirus resistance 1, interferon-inducible protein p78 | NM_002462 | 2.21 | 0.038327571 |
| ZSWIM3: zinc finger, SWIM-type containing 3 | NM_080752 | 2.21 | 0.024883066 |
| ZNF224: zinc finger protein 224 | NM_013398 | 2.21 | 0.045075848 |
| MED10: mediator complex subunit 10 | NM_032286 | 2.21 | 0.03087391 |
| C2orf63: chromosome 2 open reading frame 63 | BC029502 | 2.21 | 0.031644455 |
| OR6B2: olfactory receptor, family 6, subfamily B, member 2 | NM_001005853 | 2.21 | 0.028090634 |
| DPF2: D4, zinc and double PHD fingers family 2 | NM_006268 | 2.2 | 0.039801091 |
| PER2: period homolog 2 (Drosophila) | NM_022817 | 2.2 | 0.017620276 |
| JMJD2C: jumonji domain containing 2C | NM_015061 | 2.2 | 0.035196174 |
| SMAD7: SMAD family member 7 | NM_005904 | 2.2 | 0.014465278 |
| RSRC2: arginine/serine-rich coiled-coil 2 | NM_198261 | 2.2 | 0.020724974 |
| ARID5B: AT rich interactive domain 5B (MRF1-like) | NM_032199 | 2.2 | 0.022529909 |
| FAS: Fas (TNF receptor superfamily, member 6) | NM_000043 | 2.2 | 0.03997575 |
| HS1BP3: HCLS1 binding protein 3 | NM_022460 | 2.2 | 0.000291817 |
| BMP2: bone morphogenetic protein 2 | NM_001200 | 2.2 | 0.014071022 |
| ZNF192: zinc finger protein 192 | NM_006298 | 2.2 | 0.016789869 |
| ZNF121: zinc finger protein 121 | NM_001008727 | 2.2 | 0.02359942 |
| ZNF239: zinc finger protein 239 | NM_001099282 | 2.2 | 0.034555339 |
| ZMYM5: zinc finger, MYM-type 5 | NM_001039650 | 2.2 | 0.040914708 |
| MAP1LC3B: microtubule-associated protein 1 light chain 3 beta | NM_022818 | 2.2 | 0.016732214 |
| TBC1D3C: TBC1 domain family, member 3C | NM_001001418 | 2.19 | 0.04067972 |
| MCL1: myeloid cell leukemia sequence 1 (BCL2-related) | NM_021960 | 2.19 | 0.032247408 |
| MAP3K7IP3 | NM_152787 | 2.19 | 0.007328014 |
| MGA: MAX gene associated | NM_001080541 | 2.19 | 0.028145166 |
| MUL1: mitochondrial ubiquitin ligase activator of NFKB 1 | NM_024544 | 2.19 | 0.004891512 |
| SNORD13: small nucleolar RNA, C/D box 13 | NR_003041 | 2.19 | 0.048733597 |
| TMEM128: transmembrane protein 128 | NM_032927 | 2.19 | 0.032434558 |
| C14orf129: chromosome 14 open reading frame 129 | NM_016472 | 2.19 | 0.039150478 |
| CCDC144A: coiled-coil domain containing 144A | ENST00000360524 | 2.19 | 0.029937793 |
| STARD4: StAR-related lipid transfer (START) domain containing 4 | NM_139164 | 2.18 | 0.021618636 |
| CD72: CD72 molecule | NM_001782 | 2.18 | 0.023664087 |
| HOXD10: homeobox D10 | NM_002148 | 2.18 | 0.026435972 |
| ARMCX1: armadillo repeat containing, X-linked 1 | NM_016608 | 2.18 | 0.000866529 |
| RRAGB: Ras-related GTP binding B | NM_016656 | 2.18 | 0.013958936 |
| ADO: 2-aminoethanethiol (cysteamine) dioxygenase | NM_032804 | 2.18 | 0.021697317 |
| ZNF585B: zinc finger protein 585B | NM_152279 | 2.18 | 0.036987573 |
| ZNF619: zinc finger protein 619 | NM_173656 | 2.18 | 0.010762508 |
| IFIT5: interferon-induced protein with tetratricopeptide repeats 5 | NM_012420 | 2.18 | 0.007245129 |
| NOTUM: notum pectinacetylesterase homolog (Drosophila) | NM_178493 | 2.18 | 0.004649605 |
| CTGLF3: centaurin, gamma-like family, member 3 | NM_001077665 | 2.17 | 0.018892256 |
| ZNF251: zinc finger protein 251 | NM_138367 | 2.17 | 0.028050344 |
| LPCAT2: lysophosphatidylcholine acyltransferase 2 | NM_017839 | 2.17 | 0.028812728 |
| PARP8: poly (ADP-ribose) polymerase family, member 8 | NM_024615 | 2.17 | 0.044362176 |
| PHYH: phytanoyl-CoA 2-hydroxylase | NM_006214 | 2.17 | 0.025207118 |

TABLE 3-continued

Global gene expression profile of hFibs vs. Oct-4 transduced hFibs at Day 4

| GENES | Accession | Fold change | p-value |
|---|---|---|---|
| ZNF354B: zinc finger protein 354B | NM_058230 | 2.17 | 0.024703702 |
| ZIC5: Zic family member 5 (odd-paired homolog, Drosophila) | NM_033132 | 2.17 | 0.039267855 |
| ZNF233: zinc finger protein 233 | NM_181756 | 2.17 | 0.003416201 |
| ATP6V1C1: ATPase, H+ transporting, V1 subunit C1 | NM_001695 | 2.16 | 0.003044379 |
| ORAI3: ORAI calcium release-activated calcium modulator 3 | NM_152288 | 2.16 | 0.003893867 |
| CDC42EP1: CDC42 effector protein (Rho GTPase binding) 1 | NM_152243 | 2.16 | 0.033747645 |
| GATA1: GATA binding protein 1 | NM_002049 | 2.16 | 0.016845318 |
| NAP1L5: nucleosome assembly protein 1-like 5 | NM_153757 | 2.15 | 0.031790582 |
| ATP6V1G2: ATPase, H+ transporting, V1 subunit G2 | NM_130463 | 2.15 | 0.03127474 |
| ATP6V1G2: ATPase, H+ transporting V1 subunit G2 | NM_130463 | 2.15 | 0.03127474 |
| GOSR1: golgi SNAP receptor complex member 1 | NM_004871 | 2.15 | 0.005559571 |
| SNF1LK: SNF1-like kinase | NM_173354 | 2.15 | 0.019366348 |
| ASTE1: asteroid homolog 1 (Drosophila) | NM_014065 | 2.15 | 0.043087988 |
| ANKRD46: ankyrin repeat domain 46 | NM_198401 | 2.15 | 0.03379939 |
| CCDC148: coiled-coil domain containing 148 | NM_138803 | 2.15 | 0.041727796 |
| COQ10B: coenzyme Q10 homolog B (S. cerevisiae) | NM_025147 | 2.15 | 0.046223599 |
| TANK: TRAF family member-associated NFKB activator | NM_004180 | 2.15 | 0.005086541 |
| CDKN2B: cyclin-dependent kinase inhibitor 2B | NM_078487 | 2.15 | 0.008524239 |
| CCL5: chemokine (C-C motif) ligand 5 | NM_002985 | 2.15 | 0.04756298 |
| LRRC37A3: leucine rich repeat containing 37, member A3 | NM_199340 | 2.14 | 0.024261194 |
| ZNF813: zinc finger protein 813 | NM_001004301 | 2.14 | 0.023677455 |
| NNMT: nicotinamide N-methyltransferase | NM_006169 | 2.14 | 0.000120561 |
| TMEM41B: transmembrane protein 41B | NM_015012 | 2.14 | 0.020786008 |
| LOC730167: similar to protein tyrosine phosphatase 4a1 | XM_001134097 | 2.14 | 0.002386482 |
| DNHD1L: dynein heavy chain domain 1-like | BX647806 | 2.13 | 0.035569711 |
| SLC13A3: solute carrier family 13, member 3 | NM_022829 | 2.13 | 0.013962044 |
| SDC4: syndecan 4 | NM_002999 | 2.13 | 0.045813427 |
| MAP3K7IP2 | NM_015093 | 2.13 | 0.026103685 |
| FLJ14154: hypothetical protein FLJ14154 | NM_001083601 | 2.13 | 0.033533374 |
| GYG1: glycogenin 1 | NM_004130 | 2.13 | 0.023828816 |
| ZNF238: zinc finger protein 238 | NM_205768 | 2.13 | 0.005256296 |
| IFI27: interferon, alpha-inducible protein 27 | NM_005532 | 2.13 | 0.01497516 |
| FEM1A: fem-1 homolog a (C. elegans) | NM_018708 | 2.13 | 0.003906337 |
| GDAP1: ganglioside-induced differentiation-associated protein 1 | NM_018972 | 2.13 | 0.013787569 |
| HIST1H4E: histone cluster 1, H4e | NM_003545 | 2.13 | 0.025603216 |
| KIAA1409: KIAA1409 | NM_020818 | 2.12 | 0.018757701 |
| KIAA0247: KIAA0247 | BC064697 | 2.12 | 0.001185912 |
| ZNF518A: zinc finger protein 518A | NM_014803 | 2.12 | 0.027629382 |
| TSPYL5: TSPY-like 5 | NM_033512 | 2.12 | 0.037264815 |
| CDO1: cysteine dioxygenase, type I | NM_001801 | 2.12 | 0.017153519 |
| WDR21B: WD repeat domain 21B | NM_001029955 | 2.12 | 0.039107031 |
| INTS2: integrator complex subunit 2 | NM_020748 | 2.12 | 0.036658921 |
| TUT1: terminal uridylyl transferase 1, U6 snRNA-specific | NM_022830 | 2.12 | 0.014963223 |
| BTN2A2: butyrophilin, subfamily 2, member A2 | NM_006995 | 2.12 | 0.005036616 |
| CAB39L: calcium binding protein 39-like | NM_030925 | 2.12 | 0.011095613 |
| CCNT2: cyclin T2 | NM_058241 | 2.12 | 0.038540901 |
| UBQLN2: ubiquilin 2 | NM_013444 | 2.11 | 0.009233484 |
| ZNF574: zinc finger protein 574 | NM_022752 | 2.11 | 0.0008881 |
| ME1: malic enzyme 1, NADP(+)-dependent, cytosolic | NM_002395 | 2.11 | 0.041806037 |
| PHF21A: PHD finger protein 21A | NM_001101802 | 2.11 | 0.013287312 |
| HSPB7: heat shock 27 kDa protein family, member 7 | NM_014424 | 2.11 | 0.004007825 |
| DGKI: diacylglycerol kinase, iota | NM_004717 | 2.11 | 0.022471174 |
| SLC26A4: solute carrier family 26, member 4 | NM_000441 | 2.11 | 0.018006048 |
| C11orf1: chromosome 11 open reading frame 1 | NM_022761 | 2.11 | 0.016972505 |
| CLTB: clathrin, light chain (Lcb) | NM_007097 | 2.1 | 0.017606998 |
| SNX30: sorting nexin family member 30 | NM_001012994 | 2.1 | 0.009028901 |
| RASAL2: RAS protein activator like 2 | NM_170692 | 2.1 | 0.032913922 |
| ZNF528: zinc finger protein 528 | NM_032423 | 2.1 | 0.015144211 |
| SETD2: SET domain containing 2 | NM_014159 | 2.1 | 0.003015 |
| KIAA1737: KIAA1737 | NM_033426 | 2.1 | 0.046843473 |
| CCDC147: coiled-coil domain containing 147 | NM_001008723 | 2.1 | 0.027452863 |
| C13orf26: chromosome 13 open reading frame 26 | BC030277 | 2.1 | 0.012053578 |
| LYST: lysosomal trafficking regulator | NM_000081 | 2.1 | 0.001932627 |
| SYNGAP1: synaptic Ras GTPase activating protein 1 homolog (rat) | NM_006772 | 2.09 | 0.038516095 |
| SMURF1: SMAD specific E3 ubiquitin protein ligase 1 | NM_020429 | 2.09 | 0.01583433 |
| SNAI2: snail homolog 2 (Drosophila) | NM_003068 | 2.09 | 0.031992728 |
| LPXN: leupaxin | NM_004811 | 2.09 | 0.012244082 |
| C14orf43: chromosome 14 open reading frame 43 | NM_194278 | 2.09 | 0.025129764 |
| FHL3: four and a half LIM domains 3 | NM_004468 | 2.09 | 0.004003009 |
| KIAA1826: KIAA1826 | NM_032424 | 2.09 | 0.017918025 |
| RAG1AP1: recombination activating gene 1 activating protein 1 | NM_018845 | 2.09 | 0.033113001 |

TABLE 3-continued

Global gene expression profile of hFibs vs. Oct-4 transduced hFibs at Day 4

| GENES | Accession | Fold change | p-value |
|---|---|---|---|
| FLJ32810: hypothetical protein FLJ32810 | AK057372 | 2.09 | 0.017284005 |
| NUPR1: nuclear protein 1 | NM_001042483 | 2.09 | 0.02839574 |
| MIS12: MIS12, MIND kinetochore complex component, homolog | NM_024039 | 2.09 | 0.012018086 |
| GBA: glucosidase, beta; acid (includes glucosylceramidase) | NM_000157 | 2.09 | 0.021341145 |
| ZNF286A: zinc finger protein 286A | NM_020652 | 2.09 | 0.033090461 |
| KIAA1622: KIAA1622 | NM_058237 | 2.09 | 0.034493561 |
| LGALS3: lectin, galactoside-binding, soluble, 3 | NR_003225 | 2.09 | 0.043341144 |
| PFKFB3: 6-phosphofructo-2-kinase/fructose-2,6-biphosphatase 3 | NM_004566 | 2.08 | 0.005983533 |
| CREBBP: CREB binding protein | NM_004380 | 2.08 | 0.023457708 |
| TBC1D3H: TBC1 domain family, member 3H | NM_001123390 | 2.08 | 0.044038074 |
| ABL2: v-abl Abelson murine leukemia viral oncogene homolog 2 | NM_007314 | 2.08 | 0.017354752 |
| FSIP1: fibrous sheath interacting protein 1 | NM_152597 | 2.08 | 0.046622678 |
| JHDM1D: jumonji C domain containing histone demethylase 1 D | NM_030647 | 2.08 | 0.019417968 |
| MBD5: methyl-CpG binding domain protein 5 | NM_018328 | 2.08 | 0.019912489 |
| C17orf95: chromosome 17 open reading frame 95 | NM_001080510 | 2.08 | 0.036838072 |
| H3F3B: H3 histone, family 3B (H3.3B) | NM_005324 | 2.08 | 0.017194172 |
| REEP1: receptor accessory protein 1 | NM_022912 | 2.08 | 0.045471019 |
| ZNF227: zinc finger protein 227 | NM_182490 | 2.08 | 0.012551021 |
| ASB14: ankyrin repeat and SOCS box-containing 14 | ENST00000295941 | 2.08 | 0.008490195 |
| C2orf59: chromosome 2 open reading frame 59 | BC010491 | 2.07 | 0.048784335 |
| PLEKHM2: pleckstrin homology domain containing, family M 2 | NM_015164 | 2.07 | 0.037516178 |
| SDSL: serine dehydratase-like | NM_138432 | 2.07 | 0.021177937 |
| TAF9: TAF9 RNA polymerase II | NM_003187 | 2.07 | 0.026345397 |
| PIM1: pim-1 oncogene | NM_002648 | 2.07 | 0.017505238 |
| PATL2: protein associated with topoisomerase II homolog 2 | BC036924 | 2.07 | 0.019639638 |
| C10orf104: chromosome 10 open reading frame 104 | NM_173473 | 2.07 | 0.012142364 |
| UCN2: urocortin 2 | NM_033199 | 2.07 | 0.01472791 |
| MEF2D: myocyte enhancer factor 2D | NM_005920 | 2.07 | 0.032650793 |
| LCORL: ligand dependent nuclear receptor corepressor-like | NM_153686 | 2.07 | 0.010692901 |
| SLC38A4: solute carrier family 38, member 4 | NM_018018 | 2.07 | 0.013012561 |
| ANAPC10: anaphase promoting complex subunit 10 | NM_014885 | 2.07 | 0.039092323 |
| PTPRR: protein tyrosine phosphatase, receptor type, R | NM_002849 | 2.07 | 0.010793823 |
| ZC3H11A: zinc finger CCCH-type containing 11A | BC046137 | 2.06 | 0.044450532 |
| BAX: BCL2-associated X protein | NM_138764 | 2.06 | 0.025908071 |
| TNFRSF12A: tumor necrosis factor receptor superfamily 12A | NM_016639 | 2.06 | 0.029216252 |
| MAMLD1: mastermind-like domain containing 1 | NM_005491 | 2.06 | 0.038720553 |
| USP18: ubiquitin specific peptidase 18 | AF176642 | 2.06 | 0.012737812 |
| LSM1: LSM1 homolog, U6 small nuclear RNA associated | NM_014462 | 2.06 | 0.039256077 |
| ELF1: E74-like factor 1 (ets domain transcription factor) | NM_172373 | 2.06 | 0.002736754 |
| ZNF415: zinc finger protein 415 | NM_018355 | 2.06 | 0.031553695 |
| ZNF81: zinc finger protein 81 | NM_007137 | 2.06 | 0.006271227 |
| ARHGAP23: Rho GTPase activating protein 23 | ENST00000300901 | 2.06 | 0.011222879 |
| UFM1: ubiquitin-fold modifier 1 | NM_016617 | 2.06 | 0.010530218 |
| IHPK2: inositol hexaphosphate kinase 2 | NM_016291 | 2.06 | 0.029266685 |
| MRRF: mitochondrial ribosome recycling factor | NM_138777 | 2.06 | 0.023139286 |
| ARHGAP5: Rho GTPase activating protein 5 | NM_001030055 | 2.06 | 0.02570968 |
| RPP38: ribonuclease P/MRP 38 kDa subunit | NM_183005 | 2.06 | 0.021854645 |
| ZNF737: zinc finger protein 737 | XR_042310 | 2.06 | 0.028392291 |
| ATAD2B: ATPase family, AAA domain containing 2B | NM_017552 | 2.05 | 0.014574295 |
| SLFN5: schlafen family member 5 | NM_144975 | 2.05 | 0.006684029 |
| ZFP106: zinc finger protein 106 homolog (mouse) | NM_022473 | 2.05 | 0.01549153 |
| CLCN7: chloride channel 7 | NM_001287 | 2.05 | 0.00787186 |
| USP36: ubiquitin specific peptidase 36 | NM_025090 | 2.05 | 0.0120978 |
| TAF13: TAF13 RNA polymerase II | NM_005645 | 2.05 | 0.015411463 |
| MCC: mutated in colorectal cancers | NM_001085377 | 2.05 | 0.010015918 |
| SLC36A1: solute carrier family 36, member 1 | NM_078483 | 2.05 | 0.037843932 |
| ITPRIP: inositol 1,4,5-triphosphate receptor interacting protein | NM_033397 | 2.05 | 0.009383002 |
| TAF9: TAF9 RNA polymerase II | NM_003187 | 2.05 | 0.028770138 |
| STYXL1: serine/threonine/tyrosine interacting-like 1 | NM_016086 | 2.05 | 0.020194897 |
| NKX3-1: NK3 homeobox 1 | NM_006167 | 2.05 | 2.42E−05 |
| WDR78: WD repeat domain 78 | NM_024763 | 2.05 | 0.009053537 |
| LOC440093: histone H3-like | NM_001013699 | 2.05 | 0.023051881 |
| C21orf34: chromosome 21 open reading frame 34 | NM_001005732 | 2.05 | 0.007370088 |
| MTUS1: mitochondrial tumor suppressor 1 | NM_001001924 | 2.05 | 0.013708432 |
| PELO: pelota homolog (Drosophila) | NM_015946 | 2.04 | 0.00777595 |
| IKZF2: IKAROS family zinc finger 2 (Helios) | NM_016260 | 2.04 | 0.044649477 |
| ZNF268: zinc finger protein 268 | NM_003415 | 2.04 | 0.035073367 |

TABLE 3-continued

Global gene expression profile of hFibs vs. Oct-4 transduced hFibs at Day 4

| GENES | Accession | Fold change | p-value |
|---|---|---|---|
| CSTF2T: cleavage stimulation factor, 3' pre-RNA, subunit 2 | NM_015235 | 2.04 | 0.032105107 |
| LOC349196: hypothetical LOC349196 | BC093747 | 2.04 | 0.001722355 |
| CLIP4: CAP-GLY domain containing linker protein family 4 | NM_024692 | 2.04 | 0.031769127 |
| NHLRC1: NHL repeat containing 1 | NM_198586 | 2.04 | 0.034828117 |
| ZNF764: zinc finger protein 764 | NM_033410 | 2.04 | 0.030932324 |
| C1orf129: chromosome 1 open reading frame 129 | NM_025063 | 2.04 | 0.02969779 |
| WTAP: Wilms tumor 1 associated protein | NM_152857 | 2.03 | 0.027683281 |
| C2CD3: C2 calcium-dependent domain containing 3 | NM_015531 | 2.03 | 0.013489428 |
| HLA-B: major histocompatibility complex, class I, B | NM_005514 | 2.03 | 0.041877044 |
| HMG20A: high-mobility group 20A | NM_018200 | 2.03 | 0.031159656 |
| OPN3: opsin 3 | NM_014322 | 2.03 | 0.013455 |
| ZNF711: zinc finger protein 711 | NM_021998 | 2.03 | 0.012443614 |
| NOX4: NADPH oxidase 4 | NM_016931 | 2.03 | 0.043475629 |
| ZNF184: zinc finger protein 184 | NM_007149 | 2.03 | 0.003981512 |
| IFI6: interferon, alpha-inducible protein 6 | NM_002038 | 2.03 | 0.0038703 |
| DAZAP2: DAZ associated protein 2 | NM_014764 | 2.02 | 0.000783543 |
| LOC100132426: similar to hCG1742442 | ENST00000377415 | 2.02 | 0.022409773 |
| PPM2C: protein phosphatase 2C | NM_018444 | 2.02 | 0.041825476 |
| NPIP: nuclear pore complex interacting protein | AK294177 | 2.02 | 0.008576323 |
| TRAF3: TNF receptor-associated factor 3 | NM_145725 | 2.02 | 0.024933609 |
| KIAA1975: KIAA1975 protein similar to MRIP2 | NM_133447 | 2.02 | 0.005431778 |
| CDC42EP3: CDC42 effector protein (Rho GTPase binding) 3 | NM_006449 | 2.02 | 0.018466992 |
| LOC349196: hypothetical LOC349196 | BC093747 | 2.02 | 0.00404514 |
| LOC349196: hypothetical LOC349196 | BC093747 | 2.02 | 0.00404514 |
| LOC349196: hypothetical LOC349196 | BC093747 | 2.02 | 0.00404514 |
| LOC349196: hypothetical LOC349196 | AK090418 | 2.02 | 0.00404514 |
| AMOTL2: angiomotin like 2 | NM_016201 | 2.02 | 0.007030751 |
| CELSR3: cadherin, EGF LAG seven-pass G-type receptor 3 | NM_001407 | 2.02 | 0.044323431 |
| TLR1: toll-like receptor 1 | NM_003263 | 2.02 | 0.019328967 |
| GNA13: guanine nucleotide binding protein (G protein), alpha 13 | NM_006572 | 2.02 | 0.000922653 |
| ANKRD12: ankyrin repeat domain 12 | NM_015208 | 2.02 | 0.017191634 |
| C19orf54: chromosome 19 open reading frame 54 | NM_198476 | 2.02 | 0.001180486 |
| SYTL2: synaptotagmin-like 2 | NM_206927 | 2.02 | 0.017931379 |
| TERF2IP: telomeric repeat binding factor 2, interacting protein | NM_018975 | 2.02 | 0.011559857 |
| CCDC93: coiled-coil domain containing 93 | NM_019044 | 2.01 | 0.043888648 |
| NPIP: nuclear pore complex interacting protein | AK294177 | 2.01 | 0.018744462 |
| MST131: MSTP131 | AF176921 | 2.01 | 0.030853785 |
| KPNA5: karyopherin alpha 5 (importin alpha 6) | NM_002269 | 2.01 | 0.017091137 |
| ACTC1: actin, alpha, cardiac muscle 1 | NM_005159 | 2.01 | 0.034275937 |
| CLCN4: chloride channel 4 | NM_001830 | 2.01 | 0.023253416 |
| SOCS4: suppressor of cytokine signaling 4 | NM_199421 | 2.01 | 0.024790224 |
| PDPK1: 3-phosphoinositide dependent protein kinase-1 | AK293900 | 2.01 | 0.029054845 |
| FLJ33996: hypothetical protein FLJ33996 | AK091315 | 2.01 | 0.015558373 |
| RNF113A: ring finger protein 113A | NM_006978 | 2.01 | 0.041655818 |
| SCG5: secretogranin V (7B2 protein) | NM_003020 | 2.01 | 0.031769366 |
| FLJ46481: FLJ46481 protein | BX648674 | 2.01 | 0.033589672 |
| LRRC37A2: leucine rich repeat containing 37, member A2 | NM_001006607 | 2 | 0.009852389 |
| NPIP: nuclear pore complex interacting protein | AK294177 | 2 | 0.018766553 |
| FNIP2: folliculin interacting protein 2 | NM_020840 | 2 | 0.007031707 |
| WARS2: tryptophanyl tRNA synthetase 2, mitochondrial | NM_201263 | 2 | 0.006590314 |
| RARA: retinoic acid receptor, alpha | NM_000964 | 2 | 0.044455247 |
| CYB5D1: cytochrome b5 domain containing 1 | NM_144607 | 2 | 0.019193343 |
| LOC349196: hypothetical LOC349196 | BC093747 | 2 | 0.002961001 |
| LOC349196: hypothetical LOC349196 | BC093747 | 2 | 0.002961001 |
| LOC349196: hypothetical LOC349196 | BC093747 | 2 | 0.002961001 |
| LOC349196: hypothetical LOC349196 | BC093747 | 2 | 0.002961001 |
| LOC349196: hypothetical LOC349196 | BC093747 | 2 | 0.002961001 |
| LOC349196: hypothetical LOC349196 | BC093747 | 2 | 0.018057046 |
| LOC349196: hypothetical LOC349196 | BC093747 | 2 | 0.018057046 |
| GPRASP2: G protein-coupled receptor associated sorting protein 2 | NM_001004051 | 2 | 0.038898801 |
| ASAH2B: N-acylsphingosine amidohydrolase 2B | NM_001079516 | 2 | 0.028160166 |
| LOC100132346: similar to chaperonin 10 | ENST00000406997 | −2 | 0.036218222 |
| LIG3: ligase III, DNA, ATP-dependent | NM_013975 | −2 | 0.019468221 |
| TSGA14: testis specific, 14 | NM_018718 | −2 | 0.023783473 |
| HK2: hexokinase 2 | NM_000189 | −2 | 0.018617371 |
| IFNE1: interferon epsilon 1 | NM_176891 | −2 | 0.023047364 |
| GTF2H2: general transcription factor IIH, polypeptide 2, 44 kDa | NM_001515 | −2 | 0.00501888 |
| GTF2H2: general transcription factor IIH, polypeptide 2, 44 kDa | NM_001515 | −2 | 0.00501888 |
| IARS2: isoleucyl-tRNA synthetase 2, mitochondrial | NM_018060 | −2 | 0.048624055 |

TABLE 3-continued

Global gene expression profile of hFibs vs. Oct-4 transduced hFibs at Day 4

| GENES | Accession | Fold change | p-value |
|---|---|---|---|
| GTF2H2: general transcription factor IIH, polypeptide 2, 44 kDa | NM_001515 | −2 | 0.016689034 |
| PARP4: poly (ADP-ribose) polymerase family, member 4 | NM_006437 | −2 | 0.016709063 |
| TSEN2: tRNA splicing endonuclease 2 homolog (*S. cerevisiae*) | NM_025265 | −2 | 0.021904432 |
| STAU1: staufen, RNA binding protein, homolog 1 (*Drosophila*) | NM_017453 | −2 | 0.012233514 |
| PTGIS: prostaglandin I2 (prostacyclin) synthase | NM_000961 | −2 | 0.009340794 |
| GLMN: glomulin, FKBP associated protein | NM_053274 | −2.01 | 0.000904803 |
| L3MBTL2: l(3)mbt-like 2 (*Drosophila*) | NM_031488 | −2.01 | 0.046291942 |
| C11orf41: chromosome 11 open reading frame 41 | NM_012194 | −2.01 | 0.024004377 |
| TM9SF2: transmembrane 9 superfamily member 2 | NM_004800 | −2.01 | 0.034611134 |
| CDC5L: CDC5 cell division cycle 5-like (*S. pombe*) | NM_001253 | −2.01 | 0.047044599 |
| TMEM43: transmembrane protein 43 | NM_024334 | −2.01 | 0.015609961 |
| GTF2H2: general transcription factor IIH, polypeptide 2, 44 kDa | NM_001515 | −2.02 | 0.0164367 |
| ZMYND8: zinc finger, MYND-type containing 8 | NM_183047 | −2.02 | 0.042595975 |
| STYX: serine/threonine/tyrosine interacting protein | NM_145251 | −2.02 | 0.003486382 |
| PREP: prolyl endopeptidase | NM_002726 | −2.02 | 0.003735308 |
| KIF5B: kinesin family member 5B | NM_004521 | −2.02 | 0.008786634 |
| HNRNPA1: heterogeneous nuclear ribonucleoprotein A1 | NM_002136 | −2.02 | 0.044102459 |
| MPHOSPH10: M-phase phosphoprotein 10 | NM_005791 | −2.03 | 0.001073063 |
| GPC4: glypican 4 | NM_001448 | −2.03 | 0.017908818 |
| BLMH: bleomycin hydrolase | NM_000386 | −2.03 | 0.034451555 |
| CUL1: cullin 1 | NM_003592 | −2.03 | 0.015788274 |
| ZDHHC16: zinc finger, DHHC-type containing 16 | NM_198046 | −2.03 | 0.021864571 |
| EFTUD2: elongation factor Tu GTP binding domain containing 2 | NM_004247 | −2.03 | 0.005457825 |
| ANKRD27: ankyrin repeat domain 27 (VPS9 domain) | NM_032139 | −2.03 | 0.04681411 |
| S100PBP: S100P binding protein | NM_022753 | −2.04 | 0.038967603 |
| TOMM70A: translocase of outer mitochondrial membrane 70 A | NM_014820 | −2.04 | 0.042457828 |
| CACYBP: calcyclin binding protein | AF057356 | −2.04 | 0.015398044 |
| C5orf33: chromosome 5 open reading frame 33 | NM_001085411 | −2.04 | 0.015915104 |
| OSMR: oncostatin M receptor | NM_003999 | −2.04 | 0.029770274 |
| KIAA1731: KIAA1731 | NM_033395 | −2.04 | 0.023303606 |
| FNTB: farnesyltransferase, CAAX box, beta | NM_002028 | −2.04 | 0.012277081 |
| IKBKAP | NM_003640 | −2.04 | 0.018367629 |
| NFIA: nuclear factor I/A | NM_005595 | −2.04 | 0.027015538 |
| RBL2: retinoblastoma-like 2 (p130) | NM_005611 | −2.05 | 0.008097525 |
| PMPCA: peptidase (mitochondrial processing) alpha | NM_015160 | −2.05 | 0.023194741 |
| TOP2B: topoisomerase (DNA) II beta 180 kDa | NM_001068 | −2.05 | 0.025176793 |
| PDE7B: phosphodiesterase 7B | NM_018945 | −2.05 | 0.016073599 |
| CCDC150: coiled-coil domain containing 150 | NM_001080539 | −2.05 | 0.032422147 |
| RBM27: RNA binding motif protein 27 | NM_018989 | −2.05 | 0.015492116 |
| ZW10: ZW10, kinetochore associated, homolog (*Drosophila*) | NM_004724 | −2.05 | 0.034641085 |
| KIAA0368: KIAA0368 | NM_001080398 | −2.05 | 0.038416772 |
| MSH6: mutS homolog 6 (*E. coli*) | NM_000179 | −2.06 | 0.004560972 |
| TMEM165: transmembrane protein 165 | NM_018475 | −2.06 | 0.0109816 |
| LMNA: lamin A/C | NM_170707 | −2.06 | 0.012229609 |
| PRRC1: proline-rich coiled-coil 1 | NM_130809 | −2.06 | 0.014723547 |
| TIMP3: TIMP metallopeptidase inhibitor 3 | NM_000362 | −2.06 | 0.014243521 |
| CALM3: calmodulin 3 (phosphorylase kinase, delta) | NM_005184 | −2.06 | 0.017798429 |
| SLC6A6: solute carrier family 6, member 6 | NM_003043 | −2.06 | 0.029416714 |
| ANG: angiogenin, ribonuclease, RNase A family, 5 | NM_001145 | −2.07 | 0.031659956 |
| DDX3X: DEAD (Asp-Glu-Ala-Asp) box polypeptide 3, X-linked | NM_001356 | −2.07 | 0.018648257 |
| IPO11: importin 11 | NM_016338 | −2.07 | 0.046726189 |
| NT5DC2: 5′-nucleotidase domain containing 2 | NM_022908 | −2.07 | 0.015906693 |
| ERLIN1: ER lipid raft associated 1 | NM_001100626 | −2.07 | 0.032025552 |
| ACTN1: actinin, alpha 1 | NM_001102 | −2.07 | 0.015796693 |
| MED17: mediator complex subunit 17 | NM_004268 | −2.08 | 0.035601634 |
| DNAJC3: DnaJ (Hsp40) homolog, subfamily C, member 3 | NM_006260 | −2.08 | 0.040071418 |
| FUBP1: far upstream element (FUSE) binding protein 1 | NM_003902 | −2.08 | 0.029194926 |
| NIF3L1: NIF3 NGG1 interacting factor 3-like 1 (*S. pombe*) | NM_021824 | −2.08 | 0.011290041 |
| DHX32: DEAH (Asp-Glu-Ala-His) box polypeptide 32 | NM_018180 | −2.08 | 0.0051035 |
| C12orf30: chromosome 12 open reading frame 30 | NM_024953 | −2.08 | 0.011766507 |
| PIK3R4: phosphoinositide-3-kinase, regulatory subunit 4 | NM_014602 | −2.08 | 0.033192538 |
| SHMT1: serine hydroxymethyltransferase 1 (soluble) | NM_004169 | −2.08 | 0.039180734 |
| KDELC2: KDEL (Lys-Asp-Glu-Leu) containing 2 | NM_153705 | −2.08 | 0.026607427 |
| GEMIN4: gem (nuclear organelle) associated protein 4 | NM_015721 | −2.08 | 0.044060858 |
| ANAPC1: anaphase promoting complex subunit 1 | NM_022662 | −2.09 | 0.00878527 |
| AHSA1: AHA1, activator of heat shock protein ATPase homolog 1 | NM_012111 | −2.09 | 0.048624495 |
| LTV1: LTV1 homolog (*S. cerevisiae*) | NM_032860 | −2.09 | 0.035839743 |

TABLE 3-continued

Global gene expression profile of hFibs vs. Oct-4 transduced hFibs at Day 4

| GENES | Accession | Fold change | p-value |
|---|---|---|---|
| RPN1: ribophorin I | NM_002950 | −2.09 | 0.010225198 |
| DNM1L: dynamin 1-like | NM_012062 | −2.09 | 0.021264183 |
| QSER1: glutamine and serine rich 1 | NM_001076786 | −2.09 | 0.010855414 |
| ACOT9: acyl-CoA thioesterase 9 | NM_001037171 | −2.09 | 0.004075826 |
| ALG9: asparagine-linked glycosylation 9 homolog | NM_024740 | −2.1 | 0.032419674 |
| RNASEH2A: ribonuclease H2, subunit A | NM_006397 | −2.1 | 0.013461634 |
| BLID: BH3-like motif containing, cell death inducer | NM_001001786 | −2.1 | 0.022670321 |
| EVI5: ecotropic viral integration site 5 | NM_005665 | −2.1 | 0.029659916 |
| NPAT: nuclear protein, ataxia-telangiectasia locus | NM_002519 | −2.1 | 0.012722141 |
| KIAA1715: KIAA1715 | NM_030650 | −2.1 | 0.025609372 |
| FAM122B: family with sequence similarity 122B | NM_145284 | −2.1 | 0.009864435 |
| THAP4: THAP domain containing 4 | NM_015963 | −2.1 | 0.028339466 |
| THAP4: THAP domain containing 4 | NM_015963 | −2.1 | 0.028339466 |
| DLAT: dihydrolipoamide S-acetyltransferase | NM_001931 | −2.1 | 0.000593124 |
| FBXO11: F-box protein 11 | NM_025133 | −2.11 | 0.004285891 |
| SDF2L1: stromal cell-derived factor 2-like 1 | NM_022044 | −2.11 | 0.004808531 |
| CTGF: connective tissue growth factor | NM_001901 | −2.11 | 0.037445948 |
| FBXO3: F-box protein 3 | NM_033406 | −2.11 | 0.014945591 |
| AGPAT5: 1-acylglycerol-3-phosphate O-acyltransferase 5 | NM_018361 | −2.11 | 0.044938729 |
| RNASEN: ribonuclease type III, nuclear | NM_013235 | −2.11 | 0.030892885 |
| ZADH2: zinc binding alcohol dehydrogenase domain containing 2 | NM_175907 | −2.11 | 0.039848207 |
| TUBGCP3: tubulin, gamma complex associated protein 3 | NM_006322 | −2.12 | 0.003364525 |
| RELN: reelin | NM_005045 | −2.12 | 0.0184584 |
| FBL: fibrillarin | NM_001436 | −2.12 | 0.016591792 |
| PTPRJ: protein tyrosine phosphatase, receptor type, J | NM_002843 | −2.12 | 0.036435217 |
| TNPO3: transportin 3 | NM_012470 | −2.12 | 0.015631275 |
| PHIP: pleckstrin homology domain interacting protein | NM_017934 | −2.12 | 0.049366459 |
| HLTF: helicase-like transcription factor | NM_003071 | −2.12 | 0.034694377 |
| STX2: syntaxin 2 | NM_194356 | −2.12 | 0.024273297 |
| XPO4: exportin 4 | NM_022459 | −2.13 | 0.044881898 |
| CLPX: ClpX caseinolytic peptidase X homolog (E. coli) | NM_006660 | −2.13 | 0.0186105 |
| MBTPS1: membrane-bound transcription factor peptidase, site 1 | NM_003791 | −2.13 | 0.045645561 |
| HNRPA1L-2: heterogeneous nuclear ribonucleoprotein A1 | NR_002944 | −2.13 | 0.048491581 |
| ABCF2: ATP-binding cassette, sub-family F (GCN20), member 2 | NM_007189 | −2.14 | 0.008323273 |
| SNX9: sorting nexin 9 | NM_016224 | −2.14 | 0.02029193 |
| POLR1E: polymerase (RNA) I polypeptide E, 53 kDa | NM_022490 | −2.14 | 0.041025013 |
| IPO8: importin 8 | NM_006390 | −2.14 | 0.037105295 |
| POLE: polymerase (DNA directed), epsilon | NM_006231 | −2.14 | 0.037359493 |
| GLUL: glutamate-ammonia ligase (glutamine synthetase) | AY513283 | −2.15 | 0.032958771 |
| FHOD1: formin homology 2 domain containing 1 | NM_013241 | −2.15 | 0.040570594 |
| LAPTM4B: lysosomal protein transmembrane 4 beta | NM_018407 | −2.15 | 0.030389137 |
| MCM10: minichromosome maintenance complex component 10 | NM_182751 | −2.15 | 0.044316968 |
| IL1RL1: interleukin 1 receptor-like 1 | NM_016232 | −2.15 | 0.03462345 |
| NPAL3: NIPA-like domain containing 3 | NM_020448 | −2.15 | 0.036362629 |
| ITGA3: integrin, alpha 3 | NM_002204 | −2.15 | 0.014046025 |
| JMJD2A: jumonji domain containing 2A | NM_014663 | −2.15 | 0.024979543 |
| QARS: glutaminyl-tRNA synthetase | NM_005051 | −2.15 | 0.026387003 |
| DDX11: DEAD/H (Asp-Glu-Ala-Asp/His) box polypeptide 11 | NM_030653 | −2.15 | 0.01752887 |
| GEMIN5: gem (nuclear organelle) associated protein 5 | NM_015465 | −2.15 | 0.029127837 |
| ARSK: arylsulfatase family, member K | NM_198150 | −2.16 | 0.04639001 |
| ANTXR2: anthrax toxin receptor 2 | NM_058172 | −2.16 | 0.025925245 |
| EPS15: epidermal growth factor receptor pathway substrate 15 | NM_001981 | −2.16 | 0.045957677 |
| NAT10: N-acetyltransferase 10 | NM_024662 | −2.16 | 0.00756751 |
| AHCTF1: AT hook containing transcription factor 1 | NM_015446 | −2.16 | 0.009160004 |
| HHIP: hedgehog interacting protein | NM_022475 | −2.17 | 0.004000885 |
| SLC35C1: solute carrier family 35, member C1 | NM_018389 | −2.17 | 0.037756511 |
| ENDOD1: endonuclease domain containing 1 | NM_015036 | −2.17 | 0.0360211 |
| C1orf217: chromosome 1 open reading frame 217 | BC000988 | −2.17 | 0.019285607 |
| POLD1: polymerase (DNA directed), delta 1 | NM_002691 | −2.17 | 0.035966763 |
| C16orf88: chromosome 16 open reading frame 88 | BC117562 | −2.17 | 0.004926732 |
| COBRA1: cofactor of BRCA1 | NM_015456 | −2.17 | 0.001775062 |
| ANP32A: acidic nuclear phosphoprotein 32 family, member A | ENST00000267918 | −2.18 | 0.031801866 |
| SNORD4A: small nucleolar RNA, C/D box 4A | NR_000010 | −2.18 | 0.012684585 |
| ORC6L: origin recognition complex, subunit 6 like (yeast) | NM_014321 | −2.18 | 0.042147413 |
| PCYOX1: prenylcysteine oxidase 1 | NM_016297 | −2.18 | 0.024513574 |
| DNMT1: DNA (cytosine-5-)-methyltransferase 1 | NM_001379 | −2.18 | 0.035942748 |
| HIST1H2BI: histone cluster 1, H2bi | NM_003525 | −2.19 | 0.026472498 |
| TNFRSF1A: tumor necrosis factor receptor, member 1A | NM_001065 | −2.19 | 0.00120709 |
| DUS1L: dihydrouridine synthase 1-like (S. cerevisiae) | NM_022156 | −2.19 | 0.003838316 |

TABLE 3-continued

Global gene expression profile of hFibs vs. Oct-4 transduced hFibs at Day 4

| GENES | Accession | Fold change | p-value |
|---|---|---|---|
| PCDH18: protocadherin 18 | NM_019035 | −2.19 | 0.014273704 |
| CCDC111: coiled-coil domain containing 111 | NM_152683 | −2.19 | 0.033015758 |
| HIATL1: hippocampus abundant transcript-like 1 | NM_032558 | −2.19 | 0.001849756 |
| MLH1: mutL homolog 1, colon cancer, nonpolyposis type 2 | NM_000249 | −2.19 | 0.004129459 |
| TFPI: tissue factor pathway inhibitor | NM_006287 | −2.2 | 0.021208595 |
| ENTPD6: ectonucleoside triphosphate diphosphohydrolase 6 | NM_001247 | −2.2 | 0.011633209 |
| EIF5B: eukaryotic translation initiation factor 5B | NM_015904 | −2.2 | 0.010190315 |
| HERC4: hect domain and RLD 4 | NM_022079 | −2.2 | 0.015934335 |
| RANBP1: RAN binding protein 1 | NM_002882 | −2.2 | 0.040652233 |
| BUB3: BUB3 budding uninhibited by benzimidazoles 3 homolog | NM_004725 | −2.21 | 0.024421592 |
| MTA2: metastasis associated 1 family, member 2 | NM_004739 | −2.21 | 0.009248302 |
| LETM1: leucine zipper-EF-hand containing transmembrane protein 1 | NM_012318 | −2.21 | 0.048765841 |
| FAM73A: family with sequence similarity 73, member A | BX537792 | −2.21 | 0.034644992 |
| EPHB1: EPH receptor B1 | NM_004441 | −2.22 | 0.047452077 |
| AADAC: arylacetamide deacetylase (esterase) | NM_001086 | −2.22 | 0.031114213 |
| PHTF2: putative homeodomain transcription factor 2 | NM_001127358 | −2.22 | 0.040575959 |
| ROCK2: Rho-associated, coiled-coil containing protein kinase 2 | NM_004850 | −2.22 | 0.031094733 |
| IMPDH2: IMP (inosine monophosphate) dehydrogenase 2 | NM_000884 | −2.22 | 0.006382837 |
| COL15A1: collagen, type XV, alpha 1 | NM_001855 | −2.22 | 0.012250082 |
| C19orf2: chromosome 19 open reading frame 2 | NM_003796 | −2.22 | 0.015069324 |
| SYNCRIP: synaptotagmin cytoplasmic RNA interacting protein | NM_006372 | −2.23 | 0.048845531 |
| HSPD1: heat shock 60 kDa protein 1 (chaperonin) | NM_002156 | −2.23 | 0.042221588 |
| PRKAR2A: protein kinase, cAMP-dependent regulatory II, alpha | NM_004157 | −2.23 | 0.005848695 |
| CTPS: CTP synthase | NM_001905 | −2.23 | 0.034593254 |
| MTR: 5-methyltetrahydrofolate-homocysteine methyltransferase | NM_000254 | −2.23 | 0.039474405 |
| UBE2Q2: ubiquitin-conjugating enzyme E2Q family member 2 | NM_173469 | −2.24 | 0.049485882 |
| IGF2BP3: insulin-like growth factor 2 mRNA binding protein 3 | NM_006547 | −2.24 | 0.037683742 |
| DIRAS3: DIRAS family, GTP-binding RAS-like 3 | NM_004675 | −2.24 | 0.004124908 |
| VLDLR: very low density lipoprotein receptor | NM_003383 | −2.24 | 0.02011197 |
| FOXM1: forkhead box M1 | NM_202002 | −2.25 | 0.001919008 |
| GNB4: guanine nucleotide binding protein, beta polypeptide 4 | NM_021629 | −2.25 | 0.005083936 |
| ITGBL1: integrin, beta-like 1 (with EGF-like repeat domains) | NM_004791 | −2.25 | 0.046118361 |
| BAP1: BRCA1 associated protein-1 | NM_004656 | −2.25 | 5.21E-05 |
| NFYA: nuclear transcription factor Y, alpha | NM_002505 | −2.25 | 0.042939802 |
| NONO: non-POU domain containing, octamer-binding | NM_007363 | −2.26 | 0.035472693 |
| NMT2: N-myristoyltransferase 2 | NM_004808 | −2.26 | 0.042214394 |
| NCBP1: nuclear cap binding protein subunit 1, 80 kDa | NM_002486 | −2.26 | 0.017686678 |
| THOC3: THO complex 3 | NM_032361 | −2.26 | 0.036302901 |
| TRAIP: TRAF interacting protein | NM_005879 | −2.26 | 0.036956667 |
| LOC388796: hypothetical LOC388796 | NR_015366 | −2.27 | 0.040432333 |
| CDK5RAP2: CDK5 regulatory subunit associated protein 2 | NM_018249 | −2.27 | 0.002350224 |
| C5orf13: chromosome 5 open reading frame 13 | NM_004772 | −2.27 | 0.039757237 |
| EDEM3: ER degradation enhancer, mannosidase alpha-like 3 | NM_025191 | −2.27 | 0.030075188 |
| DDX11: DEAD/H (Asp-Glu-Ala-Asp/His) box polypeptide 11 | NM_030653 | −2.27 | 0.018080477 |
| TMEM209: transmembrane protein 209 | NM_032842 | −2.27 | 0.001701594 |
| C14orf94: chromosome 14 open reading frame 94 | BC001916 | −2.27 | 0.021331063 |
| MLKL: mixed lineage kinase domain-like | NM_152649 | −2.27 | 0.009417127 |
| THOC4: THO complex 4 | NM_005782 | −2.27 | 0.022963702 |
| DMC1: DMC1 dosage suppressor of mck1 homolog | NM_007068 | −2.28 | 0.009252845 |
| KIAA1333: KIAA1333 | NM_017769 | −2.28 | 0.049378957 |
| MRPL16: mitochondrial ribosomal protein L16 | NM_017840 | −2.28 | 0.025020015 |
| WWP1: WW domain containing E3 ubiquitin protein ligase 1 | NM_007013 | −2.28 | 0.010255632 |
| JARID2: jumonji, AT rich interactive domain 2 | NM_004973 | −2.28 | 0.010619606 |
| AOF2: amine oxidase (flavin containing) domain 2 | NM_015013 | −2.28 | 0.017536098 |
| LOC644037: hypothetical LOC644037 | XR_038280 | −2.29 | 0.010568809 |
| RPL22L1: ribosomal protein L22-like 1 | NM_001099645 | −2.29 | 0.033350508 |
| DNAJC9: DnaJ (Hsp40) homolog, subfamily C, member 9 | NM_015190 | −2.29 | 0.042661128 |
| SH3BP5L: SH3-binding domain protein 5-like | NM_030645 | −2.29 | 0.010879669 |
| FAR2: fatty acyl CoA reductase 2 | NM_018099 | −2.29 | 0.00143799 |
| CAMKK2: calcium/calmodulin-dependent protein kinase kinase 2 | NM_006549 | −2.29 | 0.01618779 |
| ADAM10: ADAM metallopeptidase domain 10 | NM_001110 | −2.29 | 0.017696884 |
| TUBGCP4: tubulin, gamma complex associated protein 4 | NM_014444 | −2.29 | 0.018548192 |
| GOLGA5: golgi autoantigen, golgin subfamily a, 5 | NM_005113 | −2.3 | 0.044082838 |

TABLE 3-continued

Global gene expression profile of hFibs vs. Oct-4 transduced hFibs at Day 4

| GENES | Accession | Fold change | p-value |
|---|---|---|---|
| EZH2: enhancer of zeste homolog 2 (Drosophila) | NM_004456 | −2.3 | 0.016344185 |
| SFXN1: sideroflexin 1 | NM_022754 | −2.3 | 0.002611512 |
| TTC14: tetratricopeptide repeat domain 14 | NM_133462 | −2.31 | 0.011708715 |
| SMURF2: SMAD specific E3 ubiquitin protein ligase 2 | NM_022739 | −2.31 | 0.017948626 |
| GALNT5 | NM_014568 | −2.31 | 0.039047442 |
| GEN1: Gen homolog 1, endonuclease (Drosophila) | NM_182625 | −2.31 | 0.003620547 |
| FLJ42986: FLJ42986 protein | AK124976 | −2.32 | 0.035510422 |
| THOC3: THO complex 3 | NM_032361 | −2.33 | 0.034985013 |
| CCDC138: coiled-coil domain containing 138 | NM_144978 | −2.33 | 0.036824721 |
| RAD54B: RAD54 homolog B (S. cerevisiae) | NM_012415 | −2.34 | 0.022132969 |
| SNORA29: small nucleolar RNA, H/ACA box 29 | NR_002965 | −2.34 | 0.030735179 |
| NUP133: nucleoporin 133 kDa | NM_018230 | −2.34 | 0.017026111 |
| CDCA7L: cell division cycle associated 7-like | NM_018719 | −2.34 | 0.036533968 |
| CANT1: calcium activated nucleotidase 1 | NM_138793 | −2.34 | 0.014074243 |
| CDCA4: cell division cycle associated 4 | NM_017955 | −2.34 | 0.008500612 |
| NDST2: N-deacetylase/N-sulfotransferase 2 | NM_003635 | −2.34 | 0.02650435 |
| NCALD: neurocalcin delta | NM_001040624 | −2.35 | 0.009881279 |
| PRPF4: PRP4 pre-mRNA processing factor 4 homolog (yeast) | NM_004697 | −2.35 | 0.004418442 |
| ATP1A1: ATPase, Na+/K+ transporting, alpha 1 polypeptide | NM_000701 | −2.35 | 0.021084011 |
| EXOSC2: exosome component 2 | NM_014285 | −2.35 | 0.024743238 |
| ABCE1: ATP-binding cassette, sub-family E (OABP), member 1 | NM_002940 | −2.36 | 0.046038604 |
| PLAUR: plasminogen activator, urokinase receptor | NM_002659 | −2.36 | 0.030171864 |
| SAAL1: serum amyloid A-like 1 | NM_138421 | −2.36 | 0.013111288 |
| DOCK5: dedicator of cytokinesis 5 | NM_024940 | −2.36 | 0.019750731 |
| LAMC1: laminin, gamma 1 (formerly LAMB2) | NM_002293 | −2.36 | 0.044570562 |
| FANCL: Fanconi anemia, complementation group L | NM_001114636 | −2.37 | 0.041089105 |
| PNPT1: polyribonucleotide nucleotidyltransferase 1 | NM_033109 | −2.37 | 0.038017589 |
| GNL3: guanine nucleotide binding protein-like 3 (nucleolar) | NM_206825 | −2.37 | 0.001394734 |
| ATP8B1: ATPase, class I, type 8B, member 1 | NM_005603 | −2.37 | 0.03613839 |
| ZYG11B: zyg-11 homolog B (C. elegans) | NM_024646 | −2.37 | 0.020663228 |
| SRGAP2: SLIT-ROBO Rho GTPase activating protein 2 | NM_015326 | −2.38 | 0.01054526 |
| SEL1L: sel-1 suppressor of lin-12-like (C. elegans) | NM_005065 | −2.38 | 0.021931558 |
| LNPEP: leucyl/cystinyl aminopeptidase | NM_005575 | −2.38 | 0.031938248 |
| ST3GAL4: ST3 beta-galactoside alpha-2,3-sialyltransferase 4 | NM_006278 | −2.39 | 0.017248347 |
| ELAC2: elaC homolog 2 (E. coli) | NM_018127 | −2.39 | 0.041509605 |
| THEX1: three prime histone mRNA exonuclease 1 | NM_153332 | −2.39 | 0.024488604 |
| H2AFZ: H2A histone family, member Z | NM_002106 | −2.4 | 0.016825189 |
| CPSF3: cleavage and polyadenylation specific factor 3, 73 kDa | NM_016207 | −2.4 | 0.013200285 |
| HDAC2: histone deacetylase 2 | NM_001527 | −2.4 | 0.018367564 |
| EPHB4: EPH receptor B4 | NM_004444 | −2.4 | 0.022324044 |
| VDAC3: voltage-dependent anion channel 3 | NM_005662 | −2.4 | 0.031428461 |
| ANKRD32: ankyrin repeat domain 32 | NM_032290 | −2.4 | 0.037922695 |
| GNL3L: guanine nucleotide binding protein-like 3 (nucleolar)-like | NM_019067 | −2.4 | 0.00705139 |
| THOC5: THO complex 5 | NM_001002878 | −2.4 | 0.01569689 |
| FUT11: fucosyltransferase 11 (alpha (1,3) fucosyltransferase) | NM_173540 | −2.41 | 0.025341384 |
| WDR3: WD repeat domain 3 | NM_006784 | −2.41 | 0.005074073 |
| GINS3: GINS complex subunit 3 (Psf3 homolog) | NM_001126129 | −2.41 | 0.013529977 |
| ATXN10: ataxin 10 | NM_013236 | −2.41 | 0.039439865 |
| NNT: nicotinamide nucleotide transhydrogenase | NM_012343 | −2.41 | 0.011197067 |
| LMNB2: lamin B2 | NM_032737 | −2.41 | 0.011722263 |
| LYCAT: lysocardiolipin acyltransferase | NM_182551 | −2.42 | 0.047366545 |
| PPT1: palmitoyl-protein thioesterase 1 | NM_000310 | −2.42 | 0.010469507 |
| PAQR5: progestin and adipoQ receptor family member V | NM_001104554 | −2.42 | 0.021249814 |
| FAM102B: family with sequence similarity 102, member B | NM_001010883 | −2.42 | 0.028835551 |
| CCBE1: collagen and calcium binding EGF domains 1 | NM_133459 | −2.43 | 0.020809114 |
| CTPS2: CTP synthase II | NM_175859 | −2.44 | 0.034632073 |
| HISPPD1: histidine acid phosphatase domain containing 1 | NM_015216 | −2.44 | 0.039062259 |
| GPD2: glycerol-3-phosphate dehydrogenase 2 (mitochondrial) | NM_001083112 | −2.44 | 0.029946883 |
| TMEM106C: transmembrane protein 106C | NM_024056 | −2.45 | 0.034569478 |
| DARS2: aspartyl-tRNA synthetase 2, mitochondrial | NM_018122 | −2.45 | 0.019519476 |
| MTHFD2: methylenetetrahydrofolate dehydrogenase 2 | NM_001040409 | −2.45 | 0.010898018 |
| EIF3A: eukaryotic translation initiation factor 3, subunit A | NM_003750 | −2.45 | 0.009415013 |
| SMC3: structural maintenance of chromosomes 3 | NM_005445 | −2.46 | 0.035234638 |
| IPO7: importin 7 | NM_006391 | −2.46 | 0.024941799 |
| PCNT: pericentrin | NM_006031 | −2.46 | 0.026897398 |
| TMPO: thymopoietin | NM_001032283 | −2.48 | 0.022817704 |
| ALG10: asparagine-linked glycosylation 10 homolog | NM_032834 | −2.48 | 0.049012163 |

TABLE 3-continued

Global gene expression profile of hFibs vs. Oct-4 transduced hFibs at Day 4

| GENES | Accession | Fold change | p-value |
|---|---|---|---|
| ETFDH: electron-transferring-flavoprotein dehydrogenase | NM_004453 | −2.48 | 0.047358705 |
| UACA | NM_018003 | −2.48 | 0.002944423 |
| DCBLD1: discoidin, CUB and LCCL domain containing 1 | NM_173674 | −2.48 | 0.013168993 |
| SEPHS1: selenophosphate synthetase 1 | NM_012247 | −2.49 | 0.016706056 |
| MCM6: minichromosome maintenance complex component 6 | NM_005915 | −2.49 | 0.026368997 |
| MYBL1: v-myb myeloblastosis viral oncogene homolog-like 1 | NM_001080416 | −2.49 | 0.03370506 |
| MGAT5 | NM_002410 | −2.49 | 0.00484168 |
| HEATR1: HEAT repeat containing 1 | NM_018072 | −2.49 | 0.004877193 |
| METTL7A: methyltransferase like 7A | NM_014033 | −2.5 | 0.03676441 |
| TNFRSF11B: tumor necrosis factor receptor 11b | NM_002546 | −2.5 | 0.011057014 |
| DGCR8: DiGeorge syndrome critical region gene 8 | NM_022720 | −2.5 | 0.036448662 |
| SLC1A5: solute carrier family 1, member 5 | NM_005628 | −2.51 | 0.001138611 |
| CYR61: cysteine-rich, angiogenic inducer, 61 | NM_001554 | −2.51 | 0.009672213 |
| VANGL1: vang-like 1 (van gogh, Drosophila) | NM_138959 | −2.52 | 0.005394434 |
| WIPI2: WD repeat domain, phosphoinositide interacting 2 | NM_015610 | −2.52 | 0.004035807 |
| SNORD4B: small nucleolar RNA, C/D box 4B | NR_000009 | −2.53 | 0.036524188 |
| C18orf55: chromosome 18 open reading frame 55 | NM_014177 | −2.54 | 0.042433254 |
| RBM25: RNA binding motif protein 25 | NM_021239 | −2.54 | 0.012195552 |
| SLC1A1: solute carrier family 1, member 1 | NM_004170 | −2.54 | 0.004826767 |
| PTTG2: pituitary tumor-transforming 2 | NM_006607 | −2.55 | 0.020964869 |
| SLC27A4: solute carrier family 27, member 4 | NM_005094 | −2.55 | 0.034498614 |
| TSR1: TSR1, 20S rRNA accumulation, homolog (S. cerevisiae) | NM_018128 | −2.55 | 0.011069433 |
| TMED5 | NM_016040 | −2.56 | 0.045843853 |
| CHMP7: CHMP family, member 7 | NM_152272 | −2.56 | 0.002316219 |
| MCM2: minichromosome maintenance complex component 2 | NM_004526 | −2.56 | 0.006446562 |
| EIF4A3: eukaryotic translation initiation factor 4A, isoform 3 | NM_014740 | −2.57 | 0.013072361 |
| C8orf32: chromosome 8 open reading frame 32 | AK293492 | −2.57 | 0.049451366 |
| NAP1L4: nucleosome assembly protein 1-like 4 | NM_005969 | −2.58 | 0.010391331 |
| RASA1: RAS p21 protein activator (GTPase activating protein) 1 | NM_002890 | −2.58 | 0.003256153 |
| SNORD5: small nucleolar RNA, C/D box 5 | NR_003033 | −2.58 | 0.000127707 |
| WNT5B: wingless-type MMTV integration site family, member 5B | NM_032642 | −2.59 | 0.033391622 |
| GOLIM4: golgi integral membrane protein 4 | NM_014498 | −2.59 | 0.041421889 |
| AHCTF1: AT hook containing transcription factor 1 | NM_015446 | −2.6 | 0.028305483 |
| ANKRD36B: ankyrin repeat domain 36B | NM_025190 | −2.6 | 0.034345414 |
| ALG8: asparagine-linked glycosylation 8 homolog | NM_024079 | −2.61 | 0.022573911 |
| HOOK3: hook homolog 3 (Drosophila) | NM_032410 | −2.61 | 0.004299545 |
| STC1: stanniocalcin 1 | NM_003155 | −2.62 | 0.010415901 |
| RCC2: regulator of chromosome condensation 2 | NM_018715 | −2.62 | 0.009369894 |
| TMEM109: transmembrane protein 109 | NM_024092 | −2.62 | 0.021866144 |
| FAM72A: family with sequence similarity 72, member A | BC035696 | −2.62 | 0.034275693 |
| DDX11: DEAD/H (Asp-Glu-Ala-Asp/His) box polypeptide 11 | NM_030653 | −2.62 | 0.002884002 |
| TGFBR2: transforming growth factor, beta receptor II (70/80 kDa) | NM_001024847 | −2.63 | 0.007912381 |
| ANKRD36B: ankyrin repeat domain 36B | NM_025190 | −2.63 | 0.019487213 |
| RPA1: replication protein A1, 70 kDa | NM_002945 | −2.63 | 0.001526936 |
| GLCE: glucuronic acid epimerase | NM_015554 | −2.64 | 0.005829522 |
| HMGB2: high-mobility group box 2 | NM_002129 | −2.65 | 0.033636663 |
| SNORD31: small nucleolar RNA, C/D box 31 | NR_002560 | −2.65 | 0.003606872 |
| EMP1: epithelial membrane protein 1 | NM_001423 | −2.65 | 0.004674523 |
| RPN2: ribophorin II | NM_002951 | −2.65 | 0.005493394 |
| FAM72A: family with sequence similarity 72, member A | BC035696 | −2.65 | 0.031854626 |
| PKMYT1: protein kinase, membrane associated tyrosine/threonine 1 | NM_182687 | −2.66 | 0.049800036 |
| TMEM107: transmembrane protein 107 | NM_032354 | −2.66 | 0.032349044 |
| XYLT2: xylosyltransferase II | NM_022167 | −2.66 | 0.004197111 |
| FAM72A: family with sequence similarity 72, member A | BC035696 | −2.66 | 0.032449273 |
| ZC3H13: zinc finger CCCH-type containing 13 | NM_015070 | −2.67 | 0.018784976 |
| WDHD1: WD repeat and HMG-box DNA binding protein 1 | NM_007086 | −2.67 | 0.006933173 |
| SNORD73A: small nucleolar RNA, C/D box 73A | NR_000007 | −2.67 | 0.013874151 |
| CSE1L: CSE1 chromosome segregation 1-like (yeast) | NM_001316 | −2.67 | 0.045684008 |
| PRPS2: phosphoribosyl pyrophosphate synthetase 2 | NM_001039091 | −2.67 | 0.036428731 |
| PPP2R3A: protein phosphatase 2, regulatory subunit B'', alpha | NM_002718 | −2.68 | 0.031629077 |
| INTS10: integrator complex subunit 10 | NM_018142 | −2.68 | 0.02143268 |
| NUP88: nucleoporin 88 kDa | NM_002532 | −2.68 | 0.020178953 |
| SLC9A6: solute carrier family 9, member 6 | NM_001042537 | −2.68 | 0.011618361 |
| LPHN2: latrophilin 2 | NM_012302 | −2.68 | 0.009407681 |
| NUP160: nucleoporin 160 kDa | NM_015231 | −2.68 | 0.021943711 |
| CLCC1: chloride channel CLIC-like 1 | NM_001048210 | −2.69 | 0.037650633 |
| RFC2: replication factor C (activator 1) 2, 40 kDa | NM_181471 | −2.69 | 0.044445519 |
| FANCG: Fanconi anemia, complementation group G | NM_004629 | −2.69 | 0.010584349 |
| KIF22: kinesin family member 22 | NM_007317 | −2.7 | 0.041646898 |

TABLE 3-continued

Global gene expression profile of hFibs vs. Oct-4 transduced hFibs at Day 4

| GENES | Accession | Fold change | p-value |
|---|---|---|---|
| METTL3: methyltransferase like 3 | NM_019852 | −2.7 | 0.034520321 |
| TMTC3: transmembrane and tetratricopeptide repeat containing 3 | NM_181783 | −2.71 | 0.011032114 |
| EFEMP1: EGF-containing fibulin-like extracellular matrix protein 1 | NM_004105 | −2.71 | 0.00709532 |
| ARHGAP19: Rho GTPase activating protein 19 | NM_032900 | −2.71 | 0.003717048 |
| GTF3C2: general transcription factor IIIC, polypeptide 2, beta | NM_001521 | −2.71 | 0.031512828 |
| ANP32B: acidic nuclear phosphoprotein 32 family, member B | NM_006401 | −2.72 | 0.042974297 |
| KIF22: kinesin family member 22 | NM_007317 | −2.73 | 0.04274961 |
| OIP5: Opa interacting protein 5 | NM_007280 | −2.73 | 0.021276651 |
| GOLM1: golgi membrane protein 1 | NM_016548 | −2.73 | 0.036043596 |
| POLD3: polymerase (DNA-directed), delta 3, accessory subunit | NM_006591 | −2.75 | 0.020758429 |
| PDS5B: PDS5, regulator of cohesion maintenance, homolog B | NM_015032 | −2.76 | 0.022177142 |
| GCS1: glucosidase I | NM_006302 | −2.76 | 0.04388769 |
| SESTD1: SEC14 and spectrin domains 1 | NM_178123 | −2.76 | 0.002883818 |
| SMC6: structural maintenance of chromosomes 6 | NM_024624 | −2.77 | 0.022699959 |
| ITGB3: integrin, beta 3 (platelet glycoprotein IIIa, antigen CD61) | NM_000212 | −2.77 | 0.010379112 |
| LRIG3: leucine-rich repeats and immunoglobulin-like domains 3 | NM_153377 | −2.78 | 0.010753728 |
| AGPAT6: 1-acylglycerol-3-phosphate O-acyltransferase 6 | NM_178819 | −2.78 | 0.034066427 |
| STIL: SCL/TAL1 interrupting locus | NM_001048166 | −2.79 | 0.017897191 |
| LOC91431: prematurely terminated mRNA decay factor-like | NM_001099776 | −2.79 | 0.006696314 |
| SERPINH1: serpin peptidase inhibitor, clade H, member 1 | NM_001235 | −2.8 | 0.000647946 |
| MMP3: matrix metallopeptidase 3 (stromelysin 1, progelatinase) | NM_002422 | −2.8 | 0.023366087 |
| TMEM19: transmembrane protein 19 | NM_018279 | −2.81 | 0.004530772 |
| CPS1: carbamoyl-phosphate synthetase 1, mitochondrial | NM_001875 | −2.81 | 0.041870042 |
| SNORD113-3: small nucleolar RNA, C/D box 113-3 | NR_003231 | −2.82 | 0.024542115 |
| ATAD5: ATPase family, AAA domain containing 5 | NM_024857 | −2.82 | 0.038184837 |
| CASP2: caspase 2, apoptosis-related cysteine peptidase | NM_032982 | −2.82 | 0.003308632 |
| POLR2B: polymerase (RNA) II (DNA directed) polypeptide B | NM_000938 | −2.82 | 0.007282975 |
| ADPGK: ADP-dependent glucokinase | NR_023318 | −2.83 | 0.007670222 |
| BZW2: basic leucine zipper and W2 domains 2 | NM_014038 | −2.83 | 0.003829986 |
| SNORA6: small nucleolar RNA, H/ACA box 6 | NR_002325 | −2.83 | 0.029880813 |
| NIN: ninein (GSK3B interacting protein) | NM_020921 | −2.83 | 0.031076246 |
| KCTD3: potassium channel tetramerisation domain containing 3 | NM_016121 | −2.84 | 0.007423643 |
| MASTL: microtubule associated serine/threonine kinase-like | NM_032844 | −2.84 | 0.012062567 |
| PLOD2: procollagen-lysine, 2-oxoglutarate 5-dioxygenase 2 | NM_182943 | −2.85 | 0.033419457 |
| BARD1: BRCA1 associated RING domain 1 | NM_000465 | −2.85 | 0.034076023 |
| FANCA: Fanconi anemia, complementation group A | NM_000135 | −2.85 | 0.019494413 |
| PSMC3IP: PSMC3 interacting protein | NM_013290 | −2.85 | 0.019857157 |
| CENPM: centromere protein M | NM_024053 | −2.87 | 0.033724716 |
| ARPC1A: actin related protein 2/3 complex, subunit 1A, 41 kDa | NM_006409 | −2.88 | 0.017661245 |
| TROAP: trophinin associated protein (tastin) | NM_005480 | −2.88 | 0.023631499 |
| DDX23: DEAD (Asp-Glu-Ala-Asp) box polypeptide 23 | NM_004818 | −2.88 | 0.018106207 |
| AKR1C3: aldo-keto reductase family 1, member C3 | NM_003739 | −2.89 | 0.030394002 |
| HMGCR: 3-hydroxy-3-methylglutaryl-Coenzyme A reductase | NM_000859 | −2.89 | 0.000592772 |
| ASF1B: ASF1 anti-silencing function 1 homolog B (*S. cerevisiae*) | NM_018154 | −2.9 | 0.007033297 |
| PSRC1: proline/serine-rich coiled-coil 1 | NM_001032290 | −2.9 | 0.026355548 |
| ZDHHC6: zinc finger, DHHC-type containing 6 | NM_022494 | −2.91 | 0.015811143 |
| LOXL2: lysyl oxidase-like 2 | NM_002318 | −2.93 | 0.027112446 |
| DPYSL2: dihydropyrimidinase-like 2 | NM_001386 | −2.93 | 0.019036817 |
| TM4SF1: transmembrane 4 L six family member 1 | NM_014220 | −2.94 | 0.023381095 |
| SPTLC2: serine palmitoyltransferase, long chain base subunit 2 | NM_004863 | −2.94 | 0.028783412 |
| MMP14: matrix metallopeptidase 14 (membrane-inserted) | NM_004995 | −2.94 | 0.014386738 |
| DKK1: dickkopf homolog 1 (*Xenopus laevis*) | NM_012242 | −2.95 | 0.010889917 |
| EME1: essential meiotic endonuclease 1 homolog 1 (*S. pombe*) | NM_152463 | −2.95 | 0.010943083 |
| NUP155: nucleoporin 155 kDa | NM_153485 | −2.95 | 0.015556838 |
| WDR40A: WD repeat domain 40A | NM_015397 | −2.95 | 0.002259207 |
| ABCD3: ATP-binding cassette, sub-family D (ALD), member 3 | NM_002858 | −2.96 | 0.028991333 |
| ITGA4: integrin, alpha 4 | NM_000885 | −2.96 | 0.013530217 |
| CENPQ: centromere protein Q | NM_018132 | −2.97 | 0.047657259 |
| APAF1: apoptotic peptidase activating factor 1 | NM_181861 | −2.97 | 0.020291148 |
| RALGPS2: Ral GEF with PH domain and SH3 binding motif 2 | NM_152663 | −2.98 | 0.013121392 |

TABLE 3-continued

Global gene expression profile of hFibs vs. Oct-4 transduced hFibs at Day 4

| GENES | Accession | Fold change | p-value |
|---|---|---|---|
| WDR4: WD repeat domain 4 | NM_018669 | −2.98 | 0.001857422 |
| PECI: peroxisomal D3,D2-enoyl-CoA isomerase | NM_206836 | −3 | 0.018600236 |
| LEPRE1: leucine proline-enriched proteoglycan (leprecan) 1 | NM_022356 | −3.01 | 0.028784846 |
| C5orf34: chromosome 5 open reading frame 34 | BC036867 | −3.01 | 0.031497145 |
| FUT8: fucosyltransferase 8 (alpha (1,6) fucosyltransferase) | NM_178155 | −3.01 | 0.023562532 |
| MCM5: minichromosome maintenance complex component 5 | NM_006739 | −3.01 | 0.035929024 |
| POLR3B: polymerase (RNA) III (DNA directed) polypeptide B | NM_018082 | −3.01 | 0.011381478 |
| PRG4: proteoglycan 4 | NM_005807 | −3.02 | 0.00601482 |
| CCDC77: coiled-coil domain containing 77 | NM_032358 | −3.03 | 0.010421873 |
| DDX46: DEAD (Asp-Glu-Ala-Asp) box polypeptide 46 | NM_014829 | −3.05 | 0.02604896 |
| FAM20B: family with sequence similarity 20, member B | BC051794 | −3.05 | 0.001425466 |
| COL6A3: collagen, type VI, alpha 3 | NM_004369 | −3.05 | 0.038940075 |
| MAD2L1: MAD2 mitotic arrest deficient-like 1 (yeast) | NM_002358 | −3.06 | 0.033827837 |
| SLC38A1: solute carrier family 38, member 1 | NM_030674 | −3.06 | 0.012108029 |
| CTR9: Ctr9, Paf1/RNA polymerase II complex component | NM_014633 | −3.06 | 0.022722617 |
| FAM72A: family with sequence similarity 72, member A | ENST00000369175 | −3.07 | 0.043211118 |
| CUL3: cullin 3 | NM_003590 | −3.07 | 0.011866288 |
| SMARCC1 | NM_003074 | −3.07 | 0.030291171 |
| MCM4: minichromosome maintenance complex component 4 | NM_005914 | −3.07 | 0.004834585 |
| CCNF: cyclin F | NM_001761 | −3.08 | 0.005114967 |
| MTHFD1: methylenetetrahydrofolate dehydrogenase 1 | NM_005956 | −3.08 | 0.010131973 |
| DDIT4: DNA-damage-inducible transcript 4 | NM_019058 | −3.08 | 0.010098044 |
| TTF2: transcription termination factor, RNA polymerase II | NM_003594 | −3.08 | 0.011153371 |
| GINS1: GINS complex subunit 1 (Psf1 homolog) | NM_021067 | −3.1 | 0.012394736 |
| TFDP1: transcription factor Dp-1 | NM_007111 | −3.1 | 0.007269234 |
| MTAP: methylthioadenosine phosphorylase | NM_002451 | −3.1 | 0.012325728 |
| MIRN21: microRNA 21 | AY699265 | −3.1 | 0.027479521 |
| SNORD58A: small nucleolar RNA, C/D box 58A | NR_002571 | −3.11 | 0.035633007 |
| NRP1: neuropilin 1 | NM_003873 | −3.12 | 0.00337744 |
| PTTG1: pituitary tumor-transforming 1 | NM_004219 | −3.14 | 0.028311698 |
| ORC1L: origin recognition complex, subunit 1-like (yeast) | NM_004153 | −3.14 | 0.028983138 |
| NAE1: NEDD8 activating enzyme E1 subunit 1 | NM_001018159 | −3.14 | 0.038143006 |
| SNORD96A: small nucleolar RNA, C/D box 96A | NR_002592 | −3.14 | 0.019451938 |
| SPCS3: signal peptidase complex subunit 3 homolog | NM_021928 | −3.15 | 0.027304589 |
| CKAP5: cytoskeleton associated protein 5 | NM_001008938 | −3.15 | 0.02351903 |
| CSGLCA-T: chondroitin sulfate glucuronyltransferase | NM_019015 | −3.16 | 0.017197107 |
| ZAK: sterile alpha motif and leucine zipper containing kinase AZK | NM_133646 | −3.17 | 0.046435057 |
| APOBEC3B | NM_004900 | −3.2 | 0.021754743 |
| AP1M1: adaptor-related protein complex 1, mu 1 subunit | NM_032493 | −3.2 | 0.001424072 |
| TIMELESS: timeless homolog (Drosophila) | NM_003920 | −3.21 | 0.007193004 |
| PDCD4: programmed cell death 4 | NM_145341 | −3.21 | 0.041665158 |
| MAN1A1: mannosidase, alpha, class 1A, member 1 | NM_005907 | −3.21 | 0.019748675 |
| SASS6: spindle assembly 6 homolog (C. elegans) | NM_194292 | −3.22 | 0.01989618 |
| NUP205: nucleoporin 205 kDa | NM_015135 | −3.22 | 0.005899841 |
| ANKRD36B: ankyrin repeat domain 36B | NM_025190 | −3.23 | 0.047475718 |
| RAD18: RAD18 homolog (S. cerevisiae) | NM_020165 | −3.23 | 0.001502957 |
| POP1: processing of precursor 1, ribonuclease P/MRP subunit | NM_015029 | −3.23 | 0.011734917 |
| TYMS: thymidylate synthetase | NM_001071 | −3.23 | 0.037215325 |
| SNORA13: small nucleolar RNA, H/ACA box 13 | NR_002922 | −3.24 | 0.017825976 |
| FANCM: Fanconi anemia, complementation group M | NM_020937 | −3.24 | 0.024199282 |
| DHFR: dihydrofolate reductase | NM_000791 | −3.24 | 0.025344887 |
| RTTN: rotatin | NM_173630 | −3.25 | 0.021737969 |
| SUV39H1: suppressor of variegation 3-9 homolog 1 (Drosophila) | NM_003173 | −3.26 | 0.017552758 |
| DHFR: dihydrofolate reductase | NM_000791 | −3.26 | 0.010689388 |
| VCP: valosin-containing protein | NM_007126 | −3.26 | 0.011120284 |
| AKR1C4: aldo-keto reductase family 1, member C4 | NM_001818 | −3.27 | 0.013531545 |
| HAT1: histone acetyltransferase 1 | NM_003642 | −3.27 | 0.025041969 |
| STARD7: StAR-related lipid transfer (START) domain containing 7 | NM_020151 | −3.28 | 0.001948089 |
| EMP2: epithelial membrane protein 2 | NM_001424 | −3.28 | 0.006424876 |
| CHEK1: CHK1 checkpoint homolog (S. pombe) | NM_001274 | −3.29 | 0.011451232 |
| CNPY4: canopy 4 homolog (zebrafish) | NM_152755 | −3.3 | 0.010311962 |
| RAD21: RAD21 homolog (S. pombe) | NM_006265 | −3.32 | 0.037218105 |
| CTSL3: cathepsin L family member 3 | NM_001023564 | −3.34 | 0.044901181 |
| MYBL2: v-myb myeloblastosis viral oncogene homolog-like 2 | NM_002466 | −3.35 | 0.002400315 |
| WDR51A: WD repeat domain 51A | NM_015426 | −3.35 | 0.015784564 |
| GLT8D1: glycosyltransferase 8 domain containing 1 | NM_001010983 | −3.38 | 0.036372 |
| APPL1 | NM_012096 | −3.38 | 0.013223775 |
| ATL3: atlastin 3 | NM_015459 | −3.38 | 0.046230649 |
| BICD2: bicaudal D homolog 2 (Drosophila) | NM_001003800 | −3.38 | 0.016766277 |

TABLE 3-continued

Global gene expression profile of hFibs vs. Oct-4 transduced hFibs at Day 4

| GENES | Accession | Fold change | p-value |
|---|---|---|---|
| THBD: thrombomodulin | NM_000361 | −3.4 | 0.005386297 |
| C15orf42: chromosome 15 open reading frame 42 | NM_152259 | −3.4 | 0.044035721 |
| NCAPD3: non-SMC condensin II complex, subunit D3 | NM_015261 | −3.4 | 0.000839888 |
| NUP107: nucleoporin 107 kDa | NM_020401 | −3.41 | 0.027814664 |
| NEDD1 | NM_152905 | −3.41 | 0.022874072 |
| XRCC2: X-ray repair complementing defective repair cells 2 | NM_005431 | −3.42 | 0.004409417 |
| HTATSF1: HIV-1 Tat specific factor 1 | NM_014500 | −3.42 | 0.019185925 |
| CDC6: cell division cycle 6 homolog (S. cerevisiae) | NM_001254 | −3.42 | 0.008710068 |
| GSTCD: glutathione S-transferase, C-terminal domain containing | NM_001031720 | −3.43 | 0.025170077 |
| STMN1: stathmin 1/oncoprotein 18 | NM_203401 | −3.43 | 0.021312021 |
| CCDC99: coiled-coil domain containing 99 | NM_017785 | −3.43 | 0.037055021 |
| LSM2: LSM2 homolog, U6 small nuclear RNA associated | NM_021177 | −3.45 | 0.023713986 |
| LSM2: LSM2 homolog, U6 small nuclear RNA associated | NM_021177 | −3.45 | 0.023713986 |
| LSM2: LSM2 homolog, U6 small nuclear RNA associated | NM_021177 | −3.45 | 0.023713986 |
| NASP: nuclear autoantigenic sperm protein (histone-binding) | NM_172164 | −3.46 | 0.021212208 |
| C6orf173: chromosome 6 open reading frame 173 | NM_001012507 | −3.46 | 0.013358256 |
| HYOU1: hypoxia up-regulated 1 | NM_006389 | −3.47 | 0.041399999 |
| GNE: glucosamine (UDP-N-acetyl)-2-epimerase | NM_005476 | −3.48 | 0.0007743 |
| tAKR: aldo-keto reductase, truncated | AB037902 | −3.49 | 0.015434682 |
| MYC: v-myc myelocytomatosis viral oncogene homolog (avian) | NM_002467 | −3.49 | 0.004252963 |
| CDK2: cyclin-dependent kinase 2 | NM_001798 | −3.49 | 0.02613663 |
| SUPT16H: suppressor of Ty 16 homolog (S. cerevisiae) | NM_007192 | −3.5 | 0.011036257 |
| LBR: lamin B receptor | NM_002296 | −3.51 | 0.004957337 |
| MRE11A: MRE11 meiotic recombination 11 homolog A | NM_005591 | −3.52 | 0.008653988 |
| RFC5: replication factor C (activator 1) 5, 36.5 kDa | NM_007370 | −3.52 | 0.02187458 |
| POLA1: polymerase (DNA directed), alpha 1, catalytic subunit | NM_016937 | −3.52 | 0.003953822 |
| NY-SAR-48: sarcoma antigen NY-SAR-48 | NM_033417 | −3.54 | 0.044014998 |
| KATNAL1: katanin p60 subunit A-like 1 | NM_001014380 | −3.54 | 0.009783192 |
| RFWD3: ring finger and WD repeat domain 3 | NM_018124 | −3.55 | 0.011324117 |
| CEP78: centrosomal protein 78 kDa | NM_001098802 | −3.57 | 0.0016975 |
| MSN: moesin | NM_002444 | −3.57 | 0.009076967 |
| CENPN: centromere protein N | NM_001100624 | −3.58 | 0.0335116 |
| DCLRE1B: DNA cross-link repair 1B (PSO2 homolog, S. cerevisiae) | NM_022836 | −3.59 | 0.010521683 |
| WHSC1: Wolf-Hirschhorn syndrome candidate 1 | NM_133330 | −3.6 | 0.002776674 |
| RGMB: RGM domain family, member B | NM_001012761 | −3.61 | 0.037945236 |
| BIRC5: baculoviral IAP repeat-containing 5 | NM_001168 | −3.62 | 0.01082439 |
| DNASE1L3: deoxyribonuclease I-like 3 | NM_004944 | −3.65 | 0.001182208 |
| LGR4: leucine-rich repeat-containing G protein-coupled receptor 4 | NM_018490 | −3.65 | 0.007489299 |
| C6orf167: chromosome 6 open reading frame 167 | NM_198468 | −3.65 | 0.014707124 |
| PENK: proenkephalin | NM_006211 | −3.66 | 0.036826868 |
| FBN1: fibrillin 1 | NM_000138 | −3.66 | 0.040182037 |
| CDCA5: cell division cycle associated 5 | NM_080668 | −3.67 | 0.006490483 |
| IL13RA2: interleukin 13 receptor, alpha 2 | NM_000640 | −3.68 | 0.033161163 |
| SGK1: serum/glucocorticoid regulated kinase 1 | NM_005627 | −3.69 | 0.015425347 |
| CENPJ: centromere protein J | NM_018451 | −3.7 | 0.042173402 |
| TPR: translocated promoter region (to activated MET oncogene) | NM_003292 | −3.7 | 0.027668604 |
| AKR1C1: aldo-keto reductase family 1, member C1 | NM_001353 | −3.71 | 0.02354857 |
| RBBP8: retinoblastoma binding protein 8 | NM_002894 | −3.73 | 0.027806512 |
| CEP97: centrosomal protein 97 kDa | NM_024548 | −3.73 | 0.011707226 |
| ZC3HAV1: zinc finger CCCH-type, antiviral 1 | NM_020119 | −3.74 | 0.043626293 |
| CDCA7: cell division cycle associated 7 | NM_031942 | −3.75 | 0.016859814 |
| KIF2A: kinesin heavy chain member 2A | NM_004520 | −3.75 | 0.013671485 |
| ITGB3BP: integrin beta 3 binding protein (beta3-endonexin) | NM_014288 | −3.75 | 0.014900666 |
| FAM29A: family with sequence similarity 29, member A | NM_017645 | −3.76 | 0.006894399 |
| ERO1L: ERO1-like (S. cerevisiae) | NM_014584 | −3.77 | 0.004412076 |
| ATL3: atlastin 3 | AK090822 | −3.77 | 0.026740981 |
| GLB1: galactosidase, beta 1 | NM_000404 | −3.77 | 0.037346081 |
| HNRNPR: heterogeneous nuclear ribonucleoprotein R | NM_001102398 | −3.78 | 0.021443364 |
| UBASH3B: ubiquitin associated and SH3 domain containing, B | NM_032873 | −3.79 | 0.01938896 |
| HIST2H2AB: histone cluster 2, H2ab | NM_175065 | −3.8 | 0.015412178 |
| KCTD20: potassium channel tetramerisation domain containing 20 | NM_173562 | −3.81 | 0.009173158 |
| GINS4: GINS complex subunit 4 (Sld5 homolog) | NM_032336 | −3.81 | 0.009179253 |
| RRM1: ribonucleotide reductase M1 | NM_001033 | −3.82 | 0.010380875 |
| KPNB1: karyopherin (importin) beta 1 | NM_002265 | −3.82 | 0.031057362 |
| DIAPH3: diaphanous homolog 3 (Drosophila) | NM_001042517 | −3.82 | 0.005890863 |
| DTL: denticleless homolog (Drosophila) | NM_016448 | −3.83 | 0.017101198 |

TABLE 3-continued

Global gene expression profile of hFibs vs. Oct-4 transduced hFibs at Day 4

| GENES | Accession | Fold change | p-value |
|---|---|---|---|
| NCSTN: nicastrin | NM_015331 | −3.84 | 0.000433316 |
| DOCK10: dedicator of cytokinesis 10 | NM_014689 | −3.85 | 0.008213513 |
| ANP32E: acidic nuclear phosphoprotein 32 family, member E | NM_030920 | −3.86 | 0.032209315 |
| CKAP2L: cytoskeleton associated protein 2-like | NM_152515 | −3.87 | 0.023411908 |
| BRCA2: breast cancer 2, early onset | NM_000059 | −3.87 | 0.002128925 |
| CDC25B: cell division cycle 25 homolog B (S. pombe) | NM_021873 | −3.9 | 0.003077211 |
| DDIT4L: DNA-damage-inducible transcript 4-like | NM_145244 | −3.94 | 0.019049984 |
| OLFML2B: olfactomedin-like 2B | NM_015441 | −3.94 | 0.003377518 |
| CD9: CD9 molecule | NM_001769 | −3.95 | 0.008545553 |
| CKS1B: CDC28 protein kinase regulatory subunit 1B | NM_001826 | −3.95 | 0.006037425 |
| CCDC80: coiled-coil domain containing 80 | NM_199511 | −3.95 | 0.006609893 |
| CKS1B: CDC28 protein kinase regulatory subunit 1B | NM_001826 | −3.96 | 0.005028013 |
| DKC1: dyskeratosis congenita 1, dyskerin | NM_001363 | −3.99 | 0.027694764 |
| MMP1: matrix metallopeptidase 1 (interstitial collagenase) | NM_002421 | −4 | 0.014418235 |
| FAM54A: family with sequence similarity 54, member A | NM_001099286 | −4.03 | 0.006364463 |
| FAM29A: family with sequence similarity 29, member A | NM_017645 | −4.05 | 0.014763219 |
| VRK1: vaccinia related kinase 1 | NM_003384 | −4.05 | 0.022044795 |
| TDP1: tyrosyl-DNA phosphodiesterase 1 | NM_018319 | −4.05 | 0.025305827 |
| HERPUD1 | NM_014685 | −4.07 | 0.013120239 |
| CDC25C: cell division cycle 25 homolog C (S. pombe) | NM_001790 | −4.08 | 0.024886353 |
| WEE1: WEE1 homolog (S. pombe) | NM_003390 | −4.09 | 0.014041834 |
| MCM7: minichromosome maintenance complex component 7 | NM_005916 | −4.13 | 0.024734886 |
| C18orf54: chromosome 18 open reading frame 54 | NM_173529 | −4.16 | 0.036455934 |
| IQGAP3: IQ motif containing GTPase activating protein 3 | NM_178229 | −4.18 | 0.000379041 |
| KRT34: keratin 34 | NM_021013 | −4.18 | 0.014644898 |
| CHAF1B: chromatin assembly factor 1, subunit B (p60) | NM_005441 | −4.19 | 0.005348677 |
| ZWILCH: Zwilch, kinetochore associated, homolog (Drosophila) | NR_003105 | −4.19 | 0.00336525 |
| RFC4: replication factor C (activator 1) 4, 37 kDa | NM_002916 | −4.19 | 0.030961838 |
| WEE1: WEE1 homolog (S. pombe) | BX641032 | −4.22 | 0.017225413 |
| POLA2: polymerase (DNA directed), alpha 2 (70 kD subunit) | NM_002689 | −4.22 | 0.013154919 |
| CYP24A1: cytochrome P450, family 24, subfamily A, polypeptide 1 | NM_000782 | −4.25 | 0.044168548 |
| CENPO: centromere protein O | NM_024322 | −4.27 | 0.029013956 |
| SLC7A11: solute carrier family 7 | NM_014331 | −4.29 | 0.009705328 |
| SPATA5: spermatogenesis associated 5 | NM_145207 | −4.29 | 0.015984863 |
| ARHGAP11B: Rho GTPase activating protein 11B | NM_001039841 | −4.31 | 0.011747473 |
| GTSE1: G-2 and S-phase expressed 1 | NM_016426 | −4.31 | 0.018713948 |
| MCM3: minichromosome maintenance complex component 3 | NM_002388 | −4.33 | 0.012084875 |
| MSH2: mutS homolog 2, colon cancer, nonpolyposis type 1 | NM_000251 | −4.33 | 0.035783705 |
| WEE1: WEE1 homolog (S. pombe) | BX641032 | −4.35 | 0.000695252 |
| C4orf21: chromosome 4 open reading frame 21 | BC044799 | −4.36 | 0.02594976 |
| FST: follistatin | NM_006350 | −4.36 | 0.01830473 |
| MALL: mal, T-cell differentiation protein-like | NM_005434 | −4.39 | 0.014343063 |
| MLF1IP: MLF1 interacting protein | NM_024629 | −4.39 | 0.022773614 |
| MATN2: matrilin 2 | NM_002380 | −4.4 | 0.009218294 |
| RECK: reversion-inducing-cysteine-rich protein with kazal motifs | NM_021111 | −4.4 | 0.003371515 |
| SKP2: S-phase kinase-associated protein 2 (p45) | NM_005983 | −4.41 | 0.000189837 |
| REEP4: receptor accessory protein 4 | NM_025232 | −4.41 | 0.024102962 |
| NID2: nidogen 2 (osteonidogen) | NM_007361 | −4.41 | 0.009245711 |
| ECT2: epithelial cell transforming sequence 2 oncogene | NM_018098 | −4.44 | 0.001371533 |
| HIST1H3B: histone cluster 1, H3b | NM_003537 | −4.47 | 0.030339315 |
| CDCA8: cell division cycle associated 8 | NM_018101 | −4.47 | 0.028564289 |
| NUP93: nucleoporin 93 kDa | NM_014669 | −4.49 | 0.019348299 |
| AURKB: aurora kinase B | NM_004217 | −4.49 | 0.009148851 |
| TEK: TEK tyrosine kinase, endothelial | NM_000459 | −4.49 | 0.018780434 |
| HSPA8: heat shock 70 kDa protein 8 | NM_006597 | −4.5 | 0.001621436 |
| ISLR: immunoglobulin superfamily containing leucine-rich repeat | NM_005545 | −4.52 | 0.027171337 |
| CDC45L: CDC45 cell division cycle 45-like (S. cerevisiae) | NM_003504 | −4.56 | 0.016054447 |
| BRIP1: BRCA1 interacting protein C-terminal helicase 1 | NM_032043 | −4.57 | 0.007308546 |
| SLC38A2: solute carrier family 38, member 2 | NM_018976 | −4.59 | 0.00620721 |
| C15orf23: chromosome 15 open reading frame 23 | NM_033286 | −4.6 | 0.012211419 |
| UBE2C: ubiquitin-conjugating enzyme E2C | NM_181802 | −4.6 | 0.02023828 |
| SHCBP1: SHC SH2-domain binding protein 1 | NM_024745 | −4.63 | 0.027145093 |
| MPHOSPH9: M-phase phosphoprotein 9 | NM_022782 | −4.64 | 0.008536058 |
| CTSL1: cathepsin L1 | NM_001912 | −4.65 | 0.004992522 |
| MAT2A: methionine adenosyltransferase II, alpha | NM_005911 | −4.69 | 0.003823851 |
| GALNTL2: UDP-N-acetyl-alpha-D-galactosamine | NM_054110 | −4.73 | 0.002123087 |
| HSPA5: heat shock 70 kDa protein 5 | NM_005347 | −4.75 | 0.027477696 |
| ALG6: asparagine-linked glycosylation 6 homolog | NM_013339 | −4.77 | 0.024806465 |
| TNC: tenascin C | NM_002160 | −4.77 | 0.0114281 |
| KNTC1: kinetochore associated 1 | NM_014708 | −4.78 | 0.001458855 |

TABLE 3-continued

Global gene expression profile of hFibs vs. Oct-4 transduced hFibs at Day 4

| GENES | Accession | Fold change | p-value |
|---|---|---|---|
| POLQ: polymerase (DNA directed), theta | NM_199420 | −4.79 | 0.026999179 |
| ADAMTS1: ADAM metallopeptidase with thrombospondin type 1 | NM_006988 | −4.81 | 0.000284897 |
| FANCI: Fanconi anemia, complementation group I | NM_001113378 | −4.83 | 0.022756296 |
| PDIA5: protein disulfide isomerase family A, member 5 | NM_006810 | −4.84 | 0.031177224 |
| TCF19: transcription factor 19 (SC1) | NM_007109 | −4.85 | 0.001920593 |
| PARP1: poly (ADP-ribose) polymerase 1 | NM_001618 | −4.86 | 0.007724835 |
| ANPEP: alanyl (membrane) aminopeptidase | NM_001150 | −4.89 | 0.017761228 |
| CENPK: centromere protein K | NM_022145 | −4.9 | 0.046603065 |
| TCF19: transcription factor 19 (SC1) | NM_007109 | −4.91 | 0.003070795 |
| TCF19: transcription factor 19 (SC1) | NM_007109 | −4.91 | 0.003070795 |
| NEIL3: nei endonuclease VIII-like 3 (E. coli) | NM_018248 | −4.92 | 0.001075466 |
| ITGA5: integrin, alpha 5 (fibronectin receptor, alpha polypeptide) | NM_002205 | −5 | 0.021315582 |
| KDELC1: KDEL (Lys-Asp-Glu-Leu) containing 1 | NM_024089 | −5.01 | 0.047199012 |
| FIBIN: fin bud initiation factor | NM_203371 | −5.01 | 0.046653181 |
| ZWINT: ZW10 interactor | NM_032997 | −5.04 | 0.027696874 |
| HIST1H1A: histone cluster 1, H1a | NM_005325 | −5.09 | 0.01356251 |
| ATAD2: ATPase family, AAA domain containing 2 | NM_014109 | −5.1 | 0.046938961 |
| TOPBP1: topoisomerase (DNA) II binding protein 1 | NM_007027 | −5.13 | 0.038866152 |
| TMEM48: transmembrane protein 48 | NM_018087 | −5.17 | 0.013425569 |
| NUP85: nucleoporin 85 kDa | NM_024844 | −5.18 | 0.022730382 |
| NT5E: 5′-nucleotidase, ecto (CD73) | NM_002526 | −5.18 | 0.005165995 |
| ERCC6L: excision repair cross-complementing repair deficiency | NM_017669 | −5.25 | 0.037116351 |
| KIF15: kinesin family member 15 | NM_020242 | −5.3 | 0.024744242 |
| SEMA7A: semaphorin 7A, GPI membrane anchor | NM_003612 | −5.36 | 0.019406028 |
| SMC1A: structural maintenance of chromosomes 1A | NM_006306 | −5.39 | 0.040588398 |
| BUB1B: budding uninhibited by benzimidazoles 1 homolog beta | NM_001211 | −5.43 | 0.030577263 |
| PODXL: podocalyxin-like | NM_001018111 | −5.44 | 0.046572766 |
| RACGAP1: Rac GTPase activating protein 1 | NM_013277 | −5.46 | 0.011950377 |
| CDC7: cell division cycle 7 homolog (S. cerevisiae) | NM_003503 | −5.49 | 0.023548326 |
| SNORD45C: small nucleolar RNA, C/D box 45C | NR_003042 | −5.51 | 0.020984632 |
| AMD1: adenosylmethionine decarboxylase 1 | NM_001634 | −5.58 | 0.017403212 |
| RAD51AP1: RAD51 associated protein 1 | NM_006479 | −5.6 | 0.03298607 |
| KIF18A: kinesin family member 18A | NM_031217 | −5.63 | 0.048229213 |
| PDGFRA: platelet-derived growth factor receptor alpha | NM_006206 | −5.63 | 0.014896088 |
| CKAP2: cytoskeleton associated protein 2 | NM_018204 | −5.63 | 0.020068434 |
| FANCD2: Fanconi anemia, complementation group D2 | NM_033084 | −5.64 | 0.016641728 |
| RBL1: retinoblastoma-like 1 (p107) | NM_002895 | −5.66 | 0.024252907 |
| DEPDC1B: DEP domain containing 1B | NM_018369 | −5.67 | 0.022605243 |
| MCM8: minichromosome maintenance complex component 8 | NM_032485 | −5.68 | 0.002917449 |
| KIF2C: kinesin family member 2C | NM_006845 | −5.7 | 0.010394746 |
| UBE2T: ubiquitin-conjugating enzyme E2T (putative) | NM_014176 | −5.73 | 0.029596772 |
| BRCA1: breast cancer 1, early onset | NM_007296 | −5.73 | 0.011735761 |
| CDCA3: cell division cycle associated 3 | NM_031299 | −5.75 | 0.028377908 |
| PLAT: plasminogen activator, tissue | NM_000930 | −5.81 | 0.017135561 |
| SMC2: structural maintenance of chromosomes 2 | NM_001042551 | −5.84 | 0.021246504 |
| KIAA1524: KIAA1524 | NM_020890 | −5.88 | 0.014262199 |
| NCAPD2: non-SMC condensin I complex, subunit D2 | NM_014865 | −5.94 | 0.009204334 |
| GPSM2: G-protein signaling modulator 2 (AGS3-like, C. elegans) | NM_013296 | −6.05 | 0.00253489 |
| CLSPN: claspin homolog (Xenopus laevis) | NM_022111 | −6.06 | 0.03807435 |
| C13orf3: chromosome 13 open reading frame 3 | NM_145061 | −6.11 | 0.031873242 |
| RFC3: replication factor C (activator 1) 3, 38 kDa | NM_002915 | −6.12 | 0.019632107 |
| C18orf24: chromosome 18 open reading frame 24 | NM_001039535 | −6.19 | 0.039810882 |
| TACC3: transforming, acidic coiled-coil containing protein 3 | NM_006342 | −6.19 | 0.017952851 |
| C14orf145: chromosome 14 open reading frame 145 | NM_152446 | −6.22 | 0.007797356 |
| NEK2: NIMA (never in mitosis gene a)-related kinase 2 | NM_002497 | −6.33 | 0.002681177 |
| NUSAP1: nucleolar and spindle associated protein 1 | NM_016359 | −6.33 | 0.049437931 |
| HIST1H2BM: histone cluster 1, H2bm | NM_003521 | −6.4 | 0.029910293 |
| HIST1H1E: histone cluster 1, H1e | NM_005321 | −6.41 | 0.004360528 |
| PRIM1: primase, DNA, polypeptide 1 (49 kDa) | NM_000946 | −6.42 | 0.002907531 |
| AURKA: aurora kinase A | NM_198433 | −6.49 | 0.033564734 |
| HJURP: Holliday junction recognition protein | NM_018410 | −6.66 | 0.000926767 |
| CEP55: centrosomal protein 55 kDa | NM_018131 | −6.68 | 0.032269904 |
| DBX2: developing brain homeobox 2 | ENST00000332700 | −6.84 | 0.047533804 |
| KIF4B: kinesin family member 4B | NM_001099293 | −6.85 | 0.02993245 |
| CDC20: cell division cycle 20 homolog (S. cerevisiae) | NM_001255 | −6.89 | 0.021541425 |
| HELLS: helicase, lymphoid-specific | NM_018063 | −6.91 | 0.028245951 |
| KIFC1: kinesin family member C1 | NM_002263 | −6.98 | 0.033788145 |
| NCAPH: non-SMC condensin I complex, subunit H | NM_015341 | −7.09 | 0.025734154 |
| TRIP13: thyroid hormone receptor interactor 13 | NM_004237 | −7.1 | 0.002615203 |
| RAD51: RAD51 homolog (RecA homolog, E. coli) (S. cerevisiae) | NM_002875 | −7.11 | 0.023887145 |
| KIF11: kinesin family member 11 | NM_004523 | −7.15 | 0.031473957 |

TABLE 3-continued

Global gene expression profile of hFibs vs. Oct-4 transduced hFibs at Day 4

| GENES | Accession | Fold change | p-value |
|---|---|---|---|
| PLK4: polo-like kinase 4 (Drosophila) | NM_014264 | −7.15 | 0.046052773 |
| KIFC1: kinesin family member C1 | NM_002263 | −7.2 | 0.033701678 |
| SPAG5: sperm associated antigen 5 | NM_006461 | −7.32 | 0.021107196 |
| RNU5F: RNA, U5F small nuclear | M77840 | −7.33 | 0.032317221 |
| ARSI: arylsulfatase family, member I | NM_001012301 | −7.39 | 0.02437027 |
| PRC1: protein regulator of cytokinesis 1 | NM_003981 | −7.48 | 0.007423876 |
| RRM2: ribonucleotide reductase M2 polypeptide | NM_001034 | −7.58 | 0.000735057 |
| CCNA2: cyclin A2 | NM_001237 | −7.72 | 0.020045463 |
| KIF20B: kinesin family member 20B | NM_016195 | −7.73 | 0.042973972 |
| CENPE: centromere protein E, 312 kDa | NM_001813 | −7.74 | 0.045689356 |
| CDCA2: cell division cycle associated 2 | NM_152562 | −7.78 | 0.002339029 |
| HIST1H1B: histone cluster 1, H1b | NM_005322 | −7.82 | 0.01239215 |
| KIAA0101: KIAA0101 | NM_014736 | −7.95 | 0.004181814 |
| KIF14: kinesin family member 14 | NM_014875 | −8.25 | 0.008367918 |
| NCAPG2: non-SMC condensin II complex, subunit G2 | NM_017760 | −8.36 | 0.018978836 |
| ITGA2: integrin, alpha 2 (CD49B) | NM_002203 | −8.43 | 0.013749967 |
| PRR11: proline rich 11 | NM_018304 | −8.47 | 0.000728434 |
| KPNA2: karyopherin alpha 2 (RAG cohort 1, importin alpha 1) | NM_002266 | −8.87 | 0.006498917 |
| KPNA2: karyopherin alpha 2 (RAG cohort 1, importin alpha 1) | NM_002266 | −9.02 | 0.006274906 |
| NCAPG: non-SMC condensin I complex, subunit G | NM_022346 | −9.23 | 0.008471132 |
| CDC2: cell division cycle 2, G1 to S and G2 to M | NM_001786 | −9.27 | 0.047076112 |
| NDC80: NDC80 homolog, kinetochore complex component | NM_006101 | −9.28 | 0.038380426 |
| EXO1: exonuclease 1 | NM_130398 | −9.52 | 0.003215089 |
| LMNB1: lamin B1 | NM_005573 | −9.53 | 0.006541627 |
| KIF23: kinesin family member 23 | NM_138555 | −9.57 | 0.013547107 |
| CASC5: cancer susceptibility candidate 5 | NM_170589 | −9.8 | 0.002491149 |
| CCNB2: cyclin B2 | NM_004701 | −9.81 | 0.034290952 |
| KIF4A: kinesin family member 4A | NM_012310 | −9.84 | 0.001147293 |
| MKI67: antigen identified by monoclonal antibody Ki-67 | NM_002417 | −10.19 | 0.042290746 |
| CCNB1: cyclin B1 | NM_031966 | −10.41 | 0.028335597 |
| PLK1: polo-like kinase 1 (Drosophila) | NM_005030 | −10.41 | 0.006026171 |
| ANLN: anillin, actin binding protein | NM_018685 | −10.45 | 0.034437444 |
| CENPF: centromere protein F, 350/400ka (mitosin) | NM_016343 | −10.56 | 0.025783454 |
| SPC25: SPC25, NDC80 kinetochore complex component, homolog | NM_020675 | −10.82 | 0.030561631 |
| TPX2: TPX2, microtubule-associated, homolog (Xenopus laevis) | NM_012112 | −10.83 | 0.012391814 |
| BUB1: BUB1 budding uninhibited by benzimidazoles 1 homolog | NM_004336 | −10.87 | 0.03037767 |
| HAS2: hyaluronan synthase 2 | NM_005328 | −10.87 | 0.009635315 |
| CENPI: centromere protein I | NM_006733 | −11.31 | 0.032980885 |
| KIF20A: kinesin family member 20A | NM_005733 | −11.45 | 0.027098763 |
| ITGA6: integrin, alpha 6 | NM_000210 | −11.81 | 0.002398135 |
| TOP2A: topoisomerase (DNA) II alpha 170 kDa | NM_001067 | −11.92 | 0.011612551 |
| PBK: PDZ binding kinase | NM_018492 | −12.25 | 0.045913184 |
| MELK: maternal embryonic leucine zipper kinase | NM_014791 | −12.29 | 0.024684383 |
| ASPM: asp (abnormal spindle) homolog, microcephaly associated | NM_018136 | −12.88 | 0.014799875 |
| TTK: TTK protein kinase | NM_003318 | −13.74 | 0.037648261 |
| DLGAP5: discs, large (Drosophila) homolog-associated protein 5 | NM_014750 | −14.61 | 0.003552502 |
| ARHGAP11A: Rho GTPase activating protein 11A | NM_014783 | −14.9 | 0.024697435 |
| NUF2: NUF2, NDC80 kinetochore complex component, homolog | NM_145697 | −15.1 | 0.042183072 |

TABLE 4

| | | Total Cell Number | | |
|---|---|---|---|---|
| Trials | Sample | Phase I | Phase II* (CD45+) | Phase III** (CD45+CD34+) |
| 1 | 1 | 10000 | 21002 | 15750 |
| | 2 | 10000 | 36410 | 27307.5 |
| | 3 | 10000 | 43103 | 25861 |
| Ave | | 10000 | 33505 | 22972.83 |
| 2 | 1 | 10000 | 18200 | 19110 |
| | 2 | 10000 | 24007 | 18005 |
| | 3 | 10000 | 38000 | 27968 |
| Ave | | 10000 | 26735.66 | 21694.33 |
| 3 | 1 | 10000 | 15490 | 14870 |
| | 2 | 10000 | 32654 | 24490 |
| | 3 | 10000 | 31800 | 23404 |
| Ave | | 10000 | 26648 | 20921.33 |

*Calculation of value: (Total cell number × frequency of CD45+ cells)
**Calculation of value: (Total cell number × frequency of CD34+CD45+ cells)

TABLE 4-continued

| | | | Total Cell Number | |
|---|---|---|---|---|
| Trials | Sample | Phase I | Phase II* (CD45+) | Phase III** (CD45+CD34+) |

Calculation of dermal patch size required to achieve full hematopoietic reconstitution:
A 60 kg individual will need $1.5 \times 10^8$ CD34+ve cells
Skin puncture of 6 mm in diameter has $1.0 \times 10^7$ cells
Per 10,000 Fibs initially plated there are ~21,000 CD34$^+$CD45$^+$ cells
Therefore, number of Fibs needed to get $1.5 \times 10^8$ CD34+ve cells
= $(10,000 \times 1.5 \times 10^8)/(21,000)$
= $7.14 \times 10^7$ Fibs Thus, 7.1 skin punctures are needed equaling to 42.84 mm (7.14 × 6 mm) diameter skin patch.

TABLE 5

| Gene | Sequence (SEQ ID NO:) |
|---|---|
| Oct-4 | Forward CTGAAGCAGAAGAGGATCAC (SEQ ID NO: 5)<br>Reverse GACCACATCCTTCTCGAGCC (SEQ ID NO: 6) |
| Nanog | Forward CGAAGAATAGCAATGGTGTGACG (SEQ ID NO: 7)<br>Reverse TTCCAAAGCAGCCTCCAAGTC (SEQ ID NO: 8) |
| Sox-2 | Forward AACGTTTGCCTTAAACAAGACCAC (SEQ ID NO: 9)<br>Reverse CGAGATAAACATGGCAATCAAATG (SEQ ID NO: 10) |
| C/EBPa | Forward CTAGAGATCTGGCTGTGGGG (SEQ ID NO: 11)<br>Reverse TCATAACTCCGGTCCCTCTG (SEQ ID NO: 12) |
| Runx1 | Forward CCGAGAACCTCGAAGACATC (SEQ ID NO: 13)<br>Reverse GTCTGACCCTCATGGCTGT (SEQ ID NO: 14) |
| SCL | Forward CATGGTGCAGCAGCTGAGTCCT (SEQ ID NO: 15)<br>Reverse CCATCTCATAGGGGGAAGGT (SEQ ID NO: 16) |
| Beta-hemoglobin | Forward AAGTCTGCCGTTACTGCCC (SEQ ID NO: 17)<br>Reverse CATGAGCCTTCACCTTAGGGT (SEQ ID NO: 18) |
| Zeta-hemoglobin | Forward GGGGGAAGTAGGTCTTGGTC (SEQ ID NO: 19)<br>Reverse CATCATTGTGTCCATGTGGG (SEQ ID NO: 20) |
| Epsilon-hemoglobin | Forward ATGGTGCATTTTACTGCTGAGG (SEQ ID NO: 21)<br>Reverse GGGAGACGACAGGTTTCCAAA (SEQ ID NO: 22) |
| Brachyury | Forward ATGAGCCTCGAATCCACATAGT (SEQ ID NO: 23)<br>Reverse TCCTCGTTCTGATAAGCAGTCA (SEQ ID NO: 24) |
| PU.1 | Forward ACGGATCTATACCAACGCCA (SEQ ID NO: 25)<br>Reverse GGGGTGGAAGTCCCAGTAAT (SEQ ID NO: 26) |
| GATA1 | Forward GGGATCACACTGAGCTTGC (SEQ ID NO: 27)<br>Reverse ACCCCTGATTCTGGTGTGG (SEQ ID NO: 28) |
| GATA2 | Forward GGGCTAGGGAACAGATCGACG (SEQ ID NO: 29)<br>Reverse GCAGCAGTCAGGTGCGGAGG (SEQ ID NO: 30) |
| GAPDH | Forward GAAATCCCATCACCAATCTTCCAGG (SEQ ID NO: 31)<br>Reverse GCAATTGAGCCCCAGCCTTCTC (SEQ ID NO: 32) |
| GUS-B | Forward CAGTCATGAAATCGGCAAAA (SEQ ID NO: 33)<br>Reverse AAACGATTGCAGGGTTTCAC (SEQ ID NO: 34) |

TABLE 6

| Gene | Sequence |
|---|---|
| Oct-4 Promoter | Forward TTAGAAGGCAGATAGAGCCACTGACC (SEQ ID NO: 35)<br>Reverse TGCCTGTCTGTGAGGGATGATGTT (SEQ ID NO: 36) |
| Nano Promoter | Forward AGCTCTATCCCCCAGCACTCG (SEQ ID NO: 37)<br>Reverse GAGAAAGCGAGAGCTCCTCGC (SEQ ID NO: 38) |
| TBX3 Promoter | Forward AACGTTTGCCTTAAACAAGACCAC (SEQ ID NO: 39)<br>Reverse CGAGATAAACATGGCAATCAAATG (SEQ ID NO: 40) |
| c-Myc Promoter | Forward AATGCCTTTGGGTGAGGGAC (SEQ ID NO: 41)<br>Reverse TCCGTGCCTTTTTTGGGG (SEQ ID NO: 42) |

TABLE 6-continued

| Gene | Sequence |
|---|---|
| Runx1 Promoter | Forward GCGTGGCTGCTTTCAACTTTCCTT(SEQ ID NO: 43)<br>Reverse TGGGTCGGTTTCTGTAATGGGTGT(SEQ ID NO: 44) |
| SCL Enhancer | Forward AACACGCCGGGAATGGATGGAT(SEQ ID NO: 45)<br>Reverse GCGGCTTTGGTGGACATATAGGAA(SEQ ID NO: 46) |
| GATA1 Promoter | Forward AGAGGCCAAAGACAGAAGTGGAGA(SEQ ID NO: 47)<br>Reverse AGAGCCACAGGCTACATCAATCCA(SEQ ID NO: 48) |
| MixL1 Promoter | Forward AAACTGCGCCGTATCCTCTGCTAA(SEQ ID NO: 49)<br>Reverse TCTTCTGCAAGCCTCCCTAACACA(SEQ ID NO: 50) |
| Oct-2 Promoter | Forward AATAGCAGGAGCAGCAACAGAAGG(SEQ ID NO: 51)<br>Reverse TTAAAGGAGCCGCGCATTTGACAG(SEQ ID NO: 52) |
| CD45 Promoter | Forward ATCTAGCTCAAGGGTATCGTACAAA(SEQ ID NO: 53)<br>Reverse CACACTTTGTGCAAATGGAAATAACCC(SEQ ID NO: 54) |
| PU.1 Promoter | Forward CAGAGACTTCCTGTATGTAGCGCA(SEQ ID NO: 55)<br>Reverse AGGGCCAGCACAAGTTCCTGATTT(SEQ ID NO: 56) |
| Myf5 Promoter | Forward AGTTGGACTGCCTTGGTCACTT(SEQ ID NO: 57)<br>Reverse ACAAACCTCCGCCTTTCCTCTACA(SEQ ID NO: 58) |
| Pol2ra Promoter | Forward ATTACAGGCCAGGAGATGCCCA(SEQ ID NO: 59)<br>Reverse CCCGGGGAAGGGCGGTTG(SEQ ID NO: 60) |
| Gadd45a Promoter | Forward ATTAGAAGAGAGGAGGCCACAGGA(SEQ ID NO: 61)<br>Reverse TTATCCTGCCAACCCTCAGCCAA(SEQ ID NO: 62) |
| Nkx2.5 Promoter | Forward GACGCATTTGGAAGGGTCTCCTTT(SEQ ID NO: 63)<br>Reverse TCCTTCTCTCTCCCATGCTGGTTT(SEQ ID NO: 64) |

TABLE 7

| RT-PCR Primers | ChIP Primers |
|---|---|
| Oct3/4<br>S: CTGAAGCAGAAGAGGATCAC<br>(SEQ ID NO: 5)<br>A: GACCACATCCTTCTCGAGCC<br>(SEQ ID NO: 6) | Oct4 Trimer from EOS Vector<br>S: ACGATTCGCAGTTAATCCTGGCCT<br>(SEQ ID NO: 73)<br>A: ATAGTATGGGCAAGCAGGGAGCTA<br>(SEQ ID NO: 74) |
| NANOG<br>S: CGAAGAATAGCAATGGTGTGACG<br>(SEQ ID NO: 7)<br>A: TTCCAAAGCAGCCTCCAAGTC<br>(SEQ ID NO: 8) | Oct3/4<br>S: TTAGAAGGCAGATAGAGCCACTGACC<br>(SEQ ID NO: 35)<br>A: TGCCTGTCTCTGTGAGGGATGATGTT<br>(SEQ ID NO: 36) |
| Sox2<br>S: AACGTTTGCCTTAAACAAGACCAC<br>(SEQ ID NO: 9)<br>A: CGAGATAAACATGGCAATCAAATG<br>(SEQ ID NO: 10) | Nanog<br>S: GACTGAGCTGGTTGCCTCAT<br>(SEQ ID NO: 75)<br>A: GGCAGCTTTAAGACTTTTCTGG<br>(SEQ ID NO: 76) |
| Tbx3<br>S: TCCATGAGGGTGTTTGATGA<br>(SEQ ID NO: 65)<br>A: CGCTGGGACATAAATCTTTGA<br>(SEQ ID NO: 66) | Sox2<br>S: GGATAACATTGTACTGGGAAGGGACA<br>CAAAGTTTCTTTTATTCGTATGTGTGAGC<br>(SEQ ID NO: 77)<br>(SEQ ID NO: 78) |
| Dppa4<br>S: ACCTCAGAAGAAGATACCAATCC<br>(SEQ ID NO: 67)<br>A: AAGGCACACAGGCGCTTA<br>(SEQ ID NO: 68) | Brachury<br>S: AGGCGCGAGAACAGCACTACTA<br>(SEQ ID NO: 79)<br>A: ATGTTTGCACCTCCATCAAAGCGG<br>(SEQ ID NO: 80) |
| hRex1<br>S: GCGTACGCAAATTAAAGTCCAGA<br>(SEQ ID NO: 69)<br>A: CAGCATCCTAAACAGCTCGCAGAAT<br>(SEQ ID NO: 70) | |

TABLE 7-continued

| RT-PCR Primers | ChIP Primers |
|---|---|

Brachyury
S: ATGAGCCTCGAATCCACATAGT
(SEQ ID NO: 23)
A: TCCTCGTTCTGATAAGCAGTCA
(SEQ ID NO: 24)

GAPDH
S: TGCACCACCAACTGCTTAGC
(SEQ ID NO: 71)
A: GGCATGGACTGTGGTCATGAG
(SEQ ID NO: 72)

REFERENCES

Aasen, T., A. Raya, et al. (2008). "Efficient and rapid generation of induced pluripotent stem cells from human keratinocytes." Nat Biotechnol 26(11): 1276-84.

Amariglio, N., Hirshberg, A., Scheithauer, B. W., Cohen, Y., Loewenthal, R., Trakhtenbrot, L., Paz, N., Koren-Michowitz, M., Waldman, D., Leider-Trejo, L., et al. (2009). Donor-derived brain tumor following neural stem cell transplantation in an ataxia telangiectasia patient. PLoS Med 6, e1000029.

Aoi, T., K. Yae, et al. (2008). "Generation of pluripotent stem cells from adult mouse liver and stomach cells." Science 321(5889): 699-702.

Atlasi, Y., S. J. Mowla, et al. (2008). "OCT4 spliced variants are differentially expressed in human pluripotent and non-pluripotent cells." Stem Cells 26(12): 3068-74.

Bendall, S. C., M. H. Stewart, et al. (2007). "IGF and FGF cooperatively establish the regulatory stem cell niche of pluripotent human cells in vitro." Nature 448(7157): 1015-21.

Bender, J. G., To, L. B., Williams, S., and Schwartzberg, L. S. (1992). Defining a therapeutic dose of peripheral blood stem cells. J Hematother 1, 329-341.

Biernaskie, J., M. Paris, et al. (2009). "SKPs derive from hair follicle precursors and exhibit properties of adult dermal stem cells." Cell Stem Cell 5(6): 610-23.

Boyer, L. A., Lee, T. I., Cole, M. F., Johnstone, S. E., Levine, S. S., Zucker, J. P., Guenther, M. G., Kumar, R. M., Murray, H. L., Jenner, R. G., et al, (2005). Core transcriptional regulatory circuitry in human embryonic stem cells. Cell 122, 947-956.

Brambrink, T., R. Foreman, et al. (2008). "Sequential expression of pluripotency markers during direct reprogramming of mouse somatic cells." Cell Stem Cell 2(2): 151-9.

Brunner, C., Marinkovic, D., Klein, J., Samardzic, T., Nitschke, L., and Wirth, T. (2003). B cell-specific transgenic expression of Bcl2 rescues early B lymphopoiesis but not B cell responses in BOB.1/OBF.1-deficient mice. J Exp Med 197, 1205-1211.

Carey, B. W., S. Markoulaki, et al. (2009). "Reprogramming of murine and human somatic cells using a single polycistronic vector." Proc Natl Acad Sci USA 106(1): 157-62.

Carpenter, M. K., Inokuma, M. S., Denham, J., Mujtaba, T., Chiu, C. P., and Rao, M. S. (2001). Enrichment of neurons and neural precursors from human embryonic stem cells. Exp Neurol 172, 383-397.

Cerdan, C., Rouleau, A., and Bhatia, M. (2004). VEGF-A165 augments erythropoietic development from human embryonic stem cells. Blood 103, 2504-2512.

Chadwick, K., L. Wang, et al. (2003). "Cytokines and BMP-4 promote hematopoietic differentiation of human embryonic stem cells." Blood 102(3): 906-15.

Chan, E. M., Ratanasirintrawoot, S., Park, I. H., Manos, P. D., Loh, Y. H., Huo, H., Miller, J. D., Hartung, O., Rho, J., Ince, T. A., et al. (2009). Live cell imaging distinguishes bona fide human iPS cells from partially reprogrammed cells. Nat Biotechnol 27, 1033-1037.

Chang, K. H., Nelson, A. M., Cao, H., Wang, L., Nakamoto, B., Ware, C. B., and Papayannopoulou, T. (2006). Definitive-like erythroid cells derived from human embryonic stem cells coexpress high levels of embryonic and fetal globins with little or no adult globin. Blood 108, 1515-1523.

Choudhary, M., X. Zhang, et al. (2007). "Putative role of hyaluronan and its related genes, HAS2 and RHAMM, in human early preimplantation embryogenesis and embryonic stem cell characterization." Stem Cells 25(12): 3045-57.

Debili, N., Coulombel, L., Croisille, L., Katz, A., Guichard, J., Breton-Gorius, J., and Vainchenker, W. (1996). Characterization of a bipotent erythro-megakaryocytic progenitor in human bone marrow. Blood 88, 1284-1296.

D'Ippolito, G., S. Diabira, et al. (2006). "Low oxygen tension inhibits osteogenic differentiation and enhances stemness of human MIAMI cells." Bone 39(3): 513-22.

Dyce, P. W., L. Wen, et al. (2006). "In vitro germline potential of stem cells derived from fetal porcine skin." Nat Cell Biol 8(4): 384-90.

Dyce, P. W., H. Zhu, et al. (2004). "Stem cells with multilineage potential derived from porcine skin." Biochem Biophys Res Commun 316(3): 651-8.

Eminli, S., A. Foudi, et al. (2009). "Differentiation stage determines potential of hematopoietic cells for reprogramming into induced pluripotent stem cells." Nat Genet 41(9): 968-76.

Eminli, S., J. Utikal, et al. (2008). "Reprogramming of neural progenitor cells into induced pluripotent stem cells in the absence of exogenous Sox2 expression." Stem Cells 26(10): 2467-74.

Emslie, D., D'Costa, K., Hasbold, J., Metcalf, D., Takatsu, K., Hodgkin, P. O., and Corcoran, L. M. (2008). Oct2 enhances antibody-secreting cell differentiation through regulation of IL-5 receptor alpha chain expression on activated B cells. J Exp Med 205, 409-421.

Feng, R., Desbordes, S. C., Xie, H., Tillo, E. S., Pixley, F., Stanley, E. R., and Graf, T. (2008). PU.1 and C/EBPalpha/beta convert fibroblasts into macrophage-like cells. Proc Natl Acad Sci USA 105, 6057-6062.

Feng, B., J. Jiang, et al. (2009). "Reprogramming of fibroblasts into induced pluripotent stem cells with orphan nuclear receptor Esrrb." Nat Cell Biol 11(2): 197-203.

Feugier, P., Bensoussan, D., Girard, F., Alla, F., Schuhmacher, A., Latger-Cannard, V., Hulin, C., Witz, F., Witz, B., Carret, A. S., et al. (2003). Hematologic recovery after autologous PBPC transplantation: importance of the number of postthaw CD34+ cells. Transfusion 43, 878-884.

Fried, W. (2009). Erythropoietin and erythropoiesis. Exp Hematol 37, 1007-1015.

Friedman, A. D. (2007). Transcriptional control of granulocyte and monocyte development. Oncogene 26, 6816-6828.

Gabbianelli, M., Pelosi, E., Montesoro, E., Valtieri, M., Luchetti, L., Samoggia, P., Vitelli, L., Barberi, T., Testa, U., Lyman, S., et al. (1995). Multi-level effects of flt3 ligand on human hematopoiesis: expansion of putative stem cells and proliferation of granulomonocytic progenitors/monocytic precursors. Blood 86, 1661-1670.

Ghozi, M. C., Bernstein, Y., Negreanu, V., Levanon, D., and Groner, Y. (1996). Expression of the human acute myeloid leukemia gene AML1 is regulated by two promoter regions. Proc Natl Acad Sci USA 93, 1935-1940.

Gonzalez, F., M. Barragan Monasterio, et al. (2009). "Generation of mouse-induced pluripotent stem cells by transient expression of a single nonviral polycistronic vector." *Proc Natl Acad Sci USA* 106(22): 8918-22.

Goolsby, J., M. C. Marty, et al. (2003). "Hematopoietic progenitors express neural genes." *Proc Natl Acad Sci USA* 100(25): 14926-31.

Guo, G., J. Yang, et al. (2009). "Klf4 reverts developmentally programmed restriction of ground state pluripotency." *Development* 136(7): 1063-9.

Hanna, J., S. Markoulaki, et al. (2008). "Direct reprogramming of terminally differentiated mature B lymphocytes to pluripotency." *Cell* 133(2): 250-64.

Hanna, J., K. Saha, et al. (2009). "Direct cell reprogramming is a stochastic process amenable to acceleration." *Nature* 462(7273): 595-601.

Hanna, J., M. Wernig, et al. (2007). "Treatment of sickle cell anemia mouse model with iPS cells generated from autologous skin." *Science* 318(5858): 1920-3.

Hassan, H. T., and Zander, A. (1996). Stem cell factor as a survival and growth factor in human normal and malignant hematopoiesis. Acta Haematol 95, 257-262.

Heng, J. C., B. Feng, et al. "The nuclear receptor Nr5a2 can replace Oct4 in the reprogramming of murine somatic cells to pluripotent cells." *Cell Stem Cell* 6(2): 167-74.

Hope, K. J., Jin, L., and Dick, J. E. (2004). Acute myeloid leukemia originates from a hierarchy of leukemic stem cell classes that differ in self-renewal capacity. Nat Immunol 5, 738-743.

Hotta, A., A. Y. Cheung, et al. (2009). "Isolation of human iPS cells using EOS lentiviral vectors to select for pluripotency." *Nat Methods* 6(5): 370-6.

Huangfu, D., K. Osafune, et al. (2008). "Induction of pluripotent stem cells from primary human fibroblasts with only Oct4 and Sox2." *Nat Biotechnol* 26(11): 1269-75.

Ichikawa, M., Asai, T., Chiba, S., Kurokawa, M., and Ogawa, S. (2004). Runx1/AML-1 ranks as a master regulator of adult hematopoiesis. Cell Cycle 3, 722-724.

Ieda, M., Fu, J. D., Delgado-Olgiun, P., Vedantham, V., Hayashi, Y., Bruneau, B. G., and Srivastava, D. (2010). Direct Reprogramming of Fibroblasts into Functional Cardiomyocytes by Defined Factors. Cell 142, 375-386.

Izadpanah, R., D. Kaushal, et al. (2008). "Long-term in vitro expansion alters the biology of adult mesenchymal stem cells." *Cancer Res* 68(11): 4229-38.

Izadpanah, R., C. Trygg, et al. (2006). "Biologic properties of mesenchymal stem cells derived from bone marrow and adipose tissue." *J Cell Biochem* 99(5): 1285-97.

Jaenisch, R., and Young, R. (2008). Stem cells, the molecular circuitry of pluripotency and nuclear reprogramming. Cell 132, 567-582.

Jensen, K. B., C. A. Collins, et al. (2009). "Lrig1 expression defines a distinct multipotent stem cell population in mammalian epidermis." *Cell Stem Cell* 4(5): 427-39.

Jiang, Y., B. N. Jahagirdar, et al. (2002). "Pluripotency of mesenchymal stem cells derived from adult marrow." *Nature* 418(6893): 41-9.

Johnson, J., J. Bagley, et al. (2005). "Oocyte generation in adult mammalian ovaries by putative germ cells in bone marrow and peripheral blood." *Cell* 122(2): 303-15.

Kaji, K., K. Norrby, et al. (2009). "Virus-free induction of pluripotency and subsequent excision of reprogramming factors." *Nature* 458(7239): 771-5.

Kanawaty, A., and Henderson, J. (2009). Genomic analysis of induced pluripotent stem (iPS) cells: routes to reprogramming. Bioessays 31, 134-138.

Kang, J., Shakya, A., and Tantin, D. (2009). Stem cells, stress, metabolism and cancer: a drama in two Octs. Trends Biochem Sci 34, 491-499.

Kawamura, T., J. Suzuki, et al. (2009). "Linking the p53 tumour suppressor pathway to somatic cell reprogramming." *Nature*.

Kim, J., J. Chu, et al. (2008). "An extended transcriptional network for pluripotency of embryonic stem cells." *Cell* 132(6): 1049-61.

Kim, J. B., Greber, B., Arauzo-Bravo, M. J., Meyer, J., Park, K. I., Zaehres, H., and Scholer, H. R. (2009). Direct reprogramming of human neural stem cells by OCT4. Nature 461, 649-643.

Kim, J. B., V. Sebastiano, et al. (2009). "Oct4-induced pluripotency in adult neural stem cells." *Cell* 136(3): 411-9.

Kistler, B., Pfisterer, P., and Wirth, T. (1995). Lymphoid- and myeloid-specific activity of the PU.1 promoter is determined by the combinatorial action of octamer and ets transcription factors. Oncogene 11, 1095-1106.

Klimchenko, O., Mori, M., Distefano, A., Langlois, T., Larbret, F., Lecluse, Y., Feraud, O., Vainchenker, W., Norol, F., and Debili, N. (2009). A common bipotent progenitor generates the erythroid and megakaryocyte lineages in embryonic stem cell-derived primitive hematopoiesis. Blood 114, 1506-1517.

Koschmieder, S., Rosenbauer, F., Steidl, U., Owens, B. M., and Tenen, D. G. (2005). Role of transcription factors C/EBPalpha and PU.1 in normal hematopoiesis and leukemia. Int J Hematol 81, 368-377.

Kragl, M., D. Knapp, et al. (2009). "Cells keep a memory of their tissue origin during axolotl limb regeneration." *Nature* 460(7251): 60-5.

Kwon, U. K., Yen, P. H., Collins, T., and Wells, R. A. (2006). Differential lineage-specific regulation of murine CD45 transcription by Oct-1 and PU.1. Biochem Biophys Res Commun 344, 146-154.

Lebofsky, R., and Walter, J. C. (2007). New Myc-anisms for DNA replication and tumorigenesis? Cancer Cell 12, 102-103.

Lengerke, C., and Daley, G. Q. (2010). Autologous blood cell therapies from pluripotent stem cells. Blood Rev 24, 27-37.

Lengner, C. J., F. D. Camargo, et al. (2007). "Oct4 expression is not required for mouse somatic stem cell self-renewal." *Cell Stem Cell* 1(4): 403-15.

Lengner, C. J., G. G. Welstead, et al. (2008). "The pluripotency regulator Oct4: a role in somatic stem cells?" *Cell Cycle* 7(6): 725-8.

Li, H., M. Collado, et al. (2009). "The Ink4/Arf locus is a barrier for iPS cell reprogramming." *Nature*.

Li, L., M. Fukunaga-Kalabis, et al. "Human dermal stem cells differentiate into functional epidermal melanocytes." *J Cell Sci* 123(Pt 6): 853-60.

Li, C. & Wong, W. H. Model-based analysis of oligonucleotide arrays: expression index computation and outlier detection. *Proc Natl Acad Sci USA* 98, 31-36 (2001).

Lin, T., Ambasudhan, R., Yuan, X., Li, W., Hilcove, S., Abujarour, R., Lin, X., Hahm, H. S., Hao, E., Hayek, A., et al. (2009). A chemical platform for improved induction of human iPSCs. Nat Methods 6, 805-808.

Loh, Y. H., Q. Wu, et al. (2006). "The Oct4 and Nanog transcription network regulates pluripotency in mouse embryonic stem cells." *Nat Genet* 38(4): 431-40.

Lowry, W. E., L. Richter, et al. (2008). "Generation of human induced pluripotent stem cells from dermal fibroblasts." *Proc Natl Acad Sci US A* 105(8): 2883-8.

Lyman, S. D., James, L., Vanden Bos, T., de Vries, P., Brasel, K., Gliniak, B., Hollingsworth, L. T., Picha, K. S., McKenna, H. J., Splett, R. R., et al. (1993). Molecular cloning of a ligand for the flt3/flk-2 tyrosine kinase receptor: a proliferative factor for primitive hematopoietic cells. Cell 75, 1157-1167.

Lyssiotis, C. A., R. K. Foreman, et al. (2009). "Reprogramming of murine fibroblasts to induced pluripotent stem cells with chemical complementation of Klf4." *Proc Natl Acad Sci USA* 106(22): 8912-7.

Manabu Ohyama, A. T., Christine L. Tock, Michael F. Radonovich, Cynthia A. Pise-Masison, Steven B. Hopping, John N. Brady, Mark C. Udey and Jonathan C. Vogel (2006). "Characterization and isolation of stem cell-enriched human hair follicle bulge cells." *The Journal of Clinical Investigation* 116(1): 249-260.

Manning, A. L. and D. A. Compton (2008). "Structural and regulatory roles of nonmotor spindle proteins." *Curr Opin Cell Biol* 20(1): 101-6.

Markoulaki, S., J. Hanna, et al. (2009). "Transgenic mice with defined combinations of drug-inducible reprogramming factors." *Nat Biotechnol* 27(2): 169-71.

Meissner, A., M. Wernig, et al. (2007). "Direct reprogramming of genetically unmodified fibroblasts into pluripotent stem cells." *Nat Biotechnol* 25(10): 1177-81.

Mikkelsen, T. S., Hanna, J., Zhang, X., Ku, M., Wernig, M., Schorderet, P., Bernstein, B. E., Jaenisch, R., Lander, E. S., and Meissner, A. (2008). Dissecting direct reprogramming through integrative genomic analysis. Nature 454, 49-55.

Moriscot, C., F. de Fraipont, et al. (2005). "Human bone marrow mesenchymal stem cells can express insulin and key transcription factors of the endocrine pancreas developmental pathway upon genetic and/or microenvironmental manipulation in vitro." *Stem Cells* 23(4): 594-603.

Nakagawa, M., M. Koyanagi, et al. (2008). "Generation of induced pluripotent stem cells without Myc from mouse and human fibroblasts." *Nat Biotechnol* 26(1): 101-6.

Nayernia, K., J. H. Lee, et al. (2006). "Derivation of male germ cells from bone marrow stem cells." *Lab Invest* 86(7): 654-63.

Ng, E. S., Azzola, L., Sourris, K., Robb, L., Stanley, E. G., and Elefanty, A. G. (2005). The primitive streak gene Mixl1 is required for efficient haematopoiesis and BMP4-induced ventral mesoderm patterning in differentiating ES cells. Development 132, 873-884.

Okita, K., T. Ichisaka, et al. (2007). "Generation of germline-competent induced pluripotent stem cells." *Nature* 448 (7151): 313-7.

Okita, K., M. Nakagawa, et al. (2008). "Generation of mouse induced pluripotent stem cells without viral vectors." *Science* 322(5903): 949-53.

Okumura-Nakanishi, S., M. Saito, H Niwa, F. Ishikawa (2005). "Oct-3/4 and Sox2 regulate Oct3/4 gene in embryonic stem cells". *Journal of Biological Chemistry* 280(7): 5307-17.

Orkin, S. H., and Zon, L. I. (2002). Hematopoiesis and stem cells: plasticity versus developmental heterogeneity. Nat Immunol 3, 323-328.

Oshima, A., et al. Cloning, sequencing, and expression of cDNA for human beta-glucuronidase. *Proc Natl Aced Sci USA* 84, 685-689 (1987).

Pardo, M., Lang, B., Yu, L., Prosser, H., Bradley, A., Babu, M. M., and Choudhary, J. (2010). An expanded Oct4 interaction network: implications for stem cell biology, development, and disease. Cell Stem Cell 6, 382-395.

Park, I. H., N. Arora, et al. (2008). "Disease-specific induced pluripotent stem cells." *Cell* 134(5): 877-86.

Park, I. H., P. H. Lerou, et al. (2008). "Generation of human-induced pluripotent stem cells." *Nat Protoc* 3(7): 1180-6.

Park, I. H., R. Zhao, et al. (2008). "Reprogramming of human somatic cells to pluripotency with defined factors." *Nature* 451(7175): 141-6.

Perlingeiro, R. C., Kyba, M., and Daley, G. Q. (2001). Clonal analysis of differentiating embryonic stem cells reveals a hematopoietic progenitor with primitive erythroid and adult lymphoid-myeloid potential. Development 128, 4597-4604.

Pfisterer, P., Konig, H., Hess, J., Lipowsky, G., Haendler, B., Schleuning, W. D., and Wirth, T. (1996). CRISP-3, a protein with homology to plant defense proteins, is expressed in mouse B cells under the control of Oct2. Mol Cell Biol 16, 6160-6168.

Pollard, S. M., Yoshikawa, K., Clarke, I. D., Danovi, D., Stricker, S., Russell, R., Bayani, J., Head, R., Lee, M., Bernstein, M., et al. (2009). Glioma stem cell lines expanded in adherent culture have tumor-specific phenotypes and are suitable for chemical and genetic screens. Cell Stem Cell 4, 568-580.

Rampalli, S., Li, L., Mak, E., Ge, K., Brand, M., Tapscott, S. J., and Dilworth, F. J. (2007). p38 MAPK signaling regulates recruitment of Ash2L-containing methyltransferase complexes to specific genes during differentiation. Nat Struct Mol Biol 14, 1150-1156.

Ren, H., Y. Cao, et al. (2006). "Proliferation and differentiation of bone marrow stromal cells under hypoxic conditions." *Biochem Biophys Res Commun* 347(1): 12-21.

Reubinoff, B. E., Itsykson, P., Turetsky, T., Pera, M. F., Reinhartz, E., Itzik, A., and Ben-Hur, T. (2001). Neural progenitors from human embryonic stem cells. Nat Biotechnol 19, 1134-1140.

Robertson, G., et al. cisRED: a database system for genome-scale computational discovery of regulatory elements. *Nucleic Acids Res* 34, D68-73 (2006).

Rodda, D. J., Chew, J. L., Lim, L. H., Loh, Y. H., Wang, B., Ng, H. H., and Robson, P. (2005). Transcriptional regulation of nanog by OCT4 and SOX2. J Biol Chem 280, 24731-24737.

Roy, N. S., Cleren, C., Singh, S. K., Yang, L., Beal, M. F., and Goldman, S. A. (2006). Functional engraftment of human ES cell-derived dopaminergic neurons enriched by coculture with telomerase-immortalized midbrain astrocytes. Nat Med 12, 1259-1268.

Sánchez Alvarado, A. (2009). "Developmental biology: A cellular view of regeneration." *Nature* 460(7251)(July 2): 39-40.

Schnerch, A., C. Cerdan, et al. "Distinguishing between mouse and human pluripotent stem cell regulation: the best laid plans of mice and men." *Stem Cells* 28(3): 419-30.

Shi, Y., C. Desponts, et al. (2008). "Induction of pluripotent stem cells from mouse embryonic fibroblasts by Oct4 and Klf4 with small-molecule compounds." *Cell Stem Cell* 3(5): 568-74.

Shivdasani, R. A., Mayer, E. L., and Orkin, S. H. (1995). Absence of blood formation in mice lacking the T-cell leukaemia oncoprotein tal-1/SCL. Nature 373, 432-434.

Silverstein, S. C., Steinman, R. M., and Cohn, Z. A. (1977). Endocytosis. Annu Rev Biochem 46, 669-722.

Simonsson, S. and J. Gurdon (2004). "DNA demethylation is necessary for the epigenetic reprogramming of somatic cell nuclei." *Nat Cell Biol* 6(10): 984-90.

Smith, Z. D., I. Nachman, et al. (2010) "Dynamic single-cell imaging of direct reprogramming reveals an early specifying event." *Nat Biotechnol* 28(5): 521-6.

Soldner, F., D. Hockemeyer, et al. (2009). "Parkinson's disease patient-derived induced pluripotent stem cells free of viral reprogramming factors." *Cell* 136(5): 964-77.

Sridharan, R., Tchieu, J., Mason, M. J., Yachechko, R., Kuoy, E., Horvath, S., Zhou, Q., and Plath, K. (2009). Role of the murine reprogramming factors in the induction of pluripotency. Cell 136, 364-377.

Stadtfeld, M., M. Nagaya, et al. (2008). "Induced pluripotent stem cells generated without viral integration." *Science* 322(5903): 945-9.

Stewart, M. H., S. C. Bendall, et al. (2008). "Deconstructing human embryonic stem cell cultures: niche regulation of self-renewal and pluripotency." *J Mol Med* 86(8): 875-86.

Strodtbeck, D., Bornhauser, M., Hanel, M., Lerche, L., Schaich, M., Illmer, T., Thiede, C., Geissler, G., Herbst, R., Ehninger, G., et al. (2005). Graft clonogenicity and intensity of pre-treatment: factors affecting outcome of autologous peripheral hematopoietic cell transplantation in patients with acute myeloid leukemia in first remission. Bone Marrow Transplant 36, 1083-1088.

Sun, H., N. Panetta, et al. (2009). "Feeder-free derivation of induced pluripotent stem cells from adult human adipose stem cells." *PNAS* 106(37): 15720-15725.

Takahashi, K., K. Okita, et al. (2007). "Induction of pluripotent stem cells from fibroblast cultures." *Nat Protoc* 2(12): 3081-9.

Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. Cell 131, 861-872.

Takahashi, K., and Yamanaka, S. (2006). Induction of pluripotent stem cells from mouse embryonic and adult fibroblast cultures by defined factors. Cell 126, 663-676.

Terunuma, A., J. W. Cross, et al. (2008). "Behavior of human foreskin keratinocytes expressing a hair follicle stem cell marker CD200." *J Invest Dermatol* 128(5): 1332-4.

Toma, J. G., I. A. McKenzie, et al. (2005). "Isolation and characterization of multipotent skin-derived precursors from human skin." *Stem Cells* 23(6): 727-37.

Tsai, F. Y., Keller, G., Kuo, F. C., Weiss, M., Chen, J., Rosenblatt, M., Alt, F. W., and Orkin, S. H. (1994). An early haematopoietic defect in mice lacking the transcription factor GATA-2. Nature 371, 221-226.

Utikal, J., N. Maherali, et al. (2009). "Sox2 is dispensable for the reprogramming of melanocytes and melanoma cells into induced pluripotent stem cells." *J Cell Sci*.

Utikal, J., J. M. Polo, et al. (2009). "Immortalization eliminates a roadblock during cellular reprogramming into iPS cells." *Nature*.

Vierbuchen, T., Ostermeier, A., Pang, Z. P., Kokubu, Y., Sudhof, T. C., and Wernig, M. (2010). Direct conversion of fibroblasts to functional neurons by defined factors. Nature.

Vijayaragavan, K., Szabo, E., Bosse, M., Ramos-Mejia, V., Moon, R. T., and Bhatia, M. (2009). Noncanonical Wnt signaling orchestrates early developmental events toward hematopoietic cell fate from human embryonic stem cells. Cell Stem Cell 4, 248-262.

Wang, L., Menendez, P., Shojaei, F., Li, L., Mazurier, F., Dick, J. E., Cerdan, C., Levac, K., and Bhatia, M. (2005). Generation of hematopoietic repopulating cells from human embryonic stem cells independent of ectopic HOXB4 expression. J Exp Med 201, 1603-1614.

Werbowetski-Ogilvie, T. E., Bosse, M., Stewart, M., Schnerch, A., Ramos-Mejia, V., Rouleau, A., Wynder, T., Smith, M. J., Dingwall, S., Carter, T., et al. (2009). Characterization of human embryonic stem cells with features of neoplastic progression. Nat Biotechnol 27, 91-97.

Wernig, M., A. Meissner, et al. (2007). "In vitro reprogramming of fibroblasts into a pluripotent ES-cell-like state." *Nature* 448(7151): 318-24.

Wojchowski, D. M., Menon, M. P., Sathyanarayana, P., Fang, J., Karur, V., Houde, E., Kapelle, W., and Bogachev, O. (2006). Erythropoietin-dependent erythropoiesis: New insights and questions. Blood Cells Mol Dis 36, 232-238.

Woltjen, K., I. P. Michael, et al. (2009). "piggyBac transposition reprograms fibroblasts to induced pluripotent stem cells." *Nature* 458(7239): 766-70.

Yamanaka, S. (2009). "Elite and stochastic models for induced pluripotent stem cell generation." *Nature* 460(7251): 49-52.

Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., et al. (2007). Induced pluripotent stem cell lines derived from human somatic cells. Science 318, 1917-1920.

Yu, H., D. Fang, et al. (2006). "Isolation of a novel population of multipotent adult stem cells from human hair follicles." *Am J Pathol* 168(6): 1879-88.

Yusa, K., R. Rad, et al. (2009). "Generation of transgene-free induced pluripotent mouse stem cells by the piggyBac transposon." *Nat Methods* 6(5): 363-9.

Zhang, S., Z. Jia, et al. (2005). "Purified human bone marrow multipotent mesenchymal stem cells regenerate infarcted myocardium in experimental rats." *Cell Transplant* 14(10): 787-98.

Zhao, X. Y., W. Li, et al. (2009). "iPS cells produce viable mice through tetraploid complementation." *Nature*.

Zhou, H., S. Wu, et al. (2009). "Generation of induced pluripotent stem cells using recombinant proteins." *Cell Stem Cell* 4(5): 381-4.

Zhou, Q., J. Brown, et al. (2008). "In vivo reprogramming of adult pancreatic exocrine cells to beta-cells." *Nature* 455(7213): 627-32.

The invention claimed is:

1. A method of generating hematopoietic progenitor cells from fibroblasts comprising:
   a) providing fibroblasts that express or are treated with a full-length Oct-4 gene or protein; wherein the fibroblasts do not overexpress or ectopically express or are not treated with Sox-2 or Nanog; and
   b) culturing the cells of step (a) under conditions that allow production of hematopoietic progenitor cells and isolating CD45+ progenitor cells;
   wherein the cells in (b) do not traverse the pluripotent state, and
   wherein the fibroblasts of step a) are not treated with any pluripotency factor protein other than said full-length Oct-4 gene or protein.

2. The method of claim 1, wherein fibroblasts that express the full-length Oct-4 gene or protein in step (a) are produced by lentiviral transduction.

3. The method of claim 1, wherein fibroblasts treated with the full-length Oct-4 gene or protein comprises providing an exogenous full-length Oct-4 gene or protein.

4. The method of claim 1, further comprising culturing the cells in step (b) in differentiation medium, wherein the differentiation medium comprises hematopoietic medium comprising at least one hematopoietic cytokine.

5. The method of claim 4, wherein the at least one hematopoietic cytokine is Flt3 ligand and/or SCF and the differentiated hematopoietic cells are of the myeloblast lineage or wherein the at least one hematopoietic cytokine is EPO and the differentiated hematopoietic cells are of the erythroid or megakaryocytic lineage.

6. The method of claim 1, wherein the fibroblasts are dermal fibroblasts.

* * * * *